US011339188B2

(12) United States Patent
Kim et al.

(10) Patent No.: US 11,339,188 B2
(45) Date of Patent: *May 24, 2022

(54) COMPOUNDS FOR THE TREATMENT OF CANCER

(71) Applicant: Eisai R&D Management Co., Ltd., Tokyo (JP)

(72) Inventors: Dae-Shik Kim, Andover, MA (US); Frank Fang, Andover, MA (US); Atsushi Endo, Andover, MA (US); Hyeong-wook Choi, Andover, MA (US); Ming-Hong Hao, Quincy, MA (US); Xingfeng Bao, Concord, MA (US); Kuan-Chun Huang, Lexington, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/781,352

(22) Filed: Feb. 4, 2020

(65) Prior Publication Data

US 2020/0299321 A1    Sep. 24, 2020

Related U.S. Application Data

(62) Division of application No. 16/277,522, filed on Feb. 15, 2019, now Pat. No. 10,618,930, which is a division of application No. 15/898,533, filed on Feb. 17, 2018, now Pat. No. 10,246,480.

(60) Provisional application No. 62/551,645, filed on Aug. 29, 2017, provisional application No. 62/551,647, filed on Aug. 29, 2017, provisional application No. 62/551,668, filed on Aug. 29, 2017, provisional application No. 62/479,169, filed on Mar. 30, 2017, provisional application No. 62/460,562, filed on Feb. 17, 2017.

(51) Int. Cl.
| | |
|---|---|
| *C07H 21/02* | (2006.01) |
| *A61P 35/02* | (2006.01) |
| *A61K 31/7084* | (2006.01) |
| *C07F 9/6587* | (2006.01) |
| *C07H 21/00* | (2006.01) |
| *A61P 31/04* | (2006.01) |
| *A61P 37/04* | (2006.01) |

(52) U.S. Cl.
CPC ......... *C07H 21/02* (2013.01); *A61K 31/7084* (2013.01); *A61P 31/04* (2018.01); *A61P 35/02* (2018.01); *A61P 37/04* (2018.01); *C07F 9/6587* (2013.01); *C07H 21/00* (2013.01)

(58) Field of Classification Search
None
See application file for complete search history.

(56) References Cited

U.S. PATENT DOCUMENTS

| | | | |
|---|---|---|---|
| 5,547,941 | A | 8/1996 | Battistini et al. |
| 7,569,555 | B2 | 8/2009 | Karaolis |
| 7,592,326 | B2 | 9/2009 | Karaolis |
| 7,709,458 | B2 | 5/2010 | Karaolis et al. |
| 8,076,303 | B2 | 12/2011 | Iyer et al. |
| 8,193,164 | B2 | 6/2012 | Fairhurst et al. |
| 9,549,944 | B2 | 1/2017 | Dubensky et al. |
| 9,770,467 | B2 | 9/2017 | Dubensky et al. |
| 2014/0205653 | A1 | 7/2014 | Dubensky et al. |
| 2014/0329889 | A1 | 11/2014 | Vance et al. |
| 2014/0341976 | A1 | 11/2014 | Dubensky et al. |
| 2015/0056224 | A1 | 2/2015 | Dubensky et al. |
| 2016/0362441 | A1 | 12/2016 | Vernejoul et al. |
| 2017/0044206 | A1 | 2/2017 | Altman et al. |
| 2017/0050967 | A1 | 2/2017 | Burai et al. |
| 2017/0158724 | A1 | 6/2017 | Adams et al. |
| 2017/0159724 | A1 | 6/2017 | Imanishi |
| 2017/0319680 | A1 | 11/2017 | Ishii et al. |
| 2017/0340658 | A1 | 11/2017 | Vernejoul et al. |

FOREIGN PATENT DOCUMENTS

| | | | |
|---|---|---|---|
| CN | 102199183 | B | 12/2013 |
| EP | 1740192 | B1 | 6/2012 |
| EP | 1729781 | B1 | 10/2012 |
| EP | 1968612 | B1 | 3/2016 |
| WO | 2009133560 | A1 | 11/2009 |
| WO | 2014179335 | A1 | 11/2014 |
| WO | 2014189805 | A1 | 11/2014 |
| WO | 2015074145 | A1 | 5/2015 |
| WO | 2015077354 | A1 | 5/2015 |
| WO | 2015185565 | A1 | 12/2015 |
| WO | 2016100261 | A2 | 6/2016 |
| WO | 2016120305 | A1 | 8/2016 |
| WO | 2016145102 | A1 | 9/2016 |
| WO | 2017011622 | A1 | 1/2017 |
| WO | 2017011920 | A1 | 1/2017 |
| WO | 2017027645 | A1 | 2/2017 |
| WO | 2017027646 | A1 | 2/2017 |
| WO | 2017040670 | A1 | 3/2017 |

(Continued)

OTHER PUBLICATIONS

Booth, J., et al., "Effect of Linker Length on DNA Duplexes Containing a Mismatched O6-2'-Deoxyguanosine-alkyl Interstrand Cross-Link," Nucleic Acids Symp. Series. No. 52, 2008, pp. 431-432.

(Continued)

*Primary Examiner* — Heidi Reese

(74) *Attorney, Agent, or Firm* — Buchanan Ingersoll & Rooney PC

(57) ABSTRACT

Provided herein are compounds useful for the treatment of cancer.

18 Claims, 21 Drawing Sheets

Specification includes a Sequence Listing.

(56) References Cited

FOREIGN PATENT DOCUMENTS

| WO | 2017075477 A1 | 5/2017 |
| WO | 2017093933 A1 | 6/2017 |
| WO | 2017123657 A1 | 7/2017 |
| WO | 2017123669 A1 | 7/2017 |
| WO | 2017161349 A1 | 9/2017 |
| WO | 2017175156 A1 | 10/2017 |
| WO | 2018060323 A1 | 4/2018 |
| WO | 2018098203 A1 | 5/2018 |
| WO | 2018140831 A2 | 8/2018 |
| WO | 2018198076 A1 | 11/2018 |
| WO | 2018198084 A1 | 11/2018 |

OTHER PUBLICATIONS

Denisov, A., et al., "Structural Basis of Interstrand Cross-Link Repair by O6-alkylguanine DNA alkyltransferase," Org. Biomol. Chem., 2017, vol. 15, pp. 8361-8370.

McManus, F., et al., "O4-Alkyl-2'deoxythymidine Cross-Linked DNA to Probe Recognition and Repair by O6-alkylguanine DNA Alkyltransferases," Org. Biomol. Chem., 2012, vol. 10, 7078-7090.

McManus, F., et al., "Preparation of Covalently Linked Complexes Between DNA and O6-Alkylguanine-DNA Alkyltransferase Using Interstrand Cross-Linked DNA," Bioconjugate Chem., 2013, vol. 24, pp. 224-233.

Notice of Reasons for Rejection in Japanese Pat. App. No. 2019-544817, dated Jan. 14, 2020, by Japanese Patent Office (Including Search Report).

Urata, H. et al., Nucleosides, Nucleotides, and Nucleic Acids 2008 vol. 27, pp. 421-430.

Chandra, Dinesh, et al., "STING ligand c-di-GMP improves cancer vaccination against metastatic breast cancer", Cancer Immunol Res., vol. 2, No. 9, pp. 901-910.

Corrales, Leticia, et al., "Direct Activation of STING in the Tumor Microenvironment Leads to Potent and Systemic Tumor Regression and Immunity", Cell Reports, vol. 11, pp. 1018-1030.

Corrales, Leticia, et al., "The host STING pathway at the interface of cancer and immunity", J. Clinical Investigation, vol. 126, No. 7, pp. 2404-2411.

Curran, Emily, et al., "STING Pathway Activation Stimulates Potent Immunity against Acute Myeloid Leukemia", Cell Reports, vol. 15, pp. 2357-2366.

Endo, Takashi, et al., "In situ cancer vaccination with a replication-conditional HSV for the treatment of liver metastasis of colon cancer", Cancer Gene Therapy, vol. 9, Nature Publishing Group, pp. 142-148.

Guanghui, Yi, et al., "Single Nucleotide Polymorphisms of Human STING Can Affect Innate Immune Response to cyclic Dinucleotides", PLOS One, vol. 8, Issue 10, pp. 1-16.

Kozlowski, James M, et al., "Metastatic Behavior of Human Tumor Cell Lines Grown in the Nude Mouse", Cancer Research, vol. 44, Aug. 1984, pp. 3522-3529.

Lioux, T, et al., "Design, Synthesis, and Biological Evaluation of Novel Cyclic Adenosine-Inosine Monophosphate (cAIMP) Analogs That Activate Stimulator of Interferon Genes (STING)", J. Med Chem., 59: , pp. 10253-10267.

Lioux, Thierry, et al., "Design, Synthesis, and Biological Evaluation of Novel Cyclic Adenosine—Inosine Monophosphate (cAIMP) Analogs That Activate Stimulator of Interferon Genes (STING)", J. Medicinal Chemistry, vol. 59, American Chemical Society, pp. 10253-10267.

Ohkuri, Takayuki, et al., "Protective role of STING against gliomagenesis: Rational use of STING agonist in anti-glioma Immunotherapy", Oncoimmunology, vol. 4, Issue 4, pp. 1-2.

International Search Report for PCT/US2018/018561 filed Feb. 17, 2018, dated May 23, 2018.

Rajendran, Simon, et al., "Murine Bioluminescent Hepatic Tumour Model", Journal of Visualized Experiments, www.jove.com, pp. 1-3.

Tang, Chih-Hang Anthony, et al., "Agonist-Mediated Activation of STING Induces Apoptosis in Malignant B Cells", Cancer Research, vol. 76, No. 8, Apr. 15, 2016, pp. 2137-2153.

Woo, Seng-Ryong, et al., "STING-Dependent Cytosolic DNA Sensing Mediates Innate Immune Recognition of Immunogenic Tumors", Immunity, vol. 41, Elsevier Inc., pp. 830-842.

Xia, Tianli, et al., "Deregulation of STING Signaling in Colorectal Carcinoma Constrains DNA Damage Responses and Correlates With Tumorigenesis", Cell Reports, vol. 14, pp. 282-297.

Xia, Tianli, et al., "Recurrent Loss of STING Signaling in Melanoma Correlates with Susceptibility to Viral Oncolysis", Cancer Research, vol. 76, No. 22, American Association for Cancer Research, pp. 6747.

Zhu, Qifan, et al., "Cutting Edge: STING Mediates Protection against Colorectal Tumorigenesis by Governing the Magnitude of Intestinal Inflammation", J. Immunol., vol. 193, American Association of Immunologists, Inc., pp. 4779-4782.

First Examination Report for India Patent Application No. 201917033410 dated Sep. 22, 2021.

Office Action dated Nov. 2, 2021, issued by the Taiwan Intellectual Property Office in R.O.C. Patent Application No. 107105846; and English translation thereof.

Search Report dated Nov. 2, 2021, issued by the Taiwan Intellectual Property Office in R.O.C. Patent Application No. 107105846; and English translation thereof.

P1: *R* configuration
P13: *S* configuration

P1: R Configuration
P13: R Configuration

FIG. 7: Study A tumor volume plots for treated and untreated tumors

FIG. 8 Study B tumor volume plots for treated and untreated tumors

FIG. 9 Tumor volume plot for treated sc tumors and survival curve

FIG. 10 Tumor volume plot for treated sc tumors and survival curve

SEQUENCE LISTING

<160> NUMBER OF SEQ ID NOS: 7

<210> SEQ ID NO 1
<211> LENGTH: 1140
<212> TYPE: DNA
<213> ORGANISM: Homo sapiens

<400> SEQUENCE: 1

```
atgccccact ccagcctgca tccatccatc ccgtgtccca ggggtcacgg ggcccagaag      60
gcagccttgg ttctgctgag tgcctgcctg gtgacccttt ggggctagg agagccacca     120
gagcacactc tccggtacct ggtgctccac ctagcctccc tgcagctggg actgctgtta    180
aacgggtct gcagcctggc tgaggagctg cgccacatcc actccaggta ccggggcagc    240
tactggagga ctgtgcgggc ctgcctgggc tgcccctcc gccgtggggc cctgttgctg    300
ctgtccatct atttctacta ctccctccca aatgcggtcg gcccgccctt cacttggatg    360
cttgccctcc tgggcctctc gcaggcactg aacatcctcc tgggcctcaa gggcctggcc    420
ccagctgaga tctctgcagt gtgtgaaaaa gggaatttca acgtggccca tgggctggca    480
tggtcatatt acatcggata tctgcggctg atcctgccag agctccaggc ccggattcga    540
acttacaatc agcattacaa caacctgcta cggggtgcag tgagccagcg gctgtatatt    600
ctcctcccat tggactgtgg ggtgcctgat aacctgagta tggctgaccc caacattcgc    660
ttcctggata aactgcccca gcagaccggt gaccgggctg gcatcaagga tcgggtttac    720
agcaacagca tctatgagct tctggagaac gggcagcggg cgggcacctg tgtcctggag    780
tacgccaccc ccttgcagac tttgtttgcc atgtcacaat acagtcaagc tggctttagc    840
cgggaggata ggcttgagca ggccaaactc ttctgccgga cacttgagga catcctggca    900
gatgcccctg agtctcagaa caactgccgc ctcattgcct accaggaacc tgcagatgac    960
agcagcttct cgctgtccca ggaggttctc cggcacctgc ggcaggagga aaaggaagag   1020
gttactgtgg gcagcttgaa gacctcagcg tgcccagta cctccacgat gtcccaagag   1080
cctgagctcc tcatcagtgg aatggaaaag cccctccctc tccgcacgga tttctcttga   1140
```

<210> SEQ ID NO 2
<211> LENGTH: 1140
<212> TYPE: DNA
<213> ORGANISM: Homo sapiens

<400> SEQUENCE: 2

```
atgcccact ccagcctgca tccatccatc ccgtgtccca ggggtcacgg ggcccagaag       60
```

```
gcagccttgg ttctgctgag tgcctgcctg gtgacccttt gggggctagg agagccacca    120
gagcacactc tccggtacct ggtgctccac ctagcctccc tgcagctggg actgctgtta    180
aacggggtct gcagcctggc tgaggagctg cgccacatcc actccaggta ccggggcagc    240
tactggagga ctgtgcgggc ctgcctgggc tgccccctcc gccgtggggc cctgttgctg    300
ctgtccatct atttctacta ctccctccca aatgcggtcg gcccgccctt cacttggatg    360
cttgccctcc tgggcctctc gcaggcactg aacatcctcc tgggcctcaa gggcctggcc    420
ccagctgaga tctctgcagt gtgtgaaaaa gggaatttca acgtggccca tgggctggca    480
tggtcatatt acatcggata tctgcggctg atcctgccag agctccaggc ccggattcga    540
acttacaatc agcattacaa caacctgcta cggggtgcag tgagccagcg gctgtatatt    600
ctcctcccat tggactgtgg ggtgcctgat aacctgagta tggctgaccc caacattcgc    660
ttcctggata aactgcccca gcagaccggt gaccatgctg gcatcaagga tcgggtttac    720
agcaacagca tctatgagct ctggagaaac gggcagcggg cggcacctg tgtcctggag    780 tacgccaccc ccttgcagac tttgtttgcc atgtcacaat acagtcaagc tggctttagc    840
cgggaggata ggcttgagca ggccaaactc ttctgccgga cacttgagga catcctggca    900
gatgcccctg agtctcagaa caactgccgc ctcattgcct accaggaacc tgcagatgac    960
agcagcttct cgctgtccca ggaggttctc cggcacctgc ggcaggagga aaaggaagag   1020
gttactgtgg gcagcttgaa gacctcagcg gtgcccagta cctccacgat gtcccaagag   1080
cctgagctcc tcatcagtgg aatggaaaag cccctccctc tccgcacgga tttctcttga   1140

<210> SEQ ID NO 3
<211> LENGTH: 1140
<212> TYPE: DNA
<213> ORGANISM: Homo sapiens

<400> SEQUENCE: 3 atgcccact ccagcctgca tccatccatc ccgtgtccca ggggtcacgg ggcccagaag     60
gcagccttgg ttctgctgag tgcctgcctg gtgacccttt gggggctagg agagccacca    120
gagcacactc tccggtacct ggtgctccac ctagcctccc tgcagctggg actgctgtta    180
aacggggtct gcagcctggc tgaggagctg cgccacatcc actccaggta ccggggcagc    240
tactggagga ctgtgcgggc ctgcctgggc tgccccctcc gccgtggggc cctgttgctg    300
ctgtccatct atttctacta ctccctccca aatgcggtcg gcccgccctt cacttggatg    360
cttgccctcc tgggcctctc gcaggcactg aacatcctcc tgggcctcaa gggcctggcc    420
ccagctgaga tctctgcagt gtgtgaaaaa gggaatttca acgtggccca tgggctggca    480
tggtcatatt acatcggata tctgcggctg atcctgccag agctccaggc ccggattcga    540
acttacaatc agcattacaa caacctgcta cggggtgcag tgagccagcg gctgtatatt    600
ctcctcccat tggactgtgg ggtgcctgat aacctgagta tggctgaccc caacattcgc    660
ttcctggata aactgcccca gcagaccgct gaccgagctg gcatcaagga tcgggtttac    720
agcaacagca tctatgagct ctggagaaac gggcagcggg cggcacctg tgtcctggag    780 tacgccaccc ccttgcagac tttgtttgcc atgtcacaat acagtcaagc tggctttagc    840
cgggaggata ggcttgagca ggccaaactc ttctgccaga cacttgagga catcctggca    900
gatgcccctg agtctcagaa caactgccgc ctcattgcct accaggaacc tgcagatgac    960
agcagcttct cgctgtccca ggaggttctc cggcacctgc ggcaggagga aaaggaagag   1020
```

```
gttactgtgg gcagcttgaa gacctcagcg gtgcccagta cctccacgat gtcccaagag    1080
cctgagctcc tcatcagtgg aatggaaaag cccctccctc tccgcacgga tttctcttga    1140
```

<210> SEQ ID NO 4
<211> LENGTH: 187
<212> TYPE: PRT
<213> ORGANISM: Homo sapiens

<400> SEQUENCE: 4

```
Val Ala His Gly Leu Ala Trp Ser Tyr Tyr Ile Gly Tyr Leu Arg Leu
1               5                   10                  15

Ile Leu Pro Glu Leu Gln Ala Arg Ile Arg Thr Tyr Asn Gln His Tyr
            20                  25                  30

Asn Asn Leu Leu Arg Gly Ala Val Ser Gln Arg Leu Tyr Ile Leu Leu
        35                  40                  45

Pro Leu Asp Cys Gly Val Pro Asp Asn Leu Ser Met Ala Asp Pro Asn
    50                  55                  60

Ile Arg Phe Leu Asp Lys Leu Pro Gln Gln Thr Gly Asp Arg Ala Gly
65                  70                  75                  80

Ile Lys Asp Arg Val Tyr Ser Asn Ser Ile Tyr Glu Leu Leu Glu Asn
                85                  90                  95

Gly Gln Arg Ala Gly Thr Cys Val Leu Glu Tyr Ala Thr Pro Leu Gln
            100                 105                 110

Thr Leu Phe Ala Met Ser Gln Tyr Ser Gln Ala Gly Phe Ser Arg Glu
        115                 120                 125

Asp Arg Leu Glu Gln Ala Lys Leu Phe Cys Arg Thr Leu Glu Asp Ile
    130                 135                 140

Leu Ala Asp Ala Pro Glu Ser Gln Asn Asn Cys Arg Leu Ile Ala Tyr
145                 150                 155                 160

Gln Glu Pro Ala Asp Asp Ser Ser Phe Ser Leu Ser Gln Glu Val Leu
                165                 170                 175

Arg His Leu Arg Gln Glu Glu Lys Glu Glu Val
            180                 185
```

<210> SEQ ID NO 5
<211> LENGTH: 311
<212> TYPE: PRT
<213> ORGANISM: Artificial Sequence
<220> FEATURE:
<223> OTHER INFORMATION: His-TEV-Sumo-WT STING construct

<400> SEQUENCE: 5

```
Met His His His His His His Ser Ser Gly Val Asp Leu Gly Thr Glu
1               5                   10                  15

Asn Leu Tyr Phe Gln Ser Asn Ala Met Ser Asp Ser Glu Val Asn Gln
            20                  25                  30

Glu Ala Lys Pro Glu Val Lys Pro Glu Val Lys Pro Glu Thr His Ile
        35                  40                  45

Asn Leu Lys Val Ser Asp Gly Ser Ser Glu Ile Phe Phe Lys Ile Lys
    50                  55                  60

Lys Thr Thr Pro Leu Arg Arg Leu Met Glu Ala Phe Ala Lys Arg Gln
65                  70                  75                  80

Gly Lys Glu Met Asp Ser Leu Arg Phe Leu Tyr Asp Gly Ile Arg Ile
                85                  90                  95

Gln Ala Asp Gln Thr Pro Glu Asp Leu Asp Met Glu Asp Asn Asp Ile
            100                 105                 110
```

```
Ile Glu Ala His Arg Glu Gln Ile Gly Gly Ser Val Ala His Gly
            115                 120                 125

Leu Ala Trp Ser Tyr Tyr Ile Gly Tyr Leu Arg Leu Ile Leu Pro Glu
130                 135                 140

Leu Gln Ala Arg Ile Arg Thr Tyr Asn Gln His Tyr Asn Asn Leu Leu
145                 150                 155                 160

Arg Gly Ala Val Ser Gln Arg Leu Tyr Ile Leu Pro Leu Asp Cys
                165                 170                 175

Gly Val Pro Asp Asn Leu Ser Met Ala Asp Pro Asn Ile Arg Phe Leu
                180                 185                 190

Asp Lys Leu Pro Gln Gln Thr Gly Asp Arg Ala Gly Ile Lys Asp Arg
                195                 200                 205

Val Tyr Ser Asn Ser Ile Tyr Glu Leu Leu Glu Asn Gly Gln Arg Ala
                210                 215                 220

Gly Thr Cys Val Leu Glu Tyr Ala Thr Pro Leu Gln Thr Leu Phe Ala
225                 230                 235                 240

Met Ser Gln Tyr Ser Gln Ala Gly Phe Ser Arg Glu Asp Arg Leu Glu
                245                 250                 255

Gln Ala Lys Leu Phe Cys Arg Thr Leu Glu Asp Ile Leu Ala Asp Ala
                260                 265                 270

Pro Glu Ser Gln Asn Asn Cys Arg Leu Ile Ala Tyr Gln Glu Pro Ala
                275                 280                 285

Asp Asp Ser Ser Phe Ser Leu Ser Gln Glu Val Leu Arg His Leu Arg
                290                 295                 300

Gln Glu Glu Lys Glu Glu Val
305                 310

<210> SEQ ID NO 6
<211> LENGTH: 187
<212> TYPE: PRT
<213> ORGANISM: Homo sapiens

<400> SEQUENCE: 6

Val Ala His Gly Leu Ala Trp Ser Tyr Tyr Ile Gly Tyr Leu Arg Leu
1               5                   10                  15

Ile Leu Pro Glu Leu Gln Ala Arg Ile Arg Thr Tyr Asn Gln His Tyr
                20                  25                  30

Asn Asn Leu Leu Arg Gly Ala Val Ser Gln Arg Leu Tyr Ile Leu Leu
                35                  40                  45

Pro Leu Asp Cys Gly Val Pro Asp Asn Leu Ser Met Ala Asp Pro Asn
50                  55                  60

Ile Arg Phe Leu Asp Lys Leu Pro Gln Gln Thr Gly Asp His Ala Gly
65                  70                  75                  80

Ile Lys Asp Arg Val Tyr Ser Asn Ser Ile Tyr Glu Leu Leu Glu Asn
                85                  90                  95

Gly Gln Arg Ala Gly Thr Cys Val Leu Glu Tyr Ala Thr Pro Leu Gln
                100                 105                 110

Thr Leu Phe Ala Met Ser Gln Tyr Ser Gln Ala Gly Phe Ser Arg Glu
                115                 120                 125

Asp Arg Leu Glu Gln Ala Lys Leu Phe Cys Arg Thr Leu Glu Asp Ile
                130                 135                 140

Leu Ala Asp Ala Pro Glu Ser Gln Asn Asn Cys Arg Leu Ile Ala Tyr
145                 150                 155                 160

Gln Glu Pro Ala Asp Asp Ser Ser Phe Ser Leu Ser Gln Glu Val Leu
                165                 170                 175
```

Arg His Leu Arg Gln Glu Glu Lys Glu Glu Val
            180             185

<210> SEQ ID NO 7
<211> LENGTH: 311
<212> TYPE: PRT
<213> ORGANISM: Artificial Sequence
<220> FEATURE:
<223> OTHER INFORMATION: His-TEV-Sumo-REF STING 155-341 construct

<400> SEQUENCE: 7

Met His His His His His Ser Ser Gly Val Asp Leu Gly Thr Glu
1               5                   10                  15

Asn Leu Tyr Phe Gln Ser Asn Ala Met Ser Asp Ser Glu Val Asn Gln
            20                  25                  30

Glu Ala Lys Pro Glu Val Lys Pro Glu Val Lys Pro Glu Thr His Ile
        35                  40                  45

Asn Leu Lys Val Ser Asp Gly Ser Ser Glu Ile Phe Phe Lys Ile Lys
    50                  55                  60

Lys Thr Thr Pro Leu Arg Arg Leu Met Glu Ala Phe Ala Lys Arg Gln
65                  70                  75                  80

Gly Lys Glu Met Asp Ser Leu Arg Phe Leu Tyr Asp Gly Ile Arg Ile
                85                  90                  95

Gln Ala Asp Gln Thr Pro Glu Asp Leu Asp Met Glu Asp Asn Asp Ile
            100                 105                 110

Ile Glu Ala His Arg Glu Gln Ile Gly Gly Ser Val Ala His Gly
        115                 120                 125

Leu Ala Trp Ser Tyr Tyr Ile Gly Tyr Leu Arg Leu Ile Leu Pro Glu
130                 135                 140

Leu Gln Ala Arg Ile Arg Thr Tyr Asn Gln His Tyr Asn Asn Leu Leu
145                 150                 155                 160

Arg Gly Ala Val Ser Gln Arg Leu Tyr Ile Leu Leu Pro Leu Asp Cys
                165                 170                 175

Gly Val Pro Asp Asn Leu Ser Met Ala Asp Pro Asn Ile Arg Phe Leu
            180                 185                 190

Asp Lys Leu Pro Gln Gln Thr Gly Asp His Ala Gly Ile Lys Asp Arg
        195                 200                 205

Val Tyr Ser Asn Ser Ile Tyr Glu Leu Leu Glu Asn Gly Gln Arg Ala
    210                 215                 220

Gly Thr Cys Val Leu Glu Tyr Ala Thr Pro Leu Gln Thr Leu Phe Ala
225                 230                 235                 240

Met Ser Gln Tyr Ser Gln Ala Gly Phe Ser Arg Glu Asp Arg Leu Glu
                245                 250                 255

Gln Ala Lys Leu Phe Cys Arg Thr Leu Glu Asp Ile Leu Ala Asp Ala
            260                 265                 270

Pro Glu Ser Gln Asn Asn Cys Arg Leu Ile Ala Tyr Gln Glu Pro Ala
        275                 280                 285

Asp Asp Ser Ser Phe Ser Leu Ser Gln Glu Val Leu Arg His Leu Arg
    290                 295                 300

Gln Glu Glu Lys Glu Glu Val
305                 310

COMPOUNDS FOR THE TREATMENT OF CANCER

CROSS-REFERENCE TO RELATED APPLICATIONS

This application claims benefit of U.S. Provisional Patent Application No. 62/460,562, filed on Feb. 17, 2017; U.S. Provisional Patent Application No. 62/479,169, filed on Mar. 30, 2017; U.S. Provisional Patent Application No. 62/551,645, filed on Aug. 29, 2017; U.S. Provisional Patent Application No. 62/551,647, filed on Aug. 29, 2017; and U.S. Provisional Patent Application No. 62/551,668, filed on Aug. 29, 2017. All of those applications are incorporated by reference as if fully rewritten herein.

BACKGROUND

STING (stimulator of interferon genes) is a signaling molecule in the innate response to dsDNA in the cytosol. STING deletion has been reported in multiple human cancers. In addition, deregulation of STING signaling in human cancers also has been reported in melanoma (Xia T, et al., "Recurrent Loss of STING Signaling in Melanoma Correlates with Susceptibility to Viral Oncolysis" *Cancer Res.* 2016) and colon cancer. (Xia T, et al., "Deregulation of STING Signaling in Colorectal Carcinoma Constrains DNA Damage Responses and Correlates With Tumorigenesis" *Cell Rep.* 2016; 14:282-97). Interestingly, in those studies, genomic analysis results showed loss expression of STING is not due to gene deletion or mutation, but through epigenetic changes. (Xia, *Cancer Res.* 2016; Xia, *Cell Rep.* 2016). STING's cancer protection activity is also supported by evidence obtained from mouse model studies. STING knockout mice have shown defective tumor control. (Woo S R, et al. "STING-dependent cytosolic DNA sensing mediates innate immune recognition of immunogenic tumors" *Immunity* 2014; 41:830-42).

In addition, STING's role in protecting ontogenesis has been demonstrated in several mouse spontaneous models, including glioma (Ohkuri T, et al., "Protective role of STING against gliomagenesis: Rational use of STING agonist in anti-glioma immunotherapy" *Oncoimmunology.* 2015; 4:e999523), and colon cancer (Zhu Q, et al., "Cutting edge: STING mediates protection against colorectal tumorigenesis by governing the magnitude of intestinal inflammation" *J. Immunol.* 2014; 193:4779-82). This anti-tumor effect may be due to its ability to counter over-activation of NF-kB and STAT3. (Okihuri 2015). Activation of STING pathway also showed potent activity in preclinical mouse tumor models. (Woo 2014; Chandra D, et al. "STING ligand c-di-GMP improves cancer vaccination against metastatic breast cancer" *Cancer Immunol Res.* 2014; 2:901-10; Corrales L, et al., "Direct Activation of STING in the Tumor Microenvironment Leads to Potent and Systemic Tumor Regression and Immunity" *Cell Rep.* 2015; 11:1018-30; Curran E, et al. "STING Pathway Activation Stimulates Potent Immunity against Acute Myeloid Leukemia" *Cell Rep.* 2016; 15:2357-66; Tang C H, et al. "Agonist-Mediated Activation of STING Induces Apoptosis in Malignant B Cells" *Cancer Res.* 2016; 76:2137-52). This anti-tumor activity is likely due to disruption of tumor vasculature and followed by induction of adaptive immune response. (Corrales L, et al., "The host STING pathway at the interface of cancer and immunity" *J. Clin. Invest.* 2016; 126:2404-11). Accordingly, direct stimulation of STING in a tumor microenvironment by an agonist may represent a novel approach for treating multiple cancer types.

BRIEF SUMMARY

Embodiments may provide a Compound of Formula (I):

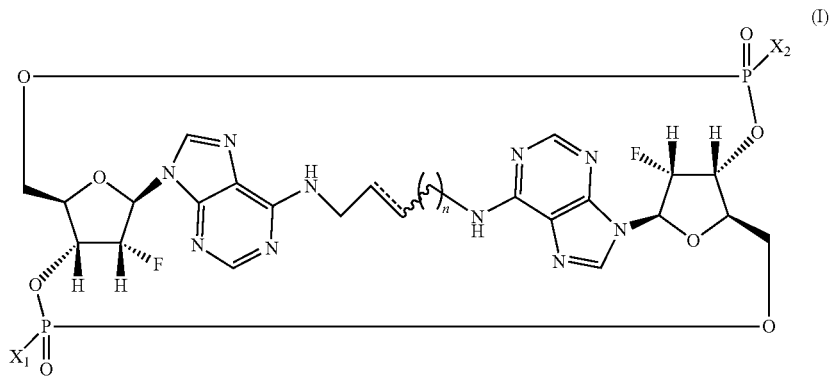

(where $P_1$ is the lower-left phosphorus and $P_2$ the upper right phosphorus as depicted above) having substituents and stereochemistry as indicated in Table 1, below, or a pharmaceutically acceptable salt thereof. The ===== indicates a single bond or double bond.
Where a phosphorous atom has four substituents that differ, that phosphorous atom will be a stereocenter. SpSp/RpRp/SpRp/RpSp refers to the phosphorous stereochemisty as indicated.

TABLE 1

| Compound # | n | Geometry (Trans, Cis, or Saturated) | $X_1$ | $X_2$ | stereochemical configuration ($P_1$) | stereochemical configuration ($P_2$) |
|---|---|---|---|---|---|---|
| 1 | 1 | Trans | SH | SH | S | R |
| 2 | 1 | Trans | SH | SH | R | R |
| 3 | 1 | Trans | SH | SH | S | S |
| 4 | 1 | Cis | SH | SH | R | R |
| 5 | 1 | Cis | SH | SH | S | R |
| 6 | 1 | Saturated | SH | SH | S | R |
| 8 | 2 | Trans | SH | SH | Undetermined | Undetermined |
| 9 | 1 | Trans | OH | OH | n/a | n/a |
| 11 | 2 | Trans | SH | SH | Undetermined | Undetermined |
| 12 | 2 | Trans | SH | SH | Undetermined | Undetermined |

Embodiments may further provide a Compound of Formula (II):

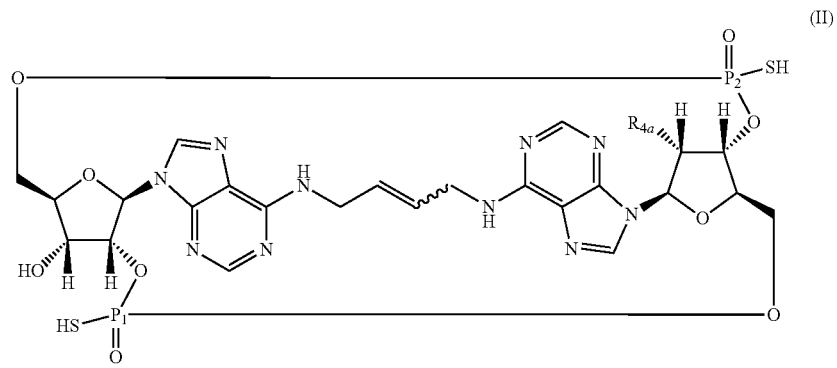

having substituents and stereochemistry as indicated in Table 2, below, or a pharmaceutically acceptable salt thereof. Where a phosphorous atom has four substituents that differ, that phosphorous atom will be a stereocenter.

TABLE 2

| Compound # | $R_{4a}$ | Geometric configuration | stereochemical configuration ($P_1$, $P_2$) |
|---|---|---|---|
| 13 | —OH | trans | S, R |
| 14 | —OH | trans | R, R |
| 15 | —F | trans | S, R |
| 16 | —F | trans | R, R |

Embodiments may provide a compound of Formula (III):

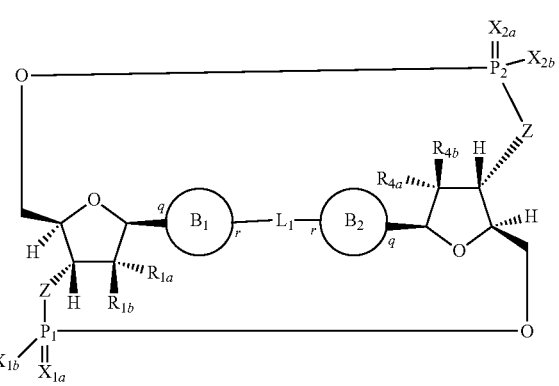

or a pharmaceutically acceptable salt thereof, wherein $R_{1a}$ is selected from the group consisting of —H, —OH, and —F;

$R_{1b}$ is selected from the group consisting of —H, —OH, and —F, wherein at least one of $R_{1a}$ and $R_{1b}$ is —H;

$R_{4a}$ is selected from the group consisting of —H, —OH, and —F;

$R_{4b}$ is selected from the group consisting of —H, —OH, and —F, wherein at least one of $R_{4a}$ and $R_{4b}$ is —H;

$P_1$ and $P_2$ each independently has an S or R stereochemical configuration;

Z is —O— or —NH—;

$X_{1a}$ and $X_{2a}$ are the same or different and are independently selected from =O or =S;

$X_{1b}$ and $X_{2b}$ are the same or different and are independently selected from —OR$_5$ and —SR$_5$;

wherein $R_5$ is selected from the group consisting of —H, $C_{1-6}$alkyl, —C(O)C$_{1-6}$alkyl, and —CH$_2$OC(O)OC$_{1-6}$alkyl;

$L_1$ in formula (III) is four, five, or six carbons in length, and is

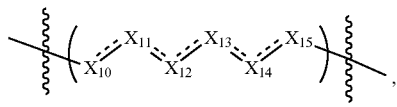

wherein ===== indicates a single bond, a double bond, or a triple bond and wherein (i) either 0 or 1 occurrence of ===== in $L_1$ indicates a triple bond; or (ii) 0, 1, or 2 occurrences of ===== in $L_1$ indicates a double bond, wherein geometry about each double bond is cis or trans; and (iii) wherein when 1 occurrence of ===== in $L_1$ indicates a triple bond, 0 occurrences of ===== in $L_1$ indicates a double bond; and (iv) wherein, when 2 occurrences of ===== in $L_1$ indicate a double bond, those double bonds are either adjacent bonds or alternating bonds;

wherein $X_{10}$, $X_{11}$, $X_{12}$, $X_{13}$, $X_{14}$, and $X_{15}$ are independently selected from a bond, —CH$_2$—, or —CH—, wherein the —CH$_2$— or —CH— is unsubstituted or substituted by (i) —OH, (ii) —F, (iii) —Cl, (iv) —NH$_2$, or (v) -D, and when $X_{10}$ or $X_{15}$ is a bond, that bond is not a double bond or triple bond;

and wherein any two adjacent members of the group including $X_{10}$, $X_{11}$, $X_{12}$, $X_{13}$, $X_{14}$, and $X_{15}$ may optionally form, with additional atoms, a $C_3$ cycloalkyl or a $C_3$ heterocycloalkyl, said $C_3$ heterocycloalkyl including an N or O atom;

wherein $B_1$ and $B_2$ are independently selected from:

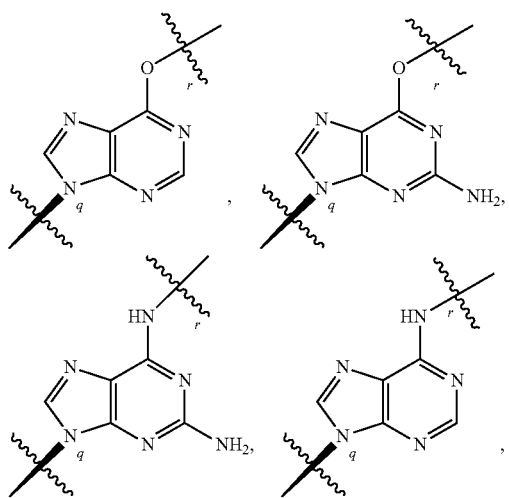

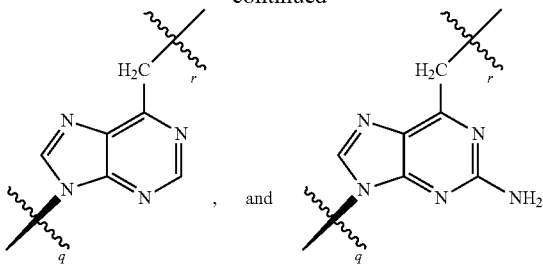

where the bonds at points q and r on $B_1$ and $B_2$ are attached at points q and r on Formula (III).

In some embodiments where $L_1$ includes a triple bond or more than one double bond, $L_1$ may be, for example,

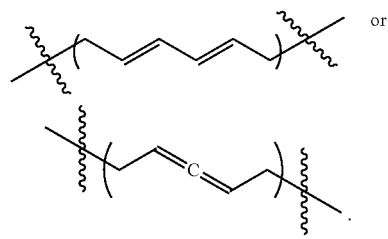

Embodiments may also provide a compound of Formula (III):

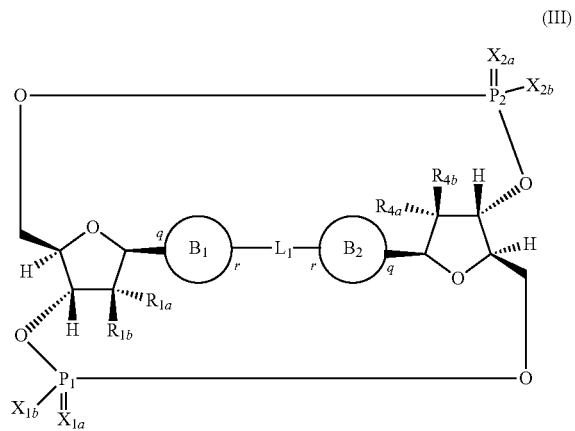

(III)

or a pharmaceutically acceptable salt thereof, wherein $R_{1a}$ is selected from the group consisting of —H and —F;

$R_{1b}$ is selected from the group consisting of —H and —F, wherein $R_{1a}$ and $R_{1b}$ may not both be —F;

$R_{4a}$ is selected from the group consisting of —H and —F;

$R_{4b}$ is selected from the group consisting of —H and —F, wherein $R_{4a}$ and $R_{4b}$ may not both be —F;

$P_1$ and $P_2$ each independently has an S or R stereochemical configuration;

$X_{1a}$ and $X_{2a}$ are the same or different and are independently selected from =O or =S;

$X_{1b}$ and $X_{2b}$ are the same or different and are independently selected from —OR$_5$ and —SR$_5$;

wherein $R_5$ is selected from the group consisting of —H, $C_{1-6}$alkyl, and —C(O)$C_{1-6}$alkyl;

$L_1$ in formula (III) is four or five carbons in length, and is

wherein ====== indicates a single bond or a double bond, and wherein either 0 or 1 occurrence of ====== in $L_1$ indicates a double bond, wherein geometry about the double bond is cis or trans;

wherein $X_{10}$ and $X_{14}$ are independently selected from a bond, —CH—, or —CH$_2$—, and wherein, when $X_{10}$ or $X_{14}$ is a bond, that bond is not a double bond;

wherein $B_1$ and $B_2$ are independently selected from:

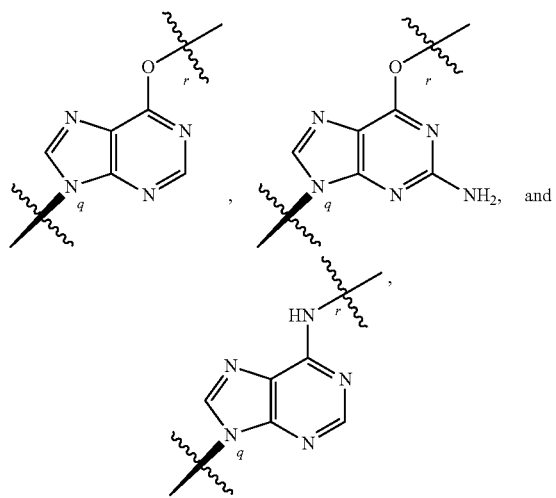

where the bonds at points q and r on $B_1$ and $B_2$ are attached at points q and r on Formula (III).

Embodiments may provide a compound of Formula (IV):

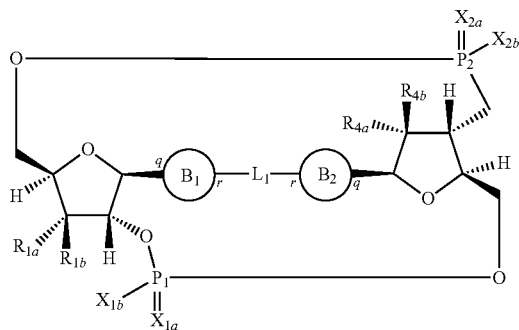

(IV)

or a pharmaceutically acceptable salt thereof, wherein $R_{1a}$ is selected from the group consisting of —H, —OH, and —F;

$R_{1b}$ is selected from the group consisting of —H, —OH, and —F, wherein at least one of $R_{1a}$ and $R_{1b}$ is —H;

$R_{4a}$ is selected from the group consisting of —H, —OH, and —F;

$R_{4b}$ is selected from the group consisting of —H, —OH, and —F, wherein at least one of $R_{4a}$ and $R_{4b}$ is —H;

$P_1$ and $P_2$ each independently has an S or R stereochemical configuration;

$X_{1a}$ and $X_{2a}$ are the same or different and are independently selected from =O or =S;

$X_{1b}$ and $X_{2b}$ are the same or different and are independently selected from —OR$_5$ and —SR$_5$;

wherein $R_5$ is selected from the group consisting of —H, $C_{1-6}$alkyl, —C(O)$C_{1-6}$alkyl, and —CH$_2$OC(O)OC$_{1-6}$alkyl;

$L_1$ in formula (IV) is four, five, or six carbons in length, and is

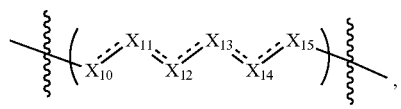

wherein ====== indicates a single bond, a double bond, or a triple bond and wherein (i) either 0 or 1 occurrence of ====== in $L_1$ indicates a triple bond; or (ii) 0, 1, or 2 occurrences of ====== in $L_1$ indicates a double bond, wherein geometry about each double bond is cis or trans; and (iii) wherein when 1 occurrence of ====== in $L_1$ indicates a triple bond, 0 occurrences of ====== in $L_1$ indicates a double bond; and (iv) wherein, when 2 occurrences of ====== in $L_1$ indicate a double bond, those double bonds are either adjacent bonds or alternating bonds;

wherein $X_{10}$, $X_{11}$, $X_{12}$, $X_{13}$, $X_{14}$, and $X_{15}$ are independently selected from a bond, —CH$_2$—, or —CH—, wherein the —CH$_2$— or —CH— is unsubstituted or substituted by (i) —OH, (ii) —F, (iii) —Cl, (iv) —NH$_2$, or (v) -D, and when $X_{10}$ or $X_{15}$ is a bond, that bond is not a double bond or triple bond;

and wherein any two adjacent members of the group including $X_{10}$, $X_{11}$, $X_{12}$, $X_{13}$, $X_{14}$, and $X_{15}$ may optionally form, with additional atoms, a $C_3$ cycloalkyl or a $C_3$ heterocycloalkyl, said $C_3$ heterocycloalkyl including an N or O atom;

wherein $B_1$ and $B_2$ are independently selected from:

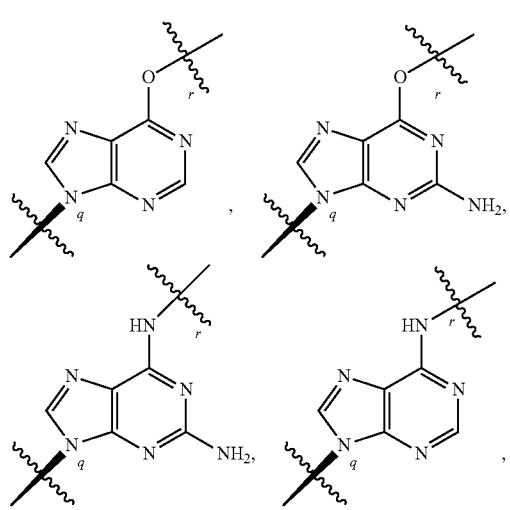

-continued

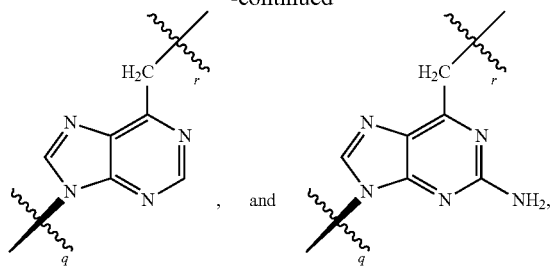

, and where the bonds at points q and r on $B_1$ and $B_2$ are attached at points q and r on Formula (IV).

Embodiments may also provide a compound of Formula (IV):

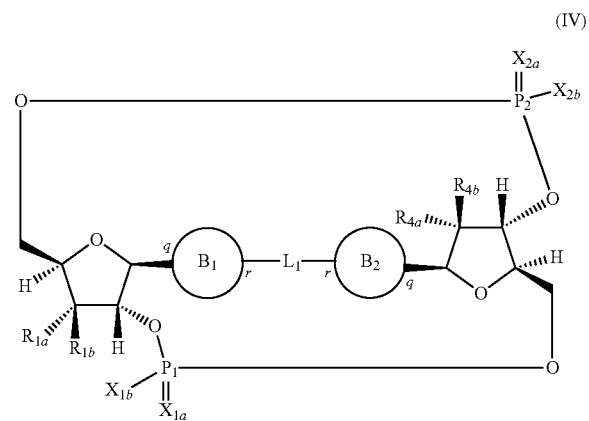

(IV)

or a pharmaceutically acceptable salt thereof, wherein
$R_{1a}$ is selected from the group consisting of —H and —F;
$R_{1b}$ is selected from the group consisting of —H and —F, wherein $R_{1a}$ and $R_{1b}$ may not both be —F;
$R_{4a}$ is selected from the group consisting of —H and —F;
$R_{4b}$ is selected from the group consisting of —H and —F, wherein $R_{4a}$ and $R_{4b}$ may not both be —F;
$P_1$ and $P_2$ each independently has an S or R stereochemical configuration;
$X_{1a}$ and $X_{2a}$ are the same or different and are independently selected from =O or =S;
$X_{1b}$ and $X_{2b}$ are the same or different and are independently selected from —$OR_5$ and —$SR_5$;
    wherein $R_5$ is selected from the group consisting of —H, $C_{1-6}$alkyl, and —C(O)$C_{1-6}$alkyl;
$L_1$ in formula (IV) is four or five carbons in length, and is

wherein ===== indicates a single bond or a double bond, and wherein either 0 or 1 occurrence of ===== in $L_1$ indicates a double bond, wherein geometry about the double bond is cis or trans;
wherein $X_{10}$ and $X_{14}$ are independently selected from a bond, —CH—, or —$CH_2$—, and wherein, when $X_{10}$ or $X_{14}$ is a bond, that bond is not a double bond;

wherein $B_1$ and $B_2$ are independently selected from:

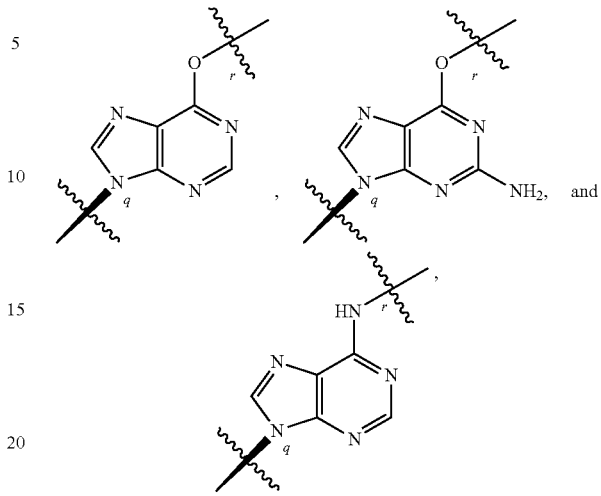

, and where the bonds at points q and r on $B_1$ and $B_2$ are attached at points q and r on Formula (IV).

Embodiments may provide a compound of Formula (V):

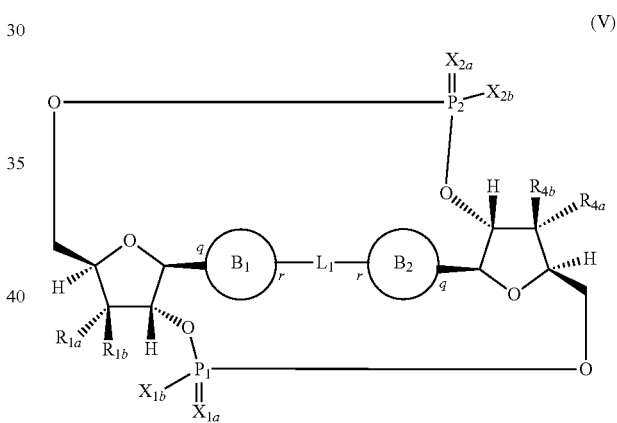

(V)

or a pharmaceutically acceptable salt thereof, wherein
$R_{1a}$ is selected from the group consisting of —H, —OH, and —F;
$R_{1b}$ is selected from the group consisting of —H, —OH, and —F, wherein at least one of $R_{1a}$ and $R_{1b}$ is —H;
$R_{4a}$ is selected from the group consisting of —H, —OH and —F;
$R_{4b}$ is selected from the group consisting of —H, —OH, and —F, and wherein at least one of $R_{4a}$ and $R_{4b}$ is —H;
$P_1$ and $P_2$ each independently has an S or R stereochemical configuration;
$X_{1a}$ and $X_{2a}$ are the same or different and are independently selected from =O or =S;
$X_{1b}$ and $X_{2b}$ are the same or different and are independently selected from —$OR_5$ and —$SR_5$;
    wherein $R_5$ is selected from the group consisting of —H, $C_{1-6}$alkyl, —C(O)$C_{1-6}$alkyl, and —$CH_2$OC(O)OC$_{1-6}$alkyl;

$L_1$ in formula (V) is four, five, or six carbons in length, and is

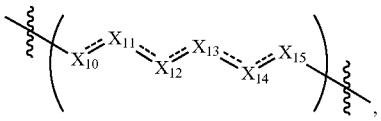

wherein ====== indicates a single bond, a double bond, or a triple bond and wherein (i) either 0 or 1 occurrence of ====== in $L_1$ indicates a triple bond; or (ii) 0, 1, or 2 occurrences of ====== in $L_1$ indicates a double bond, wherein geometry about each double bond is cis or trans; and (iii) wherein when 1 occurrence of ====== in $L_1$ indicates a triple bond, 0 occurrences of ====== in $L_1$ indicates a double bond; and (iv) wherein, when 2 occurrences of ====== in $L_1$ indicate a double bond, those double bonds are either adjacent bonds or alternating bonds;
wherein $X_{10}$, $X_{11}$, $X_{12}$, $X_{13}$, $X_{14}$, and $X_{15}$ are independently selected from a bond, —$CH_2$—, or —CH—, wherein the —$CH_2$— or —CH— is unsubstituted or substituted by (i) —OH, (ii) —F, (iii) —Cl, (iv) —$NH_2$, or (v) -D, and when $X_{10}$ or $X_{15}$ is a bond, that bond is not a double bond or triple bond;
and wherein any two adjacent members of the group including $X_{10}$, $X_{11}$, $X_{12}$, $X_{13}$, $X_{14}$, and $X_{15}$ may optionally form, with additional atoms, a $C_3$ cycloalkyl or a $C_3$ heterocycloalkyl, said $C_3$ heterocycloalkyl including an N or O atom;
wherein $B_1$ and $B_2$ are independently selected from:

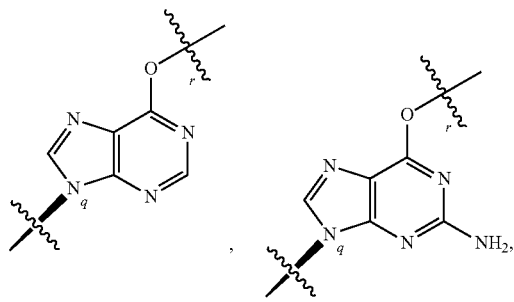

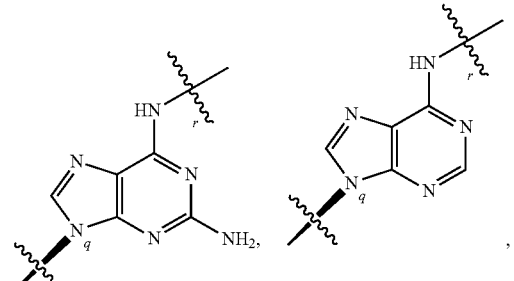

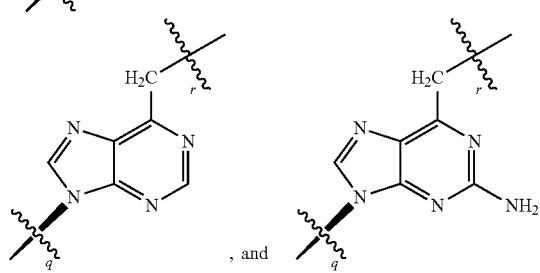
, and where the bonds at points q and r on $B_1$ and $B_2$ are attached at points q and r on Formula (V).

Embodiments may also provide a compound of Formula (V):

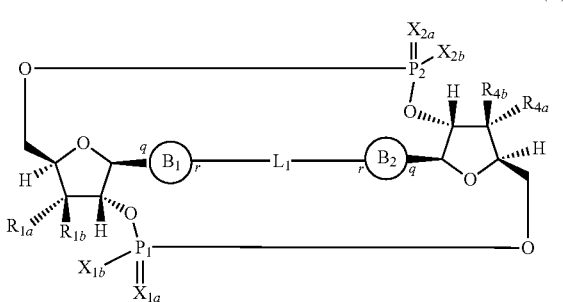

(V)

or a pharmaceutically acceptable salt thereof, wherein
$R_{1a}$ is selected from the group consisting of —H and —F;
$R_{1b}$ is selected from the group consisting of —H and —F, wherein $R_{1a}$ and $R_{1b}$ may not both be —F;
$R_{4a}$ is selected from the group consisting of —H and —F;
$R_{4b}$ is selected from the group consisting of —H and —F, wherein $R_{4a}$ and $R_{4b}$ may not both be —F;
$P_1$ and $P_2$ each independently has an S or R stereochemical configuration;
$X_{1a}$ and $X_{2a}$ are the same or different and are independently selected from =O or =S;
$X_{1b}$ and $X_{2b}$ are the same or different and are independently selected from —$OR_5$ and —$SR_5$;
wherein $R_5$ is selected from the group consisting of —H, $C_{1-6}$alkyl, and —$C(O)C_{1-6}$alkyl;
$L_1$ in formula (V) is four or five carbons in length and is

wherein ====== indicates a single bond or a double bond, and wherein either 0 or 1 occurrence of ====== in $L_1$ indicates a double bond, wherein geometry about the double bond is cis or trans;
wherein $X_{10}$ and $X_{14}$ are independently selected from a bond, —CH—, or —$CH_2$—, and wherein, when $X_{10}$ or $X_{14}$ is a bond, that bond is not a double bond;
wherein $B_1$ and $B_2$ are independently selected from:

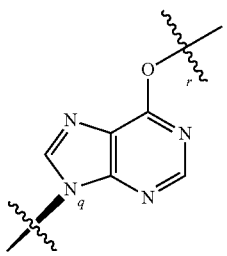

-continued

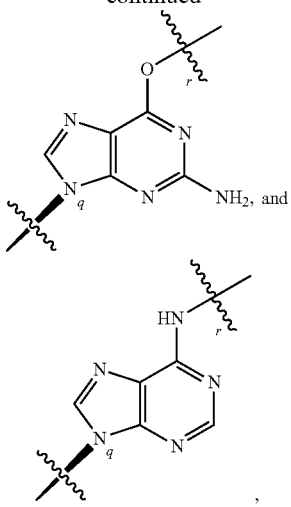

NH₂, and

, where the bonds at points q and r on B₁ and B₂ are attached at points q and r on Formula (V).

In some embodiments of compounds and/or salts as reported in the Formulas above, (i) the stereochemical configuration of P₁ and P₂ are both R, the stereochemical configuration of P₁ is R and and P₂ is S, or the stereochemical configuration of P₁ is S and P₂ is R; (ii) one occurrence of ===== in L₁ indicates a double bond, wherein geometry about the double bond is trans; and (iii) Z is —O—.

Further embodiments of compounds and/or salts as reported in the Formulas above may be found in other aspects herein. For example, some embodiments provide a compound or pharmaceutically acceptable salt wherein $R_{1a}$ and $R_{4a}$ are each —F. In some embodiments $R_{1b}$ and $R_{4b}$ are each —F. In some embodiments B₁ and B₂ are each

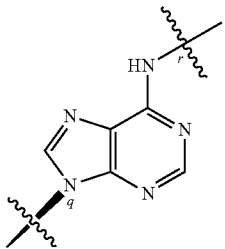

,

In some embodiments $X_{1a}$ and $X_{2a}$ are both =O, and $X_{1b}$ and $X_{2b}$ are both —SH. In some embodiments L₁ is

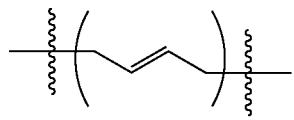

.

In some embodiments the linker is four carbons long. In some embodiments the linker is five carbons long.

Some embodiments provide a compound selected from the group consisting of:

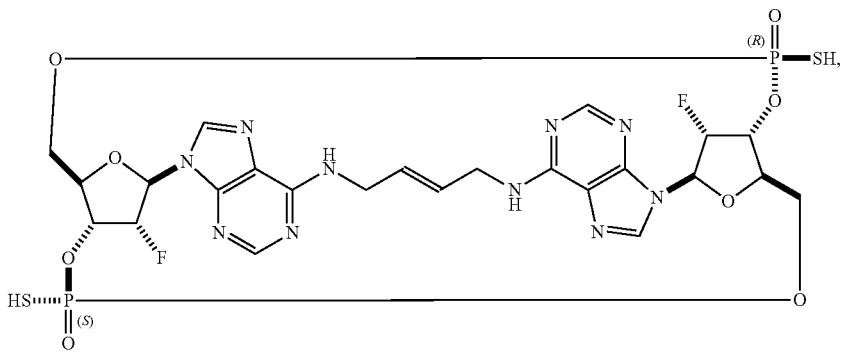

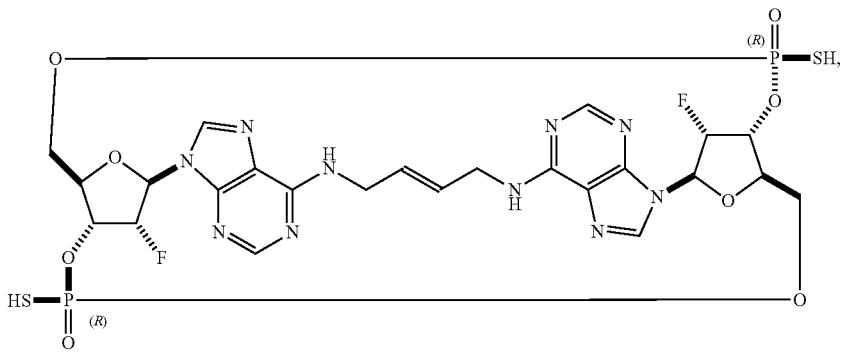

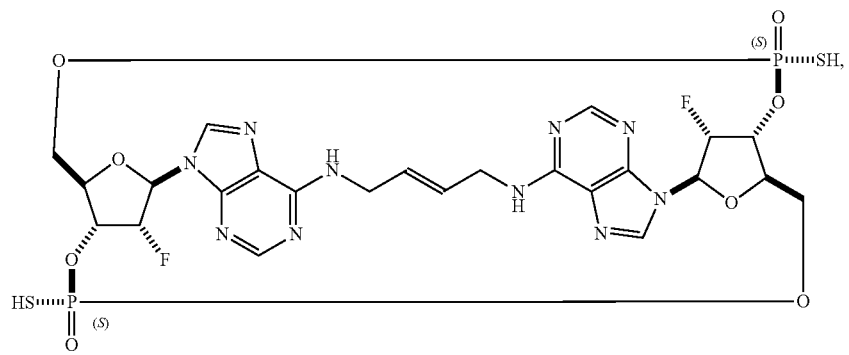
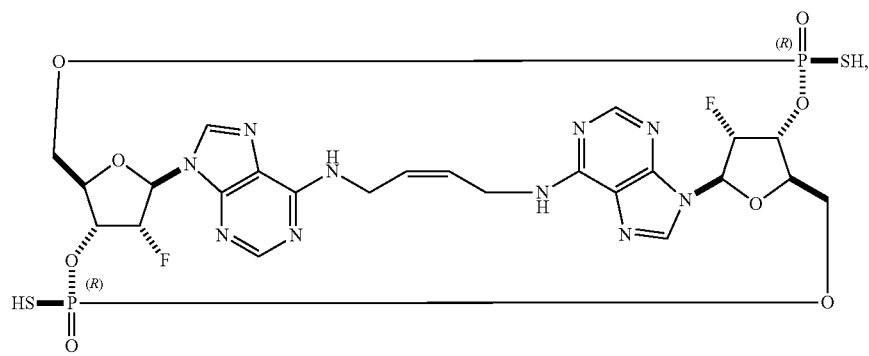
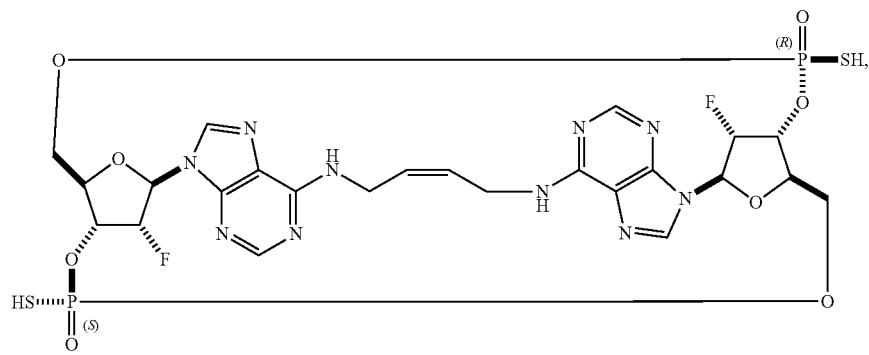
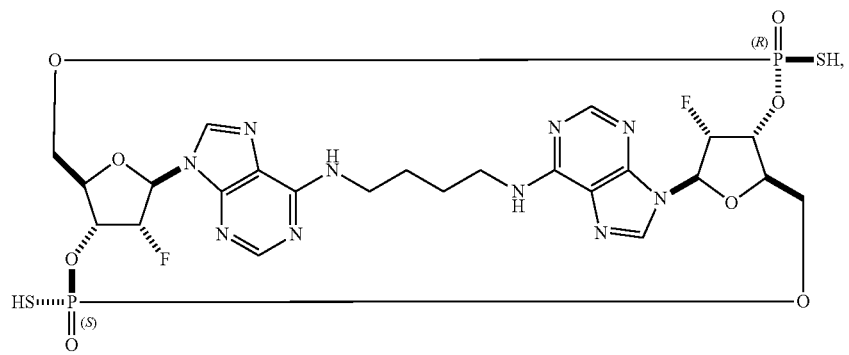

-continued
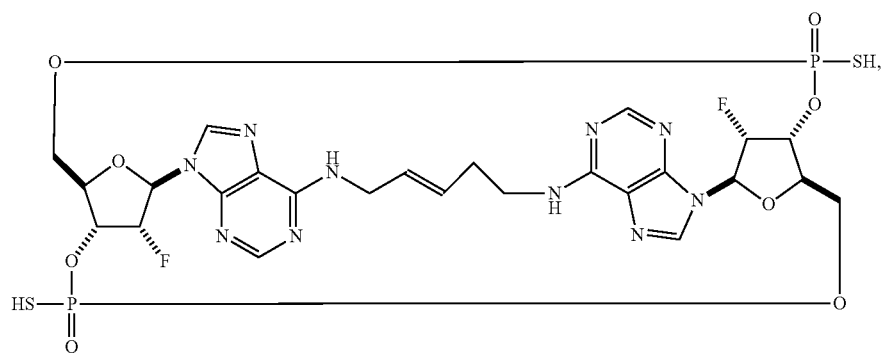
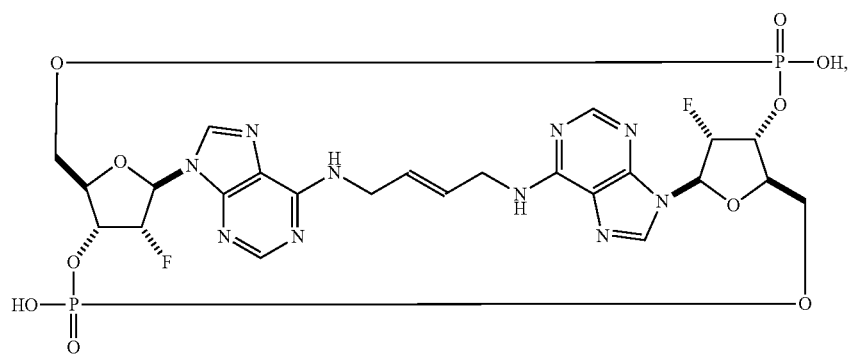
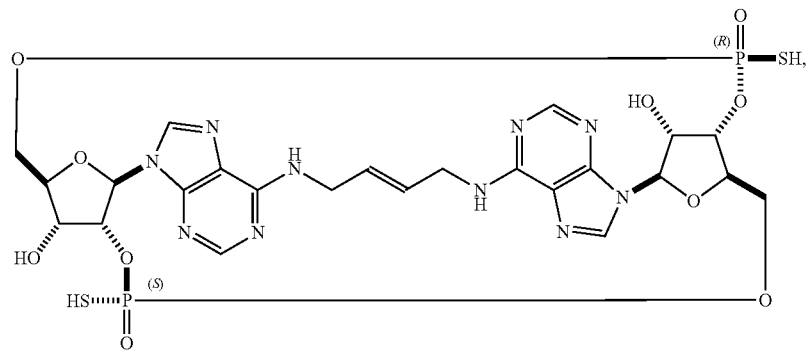
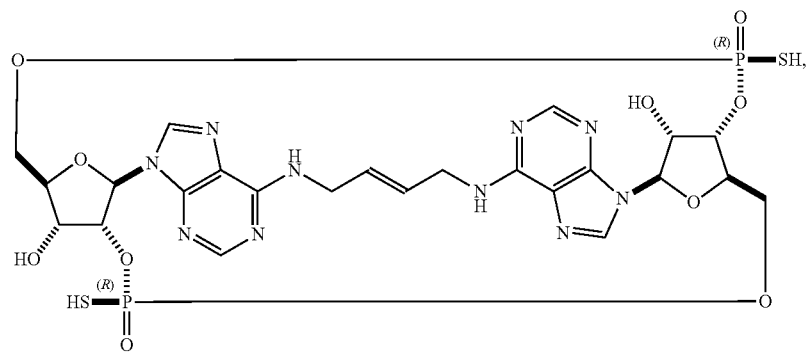

-continued
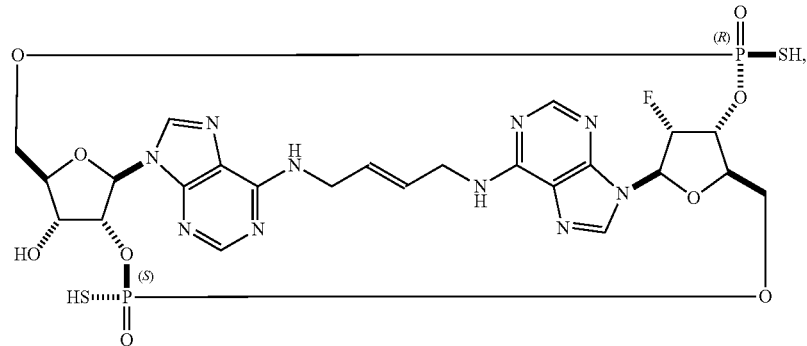
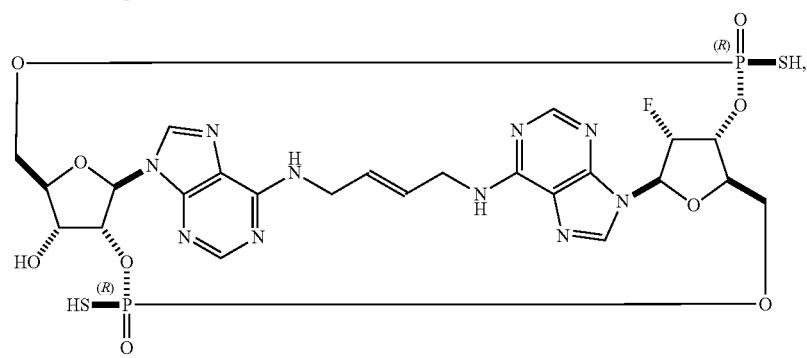
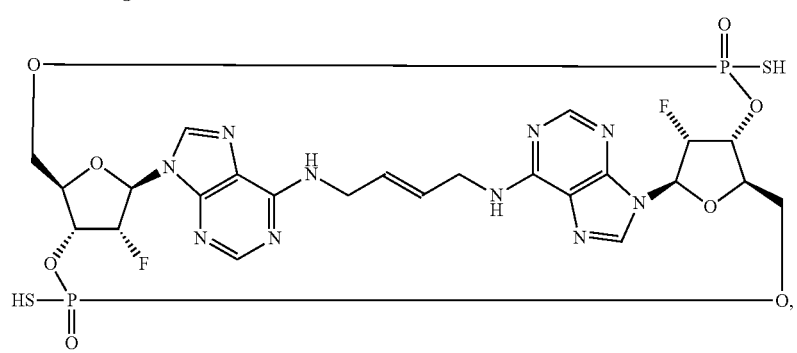
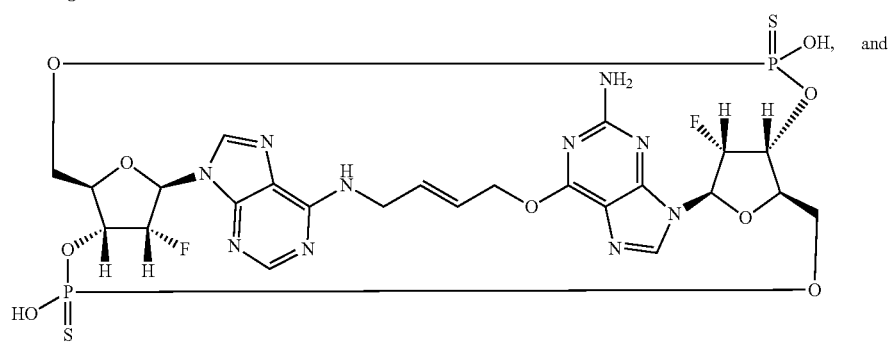
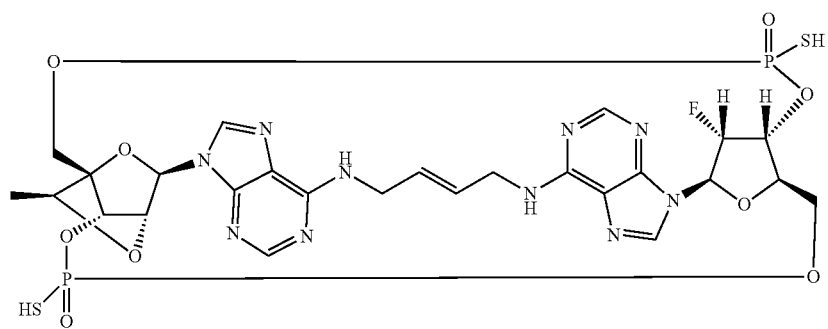

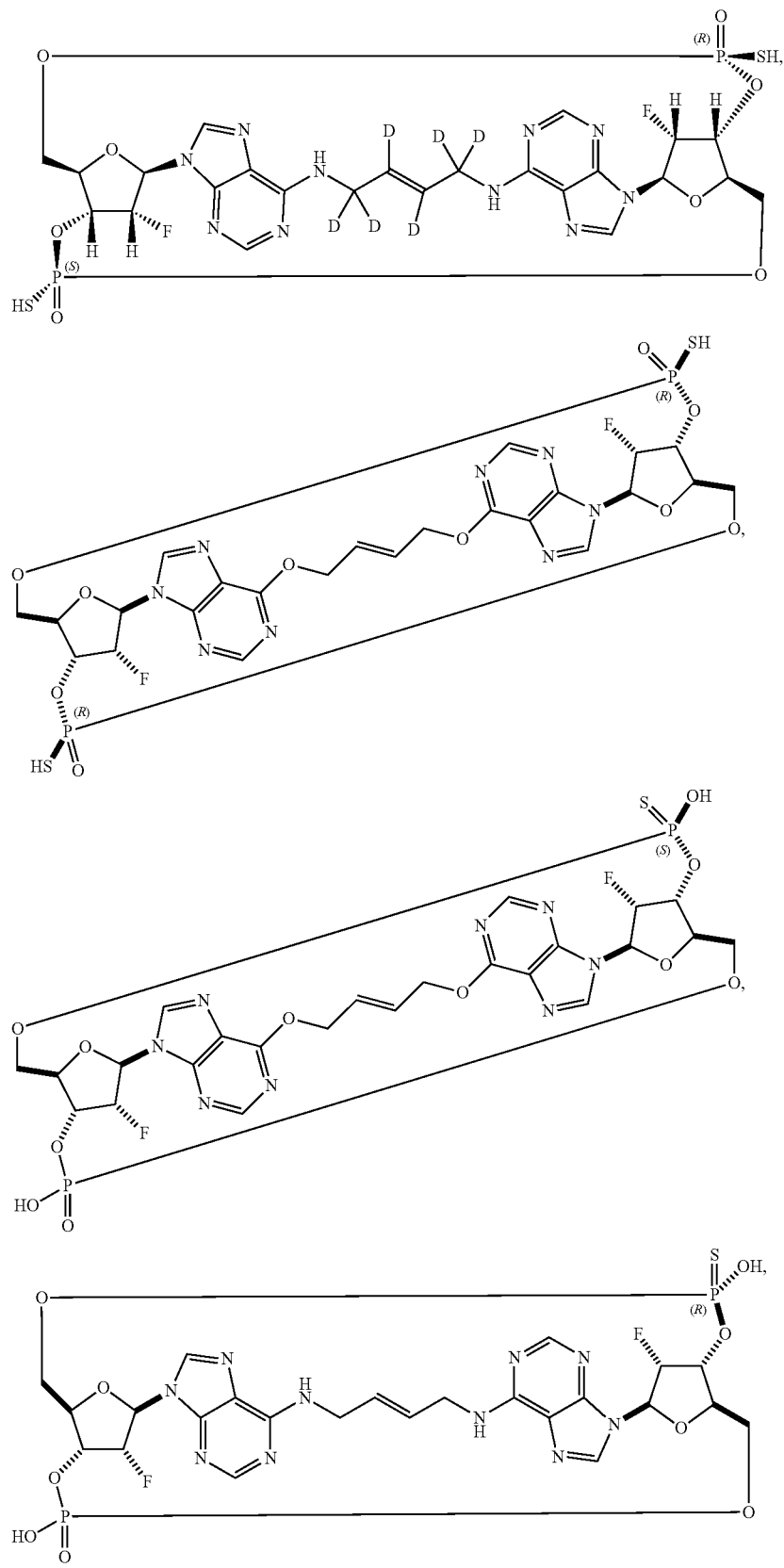

-continued
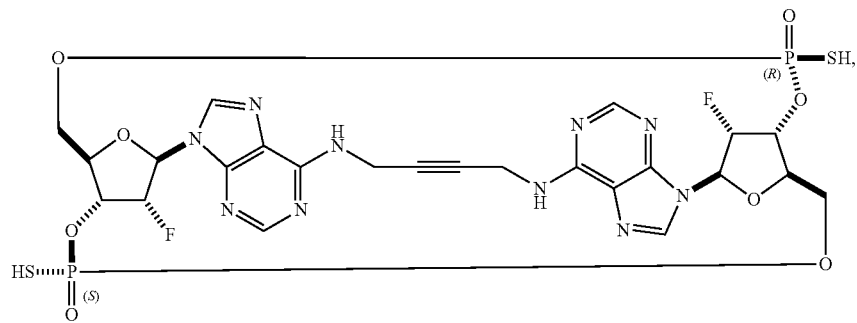
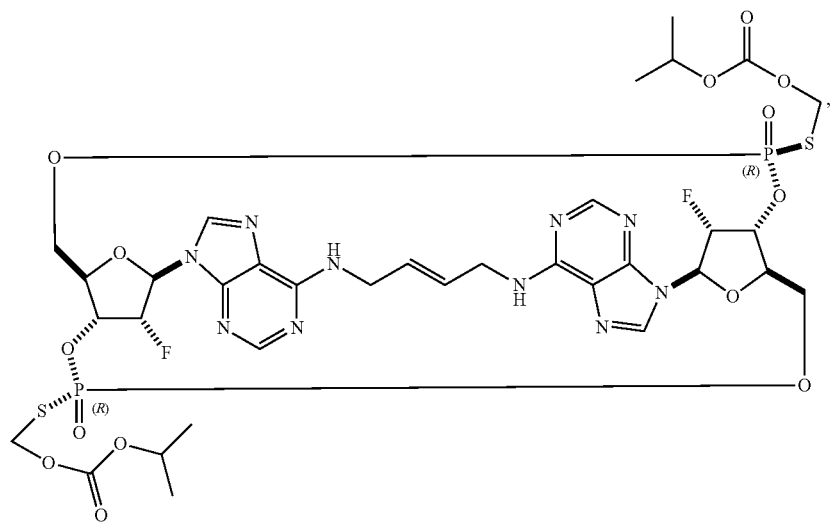
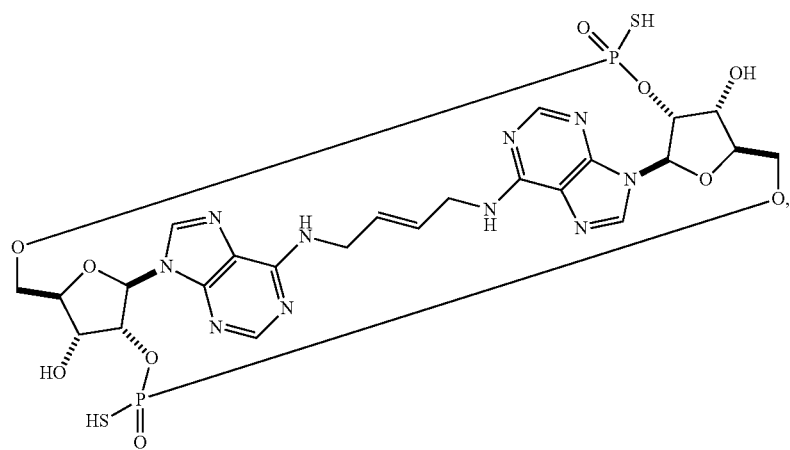

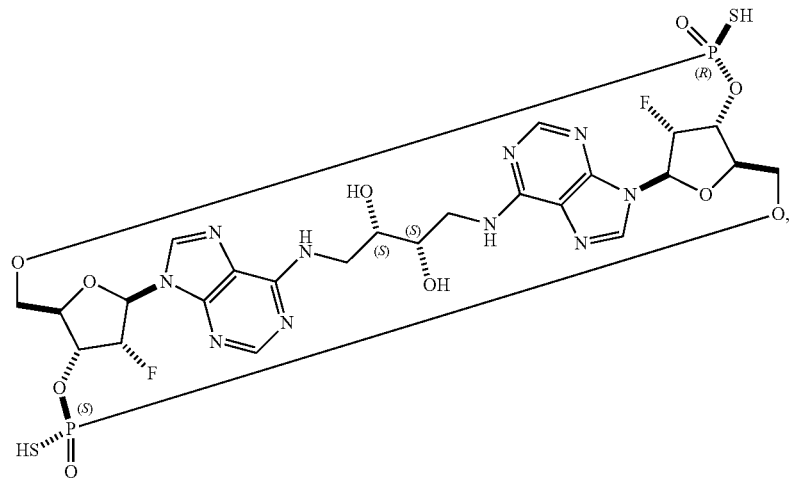
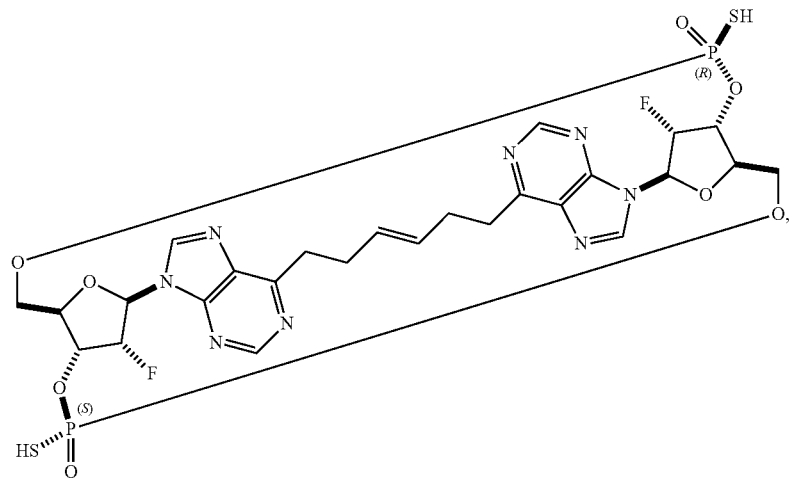
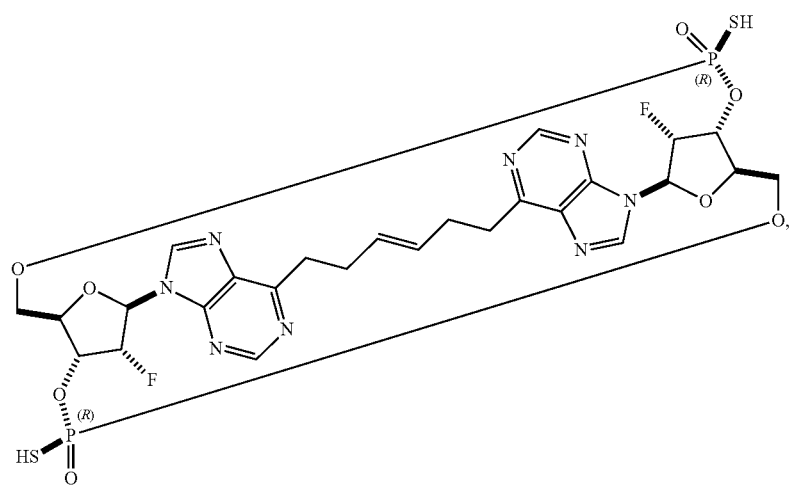

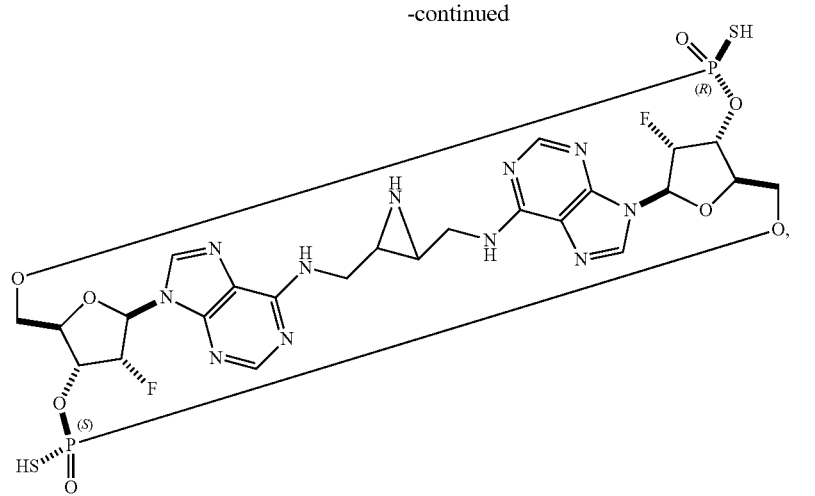
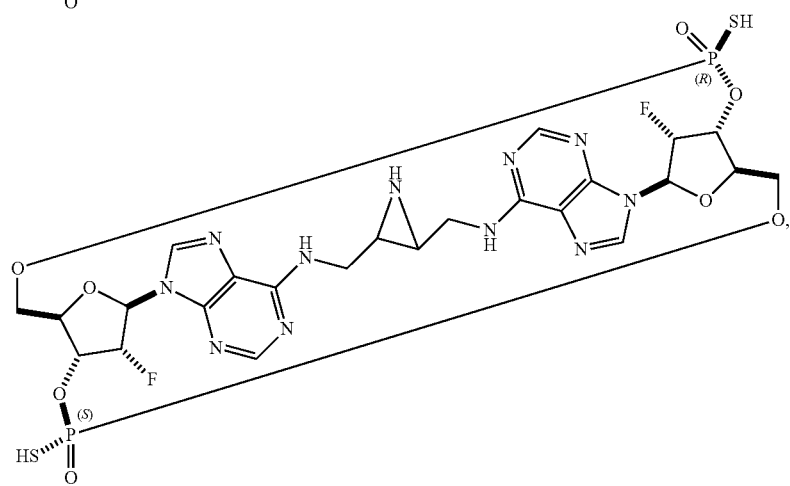
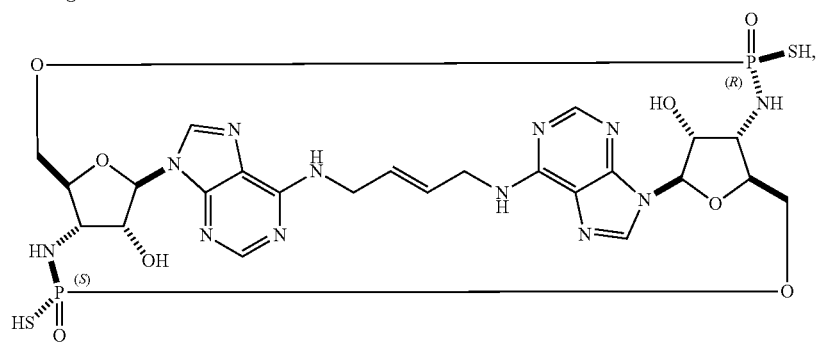
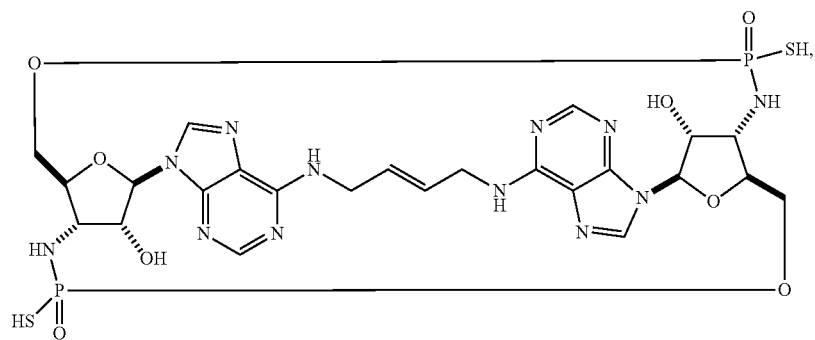
or a pharmaceutically acceptable salt thereof.

Embodiments may provide a compound or pharmaceutically acceptable salt with one or more of (i) an $EC_{50}$ value below 100 micromolar in a cell reporter assay expressing STING HAQ genetic variant; (ii) an $EC_{50}$ value below 100 micromolar in reporter cells expressing human STING AQ variant; (iii) an $EC_{50}$ value below 100 micromolar in reporter cells expressing human STING WT variant; and (iv) an $EC_{50}$ value below 100 micromolar in reporter cells expressing human STING REF variant. One embodiment provides a compound having the following structure:

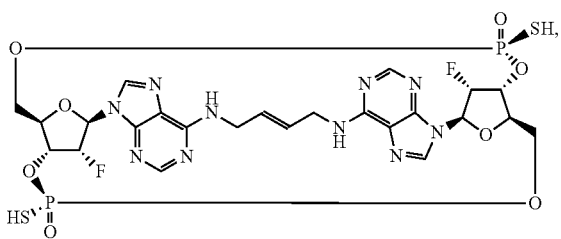 [SMILES: O=[P@]1(S)OC[C@H]2O[C@@H]3[C@H](F)[C@@H]2O[P@](=O)(S)OC[C@H]2O[C@H]([C@H](F)[C@@H]2O1)n1cnc2c(ncnc21)NC/C=C/CNc1ncnc2c1ncn23]

or a pharmaceutically acceptable salt thereof.

Further embodiments may provide a pharmaceutically acceptable salt of a compound reported herein, wherein the salt is a diammonium salt. Further embodiments may provide compounds reported herein as a triethyl amine (TEA) salt. Further embodiments may provide a pharmaceutical composition including a compound or salt as reported herein and a pharmaceutically acceptable excipient.

Embodiments may provide a method of treating cancer comprising administering to a patient a compound, pharmaceutically acceptable salt, or pharmaceutical composition as reported herein.

Use of a compound or pharmaceutically acceptable salt thereof as reported herein for preparation of a pharmaceutical composition for treating cancer.

Embodiments may provide use of a compound, pharmaceutically acceptable salt, or pharmaceutical composition reported herein in a treatment for cancer.

Embodiments may provide a method of treating cancer comprising identifying an individual having a cancer treatable by a compound, a pharmaceutically acceptable salt, or a pharmaceutical composition reported herein; and administering to said individual a pharmaceutically effective amount of the compound, pharmaceutically acceptable salt or pharmaceutical composition by which the cancer has been identified as treatable.

In some embodiments the individual is identified as having a cancer treatable by a compound, pharmaceutically acceptable salt or pharmaceutical composition reported herein by a presence of a REF STING variant allele in the patient.

Some embodiments provide a method of treating cancer in a patient having REF STING allele comprising administering to said patient a compound, pharmaceutically acceptable salt or pharmaceutical composition as reported herein.

Some embodiments provide a method of treating cancer in a patient having WT STING allele comprising administering to said patient a compound, pharmaceutically acceptable salt or pharmaceutical composition as reported herein.

Some embodiments provide a method of treating cancer in a patient having AQ STING allele comprising administering to said patient a compound, pharmaceutically acceptable salt or pharmaceutical composition as reported herein.

Some embodiments provide a method of treating cancer in a patient having HAQ STING allele comprising administering to said patient a compound, pharmaceutically acceptable salt or pharmaceutical composition as reported herein.

In some embodiments the cancer is selected from the group consisting of lymphoma, melanoma, colorectal cancer, breast cancer, acute myeloid leukemia, colon cancer, liver cancer, prostate cancer, pancreatic cancer, renal cancer, and glioma. In some embodiments the cancer is metastatic.

In some embodiments of compounds of formulas presented herein, one of the bonds in $L_1$ is a double bond. In further embodiments that double bond has a trans geometry. In further embodiments $L_1$ is saturated. In certain embodiments $L_1$ includes five carbon atoms. In other embodiments $L_1$ includes 4 carbon atoms.

Embodiments may further provide mixtures of compounds as reported herein, including mixtures of stereoisomers of these compounds. For example, a mixture may be provided of Compound 11 and Compound 12, or a mixture may be provided of Compound 2 and Compound 4. Of course, these are not limiting examples and other mixtures are possible.

Particular embodiments are set forth in Table 3 below.

TABLE 3

| Compound No. | Structure |
|---|---|
| 1 | 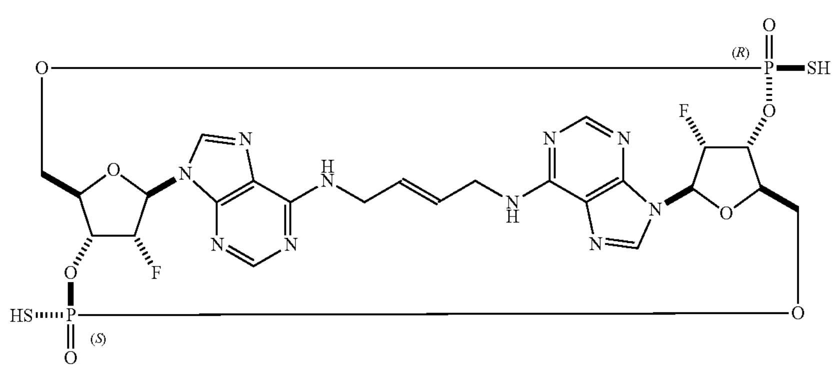 |

TABLE 3-continued

| Compound No. | Structure |
| --- | --- |
| 2 | 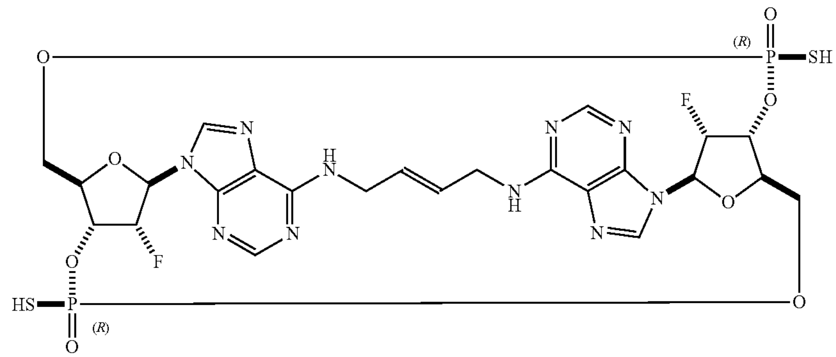 |
| 3 | 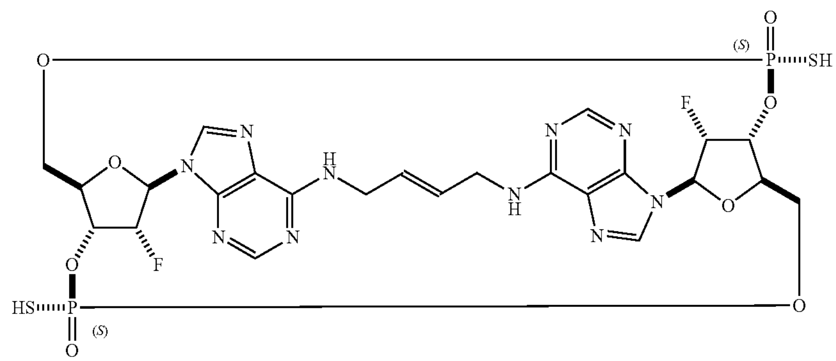 |
| 4 | 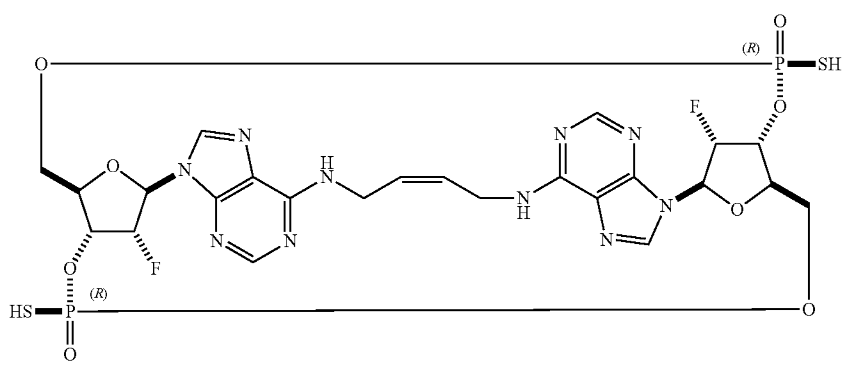 |
| 5 | 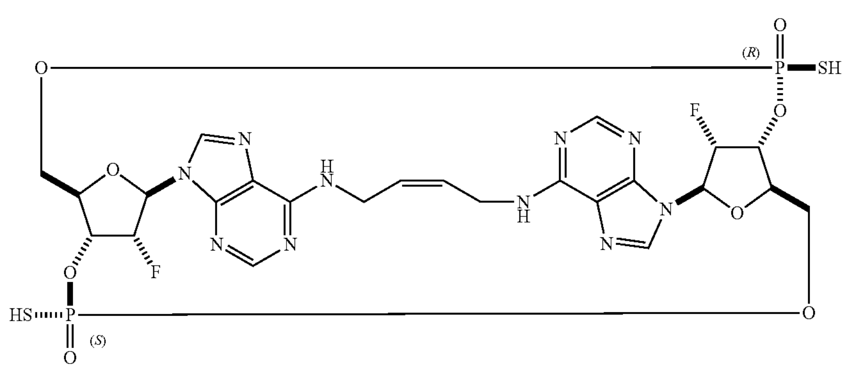 |

TABLE 3-continued

| Compound No. | Structure |
|---|---|
| 6 | (chemical structure) |
| 8 | (chemical structure) (Stereoisomer 1) |
| 9 | (chemical structure) |
| 11 | (chemical structure) (Stereoisomer 2) |

TABLE 3-continued
| Compound No. | Structure |
|---|---|
| 12 | 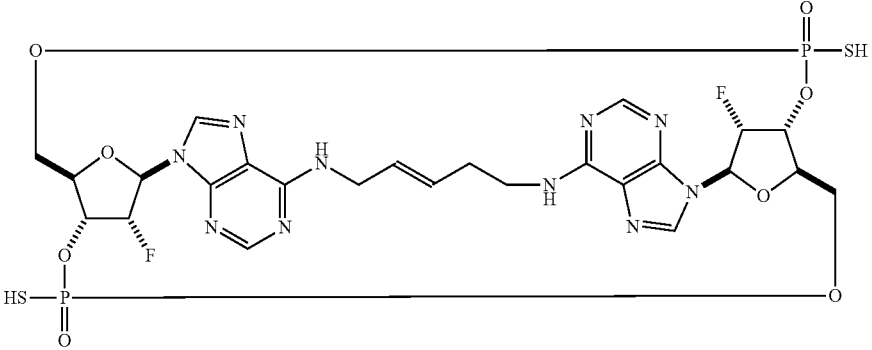<br>(Stereoisomer 3) |
| 13 | 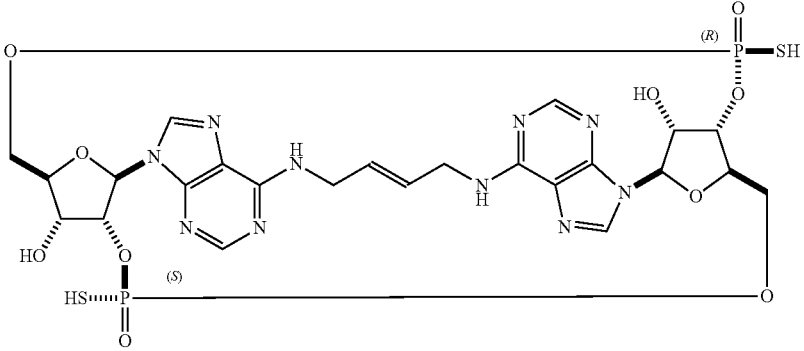 |
| 14 | 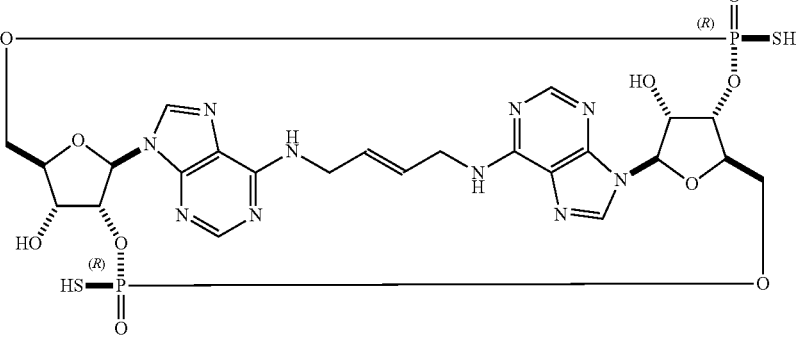 |
| 15 | 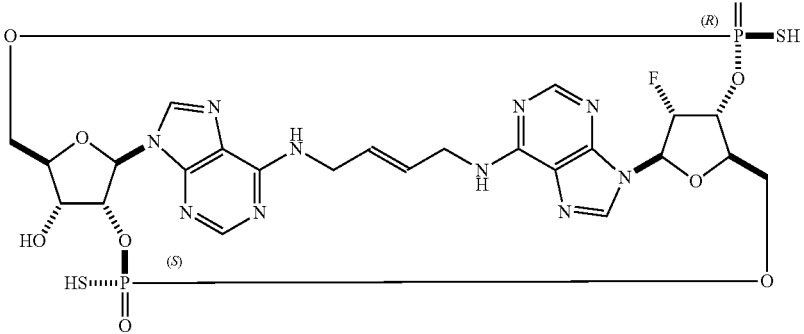 |

TABLE 3-continued

| Compound No. | Structure |
|---|---|
| 16 | [chemical structure of cyclic dinucleotide with two adenine bases connected by N-H-CH2-CH=CH-CH2-N-H linker, with (R)-configured phosphorothioate groups, one ribose bearing OH and the other bearing F] |
| 18 | [chemical structure of cyclic dinucleotide analog with butenyl-diamine linker between two adenines, phosphorothioate linkages, one 2'-F sugar] (Stereoisomer 1) |
| 19 | [chemical structure — Stereoisomer 2 of the cyclic dinucleotide with butenyl-diamine linker, phosphorothioate, 2'-F sugar] (Stereoisomer 2) |
| 20 | [chemical structure — Stereoisomer 3 of the cyclic dinucleotide with butenyl-diamine linker, phosphorothioate, 2'-F sugar] (Stereoisomer 3) |

TABLE 3-continued

| Compound No. | Structure |
|---|---|
| 21 | (Stereoisomer 1) |
| 22 | (Stereoisomer 2) |
| 23 | (Stereoisomer 3) |
| 24 | 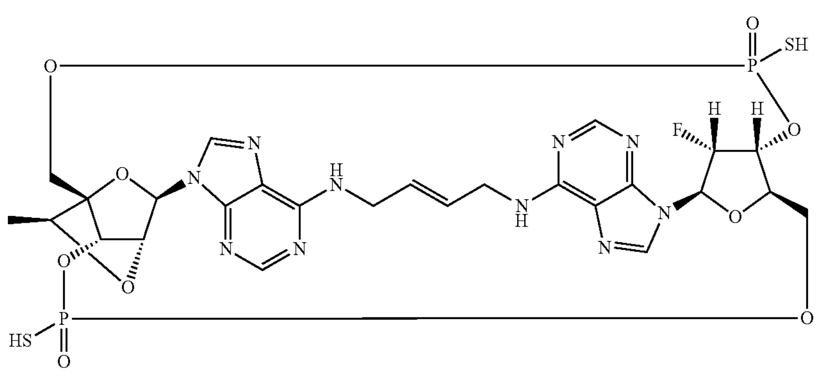 |

TABLE 3-continued

| Compound No. | Structure |
|---|---|
| 25 | 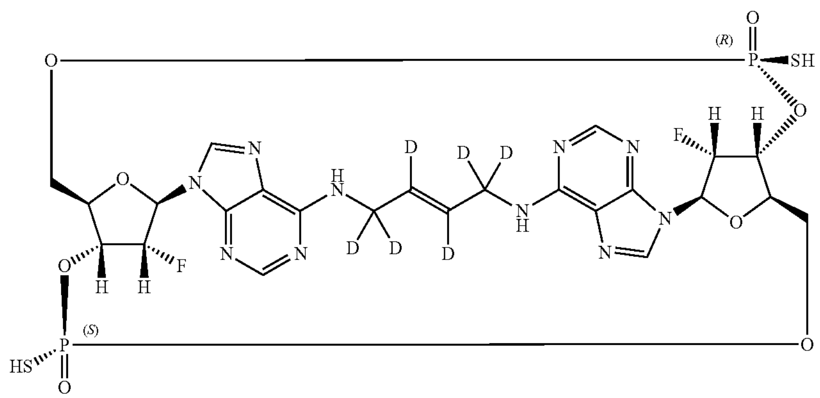 |
| 26 | 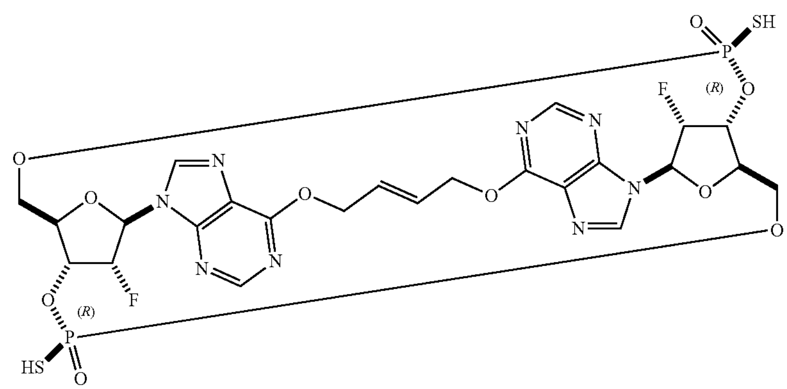 |
| 27 | 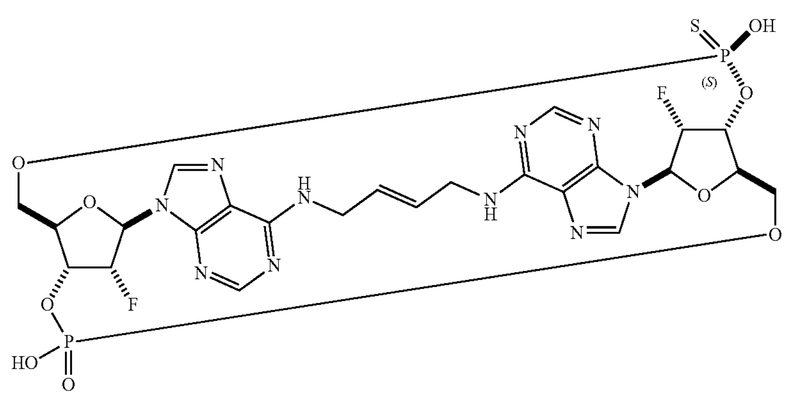 |
| 28 | 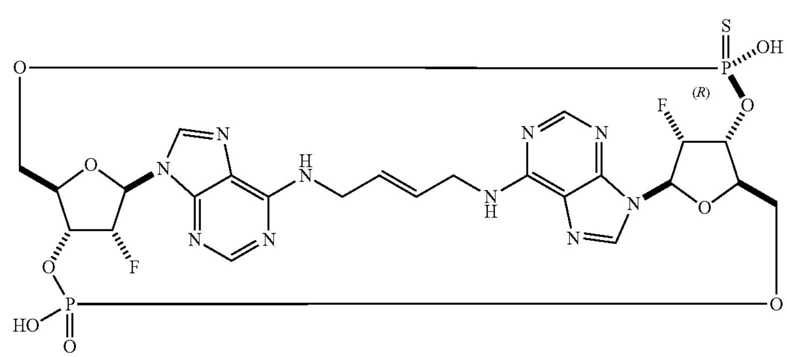 |

TABLE 3-continued

| Compound No. | Structure |
|---|---|
| 29 | 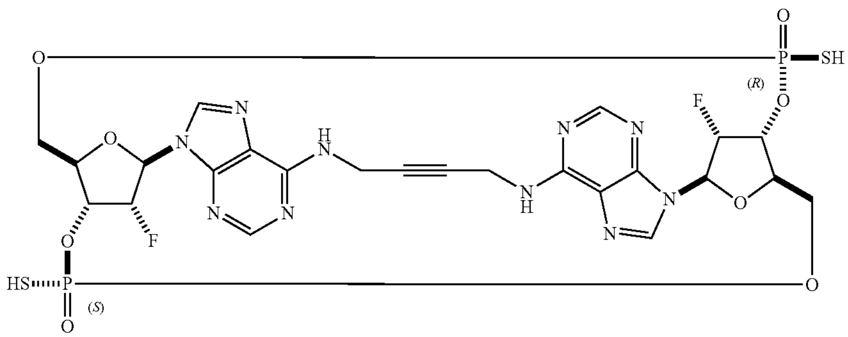 |
| 30 | 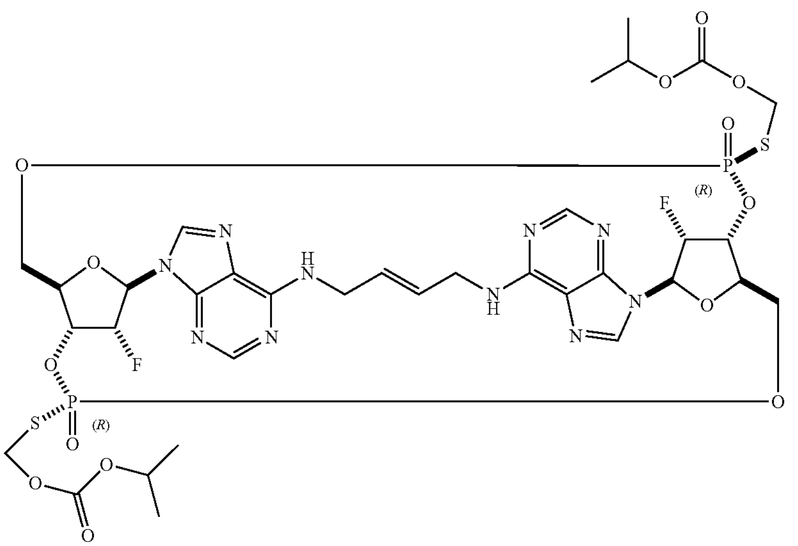 |
| 31 | 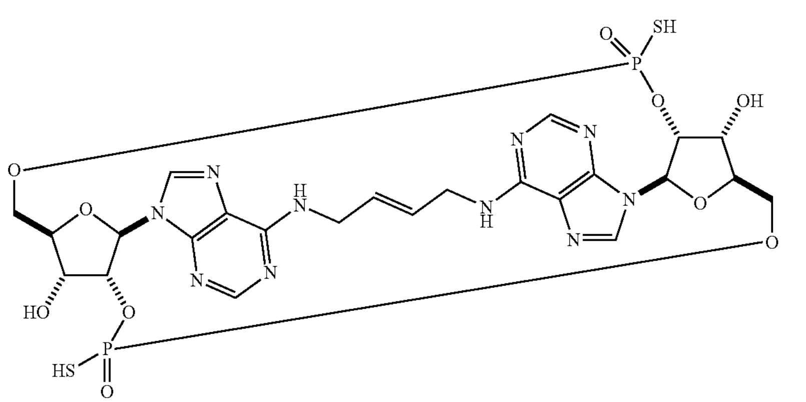 |

TABLE 3-continued

| Compound No. | Structure |
|---|---|
| 32 | 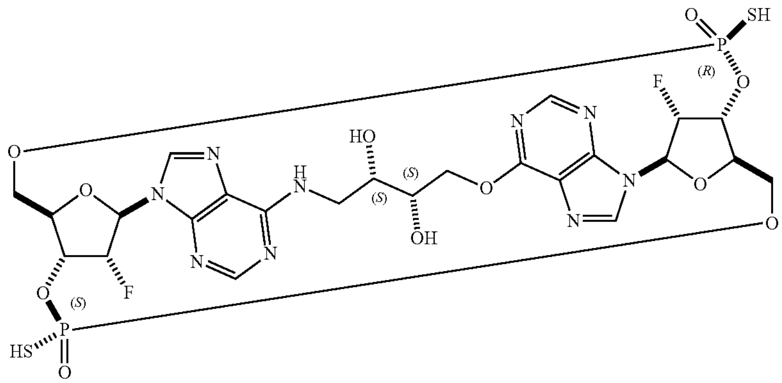 |
| 33 | 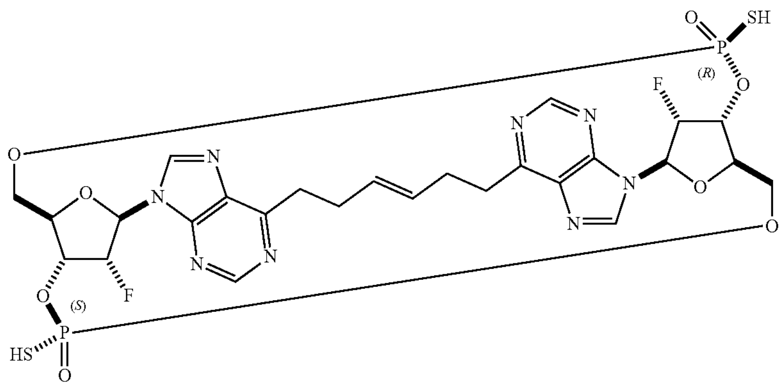 |
| 34 | 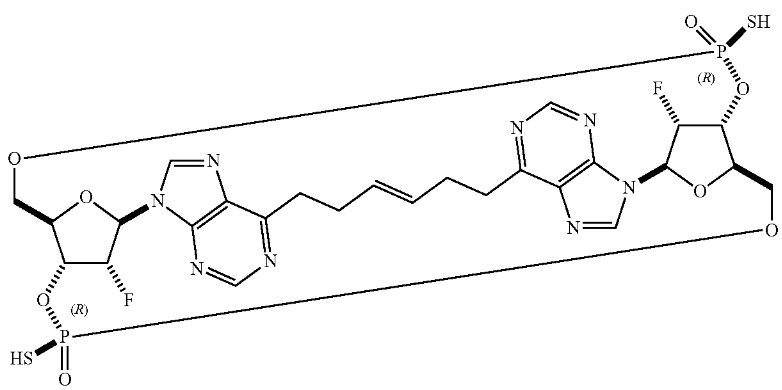 |
| 35 | (Stereoisomer 1) |

TABLE 3-continued

| Compound No. | Structure |
|---|---|
| 36 | (Stereoisomer 2) |
| 37 | stereoisomer 4 |
| 38 | 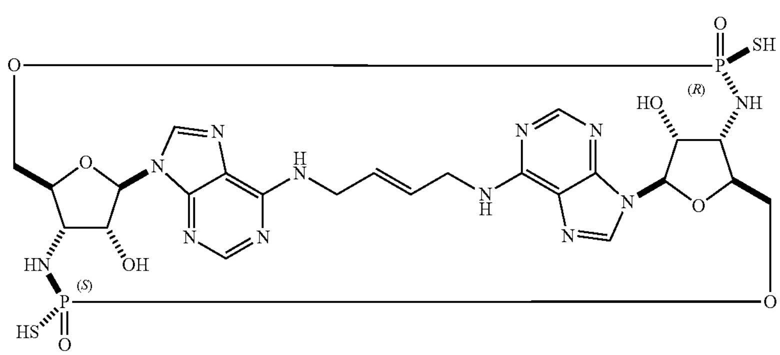 |
| 39 | 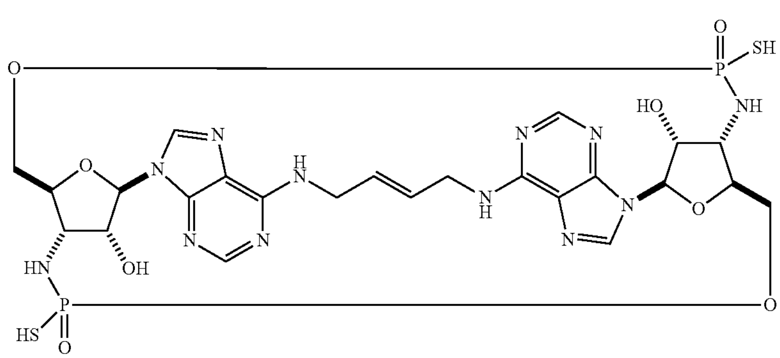 |

In the table above, Compounds 8, 11, and 12 are drawn with the same structural formula and relate to three separate stereoisomers. The applicant notes, however, that the phosphorous chirality of Compound 8 is not necessarily the same as the phosphorous chirality for other compounds labeled "Stereoisomer 1," such as, for example, Compound 21. The same holds true for the other stereoisomers.

Embodiments may relate to $C_4$-$C_6$ linkers that may be covalently bound at either end to purine or pyrimidine bases that form part of a cyclic dinucleotide. In an embodiment, the linkers are butene, pentene or hexene linkers bound at either end to purine bases. In another embodiment, the linkers are butene linkers bound at either end to purine bases; in another embodiment, the linkers are transbutene linkers with the double bond located between the center two carbons.

The following numbered embodiments are illustrative of use of these $C_4$-$C_6$ linkers:

1. A compound of Formula (X):

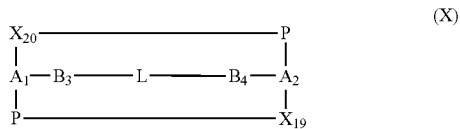

or a pharmaceutically acceptable salt thereof, wherein:

$A_1$ and $A_2$ are sugar moieties and may be the same or different;

$B_3$ and $B_4$ are purine or pyrimidine bases that may be the same or different and that form nucleotides with, respectively, $A_1$ and $A_2$;

L is a alkyl linker;

$X_{19}$ and $X_{20}$ are the same or different and are selected from the group consisting of —O—, —CH—, —NH—, and —S—, wherein —CH— and —NH— may be substituted or unsubstituted.

2. The compound or pharmaceutically acceptable salt of numbered embodiment 1, wherein —CH— and —NH— of $X_{19}$ and $X_{20}$ may be substituted with $C_{1-6}$ alkyl.

3. The compound or pharmaceutically acceptable salt of numbered embodiment 1, wherein L is butene, pentene, or hexane.

4. The compound or pharmaceutically acceptable salt of numbered embodiment 3, wherein L is a transbutene linker with a double bond at its center.

Compounds or pharmaceutically acceptable salts of the numbered embodiments may be useful, for example, for treating cancer. $A_1$, $A_2$, $B_3$, and $B_4$ may be further substituted with, for example, hydroxyl, halogen, or methoxy. Each phosphorous in Formula (X) may be substituted, for example, with —SH, —OH, =O, or =S until its valence has been satisfied.

Examples of cyclic dinucleotide analogs that may benefit from linkers of the present invention include but are not limited to those identified in US 2014/0205653 A1; US 2014/0329889 A1; US 2014/0341976 A1; US 2015/0056224 A1; US 2016/0362441 A1; US 2017/0158724 A1; US 2017/044206 A1; U.S. Pat. Nos. 5,547,941; 7,569,555 B2; 7,592,326 B2; 7,709,458 B2; 9,549,944 B2; WO 2009/133560 A1; WO 2015/074145 A1; WO 2015/077354 A1; WO 2015/185565 A1; WO 2016/100261 A1; WO 2016/120305 A1; WO 2016/145102 A1; WO 2017/027645 A1; WO 2017/027646 A1; WO 2017/075477 A1; WO 2017/093933 A1; WO 2017/123657 A1; WO 2017/175156 A1; EP 1740,192 B1; CN 102199183 A; Corrales, L. et al., "Direct Activation of STING in the Tumor Microenvironment Leads to Potent and Systemic Tumor Regression and Immunity," *Cell Reports,* 11: 1018-1030 (2015); and Lioux, T. et al., "Design, Synthesis, and Biological Evaluation of Novel Cyclic Adenosine-Inosine Monophosphate (cAIMP) Analogs That Activate Stimulator of Interferon Genes (STING)," *J. Med. Chem.,* 59: 10253-10267 (2016). All of those documents, including the compounds therein, are incorporated by reference herein; if any component of any of those documents contradicts or is otherwise inconsistent with anything in this specification, then this specification controls.

In some embodiments, a compound as reported herein is provided as a free acid. In some embodiments, the compound is provided as an $NH_4$ salt or as a triethyl amine (TEA) salt.

Embodiments may provide a method of treating cancer in a patient in need thereof, including administering to the patient a therapeutically effective amount of a compound reported herein, or a pharmaceutically acceptable salt thereof, as recited above.

In some embodiments, the compound is administered as a free acid. In some embodiments, the compound is administered as a diammonium salt ($NH_4$). Pharmaceutical compositions including a Compound of Formula I, Formula II, Formula III, Formula IV, Formula V, Table 3, or a pharmaceutically acceptable salt thereof, as well as a pharmaceutically acceptable excipient, are contemplated. Embodiments may provide a compound according to Formula I in which n is 1; geometry about the double bond is trans; $X_1$ and $X_2$ are each SH; stereochemistry at $P_1$ is S; and stereochemistry at $P_2$ is R; or a pharmaceutically acceptable salt thereof.

Embodiments may provide a method of treating cancer in a patient comprising administering to said patient a compound or pharmaceutically acceptable salt thereof, or a pharmaceutical composition, as reported herein. Cancers treated as reported herein may be metastatic cancers. They may be selected from, for example, lymphoma, melanoma, colorectal cancer, breast cancer, acute myeloid leukemia, colon cancer, liver cancer, prostate cancer, pancreatic cancer, renal cancer, and glioma. Uses of compounds, salts, and pharmaceutical compositions for treatment of cancer and/or preparation of a medicament for treatment of cancer are also contemplated.

Embodiments may provide a method of treating cancer including identifying an individual having a cancer treatable by a compound, pharmaceutically acceptable salt, or pharmaceutical composition as reported herein, and administering to the individual a compound, pharmaceutically acceptable salt, or pharmaceutical composition by which the patient has been identified as treatable. In some embodiments the individual is identified as having a cancer treatable by a compound, pharmaceutically acceptable salt, or pharmaceutical composition as reported herein by presence of a human REF STING variant allele in the patient.

Embodiments may provide a method of treating cancer in a patient having REF STING allele comprising administering to said patient a compound or pharmaceutically acceptable salt thereof, or pharmaceutical composition as reported herein.

Embodiments may provide a method of treating cancer in a patient having WT STING allele comprising administering to said patient a compound or pharmaceutically acceptable salt thereof, or pharmaceutical composition as reported herein.

Embodiments may provide a method of treating cancer in a patient having AQ STING allele comprising administering to said patient a compound or pharmaceutically acceptable salt thereof, or pharmaceutical composition as reported herein.

Embodiments may provide a method of treating cancer in a patient having HAQ STING allele comprising administering to said patient a compound or pharmaceutically acceptable salt thereof, or pharmaceutical composition as reported herein.

BRIEF DESCRIPTION OF THE FIGURES

FIG. 1 shows a synthesis of Compound 1a and Compound 2a.

DETAILED DESCRIPTION OF EMBODIMENTS

Figure 1:
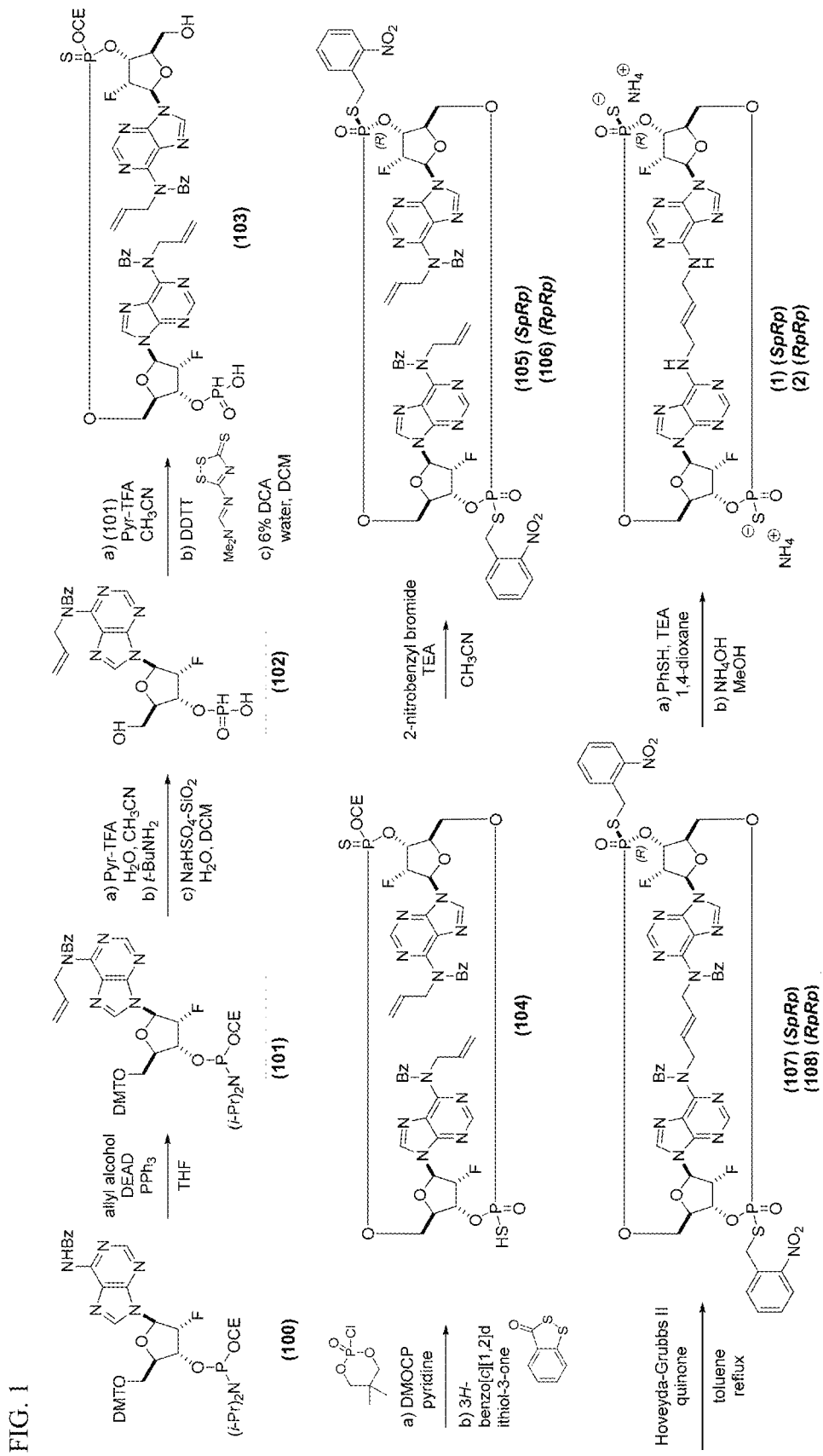

Provided herein are compounds that may be useful in treating cancer. The compounds may activate stimulator of interferon genes (STING).

In some embodiments, the compound is provided as a free acid. In some embodiments, the compound is provided as, for example, an $NH_4$ salt. Reference to a compound number followed by an "a" will indicate a diammonium salt of the given compound. For example, "Compound 1a" refers to the diammonium salt of Compound 1.

Embodiments may provide a method of treating cancer in a patient in need thereof, including administering to the patient a therapeutically effective amount of a Compound of Formula I, Formula II, Formula III, Formula IV, or Formula V, or pharmaceutically acceptable salt thereof.

In some embodiments, the compound is administered as a free acid. In some embodiments, the compound is administered as, for example, a diammonium salt ($NH_4$). Pharmaceutical compositions for treating cancer may also be provided including a compound reported herein or a pharmaceutically acceptable salt thereof, as well as a pharmaceutically acceptable excipient.

Embodiments as reported herein may be used to treat cancer or to prepare medicaments useful for treatment of cancer. "Cancer" may include, but is not limited to, colon cancer, liver cancer, melanoma, colorectal cancer, breast cancer, acute myeloid leukemia, and glioma.

Those of skill in the art will recognize that where substituents bound to the phosphorous atoms ($P_1, P_2$) have both single and double bonds, they may be susceptible to tautomerization. For example, the the compounds may tautomerize at equilibrium. One example is shown below:

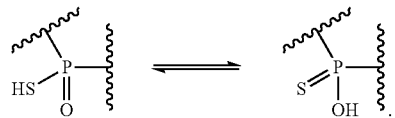 [SMILES: *P(*)(=O)S ; *P(*)(O)=S]

Such tautomers should be considered to be within the scope of the claims. A structural representation of either tautomer for a given compound will represent the same compound.

In some embodiments, the compound selected from the group consisting of the compounds reported herein is provided as a free acid or a pharmaceutically acceptable salt thereof. In some embodiments, the compound selected from the group consisting of the compounds reported herein is provided as an $NH_4$ salt, which may be a diammonium salt.

As used herein, "$C_{1-6}$alkyl" or "$C_1$-$C_6$" alkyl is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_{1-6}$ alkyl is intended to include $C_1$, $C_2$, $C_3$, $C_4$, $C_5$ and $C_6$ alkyl groups. Examples of alkyl include moieties having from one to six carbon atoms, such as, but not limited to, methyl, ethyl, n-propyl, i-propyl, n-butyl, s-butyl, t-butyl, n-pentyl, s-pentyl or n-hexyl. Similarly, "$C_{1-3}$alkyl" or "$C_1$-$C_3$alkyl" is intended to include $C_1$, $C_2$, or $C_3$ straight chain (linear) saturated aliphatic hydrocarbon groups and $C_3$ branched saturated aliphatic hydrocarbon groups.

As used herein, the term "$C_{3-6}$cycloalkyl" or "$C_3$-$C_6$cycloalkyl" refers to a saturated or unsaturated nonaromatic hydrocarbon ring having 3 to 6 carbon atoms (e.g., $C_3$-$C_6$). Examples of cycloalkyl include, but are not limited to, cyclopropyl, cyclobutyl, cyclopentyl, cyclohexyl, cycloheptyl, cyclopentenyl, and cyclohexenyl. The term "$C_{5-6}$cycloalkyl" or "$C_5$-$C_6$cycloalkyl" refers to a saturated or unsaturated nonaromatic hydrocarbon ring having 5 or 6 carbon atoms (e.g., $C_5$-$C_6$).

The term "$C_{5-6}$heterocycloalkyl" or "$C_5$-$C_6$heterocycloalkyl" refers to a saturated or unsaturated nonaromatic 5-6 membered monocyclic having one or more heteroatoms (such as O, N, or S), unless specified otherwise. The term "$C_{4-6}$heterocycloalkyl" or "$C_4$-$C_6$heterocycloalkyl" refers to a saturated or unsaturated nonaromatic 4-6 membered monocyclic having one or more heteroatoms (such as O, N, or S), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, tetrahydrothiophene, dihydropyranyl, pyranyl, morpholinyl, 1,4-diazepanyl, 1,4-oxazepanyl, and the like.

Additional examples of heterocycloalkyl groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

As used herein, the term "$C_{5-6}$aryl" or "$C_5-C_6$aryl" refers to an aromatic hydrocarbon ring having 5 to 6 carbon atoms (e.g., $C_5-C_6$) that does not contain any heteroatom in the ring structure. The term "$C_{3-6}$heteroaryl" or "$C_3-C_6$heteroaryl" refers to an aromatic 3-6 membered monocyclic having one or more heteroatoms (such as O, N, or S), unless specified otherwise, except that a heteroaryl ring will include no more than one oxygen atom or one sulfur atom. The term "$C_{2-6}$alkenyl" includes unsaturated aliphatic groups having 2, 3, 4, 5, or 6 carbons and that contain at least one double bond. For example, the term "$C_{2-6}$alkenyl" includes straight chain alkenyl groups (e.g., ethenyl, propenyl, butenyl, pentenyl, hexenyl), and branched alkenyl groups. In certain embodiments, a straight chain or branched alkenyl group has six or fewer carbon atoms in its backbone (e.g., $C_2-C_6$ for straight chain, $C_3-C_6$ for branched chain). The term "$C_{2-6}$alkenyl" includes alkenyl groups containing two to six carbon atoms.

The term "$C_{2-6}$alkynyl" includes unsaturated aliphatic groups having 2, 3, 4, 5, or 6 carbon atoms, but which contain at least one triple bond. For example, "alkynyl" includes straight chain alkynyl groups (e.g., ethynyl, propynyl, butynyl, pentynyl, hexynyl), and branched alkynyl groups. In certain embodiments, a straight chain or branched alkynyl group has six or fewer carbon atoms in its backbone (e.g., $C_2-C_6$ for straight chain, $C_3-C_6$ for branched chain). The term "$C_{2-6}$alkynyl" includes alkynyl groups containing two to six carbon atoms.

Methods of Treatment

Embodiments may provide a method of treating cancer in a patient in need thereof, including administering to the patient a therapeutically effective amount of a compound reported herein or a pharmaceutically acceptable salt thereof.

In some embodiments, the administered compound is provided as a free acid or a pharmaceutically acceptable salt thereof. In some embodiments, the administered compound is provided as an $NH_4$ salt a free acid or a pharmaceutically acceptable salt thereof. In some embodiments, the compound is provided as an $NH_4$ salt.

The term "optionally substituted" refers to a moiety having designated substituents replacing one or more hydrogen atoms on one or more atoms bearing hydrogen in the moiety.

Chemicals as named or depicted are intended to include all naturally occurring isotopes of atoms occurring in the present compounds. Isotopes include those atoms having the same atomic number but different mass numbers. By way of general example and without limitation, isotopes of $^1H$ hydrogen include tritium and deuterium, and isotopes of $^{12}C$ carbon include $^{13}C$ and $^{14}C$.

Dosages

The optimal dose for treatment of cancer can be determined empirically for each individual using known methods and will depend upon a variety of factors, including the activity of the agents; the age, body weight, general health, gender and diet of the individual; the time and route of administration; and other medications the individual is taking. Optimal dosages may be established using routine testing and procedures that are well known in the art. Administration of the above compounds may be by any suitable route.

"Pharmaceutically acceptable salt" as used herein refers to acid addition salts or base addition salts of the compounds in the present disclosure. A pharmaceutically acceptable salt is any salt which retains the activity of the parent compound and does not impart any unduly deleterious or undesirable effect on a subject to whom it is administered and in the context in which it is administered. Pharmaceutically acceptable salts include, but are not limited to, metal complexes and salts of both inorganic and carboxylic acids. Pharmaceutically acceptable salts also include metal salts such as aluminum, calcium, iron, magnesium, manganese and complex salts. In addition, pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolic, glycolylarsanilic, hexamic, hexylresorcinoic, hydrabamic, hydrobromic, hydrochloric, hydrochloride, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like. Sodium salts and potassium salts may also be prepared.

Embodiments may be diammonium salts. Pharmaceutically acceptable salts may be derived from amino acids including, but not limited to, cysteine. Methods for producing compounds as salts are known to those of skill in the art (see, e.g., Stahl et al., Handbook of Pharmaceutical Salts: Properties, Selection, and Use, Wiley-VCH; Verlag Helvetica Chimica Acta, Zurich, 2002; Berge et al., J. Pharm. Sci. 66: 1, 1977).

An "effective amount" of a therapeutic agent is an amount sufficient to provide an observable therapeutic benefit compared to cancer left untreated in a subject or patient.

Active agents as reported herein can be combined with a pharmaceutically acceptable carrier to provide pharmaceutical formulations thereof. The particular choice of carrier and formulation will depend upon the particular route of administration for which the composition is intended. "Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, sorbic acid, potassium sorbate, partial glyceride mixtures of saturated vegetable fatty acids, water, salts or electrolytes, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene glycol and wool fat.

The compositions of the present invention may be suitable for parenteral, oral, inhalation spray, topical, rectal, nasal, buccal, vaginal or implanted reservoir administration, etc. In some embodiments, the formulation comprises ingredients that are from natural or non-natural sources. In some embodiments, the formulation or carrier may be provided in a sterile form. Non-limiting examples of a sterile carrier include endotoxin-free water or pyrogen-free water.

The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds are administered intravenously, orally, subcutaneously, or via intramuscular administration. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids and their glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents that are commonly used in the manufacture of pharmaceutically acceptable solid, liquid, or other dosage forms may also be used for the purposes of formulation.

For oral administration, a compound or salt may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient may be combined with emulsifying and suspending agents. If desired, certain sweetening, flavoring or coloring agents may also be added. In addition preservatives may also be added. Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

"Immediate-release" is meant to include a conventional release, in which release of the drug starts immediately after administration. As used herein, the term "immediate release" includes dosage forms that allow the drug to dissolve in the gastrointestinal contents, with no intention of delaying or prolonging the dissolution or absorption of the drug. The objective is for the drug to be released rapidly after administration, for example for it to be possible to release at least 80% of the drug within approximately 30 minutes after commencement of dissolution in a dissolution test. "Sustained-release" or "extended-release" includes dosage forms whose drug-release characteristics of time course and/or location are chosen to accomplish therapeutic or convenience objectives not offered by conventional dosage forms such as a solution or an immediate release dosage form. The term "steady-state" means that a plasma level for a given active agent has been achieved and which is maintained with subsequent doses of the active agent at a level which is at or above the minimum effective therapeutic level and is below the minimum toxic plasma level for a given active agent.

The term "single formulation" as used herein refers to a single carrier or vehicle formulated to deliver effective amounts of both therapeutic agents to a patient. The single vehicle is designed to deliver an effective amount of each of the agents along with any pharmaceutically acceptable carriers or excipients. In some embodiments, the vehicle is a tablet, capsule, pill, or a patch.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of an agent along with pharmaceutically acceptable carriers and excipients. In some embodiments, the unit dose is one or more tablets, capsules, pills, or patches administered to the patient at the same time.

The term "dose range" as used herein refers to an upper and a lower limit of an acceptable variation of the amount of agent specified. Typically, a dose of an agent in any amount within the specified range can be administered to patients undergoing treatment.

The term "treat" is used herein to mean to relieve, reduce or alleviate at least one symptom of a disease in a subject. For example, in relation to cancer, the term "treat" may mean to arrest, delay the onset (i.e., the period prior to clinical manifestation of a disease or symptom of a disease) and/or reduce the risk of developing or worsening a symptom of a disease. The term "protect" is used herein to mean prevent delay or treat, or all, as appropriate, development or continuance or aggravation of symptoms of the disease in a subject.

The term "subject" or "patient" is intended to include animals, which are capable of suffering from or afflicted with cancer. Examples of subjects or patients include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer.

The term "about" or "approximately" usually means within 20%, more preferably within 10%, and most preferably still within 5% of a given value or range. Alternatively, especially in biological systems, the term "about" means approximately within a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

Exemplary cell proliferative disorders that may be treated using one or more compounds disclosed herein include, but are not limited to cancer, a precancer or precancerous condition, and metastatic lesions in tissue and organs in the body. Cell proliferative disorders may include hyperplasia, metaplasia, and dysplasia.

A compound disclosed herein, or a pharmaceutically acceptable salt thereof, may be used to treat or prevent a cell proliferative disorder, or to treat or prevent cancer, in a subject having an increased risk of developing cancer relative to the population at large, or used to identify suitable candidates for such purposes.

Pharmaceutical Formulations and Routes of Administration

Provided herein are pharmaceutical formulations comprising a compound or pharmaceutically acceptable salt thereof for the treatment of cancer. The pharmaceutical formulations may additionally comprise a carrier or excipient, stabilizer, flavoring agent, and/or coloring agent.

The compound or pharmaceutically acceptable salt thereof may be administered using a variety of routes of administration known to those skilled in the art. Routes of administration include oral administration. In certain embodiments, a pharmaceutical formulation comprising the compound or pharmaceutically acceptable salt thereof may be taken orally in the form of liquid, syrup, tablet, capsule, powder, sprinkle, chewtab, or dissolvable disk. Alternatively, pharmaceutical formulations of the present invention can be administered intravenously or transdermally. Additional routes of administration are known to those skilled in the art (see, e.g., Remington's Pharmaceutical Sciences, Gennaro A. R., Ed., 20.sup.th Edition, Mack Publishing Co., Easton, Pa.).

In some embodiments, the compound or pharmaceutically acceptable salt is formulated as a paste, jelly, or suspension. For example, the drug is dissolved, entrapped or suspended in the form of drug particles, microencapsulated particles, or drug-polymer particles in a gelatinous solution or semi-solid. An advantage of an oral jelly formulation is that it is easier to administer the drug to patients who have difficulty swallowing tablets, capsules or pills. In certain embodiments, the compound is thoroughly mixed and suspended in an appropriate medium to form a paste or a gel. Additional agents can optionally be mixed to provide flavor during oral administration. Peanut butter or alginate, flavored with raspberry and a sweetener are examples of the many suitable taste masking agents. In various embodiments, the paste or jelly can also be formulated with suitable binders or excipients known in the art for topical administration.

Methods of preparing sustained release formulations in the form of tablets, capsules or pills are known in the art. In some embodiments, the sustained release formulation is prepared by coating the active ingredient of the drug with a polymer, preferably a water-insoluble polymer. For example, a water-insoluble polymer used in the pharmaceutical field as a sustained release coating agent, an enteric coating agent, or a gastric coating agent. The water-insoluble polymer can include, for example, ethyl cellulose, purified shellac, white shellac, aminoalkyl methacrylate copolymer RS, hydroxypropyl methylcellulose phthalate, hydroxypropyl methylcellulose acetate succinate, carboxymethylethylcellulose, cellulose acetate phthalate, methacrylic acid copolymer L, methacrylic acid copolymer LD, methacrylic acid copolymer S, aminoalkyl methacrylate copolymer E, or polyvinyl acetal diethylaminoacetate.

The type, degree of substitution and molecular weight of the water-insoluble polymers can depend on solubility of the active ingredient in water or an alcohol, the desired sustained release level and the like. The water-insoluble polymers can be used either alone or in combination. There can be further incorporated a hydrogenated oil, stearic acid, or cetanol as a coating auxiliary agent, and a middle-chain triglyceride, triacetin, triethyl citrate, or cetanol as a plasticizer. In some embodiments, the sustained release formulation is a matrix-type tablet or granule. The active ingredient can be coated with up to 3 different types of polymers. These three different types of polymers can include: 1) a water insoluble polymer, such as ethylcellulose; 2) a pH independent gelling polymer, such as hydroxypropyl methylcellulose; and 3) a pH dependent gelling polymer, such as sodium alginate. These three different types of polymers can be used together to attenuate the release rate of the drugs.

Dosage Forms: Release Properties

Sustained-release formulations can achieve a degree of sustained effect. However, the exposure and/or the bioavailability of the active ingredient may vary based on a variety of factors, such as for example, the absorption window, the carriers or excipients used in the formulation, the mode of delivery of the formulation, and/or the transit time of the active ingredient through the gastrointestinal tract of the patient.

A therapy can contain at least one sustained-release portion for performing a sustained-release function and one immediate release portion for performing an immediate release function. In certain embodiments, when the therapy is in a single dosage form, it can be in the form of tablets formed from a mixture of sustained-release granules constituting a sustained-release portion and immediate-release granules constituting an immediate-release portion, a capsule preparation obtained by filling a capsule with sustained-release granules and immediate-release granules, or press-coated tablets in which an outer layer constituting an immediate-release portion is formed on an inner core constituting a sustained-release portion. There is, however, no limitation to the above embodiments.

Moreover, there are no particular limitations on the state of containment of the drug in the composition or in an immediate-release portion or a sustained-release portion; the compound may be dispersed uniformly in the composition, immediate release portion or sustained release portion, or may be contained in only one part of the composition, immediate-release portion or sustained-release portion, or may be contained such that there is a concentration gradient. A sustained-release portion in the composition according to the present invention can contain at least one non-pH-dependent polymeric substance or pH-dependent polymeric substance for controlling drug release.

A non-pH-dependent polymeric substance used herein can comprise a polymeric substance whose charge state hardly changes under pH conditions generally found in the gastrointestinal tract, specifically from pH 1 to pH 8. This means, for example, a polymeric substance that does not have functional groups whose charge state changes depending on the pH such as basic functional groups such as amino groups or acidic functional groups such as carboxylic acid groups. Note that the non-pH-dependent polymeric substance can be included for giving the composition according to the present invention a sustained-release function, but may also be included for another purpose. Moreover, the non-pH-dependent polymeric substance used in the present invention may be water-insoluble, or may swell in water or dissolve in water to form a gel.

Examples of water-insoluble non-pH-dependent polymeric substances include, but are not limited to, cellulose ethers, cellulose esters, and methacrylic acid-acrylic acid copolymers (trade name Eudragit, manufactured by Rohm GmbH & Co. KG, Darmstadt, Germany). Examples include, but are not limited to, cellulose alkyl ethers such as ethylcellulose (trade name Ethocel, manufactured by Dow Chemical Company, USA), ethyl methylcellulose, ethyl propylcellulose or isopropylcellulose, and butylcellulose, cellulose aralkyl ethers such as benzyl cellulose, cellulose cyanoalkyl ethers such as cyanoethylcellulose, cellulose organic acid esters such as cellulose acetate butyrate, cellulose acetate, cellulose propionate or cellulose butyrate, and cellulose acetate propionate, ethyl acrylate-methyl methacrylate copolymers (trade name Eudragit NE, manufactured by Rohm GmbH & Co. KG, Darmstadt, Germany), and aminoalkyl methacrylate copolymer RS (trade names Eudragit RL, Eudragit RS). There are no particular limitations on the mean particle diameter of a water-insoluble polymer used in the present invention, but usually the lower this mean particle diameter the better the performance, with the mean particle diameter preferably being from 0.1 to 100 μm, more preferably from 1 to 50 μm, particularly preferably from 3 to 15 μm, most preferably from 5 to 15 μm. Moreover, examples of water-soluble or water-swelling non-pH-dependent polymeric substances include, but are not limited to, polyethylene oxide (trade name Polyox, manufactured by Dow Chemical Company, molecular weight 100,000 to 7,000,000), low-substituted hydroxypropyl cellulose (trade name L-HPC, manufactured by Shin-Etsu Chemical, Japan), hydroxypropyl cellulose (trade name HPC, manufactured by Nippon Soda, Co., Ltd, Japan), hydroxypropyl methylcellulose (trade names Metolose 60SH, 65SH, 90SH, manufactured by Shin-Etsu Chemical, Japan), and methylcellulose (trade name Metolose SM, manufactured by Shin-Etsu Chemical, Japan).

In some embodiments a single non-pH-dependent polymeric substance may be contained in the composition, or a plurality of the non-pH-dependent polymeric substances may be contained. The non-pH-dependent polymeric substance, if used in embodiments reported herein, may be a water-insoluble polymeric substance, more preferably ethylcellulose, an ethyl acrylate-methyl methacrylate copolymer (trade name Eudragit NE), or an aminoalkyl methacrylate copolymer RS (trade name Eudragit RL, Eudragit RS). Particularly preferable is at least one of ethylcellulose and an aminoalkyl methacrylate copolymer RS. Most preferable is ethylcellulose. There are no particular limitations on the amount of the non-pH-dependent polymeric substance contained in the composition; this amount can be adjusted as appropriate in accordance with the purpose such as controlling sustained drug release.

A pH-dependent polymeric substance that can be used in embodiments reported herein may be a polymeric substance whose charge state changes under pH conditions generally found in the gastrointestinal tract, specifically from pH 1 to pH 8. This means, for example, a polymeric substance having functional groups whose charge state changes depending on the pH such as basic functional groups such as amino groups or acidic functional groups such as carboxylic acid groups. The pH-dependent functional groups of the pH-dependent polymeric substance are preferably acidic functional groups, with the pH-dependent polymeric substance most preferably having carboxylic acid groups.

A pH-dependent polymeric substance used in the present invention may be water-insoluble, or may swell in water or dissolve in water to form a gel. Examples of pH-dependent polymeric substances used in the present invention include, but are not limited to, enteric polymeric substances. Examples of enteric polymeric substances include, but are not limited to, methacrylic acid-methyl methacrylate copolymers (Eudragit L100, Eudragit S100, manufactured by Rohm GmbH & Co. KG, Darmstadt, Germany), methacrylic acid-ethyl acrylate copolymers (Eudragit L100-55, Eudragit L30D-55, manufactured by Rohm GmbH & Co. KG, Darmstadt, Germany), hydroxypropyl methylcellulose phthalate (HP-55, HP-50, manufactured by Shin-Etsu Chemical, Japan), hydroxypropyl methylcellulose acetate succinate (AQOAT, manufactured by Shin-Etsu Chemical, Japan), carboxymethyl ethylcellulose (CMEC, manufactured by Freund Corporation, Japan), and cellulose acetate phthalate.

Examples of pH-dependent polymeric substances that swell in water or dissolve in water to form a gel include, but are not limited to, alginic acid, pectin, carboxyvinyl polymer, and carboxymethyl cellulose. In the present invention, a single pH-dependent polymeric substance may be contained in the composition, or a plurality of pH-dependent polymeric substances may be contained. The pH-dependent polymeric substance used in the present invention is preferably an enteric polymeric substance, more preferably a methacrylic acid-ethyl acrylate copolymer, a methacrylic acid-methyl methacrylate copolymer, hydroxypropyl methylcellulose phthalate, or hydroxypropyl methylcellulose acetate succinate, particularly preferably a methacrylic acid-ethyl acrylate copolymer.

When using a pH-dependent polymeric substance in the manufacturing process of a composition according to the present invention, a commercially available product of a powder type or a granular type, or a suspension type in which the pH-dependent polymeric substance has been dispersed in a solvent in advance can be used as is, or such a commercially available product can be used dispersed in water or an organic solvent. The lower the particle diameter of the pH-dependent polymeric substance the better the performance, with the pH-dependent polymeric substance preferably being of the powder type. In the case of a methacrylic acid-ethyl acrylate copolymer, an example is Eudragit L100-55. There are no particular limitations on the mean particle diameter of a pH-dependent polymeric substance used in the present invention, but the mean particle diameter is preferably from 0.05 to 100 μm, more preferably from 0.05 to 70 μm, most preferably from 0.05 to 50 μm. Moreover, there are no particular limitations on the amount of the pH-dependent polymeric substance, for example, in the case of an enteric polymeric substance, the amount is generally from 0.1 to 90 parts by weight, preferably from 1 to 70 parts by weight, more preferably from 5 to 60 parts by weight, particularly preferably from 10 to 50 parts by weight, based on 100 parts by weight of the composition.

A therapy according to embodiments reported herein may further contain any of various additives, such as any of various pharmacologically acceptable carriers such as diluents, lubricants, binders and disintegrants, as well as preservatives, colorants, sweeteners, plasticizers, film coating agents and so on, as necessary. Examples of diluents include, but are not limited to, lactose, mannitol, dibasic calcium phosphate, starch, pregelatinized starch, crystalline cellulose, light silicic anhydride, synthetic aluminum silicate, magnesium aluminate metasilicate or the like. Examples of lubricants include, but are not limited to, magnesium stearate, calcium stearate, talc, sodium stearyl fumarate or the like. Examples of binders include, but are not limited to, hydroxypropyl cellulose, methylcellulose, sodium carboxymethyl cellulose, hydroxypropyl methylcellulose, polyvinylpyrrolidone or the like. Examples of disintegrants include, but are not limited to, carboxymethyl cellulose, calcium carboxymethyl cellulose, croscarmellose sodium, sodium carboxymethyl starch, low-substituted hydroxypropyl cellulose or the like. Examples of preservatives include, but are not limited to, paraoxybenzoic acid esters, chlorobutanol, benzyl alcohol, phenethyl alcohol, dehydroacetic acid, sorbic acid or the like. Preferable examples of colorants include, but are not limited to, water-insoluble lake pigments, natural pigments (e.g., .beta.-carotene, chlorophyll, red ferric oxide), yellow ferric oxide, red ferric oxide, black ferric oxide or the like. Preferable examples of sweeteners include, but are not limited to, sodium saccharin, dipotassium glycyrrhizate, aspartame, stevia or the like. Examples of plasticizers include, but are not limited to, glycerol fatty acid esters, triethyl citrate, propylene glycol, polyethylene glycol or the like. Examples of film coating agents include, but are not limited to, hydroxypropyl methylcellulose, hydroxypropyl cellulose or the like.

Manufacturing Methods

To manufacture embodiments as reported herein, a single conventional method, or a combination of conventional methods, can be used. For example, when manufacturing drug-containing granules as a sustained-release portion or an immediate-release portion, granulation is the main operation, but this may be combined with other operations such as mixing, drying, sieving, and classification. As the granulation method, for example, a wet granulation method in which a binder and a solvent are added to the powder and granulation is carried out, a dry granulation method in which the powder is compressed and granulation is carried out, a molten granulation method in which a binder that melts on heating is added and heating and granulation are carried out, or the like can be used.

Furthermore, in accordance with the granulation method, an operating method such as a mixing granulation method using a planetary mixer, a screw mixer or the like, a high-speed mixing granulation method using a Henschel mixer, a Super mixer or the like, an extruding granulation method using a cylindrical granulator, a rotary granulator, a screw extruding granulator, a pellet mill type granulator or the like, a wet high-shear granulation method, a fluidized-bed granulation method, a compression granulation method, a crushing granulation method, or a spraying granulation method can be used. After the granulation, drying using a dryer, a fluidized bed or the like, cracking, and sieving can be carried out to obtain the granules or fine granules for use. Moreover, a granulation solvent may be used when preparing the composition according to the present invention. There are no particular limitations on such a granulation solvent, which may be water or any of various organic solvents, for example, water, a lower alcohol such as methanol or ethanol, a ketone such as acetone or methyl ethyl ketone, methylene chloride, or a mixture thereof.

For sustained-release granules contained in embodiments, at least one drug and at least one selected from non-pH-dependent polymeric substances and pH-dependent polymeric substances are mixed together, a diluent and a binder are added as necessary, and granulation is carried out to obtain granular matter. The granular matter obtained is dried using a tray dryer, a fluidized bed dryer or the like, and sieving is carried out using a mill or an oscillator, whereby the sustained-release granules can be obtained. Alternatively, as a method of manufacturing sustained-release granules in the present invention, it is possible to add at least one drug, at least one selected from non-pH-dependent polymeric substances and pH-dependent polymeric substances, and as necessary a diluent and a binder using a dry compactor such as a roller compactor or a slug tabletting machine, and carry out compression-molding while mixing, and then carry out granulation by cracking down to a suitable size. The granular matter prepared using such a granulator may be used as is as granules or fine granules according to the present invention, or may be further cracked using a power mill, a roll granulator, a rotor speed mill or the like, and sieved to obtain sustained-release granules. Note that immediate-release granules can also be manufactured as for the sustained-release granules.

A compression-molded product can be manufactured as a drug-containing sustained-release portion or immediate-release portion, or as a composition reported herein using a single conventional method, or a combination of conventional methods. For example, at least one drug, at least one selected from non-pH-dependent polymeric substances and pH-dependent polymeric substances, a diluent such as mannitol or lactose, a binder such as polyvinylpyrrolidone or crystalline cellulose, a disintegrant such as carmellose sodium or crospovidone, and a lubricant such as magnesium stearate or talc are used, and tabletting is carried out using an ordinary method, whereby the compression-molded product can be obtained. In this case, tabletting is the main operation in the method of manufacturing the compression-molded product, but this may be combined with other operations such as mixing, drying, sugar coating formation, and coating.

Examples of the method for the tabletting include, but are not limited to, direct compression molding in which at least one drug and pharmacologically acceptable additives are mixed together and then the mixture is directly compression-molded into tablets using a tabletting machine, and dry granule compression or wet granule compression in which sustained-release granules or immediate-release granules according to the present invention are subjected to compression-molding after adding a lubricant or a disintegrant as necessary. There are no particular limitations on the tabletting machine used in the compression molding; for example, a single-punch tabletting machine, a rotary tabletting machine, or a press-coated tabletting machine can be used.

Drug-containing sustained-release granules or immediate-release granules, or compression-molded product according to embodiments herein can be used as is in the form of granules or a tablet as the composition, but may also be subjected to further processing to manufacture the composition. For example, the compression-molded product or granules can be given a film coating using a film base material such as ethylcellulose, casein, methylcellulose, hydroxypropyl methylcellulose, methacrylic acid copolymer L, cellulose acetate phthalate, shellac or the like, or given a sugar coating using a sugar coating liquid containing saccharose, sugar alcohol, gum arabic powder, talc or the like, thus producing film-coated tablets or sugar-coated tablets. One solvent in this coating technique may be purified water, but an organic solvent such as an alcohol, a ketone, an ether or a chlorinated hydrocarbon, or a mixture thereof can also be used. For example, ethanol, acetone, methylene chloride or the like can be used as an organic solvent. Moreover, as the coating apparatus, an apparatus ordinarily used in coating techniques for manufacturing medicines can be used, with examples including a spray coating apparatus in which the coating is carried out by spraying a coating liquid or the like, and a rotor fluidized bed granulator for layering.

In the case of manufacturing capsule preparations, capsule preparations can be manufactured by filling sustained-release granules or immediate-release granules as above, or mini-tablets into hard gelatin capsules or HPMC capsules using an automatic capsule filling machine. Alternatively, in the case of the preparations for per-tube administration or a dry syrup that is used mixed with water or the like when taken, sustained-release granules or immediate-release granules as above can be mixed with a thickener or a dispersant so as to disperse these granules, the mixture then being made into granules or tablets. Furthermore, a liquid or jelly can be made using water, and substances selected from dispersants, emulsifiers, thickeners, preservatives, pH adjustors, sweeteners, flavorings, fragrances and so on. However, with respect to other manufacturing methods, there are no limitations to the above.

So that embodiments described herein may be more fully understood, the following examples are set forth. It should be understood that these examples are for illustrative purposes only and are not to be construed as limiting.

EXAMPLES

The following abbreviations may be used throughout the examples.
All: allyl
BOP: (Benzotriazol-1-yloxy)tris(dimethylamino)phosphonium hexafluorophosphate
DMT: 4,4'-Dimethoxytrityl (DMTO-: 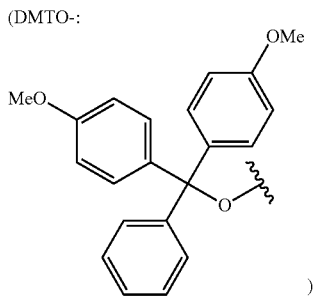 [SMILES: *OC(c1ccccc1)(c1ccc(OC)cc1)c1ccc(OC)cc1])

Bz: benzoyl
ib: isobutyryl
Hunig's Base: i-Pr$_2$NEt (diisopropylethylamine)
AllylOH: allyl alcohol
OAll: —OCH$_2$CHCH$_2$
ACN: acetonitrile
All: —CH$_2$CHCH$_2$
2-NitroBnBr: 2-nitrobenzyl bromideBz: benzoyl
ib: isobutyryl
i-Pr: isopropyl
CE: cyanoethyl (-OCE: 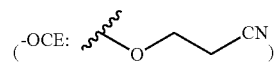 [SMILES: *OCCC#N])

DEAD: diethyl azodicarboxylate
DIAD: diisopropyl azodicarboxylate
DCM: dichloromethane
DDTT: N,N-dimethyl-N'-(3-thioxo-3H-1,2,4-dithiazol-5-yl)formimidamide

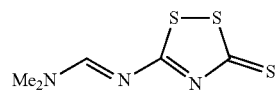

DMOCP: 2-chloro-5,5-dimethyl-1,3,2-dioxaphosphinane 2-oxide

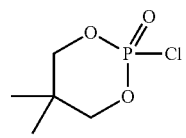

TBS: t-butyldimethylsilyl
3H-benzo[c][1,2]dithiol-3-one:

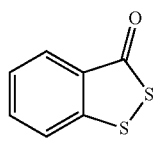

Example 1—Synthesis of Compound 1a

A full scheme of this synthesis is available in FIG. 1.
Step A

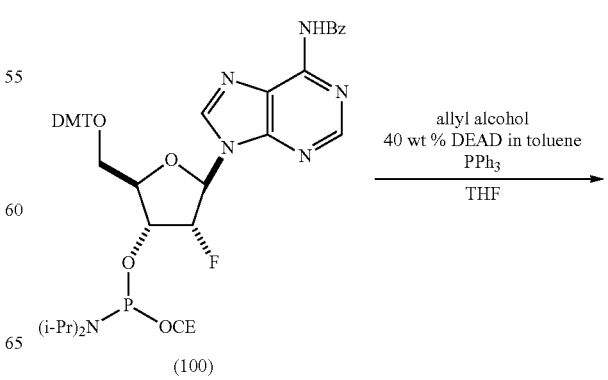
(100)

-continued

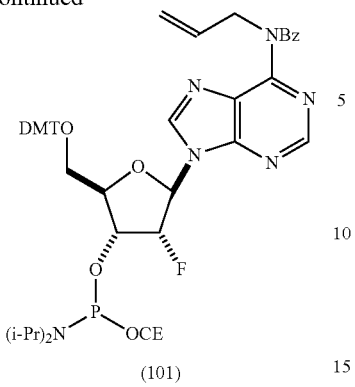

(101)

To a mixture of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (Compound 100) (mixture of phosphorous diastereomers; 80.0 g, 91.332 mmol, 1 eq, ChemGenes Corporation catalog #ANP-9151), allyl alcohol (9.63 ml, 142 mmol, 1.55 eq) and triphenylphosphine (38.3 g, 146 mmol, 1.60 eq) in THF (1.1 L) was added DEAD (40 wt % solution in toluene; 54.2 ml, 137 mmol, 1.5 eq.) at ambient temperature. Stirring was continued at ambient temperature and the reaction was monitored by LC/MS. Upon completion (19 h), the mixture was concentrated in vacuo (35° C.) and resultant mixture was purified by silica gel column chromatography (800 g×2 columns, 40 to 60% EtOAc in n-heptane buffered with 0.5% triethylamine) to give Compound 101 as a white foam (84.2 g, quantitative yield, mixture of phosphorous diastereomers).

$^1$H NMR (3:2 mixture of phosphorous diastereomers, 400 MHz, CDCl$_3$) δ 1.14-1.21 (m, 12H) 2.40 (t, J=6.2 Hz, 1.2H) 2.59 (t, J=6.2 Hz, 0.8H) 3.27 (d, J=8.6 Hz, 1H) 3.52-3.66 (m, 5H) 3.78 (s 2.4H) 3.79 (s 3.6H) 4.28-4.34 (m, 1H) 4.84-4.96 (m, 0.4H) 4.99 (d, J=5.5 Hz, 2H) 4.95-5.10 (m, 0.6H) 5.05 (d, J=10.9 Hz, 1H) 5.22 (br d, J=17.6 Hz, 1H) 5.64 (br d, J=53.2 Hz, 0.6H) 5.70 (br d, J=51.6 Hz, 0.4H) 5.96-6.75 (m, 1H) 6.20 (d, J=16.0 Hz, 0.6H) 6.24 (d, J=17.2 Hz, 0.4H) 6.74-6.79 (m, 4H) 7.02-7.06 (m, 2H) 7.17-7.24 (m, 8H) 7.32-7.34 (m, 2H) 7.41-7.44 (m, 2H) 8.11 (s, 1H) 8.52 (s, 0.4H) 8.54 (s, 0.6H).

Step B

-continued

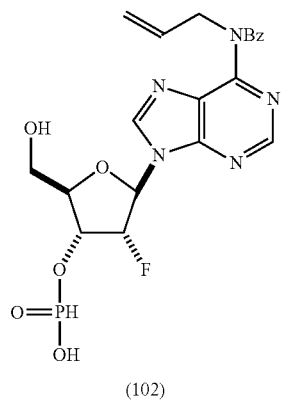

(102)

To a solution of Compound 101 (3.00 g, 3.28 mmol, 1 eq) in acetonitrile (30 ml) was added water (0.118 ml, 6.55 mmol, 2.0 eq) and pyridine trifluoroacetate salt (0.759 g, 3.93 mmol, 1.2 eq). After stirring at ambient temperature for 1 minute, tert-butylamine (14.5 g, 21.0 ml, 0.20 mol, 60 eq) was added. Upon complete cleavage of cyanoethyl group (monitored by LC/MS), the reaction mixture was concentrated in vacuo and azeotroped twice with acetonitrile. The crude mixture was dissolved in DCM (45.0 ml) and treated with water (0.118 ml, 6.55 mmol, 2.0 eq) and NaHSO$_4$—SiO$_2$ (1.18 g, 6.55 mmol, 2 eq) at ambient temperature. Upon complete cleavage of DMT group (monitored by LC/MS, approximately 1 hour), the reaction mixture was filtered and rinsed twice with DCM/MeOH (9/1, 20 ml). The combined filtrates were concentrated in vacuo and treated with 1:1 mixture of n-heptane/toluene (~30 ml). The top layer was removed by decantation. The same operation was repeated once more with n-heptane/toluene (1/1, 30 ml) and the bottom layer was azeotroped twice with acetonitrile to give Compound 102 (100% theoretical yield assumed). The product was used in the next step without further purification.

Step C

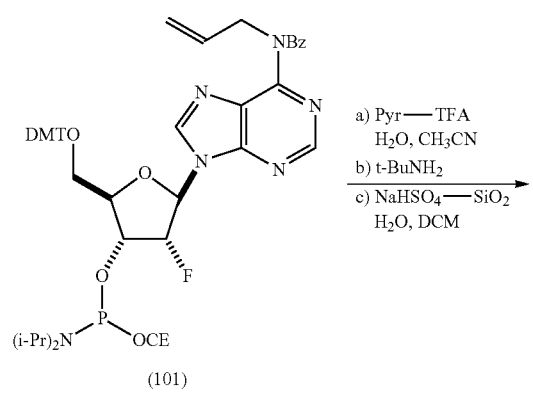

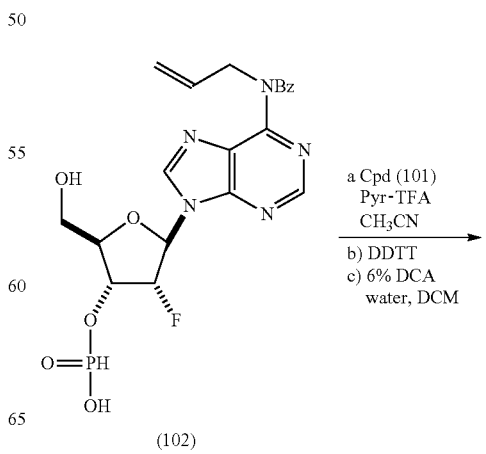

-continued

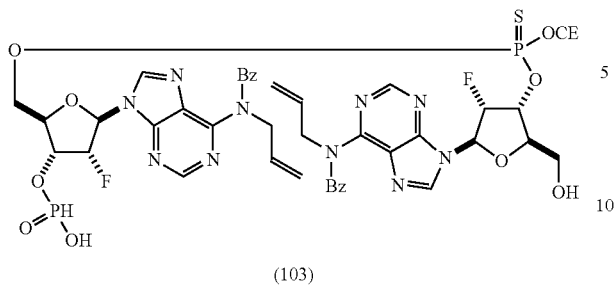

(103)

To a mixture of Compound 102 (1.56 g, 3.27 mmol, 1 eq) and Compound 101 (3.00 g, 3.28 mmol, 1 eq) in acetonitrile (30 ml) was added pyridine trifluoroacetate salt (azeotropically dried with pyridine; 0.760 g, 3.94 mmol, 1.25 eq). After 5 minutes, DDTT (0.840 g, 4.09 mmol, 1.30 eq, ChemGenes Corporation catalog #RN-1588) was added and, upon complete sulfurization (monitored by LC/MS), the reaction mixture was concentrated in vacuo. The residue was dissolved in DCM (30 ml) and treated with water (0.57 ml, 32 mmol, 10 eq) and 6% dichloroacetic acid (1.56 ml, 18.9 mmol, 6.0 eq) in DCM (30 ml). After 20 minutes, the reaction was quenched with pyridine (20 ml) and concentrated in vacuo. The residue was azeotroped with pyridine to give Compound 103 (3.22 g, 100% theoretical yield assumed). The product was used in next the step without further purification.

Step D

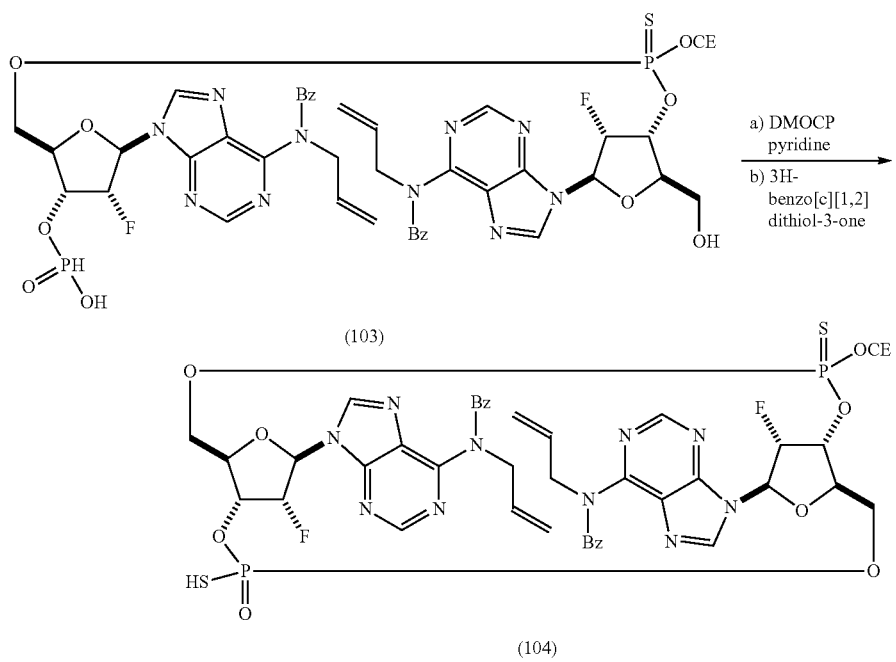

To a solution of Compound 103 (3.22 g, 3.15 mmol, 1 eq) in pyridine (100 ml) was added DMOCP (1.45 g, 7.88 mmol, 2.50 eq) at ambient temperature. Upon complete macrocyclization (monitored by LC/MS), water (1.7 ml, 94.5 mmol, ×10 fold relative to DMOCP) was added followed by 3H-benzo[c][1,2]dithiol-3-one (0.795 g, 4.73 mmol, 1.5 eq). Upon complete sulfurization (approximately 40 minutes), the reaction mixture was partially concentrated in vacuo to approximately 15 ml and poured into a mixture of saturated aqueous NaHCO$_3$ (50 ml) and water (30 ml). After 10 min stirring at ambient temperature, the mixture was extracted with 1:1 mixture of EtOAc/MTBE (60 ml×3 times). The organic layers were combined, washed with brine (25 ml), dried over Mg$_2$SO$_4$ and concentrated in vacuo. The residue was purified by silica gel column chromatography (0-20% MeOH in DCM) to give Compound 104 (3.31 g, 3.20 mmol, 100% theoretical yield assumed) as a brown oil. The product was used in the next step without further purification.

Step E

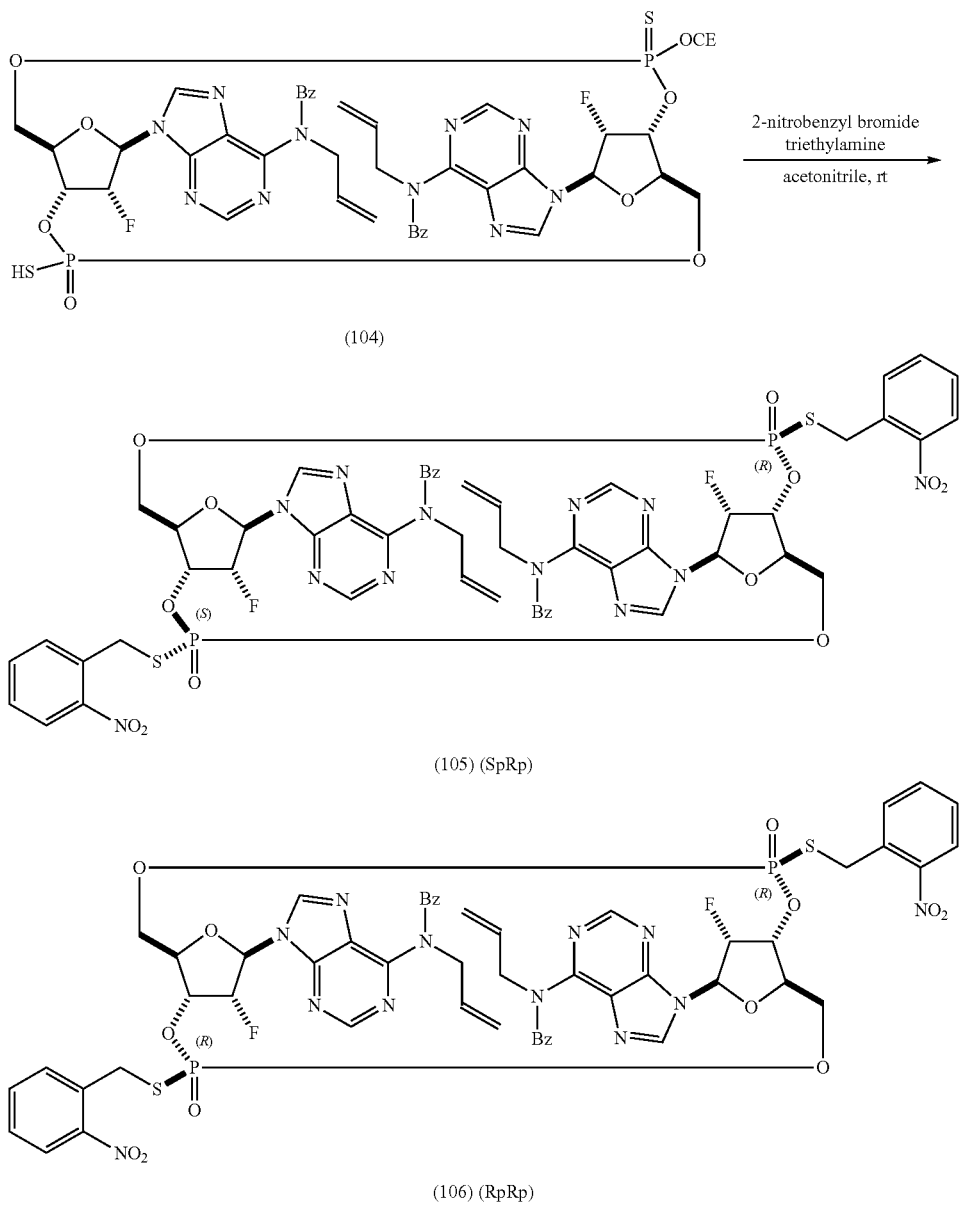

(104)

(105) (SpRp)

(106) (RpRp)

To a solution of Compound 104 (3.31 g, 3.20 mmol, 1 eq) in acetonitrile (66.2 ml) was added 2-nitrobenzyl bromide (2.42 g, 11.2 mmol, 3.50 eq) and triethylamine (1.78 ml, 12.8 mmol, 4.00 eq). Upon complete reaction (monitored by LC/MS, approximately 20 hours at ambient temperature), the reaction mixture was concentrated in vacuo and purified by silica gel column chromatography (60% ethyl acetate/n-heptane to 100% ethyl acetate) to give 0.568 g product as a mixture of phosphorous diastereomers. Preparative HPLC separation of the diastereomers gave Compound 105 (SR isomer; 0.225 g, 0.180 mmol, 5.6% overall yield from Compound 101) and Compound 106 (RR isomer; 0.187 g, 0.149 mmol, 4.7% overall yield from Compound 1).

Compound 105 (SpRp) $^1$H NMR (400 MHz, CDCl$_3$) δ=8.63 (s, 1H), δ=8.61 (s, 1H), 8.04-8.00 (m, 2H), 7.99 (s, 1H), 7.90 (s, 1H), 7.65-7.44 (m, 8H), 7.40-7.31 (m, 4H), 7.25-7.21 (m, 4H), 6.15-5.89 (m, 5H), 5.61 (dd, J=52.0, 5.1 Hz, 1H), 5.55 (ddd, J=51.2, 4.7, 2.7 Hz, 1H) 5.51-5.42 (m, 1H), 5.31-5.22 (m, 2H), 5.11 (dd, J=3.9, 9.8 Hz, 2H), 5.04-4.95 (m, 4H), 4.55-4.37 (m, 7H), 4.29-4.12 (m, 3H)

Compound 106 (RpRp) $^1$H NMR (400 MHz, CDCl$_3$) δ=8.65 (s, 2H), 8.06 (dd, J=1.4, 8.0 Hz, 2H), 7.98 (s, 2H), 7.57-7.52 (m, 6H), 7.47-7.32 (m, 6H), 7.25-7.21 (m, 4H), 6.15 (d, J=18.7 Hz, 2H), 6.09-5.99 (m, 2H), 5.82-5.76 (m, 2H), 5.60 (dd, J=51.8, 4.9 Hz, 2H), 5.27 (dd, J=1.2, 17.2 Hz, 2H), 5.12 (dd, J=1.0, 10.4 Hz, 2H), 5.06-4.96 (m, 4H), 4.55-4.40 (m, 4H), 4.36-4.24 (m, 4H), 4.21-4.02 (m, 2H)

Preparative HPLC Conditions:

| | |
|---|---|
| Instrument | Agilent 1200 |
| HPLC column | Waters Sunfire Prep C18 OBD column, 5 um, 30 × 250 mm, #186003969 |

| | | | | | | |
|---|---|---|---|---|---|---|
| Flow rate | | 50 ml/min | | | | |
| mobile phase | | A: water, B: acetonitrile | | | | |
| Gradient | Time (min) | 0 | 8 | 9.9 | 10 | 12 |
| | B % | 50 | 99 | 99 | 50 | 50 |
| Run time | | 12 min | | | | |
| Injection volume | | 150 ul (0.08 g/ml in acetonitrile) | | | | |
| detection | | UV 254 nm | | | | |
| Retention time | Compound 105 (SpRp) | 7.7 min | | | | |
| | Compound 106 (RpRp) | 8.0 min | | | | |

Step F

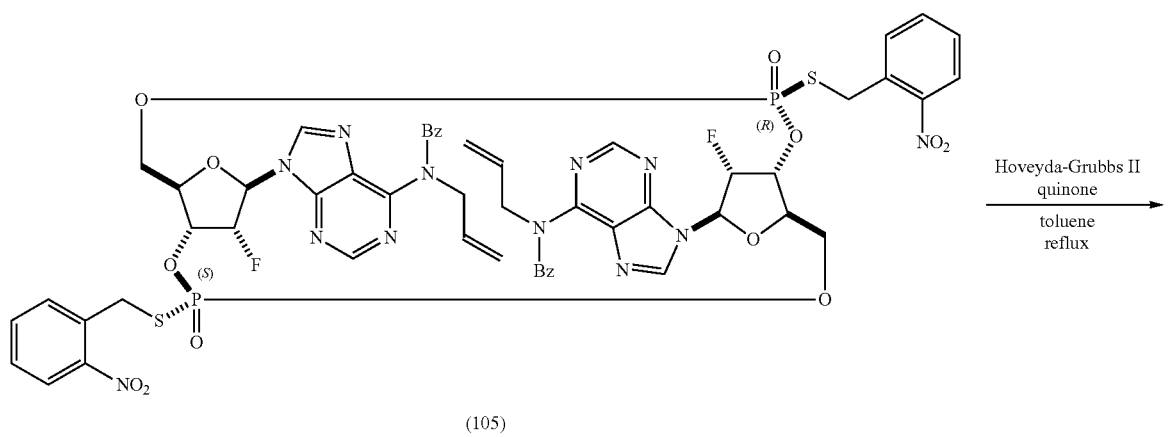

(105)

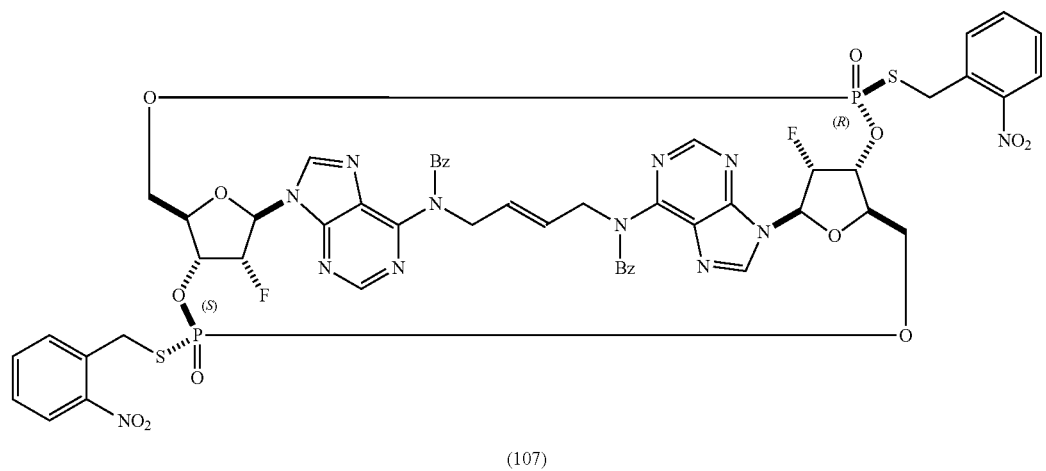

(107)

To a heated (90° C.) solution of Compound 105 (519 mg, 0.414 mmol, 1 eq) in toluene (519 ml) was added Hoveyda-Grubbs Catalyst™ 2nd generation ((1,3-Bis-(2,4,6-trimethylphenyl)-2-imidazolidinylidene)dichloro(o-isopropoxyphenylmethylene)ruthenium; available at SIGMA-ALDRITCH® Catalog No. 569755; CAS 301224-40-8; 91 mg, 0.15 mmol, 0.35 eq) and quinone (0.102 ml, 1.243 mmol, 3.0 eq). The mixture was heated to reflux and reaction progress was monitored by LC/MS. After 3 hours an additional catalyst was added (91 mg, 0.15 mmol, 0.35 eq) and the reaction was continued for additional 3 hours. After cooling down, the mixture was treated with DMSO (0.59 ml, 8.3 mmol, 20 eq) at ambient temperature for 15 hours, concentrated in vacuo and purified by silica gel column chromatography (SiO$_2$ 25 g, 66% ethyl acetate in n-heptane to 100% ethyl acetate) to give Compound 107 (200 mg, 0.163 mmol, 39% yield) as a brown dry foam.

$^1$H NMR (400 MHz, CDCl$_3$) δ=8.19 (s, 1H), 8.12 (dd, J=7.8 Hz, 1.9 Hz, 1H), 8.10 (s, 1H), 8.02 (d, J=8.2 Hz, 1H), 7.89 (s, 1H), 7.63 (br d, J=7.0 Hz, 1H), 7.53-7.41 (m, 10H), 7.35-7.30 (m, 2H), 7.25-7.20 (m, 4H), 6.23 (d, J=17.6 Hz, 1H), 6.14 (d, J=18.8 Hz, 1H), 5.86-5.75 (m, 1H), 5.75 (dt, J=15.3, 5.0 Hz, 1H), 5.67 (dt, J=15.3, 4.7 Hz, 1H), 5.60 (dd, J=52.0, 3.9 Hz, 1H), 5.48 (dd, J=50.4, 3.9 Hz, 1H) 5.50-5.39 (m, 1H), 4.91-4.64 (m, 4H), 4.57-4.25 (m, 9H), 4.15 (d, J=7.03 Hz, 1H), 4.11 (d, J=7.03 Hz, 1H).

Step G

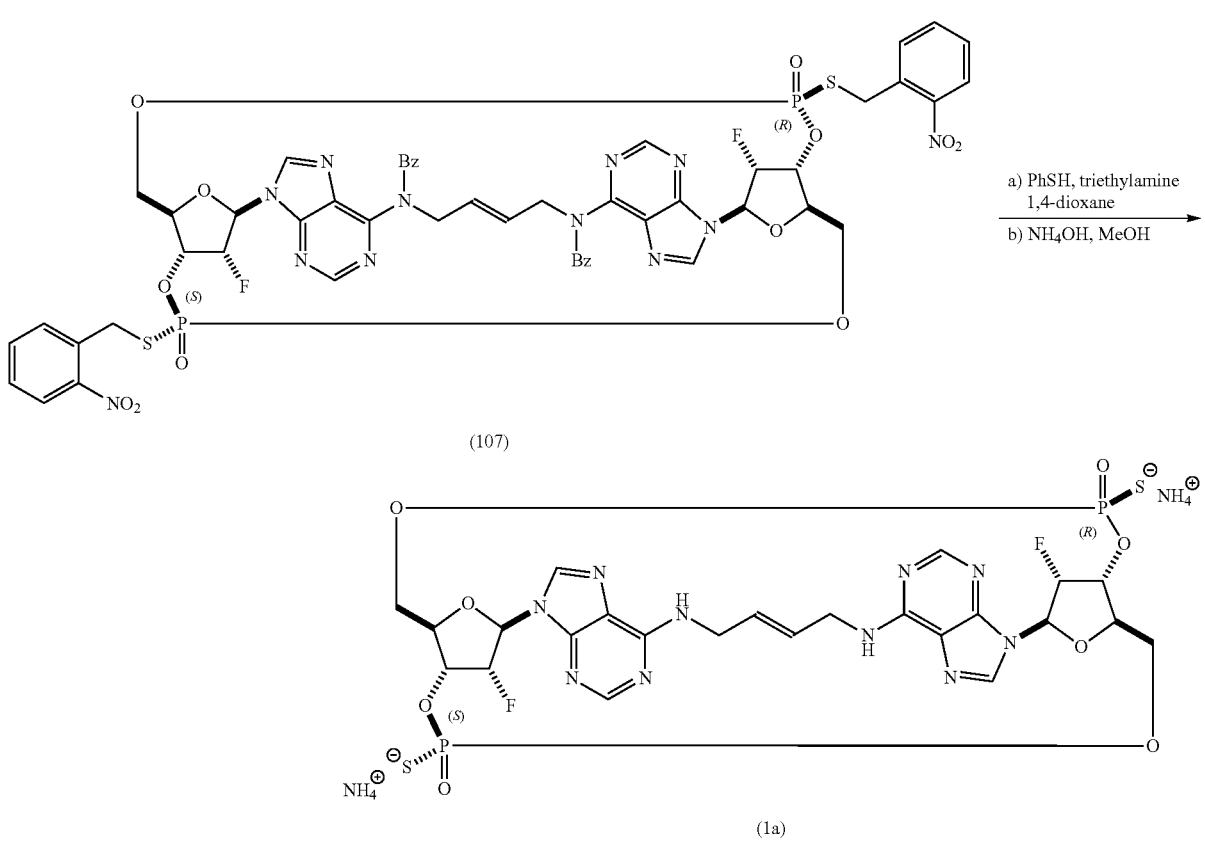

To a solution of Compound 107 (88 mg, 0.072 mmol, 1 eq) in 1,4-dioxane (1.76 ml) was added thiophenol (0.88 mL, 8.55 mmol, 119 eq) and triethylamine (0.88 mL, 6.31 mmol, 88 eq). The resulting mixture was stirred at ambient temperature. Upon complete reaction (monitored by LC/MS, 13 hours), methanol (5.28 ml) and 28% ammonium hydroxide (3.52 ml) were added and resultant mixture was heated to 50° C. Upon complete reaction (monitored by LC/MS, 5 hours), the mixture was cooled to ambient temperature and the resultant brownish slurry was filtered and rinsed with water (15 ml). The filtrate was filtered again to remove additional solids. The final filtrate was extracted twice with a 1:1 mixture of toluene and heptane (30 ml). The aqueous layer was concentrated in vacuo and then re-suspended in water (6 ml). The resulting solid was filtered off and the filtrate was subjected to preparative HPLC to give Compound 1 diammonium salt (also referred to as Compound 1a) (39 mg, 0.050 mmol, 70% yield) as a white solid.

Compound 1a (SpRp, trans) $^1$H NMR (400 MHz, CD$_3$OD) δ=9.05 (s, 1H), 8.33 (s, 1H), 8.25 (s, 1H), 8.12 (s, 1H), 6.34 (br s, 2H), 5.88 (br s, 2H), 5.66 (br d, J=51.6 Hz, 1H), 5.59 (br d, J=52.2 Hz, 1H) 5.01 (br s, 2H), 4.68-4.34 (m, 6H), 4.07-3.82 (m, 2H), 3.79-3.55 (m, 2H); $^{31}$P NMR (162 MHz, CD$_3$OD) δ=55.48 (s, 1P), 55.16 (s, 1P).

Compound 1a Preparative HPLC Conditions:

| Instrument | Agilent 1200/1260 AS/FC |
|---|---|
| HPLC column | Waters XBridge C18, 10 × 100 mm # 1413 |

-continued

| Flow rate | 3.0 ml/min |
|---|---|
| Column temperature | 35° C. |
| mobile phase | A: 0.1% NH$_4$OH in water, B: 0.1% NH$_4$OH in acetonitrile |
| Gradient (B %) | 0 → 5 |
| Run time | 20 min |
| Injection volume | 50 ul (4 mg/ml in water) |
| detection | UV 260 nm |
| Retention times | 6.5 min |

Example 1.1—Alternative Synthesis for Compound 1a

Figure 2A:
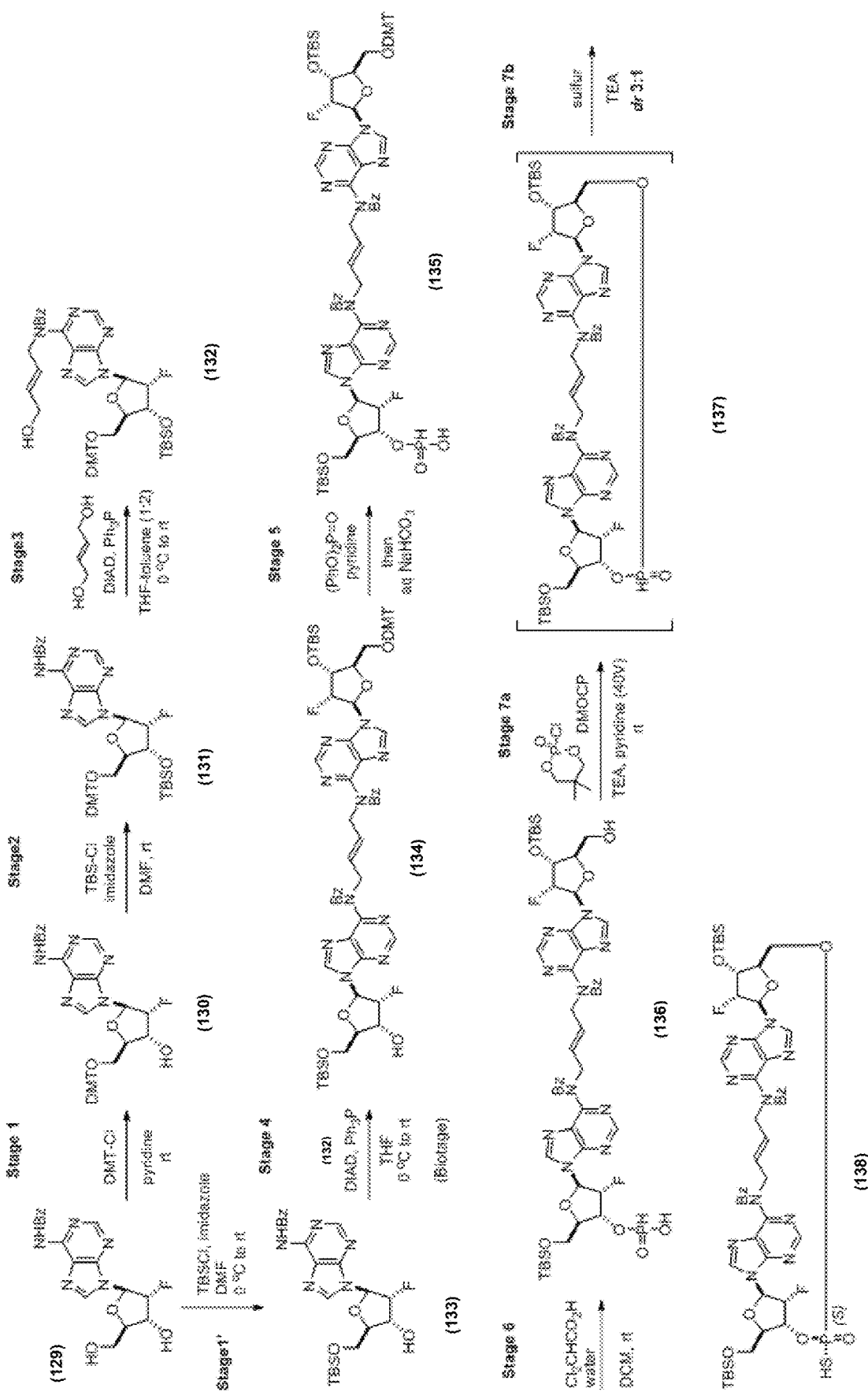
FIG. 2A and FIG. 2B show an alternate synthesis of Compound 1 and Compound 1a. That alternate synthesis is also shown in FIG. 2C through FIG. 2E.

An alternative synthetic route for Compound 1a is set out in FIG. 2A and FIG. 2B, as well as in FIG. 2C and reported below.

Stage 1

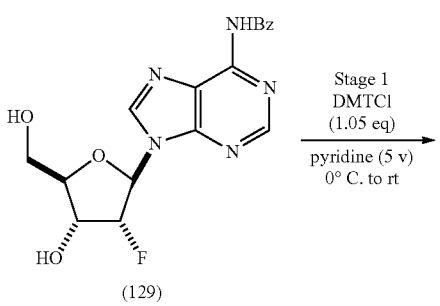

-continued

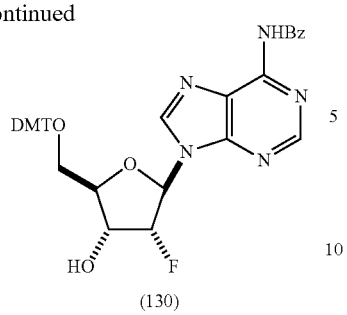

(130)

-continued

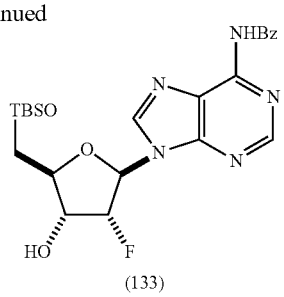

(133)

Compound 129 (570 g, 1.53 mol, 1 wt, 1 vol, 1 eq) was dissolved in pyridine (2.85 L, 35.2 mol, 4.89 wt, 5.0 vols, 23 eq). The mixture was cooled to 2.6° C. and treated with 4,4'-dimethoxytrityl chloride (DMTCl; 543 g, 1.60 mol, 0.953 wt, 1.05 eq). The mixture was stirred at 0 to 5° C. for 2 h and then allowed to warm to ambient temperature. The reaction was monitored by LC/MS and complete conversion was confirmed after overnight stirring. The reaction mixture was cooled to below 5° C. and quenched by treatment with MeOH (124 ml, 3.05 mol, 0.172 wt, 0.217 vol, 2.0 eq) for 15 minutes. The mixture was co-evaporated with toluene (2.00 L, 3.04 wt, 3.51 vol) under vacuum and then diluted with a mixture of EtOAc (2.850 L, 4.5 wt, 5.0 vol) and n-heptane (2.85 L, 3.42 wt, 5.0 vol). The organic layer was washed with saturated NaHCO$_3$ (9 wt % solution in water; 2.0 L, 3.5 vol). An additional EtOAc (2.85 L, 4.5 wt, 5.0 vol) was added to completely dissolve the crude product. After stirred for 5 minutes, the two layers were separated. The organic layer was washed with water (2.0 L, 3.5 wt, 3.5 vol). Solid began slowly precipitating out of the organic layer. The water layer was separated. The organic layer was then concentrated to approx. 1 vol. The crude product was slurried with a mixture of n-heptane (2.00 L, 2.40 wt, 3.51 vol) and toluene (0.50 L, 0.76 wt, 0.88 vol). After stirring for 15 minutes, the pale yellow solid was collected by vacuum filtration. The filter cake was sequentially rinsed with: (1) a mixture of n-heptane (0.60 L, 0.72 wt, 1.05 vol) and toluene (0.30 L, 0.46 wt, 0.53 vol), and then (2) n-heptane (3.00 L, 3.6 wt, 5.26 vol). The solid was dried with no heat for 30 minutes and then transferred to trays for drying at 50° C. in a vacuum oven overnight to give Compound 130 as pale yellow solid (996.7 g, 1.47 mol, 1.75 wt, 97% yield).

$^1$H NMR (400 MHz, CHLOROFORM-d) δ=8.99 (s, 1H), 8.76 (s, 1H), 8.21 (s, 1H), 8.04-8.00 (m, 2H), 7.64-7.59 (m, 1H), 7.57-7.50 (m, 2H), 7.41-7.36 (m, 2H), 7.32-7.15 (m, 7H), 6.83-6.76 (m, 4H), 6.31 (dd, J=2.5, 17.0 Hz, 1H), 5.68 (ddd, J=2.3, 4.7, 52.7 Hz, 1H), 4.88-4.77 (m, 1H), 4.26-4.21 (m, 1H), 3.77 (s, 6H), 3.57 (dd, J=3.1, 10.9 Hz, 1H), 3.43 (dd, J=4.1, 10.7 Hz, 1H), 2.60 (br s, 1H)

Stage 1'

Compound 129 (430 g, 1.15 mol, 1 wt, 1 vol, 1 eq) and imidazole (118 g, 1.73 mol, 0.274 wt, 1.50 eq) were dissolved in DMF (1.72 L, 3.78 wt, 4.0 vol) and the resultant mixture was cooled to 5° C. TBS-Cl (191 g, 1.27 mol, 0.444 wt, 1.10 eq) was added. The mixture was stirred at 0 to 11° C. for 2 h, allowed to slowly warm to ambient temperature (progress monitored by LCMS). The reaction was complete 6 h after TBS-Cl addition, yet allowed to stir at ambient temperature for an additional 20 h. The mixture was cooled to 2° C. and treated with methanol (93 ml, 74 g, 2.3 mol, 0.17 wt, 0.22 wt, 2.0 eq) for 10 minutes. The reaction mixture was diluted with a mixture of MTBE (1.72 L, 1.23 kg, 2.96 wt, 4.0 vol) and EtOAc (1.72 L, 1.55 kg, 3.60 wt, 4.0 vol) followed by saturated NH$_4$Cl (28 wt % solution in water; 2.15 L, 5.0 vol). Solids began slowly falling out of solution. The mixture was allowed to warm to 24° C. and water (1.08 L, 1.08 kg, 2.5 wt, 2.5 vol) was added to the (T-internal=22° C.). More solids began precipitating out of the mixture. An additional water (1.08 L, 1.08 kg, 2.5 wt, 2.5 vol) and MTBE (1.40 L, 1.04 kg, 2.4 wt, 3.3 vol) were added to the mixture. The off-white solid was collected by vacuum filtration. The reactor was rinsed with water (320 ml, 0.74 vol) and then MTBE (1.80 L, 1.33 kg, 3.10 wt, 4.19 vol) to transfer any remaining solid to the filter. The filter cake was rinsed sequentially with: (1) water (1.80 L, 1.80 kg, 4.2 wt, 4.2 vol). (2) water (1.80 L, 1.80 kg, 4.2 wt, 4.2 vol), (3) a mixture of MTBE (0.90 L, 0.67 kg, 1.5 wt, 2.1 vol) and n-heptane (0.90 L, 0.62 kg, 1.4 wt, 2.1 vol), (4) a mixture of MTBE (0.90 L, 0.67 kg, 1.5 wt, 2.1 vol) and n-heptane (0.90 L, 0.62 kg, 1.4 wt, 2.1 vol). The recovered solid was dried under vacuum at 40° C. over 2 days to give Compound 133 as white solid (483 g, 0.991 mol, 1.12 wt, 86% yield).

$^1$H NMR (400 MHz, CHLOROFORM-d) δ=8.97 (s, 1H), 8.82 (s, 1H), 8.36 (s, 1H), 8.04-8.00 (m, 2H), 7.64-7.58 (m, 1H), 7.56-7.51 (m, 2H), 6.40 (dd, J=2.3, 16.0 Hz, 1H), 5.45 (ddd, J=2.7, 4.3, 53.1 Hz, 1H), 4.75-4.66 (m, 1H), 4.22-4.17 (m, 1H), 4.07 (dd, J=2.3, 11.7 Hz, 1H), 3.91 (dd, J=2.7, 11.7 Hz, 1H), 2.38 (dd, J=2.7, 7.0 Hz, 1H), 0.92 (s, 9H), 0.11 (s, 3H), 0.11 (s, 3H).

Stage 2

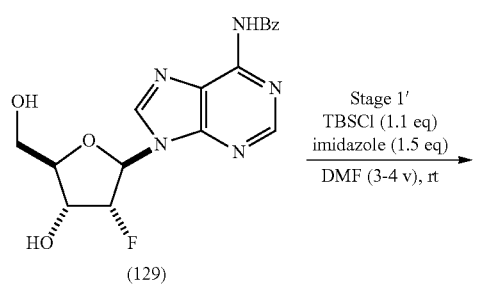

(129)

Stage 1'
TBSCl (1.1 eq)
imidazole (1.5 eq)
⟶
DMF (3-4 v), rt

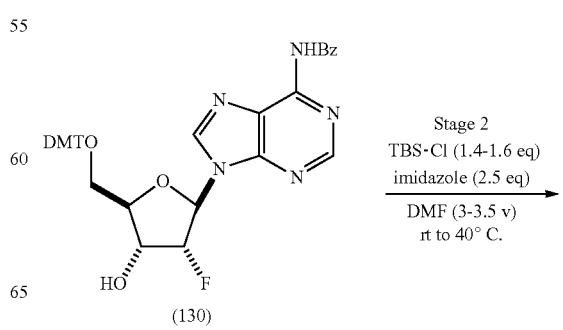

(130)

Stage 2
TBS-Cl (1.4-1.6 eq)
imidazole (2.5 eq)
⟶
DMF (3-3.5 v)
rt to 40° C.

-continued

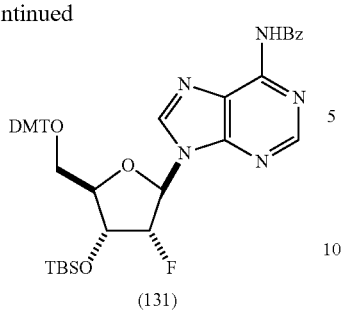

(131)

-continued

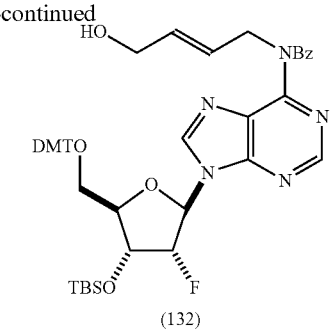

(132)

Compound 130 (993 g, 1.47 mol, 1 wt, 1 vol, 1 eq) and imidazole (150 g, 2.20 mol, 0.151 wt, 1.5 eq) were dissolved in DMF (3.48 L, 3.28 kg, 3.3 wt, 3.5 vol) and the mixture was cooled to 5° C. TBS-Cl (244 g, 1.62 mol, 0.245 wt, 1.10 eq) was added. The reaction was stirred at 0 to 5° C. for 2 h, allowed to slowly warm to ambient temperature and monitored by LCMS. After 17 h, an additional imidazole (100 g, 1.47 mol, 0.10 wt, 1.0 eq) and TBS-Cl (111 g, 735 mmol, 0.112 wt, 0.50 eq) were added and stirring was continued at ambient temperature for 2 h and at 35° C. for 2 h. The resulting mixture was cooled to 13.6° C. and treated with MeOH (119 ml, 2.94 mol, 2 eq) for 10 minutes. In a separate reactor was added ice (5 kg, 5 wt) and saturated NH$_4$Cl (28 wt % solution in water; 5.0 L, 5 vol). The reaction mixture was added to the ice/NH$_4$Cl mixture. An off white solid began precipitating out of solution immediately. An additional 2 kg of ice (2 kg, 2 wt) and water (3.0 L, 3 vol) were added to the mixture. The reaction flask was rinsed with water (0.50 L, 0.5 vol) and the rinsate was added to the mixture. n-heptane (2.00 L, 2 vol) was added to the mixture and stirring was continued for 10 minutes. The off white solid was collected by vacuum filtration. The filter cake was rinsed with: (1) water (4.0 L, 4.0 vol), (2) water (4.0 L, 4.0 vol), (3) n-heptane (4.0 L, 4.0 vol), (4) n-heptane (4.0 L, 4.0 vol). The recovered solid was dried under vacuum at 45° C. for 4 days to give Compound 131 as off-white solid (1.095 kg, 1.39 mol, 1.10 wt, 94% yield).

$^1$H NMR (400 MHz, CHLOROFORM-d) δ=9.09 (s, 1H), 8.78 (s, 1H), 8.28 (s, 1H), 8.02 (d, J=7.4 Hz, 2H), 7.63-7.59 (m, 1H), 7.55-7.50 (m, 2H), 7.37 (d, J=7.1 Hz, 2H), 7.29-7.17 (m, 7H), 6.79 (d, J=7.9 Hz, 4H), 6.29 (dd, J=2.9, 16.2 Hz, 1H), 5.60 (ddd, J=2.7, 3.9, 53.1 Hz, 1H), 4.78 (ddd, J=4.7, 6.4, 15.8 Hz, 1H), 4.26-4.22 (m, 1H), 3.77 (s, 6H), 3.58 (dd, J=3.1, 10.9 Hz, 1H), 3.26 (dd, J=3.7, 10.7 Hz, 1H), 0.85 (s, 9H), 0.10 (s, 3H), 0.02 (s, 3H)

Stage 3

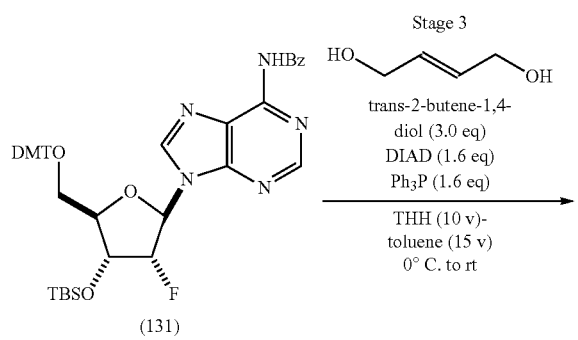

Compound 131 (1000 g, 1.27 mol, 1 wt, 1 vol, 1 eq) and trans-2-butene-1,4-diol (olefin geometry confirmed by $^1$H-NMR; 335 g, 3.80 mol. 0.335 wt, 3.0 eq) were azeotroped twice with THF (3.0 L, 3.0 vol). The residue was dissolved in a mixture of THF (10 L, 10 vol) and toluene (15 L, 15 vol). Triphenylphosphine (432 g, 1.65 mol, 0.432 wt, 1.3 eq) was added and then the reaction mixture was cooled to −5° C. DIAD (0.320 L, 1.65 mol, 333 g, 0.333 wt, 0.320 vol, 1.3 eq) was added slowly over 20 minutes while keeping T-internal below 5° C. The reaction was stirred at 0-5° C. for 1 h and monitored by LCMS. The ice bath was removed and the mixture was allowed to warm up to rt. After overnight stirring (17 h), an triphenylphosphine (83 g, 0.32 mol, 0.083 wt, 0.25 eq) and DIAD (62 ml, 0.32 mol, 64 g, 0.064 wt, 0.062 vol, 0.25 eq) were added. After additional 1 h at rt, the reaction mixture was diluted with MTBE (10 L, 10 vol), washed twice with half-saturated NaCl (18 wt % solution in water; 2×4 L) and concentrated in vacuo to a thick oil. The mixture was re-dissolved in a mixture of MTBE (4.00 L, 4 vol) and n-heptane (0.50 L, 0.5 vol) and then cooled to 0° C. A seed crystal of triphenylphosphine oxide was added to the solution. Solids slowly began precipitating out of solution and was stirred overnight. The white solid was collected by vacuum filtration and rinsed with MTBE (2 L, 2 vol) to isolate 540 g of triphenylphosphine oxide. The filtrate was concentrated and purified via Biotage 150 L KP-Sil (SiO$_2$ 5 kg; pretreated with 1% TEA in Hep/etOAc; eluents: heptane/EtOAc (48 L of 33% EtOAc with 1% TEA, 24 L of 50% EtOAc with 1% TEA, 24 L of 66% EtOAc with 1% TEA)→100% EtOAc with 1% TEA). The column was monitored by TLC (2:1 EtOAc/n-heptane). The clean product fractions were combined and concentrated under vacuum to give Compound 132 as pale white foam solid (634 g, contained 14 wt % DIAD derived co-product, net 545 g, 0.63 mol, 50% adjusted yield). The mixture fractions were combined and concentrated under vacuum to give pale yellow foam solid (750 g), which was subjected to repurification via Biotage 150M HP-Sphere (2.5 kg SiO$_2$; pretreated with 1% TEA in Hep/EtOAc; loaded sample with toluene eluents: Hep/EtOAc/1% TEA (12 L of 50% EtOAc with 1% TEA, 16 L 66% EtOAc with 1% TEA)→EtOAc with 1% TEA). The column was monitored by TLC (2/1/0.03 EtOAc/n-hep/TEA). The clean product fractions were combined and concentrated under vacuum to give additional Compound 132 as pale white foam solid (206 g, 0.24 mol, 18% yield).

$^1$H NMR (400 MHz, CHLOROFORM-d) δ=8.58 (s, 1H), 8.10 (s, 1H), 7.43-7.37 (m, 2H), 7.32-7.28 (m, 2H), 7.24-7.15 (m, 8H), 7.03-6.98 (m, 2H), 6.78-6.73 (m, 4H), 6.18 (dd, J=2.7, 17.2 Hz, 1H), 5.88 (td, J=5.5, 15.6 Hz, 1H), 5.77 (td, J=5.1, 15.6 Hz, 1H), 5.60 (ddd, J=2.7, 4.3, 53.1 Hz, 1H), 5.03-4.96 (m, 2H), 4.91 (ddd, J=4.5, 6.6, 16.6 Hz, 1H), 4.18-4.14 (m, 1H), 3.88-3.82 (m, 2H), 3.78 (s, 6H), 3.52 (dd, J=2.7, 10.9 Hz, 1H), 3.14 (dd, J=3.5, 10.9 Hz, 1H), 0.85 (s, 9H), 0.10 (s, 3H), 0.01 (s, 3H).

Stage 4

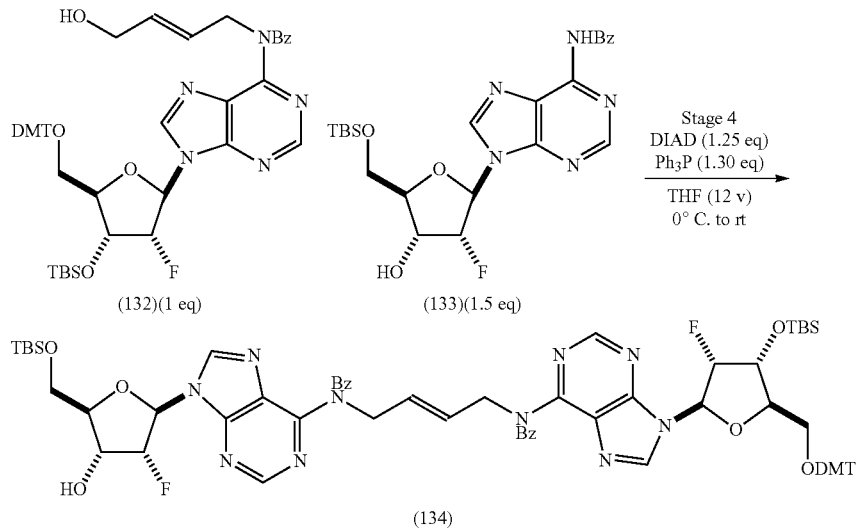

Compound 132 (800 g, 0.930 mol, 1 wt, 1 vol, 1 eq) and Compound 133 (522 g, 1.07 mol, 0.652 wt, 1.15 eq) were azeotropically dried with THF (2×3 L, 2×3.8 vol) and re-dissolved in THF (9.60 L, 8.45 kg, 12.0 vol) at rt. Triphenylphosphine (317 g, 1.21 mol, 0.396 wt, 1.30 eq) was added and the mixture was cooled below −5° C. DIAD (226 ml, 1.16 mol, 235 g, 0.294 wt, 0.283 vol, 1.25 eq) was added T-internal below 7° C. The reaction was allowed to warm to rt slowly. The reaction was monitored by LCMS. After 21 h, the reaction mixture was concentrated in vacuo to a thick oil, azeotroped with n-heptane (2.00, 1.37 kg, 1.71 wt, 2.50 vol) and then re-dissolved in a mixture of MTBE (2.40 L, 1.78 kg, 2.2 wt, 3.0 vol) and n-heptane (800 ml, 547 g, 0.68 wt, 1.0 vol). The solution was seeded with triphenylphosphine oxide and cooled to 5° C., diluted with n-heptane (400 ml, 274 g, 0.34 wt, 0.50 vol) and stirred at 5° C. for 30 minutes. The white solid precipitate was collected by vacuum filtration and rinsed with with 2:1 (v/v) mixture of MTBE and n-Heptane (1.8 L) to give triphenylphosohine oxide (455 g). The filtrate was concentrated under vacuum and purified via Biotage 150 L KP-Sil (SiO$_2$ 5 kg; pretreated wit 1% TEA; loaded sample by dissolving in toluene eluents: 9:1 heptane/EtOAc (16 L) and 15 TEA, 3.6:1 (46 L), 2:1 (20 L) and 1% TEA, 1:1 (30 L) and 1% TEA, and 100% EtOAc (16 L) and 1% TEA). The combined clean product fractions were concentrated under vacuum to give Compound 134 as off white solid foam (662.2 g). The mixture fractions were combined and concentrated under vacuum (480 g). A white insoluble solid formed by dilution with toluene (300 ml) prior to loading on Biotage 150 L was removed by vacuum filtration. The material soluble in toluene was purified via Biotage 150M HP-Sphere (SiO$_2$ 2.5 kg (pretreated wit 1% TEA); sample loading with toluene; eluents: 2:1 heptane/EtOAc (26 L) w/ 1% TEA, 1:1 (25 L) w/ 1% TEA, 1:4 (34 L) w/ 1% TEA). The column was monitored by TLC (1:1 heptane/EtOAc). The combined clean product fractions were concentrated under vacuum to give additional Compound 134 as off white solid foam (165.5 g. Total 662.2+165.5 g=827.7 g, 930 mmol, 1.03 wt, 67% yield).

$^1$H NMR (400 MHz, CHLOROFORM-d) δ=8.47 (s, 1H), 8.39 (s, 1H), 8.20 (s, 1H), 8.01 (s, 1H), 7.38-7.31 (m, 5H), 7.27-7.19 (m, 6H), 7.14-7.06 (m, 3H), 6.93-6.87 (m, 2H), 6.76 (d, J=8.6 Hz, 4H), 6.26 (dd, J=2.0, 16.0 Hz, 1H), 6.15 (dd, J=2.7, 17.2 Hz, 1H), 5.86 (dd, J=4.7, 15.2 Hz, 1H), 5.80 (dd, J=4.7, 15.2 Hz, 1H), 5.51 (ddd, J=2.7, 4.3, 52.8 Hz, 1H), 5.31 (ddd, J=2.0, 4.3, 52.8 Hz, 1H), 4.87 (d, J=4.7 Hz, 2H), 4.85-4.81 (m, 1H), 4.79 (d, J=4.3 Hz, 2H), 4.71-4.59 (m, 1H), 4.20-4.13 (m, 2H), 4.06 (dd, J=2.7, 11.3 Hz, 1H), 3.90 (dd, J=2.7, 11.7 Hz, 1H), 3.77 (s, 6H), 3.52 (dd, J=3.1, 10.9 Hz, 1H), 3.18 (dd, J=3.9, 10.9 Hz, 1H), 0.92 (s, 9H), 0.84 (s, 9H), 0.10 (s, 3H), 0.09 (s, 6H), 0.07 (s, 3H)

Stage 5-6

-continued

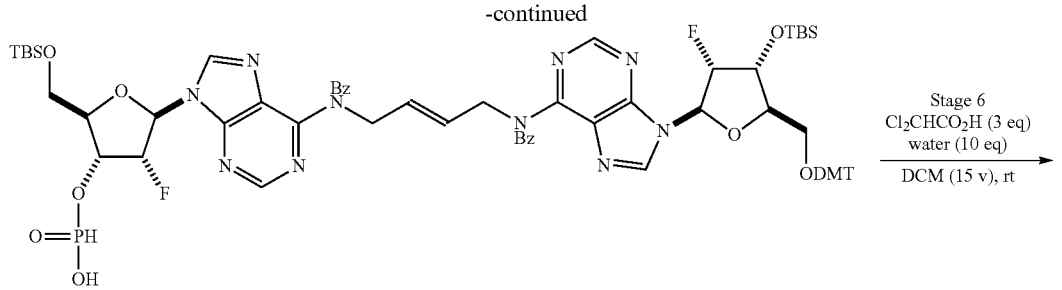

(135)

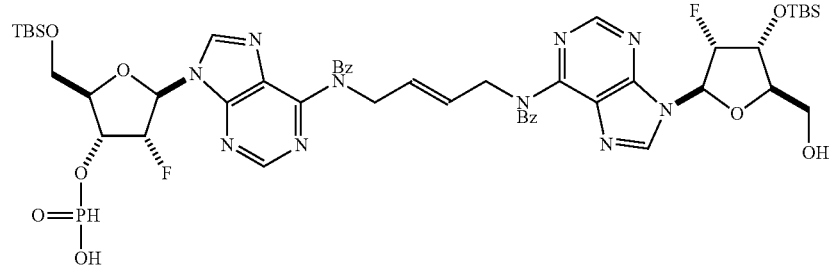

(136)

To a solution of Compound 134 (410.7 g, 309 mmol, 1 wt, 1 vol, 1 eq) in pyridine (1.23 L, 1.21 kg, 15.2 mol, 2.9 wt, 3.0 vol, 49 eq) was added diphenyl phosphite (90 ml, 109 g, 0.46 mol, 0.26 wt, 0.22 vol, 1.5 eq). The reaction was stirred at rt and was monitored by LCMS. After 2 h (80% conversion) an additional diphenyl phosphite (29.9 ml, 36.2 g, 155 mmol, 0.088 wt, 0.073 vol, 0.50 eq) was added. After an additional 1 h an extra diphenyl phosphite (6.0 ml, 7.2 g, 31 mmol, 0.018 wt, 0.015 vol, 0.10 eq) was added and the reaction was continued for an additional 0.5 h (98% conversion). The reaction mixture was added to a mixture of saturated NaHCO$_3$ (9 wt % solution in water; 2.1 L, 5 vol) and water (1.0 L ml, 2.5 vol) while keeping T-internal 4.7 to 12° C. The reactor was rinsed with a small volume of EtOAc. Stirring was continued at rt for 30 minutes and monitored the reaction by LCMS (100% conversion). The reaction mixture was extracted twice with 1:1 mixture of EtOAc and MTBE (2×8.2 L, 2×20 vol). The combined organic layers were washed with water (4.1 L, 10 vol), concentrated in vacuo and azeotroped with toluene (3×4.1 L, 3×10 vol; continuous feeding) for removal of pyridine to give Compound 135 (0.55 eq pyridine remained).

Stage 6—

The crude Compound 135 was dissolved in dichloromethane (3.08 L, 4.07 kg, 9.9 wt, 7.5 vol) at ambient temperature. Water (55.7 ml, 0.136 vol, 10 eq) was added followed by a solution of dichloroacetic acid (77 ml, 120 g, 0.93 mol, 0.29 wt, 0.19 vol, 3.0 eq) in DCM (3.08 L, 7.5 vol) while keeping the internal T below 25° C. (Turned into an orange solution). After 30 min, triethylsilane (Et$_3$SiH; 494 ml, 359 g, 3.09 mol, 0.875 wt, 1.20 vol, 10.0 eq) (T-internal went from 18.2° C. to 17° C.) was added and stirring was continued for 20 min. Triethylamine (431 ml, 313 g, 3.09 mol, 0.762 wt, 1.05 vol, 10.0 eq) was added (T-internal went from 17.8° C. to 22° C.). The mixture was concentrated to 1.55 kg (3.8 wt), redissolved in EtOAc (6.2 L, 5.5 kg, 14 wt, 15 vol), sequentially washed with: (1) water (1.0 L, 2.5 vol) and saturated NaHCO$_3$ (9 wt % solution in water, 0.82 L, 2.0 vol). The crude product EtOAc solution was stored at −20° C. over night.; 0.82 L, 2.0 vol) and in next day, the solution was concentrated in vacuo at 25° C. The crude mixture thus obtained (654 g) was triturated with: (1) n-heptane (3.01 L, 7.5 vol), (2) a mixture of n-heptane (2.46 L, 6.0 vol) and toluene (0.82 L, 2.0 vol). The solution part (supernatant) was decanted off and the solid remained at the bottom was dissolved in acetonitrile (4.1 L, 10 vol). The mixture was concentrated in vacuo at 25° C. and azeotroped with acetonitrile twice to give Compound 136. The product was used for the subsequent stage without purification (theoretical 100% yield assumed).

Stage 7

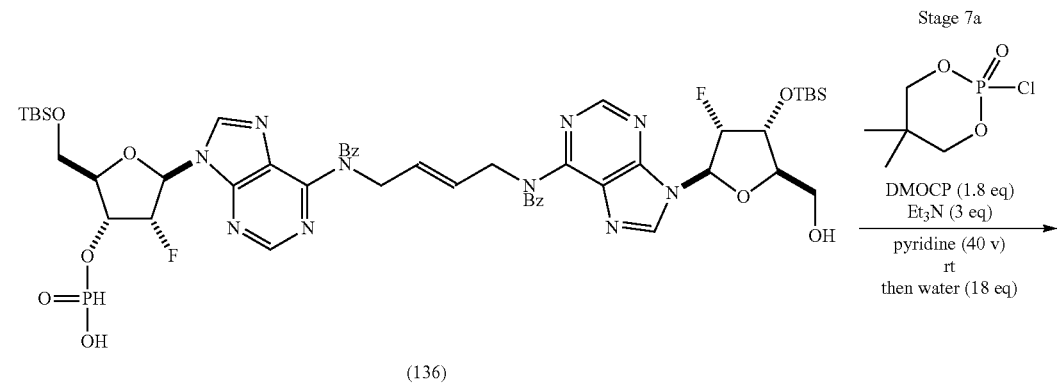

(136)

-continued

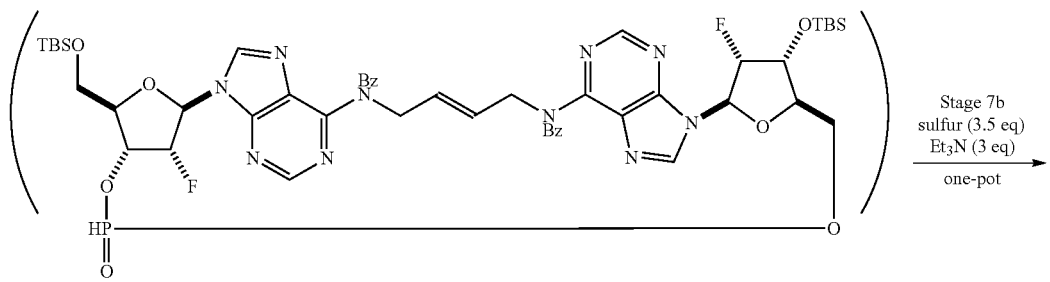

(137)
dr 3-4:1

Stage 7b
sulfur (3.5 eq)
Et₃N (3 eq)
―――――――→
one-pot

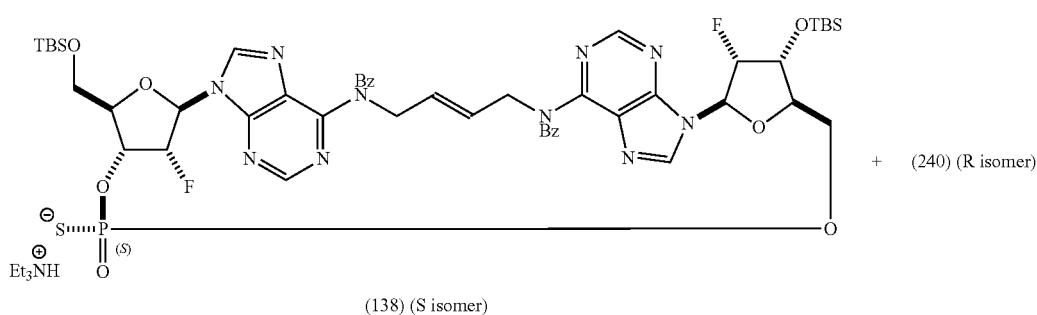

(138) (S isomer)

+ (240) (R isomer)

Stage 7a

Compound 136 (337 g, 309 mmol, 1 wt, 1 vol, 1 eq) was dissolved in in anhydrous pyridine (13.5 L, 13.2 kg, 39 wt, 40 vol) at rt. Triethylamine (129 ml, 927 mmol, 94 g, 0.28 wt, 0.38 vol, 3.0 eq) was added followed by 2-chloro-5,5-dimethyl-1,3,2-dioxaphosphinane 2-oxide (DMOCP; 103 g, 556 mmol, 0.31 wt, 1.80 eq). The resultant mixture was stirred at ambient temperature for 30 minutes and monitored by LCMS (100% conversion) to generate Compound 137.

Stage 7b

TEA (129 ml, 927 mmol, 94 g, 0.28 wt, 0.38 vol, 3.0 eq), water (100 ml, 5.56 mol, 0.30 wt, 0.30 wt, 18 eq) and sulfur (34.7 g, 1.08 mol, 0.10 wt, 3.5 eq) were added to the above mixture of Compound 137. After 90 minutes (100% conversion), NaHCO₃ (9 wt % solution in water; 3.37 L, 10 vol) was added while keeping T-internal below 30° C. (16.6° C. to 27° C.). The resultant mixture was filtered for removal of salts. The filtrate was concentrated the mixture in vacuo, diluted with MTBE (5.1 L, 15 vol), and wash twice with NaCl (30 wt % solution in water; 2×1.35 L, 2×4 vol). Insoluble solids were filtered off and the filtrate was concentrated in vacuo and azeotroped with toluene (4.0 L, 12 vol). The resulting solid was removed by filtration and the crude mixture was dissolved in toluene and purified via Biotage 150 L KP-Sil (SiO₂ 5 kg; pretreated with Hep/EtOAc/TEA (1.5/1.5/0.03 CV); eluted with: EtOAc/TEA (3/0.03 CV), EtOAc/MeOH/TEA (4/0.2/0.04 CV), EtOAC/MeOH/TEA (2/0.2/0.02CV) The column was monitored by TLC (EtOAC/MeOH/TEA=9/1/0.1). Fractions containing the Sp isomer were combined and concentrated under vacuum to give Compound 138 as light pink foam solid (Sp isomer; 154 g, 128 mmol, 0.46 wt, 41.3% yield). Fractions containing the Rp isomer were combined and concentrated under vacuum to give Compound 240 as light pink foam solid (Rp isomer; 64 g, 53 mmol, 0.19 wt, 17% yield).

Compound 138 (Sp Isomer):

¹H NMR (400 MHz, CHLOROFORM-d) δ=8.51 (s, 1H), 8.50 (s, 1H), 8.22 (s, 1H), 8.14 (s, 1H), 7.49-7.44 (m, 2H), 7.38-7.27 (m, 4H), 7.25-7.21 (m, 2H), 7.14 (t, J=7.1 Hz, 2H), 6.44 (dd, J=2.5, 13.9 Hz, 1H), 6.18 (d, J=15.2 Hz, 1H), 5.78 (td, J=6.3, 15.6 Hz, 1H), 5.69 (td, J=4.7, 15.6 Hz, 1H), 5.56 (dd, J=3.9, 50.8 Hz, 1H), 5.20-5.06 (m, 1H), 4.95-4.79 (m, 4H), 4.69 (dd, J=4.3, 16.0 Hz, 1H), 4.54-4.38 (m, 3H), 4.35 (d, J=5.5 Hz, 1H), 4.32-4.29 (m, 1H), 4.05 (dd, J=1.6, 11.7 Hz, 1H), 3.91 (dd, J=3.1, 11.7 Hz, 1H), 3.14-3.06 (m, 6H), 1.30 (t, J=7.4 Hz, 9H), 0.91 (s, 9H), 0.90 (s, 9H), 0.12 (s, 3H), 0.08 (s, 3H), 0.06 (s, 3H), 0.05 (s, 3H)

Compound 240 (Rp Isomer):

¹H NMR (400 MHz, CHLOROFORM-d) δ=8.54 (s, 1H), 8.38 (s, 1H), 8.33 (s, 1H), 8.01 (s, 1H), 7.39-7.09 (m, 10H), 6.39 (dd, J=2.3, 14.1 Hz, 1H), 6.13 (d, J=17.2 Hz, 1H), 5.72 (d, J=3.1 Hz, 2H), 5.68 (dd, J=4.3, 51.2 Hz, 1H), 5.43-5.29 (m, 1H), 5.10-4.96 (m, 3H), 4.90-4.83 (m, 2H), 4.78-4.72 (m, 1H), 4.52 (ddd, J=3.9, 6.6, 17.2 Hz, 1H), 4.44-4.35 (m, 2H), 4.31-4.26 (m, 1H), 4.20-4.12 (m, 2H), 3.87 (dd, J=3.5, 11.7 Hz, 1H), 3.79-3.77 (m, 1H), 3.15-3.09 (m, 6H), 1.33 (t, J=7.4 Hz, 9H), 0.94 (s, 9H), 0.89 (s, 9H), 0.13 (s, 3H), 0.12 (s, 3H), 0.10 (s, 3H), 0.09 (s, 3H)

Stage 8

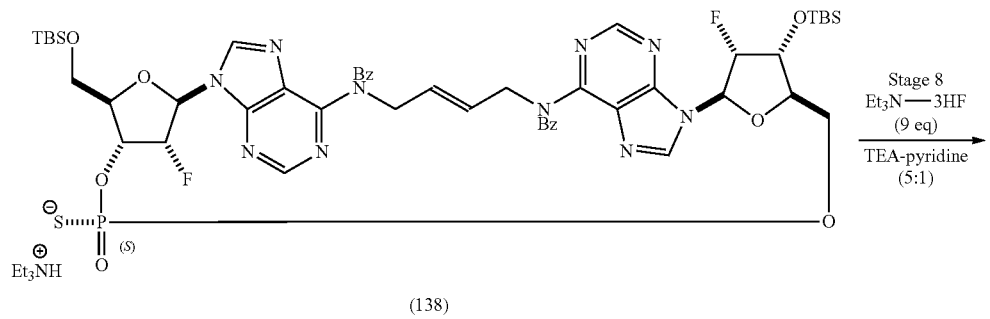

(138)

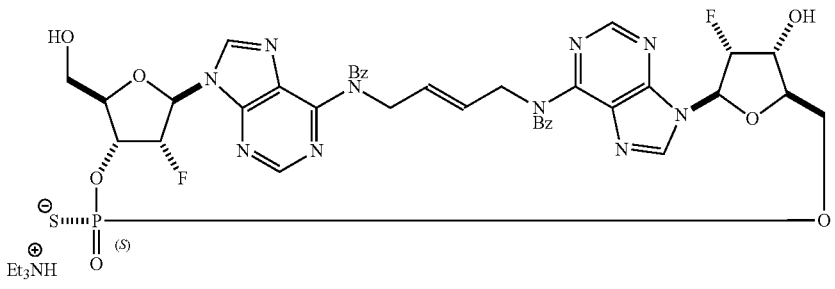

(139)

Compound 138 (221 g, 183 mmol, 1 wt, 1 vol, 1 eq) was dissolved in a mixture of pyridine (530 ml, 6.56 mol, 519 g, 2.3 wt, 2.4 vol) and TEA (2.65 L, 19.0 mol, 1.93 kg, 8.7 wt, 12 vol, 104 eq). Triethylamine trihydrofluoride (264 ml, 1.62 mol, 262 g, 1.2 wt, 1.2 vol, 8.9 eq as complex, 27 eq HF) was added and the mixture was stirred at RT while the conversion was monitored by LCMS. After 3 h (97% conversion), methoxytrimethylsilane (TMSOMe; 1.40 L, 10.2 mol, 1.06 kg, 4.8 wt, 6.3 vol, 55 eq) was added and stirring was continued for 30 minutes. A sticky solid coated the reactor. The solution part (supernatant) was decanted off. The solid was triturated twice with toluene (2×2.2 L, 2×10 vol; supernatant decanted off). The crude solid remained in the reactor was dissolved in dichloromethane (2.2 L, 10 vol) and washed with NH₄Cl (28 wt % solution in water; 2.2 L, 10 vol). The aqueous layer was back-extracted with dichloromethane (2.2 L, 10 vol). The combined organic layers were washed with a mixture of NaCl (36 wt % solution in water; 1.1 L, 5 vol) and water (1.1 L, 5 vol), and then concentrated under vacuum to give Compound 139 as tan dry foam (152 g, 155 mmol, 0.70 wt, 85% yield). The crude product was taken onto the next step without purification.

Stage 9

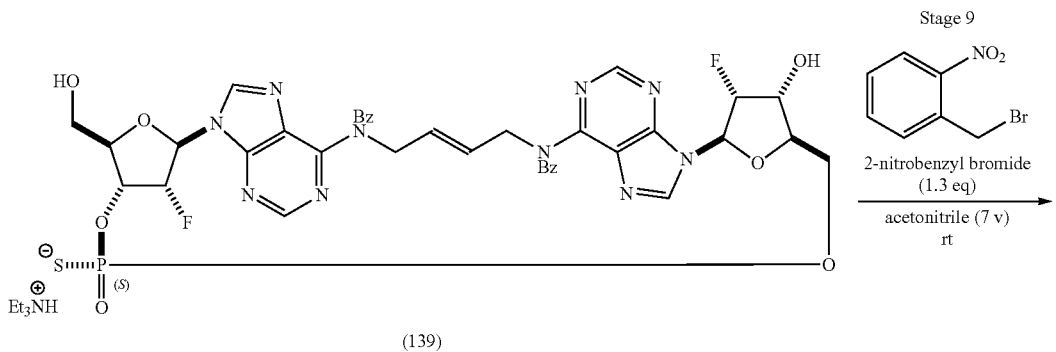

(139)

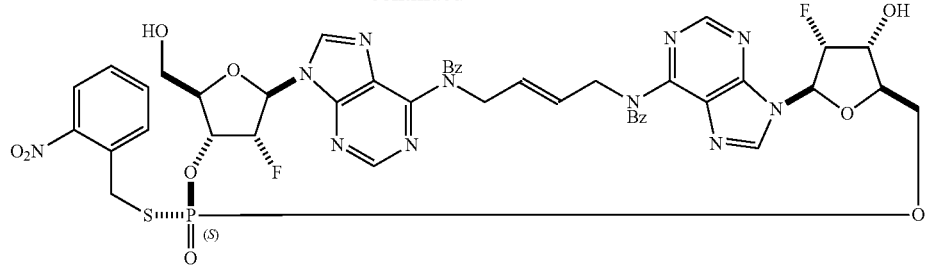

(140)

Compound 139 (150 g, 153 mmol, 1 wt, 1 vol, 1 eq) was azeotroped with acetonitrile (4 L, 27 vol) and then redissolved in acetonitrile (1.05 L, 0.83 kg, 5.5 wt, 7.0 vol) at rt. 2-Nitrobenzyl bromide (44.4 g, 205 mmol, 0.30 wt, 1.34 eq) was added at rt and the reaction was monitored by LCMS. After 23 h (100% conversion), EtOAc (1.50 L, 10 vol), NH$_4$Cl (28 wt % solution in water; 300 ml, 2 vol) and water (300 ml, 2 vol) were added (pH=6) and the resultant mixture was partially concentrated under vacuum at 25° C. to a weight of 1.11 kg. EtOAc (2.25 L, 15 vol) was added and the mixture was stirred for 5 minutes. The two layers were separated. The aqueous layer was extracted with ethyl acetate (750 ml, 5 vol). The combined organic layers were sequentially washed with: (1) a mixture of NaCl (36 wt % solution in water; 300 ml, 2 vol) and water (300 ml, 2 vol) and (2) water (600 ml, 4 vol). The organic layer was then concentrated under vacuum and azeotroped with n-heptane (1.50 L, 10 vol). MTBE (0.95 L, 6.3 vol) was added to the crude solid and the mixture was heated at 40° C. The mixture was diluted with EtOAc (300 ml, 2 vol) and slowly cooled to 0° C. The dense solid was allowed to settle and the supernatant was pumped off through a filter frit tube. The solid was rinsed twice with MTBE (2×300 ml, 2×2 vol; supernatant pumped off through the filter frit tube each time) and dried under vacuum at 40° C. overnight to give Compound 140 as pale yellow solid (156 g). The filtrate was concentrated under vacuum yielding a brown oil (17.8 g), which was subjected to purification via Biotage Snap-Ultra 340 g (eluents: 0 to 5% MeOH in EtOAc) to give additional Compound 140 as pale yellow solid (5.8 g). Total 156 g+5.8 g=161.8 g (net 152 mmol, 95% pure, 99% yield)

$^1$H NMR (400 MHz, CHLOROFORM-d) δ=8.46 (s, 1H), 8.15 (s, 1H), 8.10 (s, 1H), 8.09-8.06 (m, 1H), 7.89 (s, 1H), 7.54-7.51 (m, 1H), 7.49-7.45 (m, 4H), 7.37-7.28 (m, 3H), 7.24-7.19 (m, 3H), 7.16-7.11 (m, 2H), 6.22 (d, J=16.8 Hz, 1H), 6.14 (dd, J=2.7, 17.2 Hz, 1H), 5.83-5.61 (m, 3H), 5.60-5.48 (m, 1H), 5.07 (dd, J=3.5, 51.6 Hz, 1H), 5.06-4.96 (m, 1H), 4.79 (dd, J=4.9, 15.8 Hz, 1H), 4.69 (d, J=5.9 Hz, 2H), 4.67-4.56 (m, 1H), 4.48-4.40 (m, 3H), 4.37-4.30 (m, 1H), 4.27 (d, J=5.9 Hz, 2H), 4.19-4.13 (m, 1H), 3.93-3.85 (m, 1H), 3.85-3.78 (m, 1H)

Stage 10-11

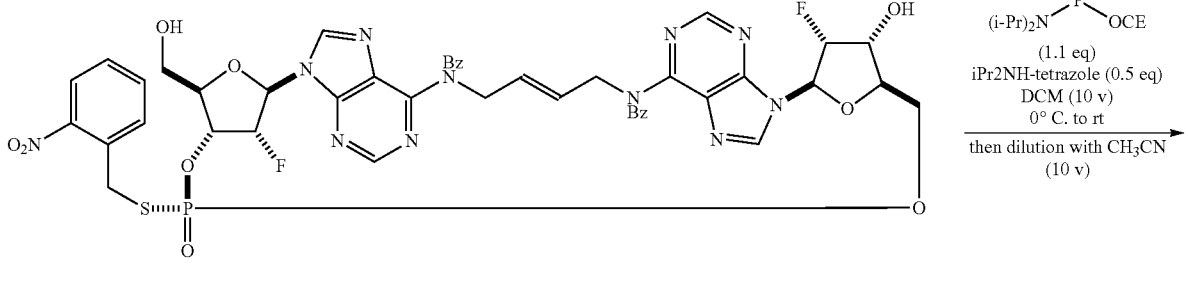

(140)

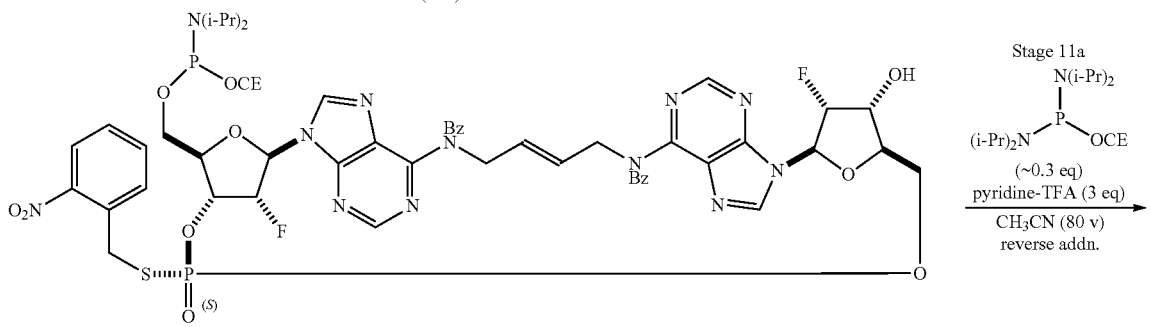

(141)

-continued

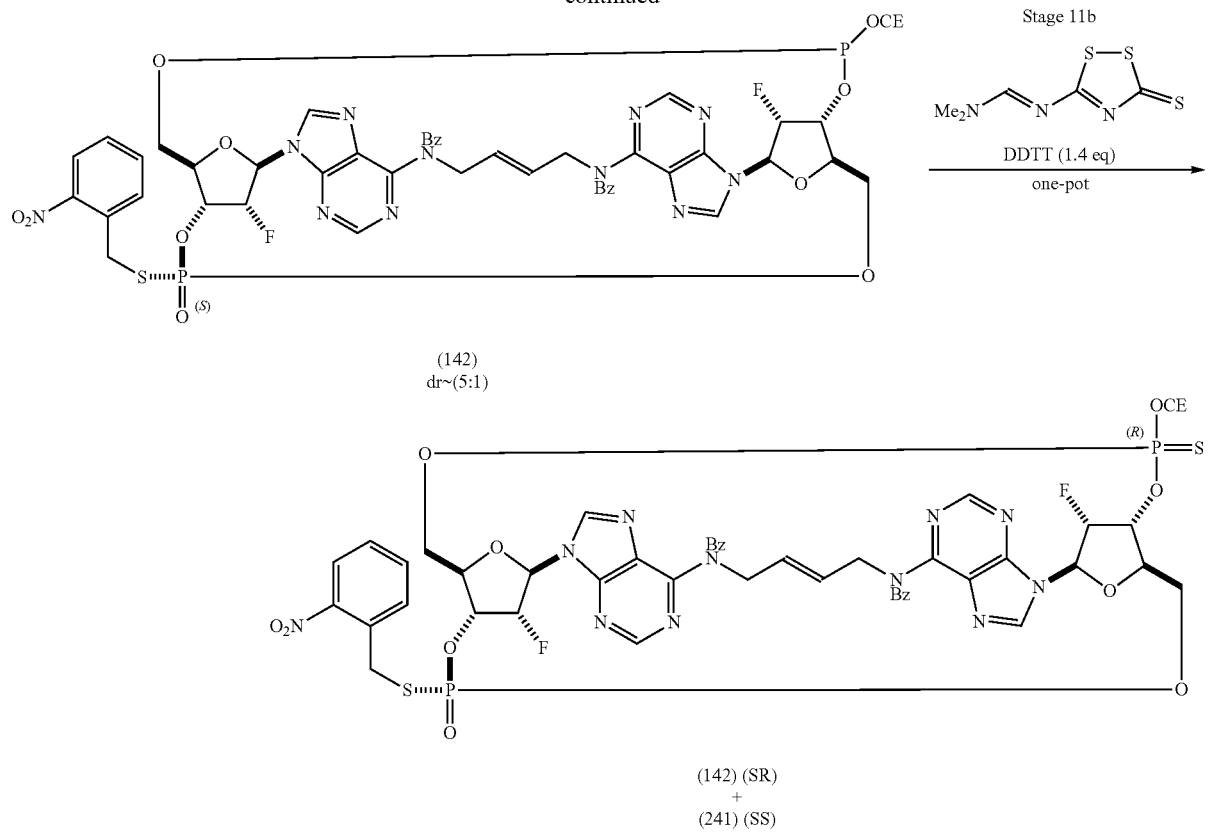

Stage 10

Compound 140 (95% pure, net 73.2 g, 72.3 mmol, 1 wt, 1 vol, 1 eq) and 2-cyanoethyl N,N,N',N'-tetraisopropylphosphorodiamidite (25.3 ml, 79.5 mmol, 0.33 wt, 0.35 vol, 1.10 eq) were azeotroped with anhydrous acetonitrile three times (3×2 L), re-dissolved in dichloromethane (0.73 L, 10 vol) and cooled to 0-5° C. Diisopropylammonium tetrazolide (6.19 g, 36.1 mmol, 0.085 wt, 0.50 eq) was added. The resulting reaction mixture was stirred at 0° C. for 10 h, warmed to 10° C. over 2 h, held at 10° C. for 10 h and warmed up to rt over 2 h. The reaction was monitored by LCMS and TLC (EtOAc with 0.5% TEA). After 18 h, anhydrous acetonitrile (0.73 L, 10 vol) was added and the mixture was stored at −20° C. over 3 days.

Stage 11a

The mixture from Stage 10 was warmed to ambient temperature and added via a dropping funnel in portions (100 mL every 30 minutes, over 9 h) into a mixture of pyridine trifluoroacetate salt (azeotroped in advance with pyridine twice; 41.9 g, 217 mmol, 0.57 wt, 3.0 eq) and acetonitrile (5.85 L, 80 vol). The reaction was monitored by LCMS. After 13 h, a solution of 2-cyanoethyl N,N,N',N'-tetraisopropylphosphorodiamidite (5.8 mL, 18 mmol, 0.25 eq) in acetonitrile (24 mL) was added over 4 h. Amount of the additional reagent was determined based on the remaining Compound 140 (~30% based on LCMS). More conversion of the diol was observed after 6 h.

Stage 11b ((Dimethylaminomethylidene)amino)-3H-1,2,4-dithiazoline-3-thione (DDTT; 20.8 g, 101 mmol, 0.28 wt, 1.4 eq) was added and stirring was continued for 1 h. The reaction mixture was partially concentrated to ~800 mL and diluted with MTBE (1.46 L, 20 vol), NaHCO$_3$ (9 wt % solution in water; 1.1 L, 15 vol) and water (0.37 L, 5 vol). pH=8. The layers were separated and the aqueous layer was extracted with a mixture of MTBE (1.46 L, 20 vol) and EtOAc (1.10 L, 15 vol). The combined organic layers were washed twice with 30% aq NaCl (2×0.73 L, 2×10 vol), concentrated under vacuum at 35° C. and azeotroped with toluene (1.46 L, 20 vol). LCMS and TLC (EtOAc) indicated Compound 143 (SpRp, desired):Compound 241 (SpSp)=5:1

The crude product was purified via Biotage 150M KP-Sil, (SiO$_2$ 2.5 kg; eluents: EtOAc/Hep: 2:1 (4 CV), 3:1 (2.5 CV), 4:1 (2.5 CV), 100% EA (3 CV), 5-10% MeOH in EA 4 CV) to give Compound 143 (36 g, 31.5 mmol, 44% yield).

Compound 143 (SpRp): $^1$H NMR (400 MHz, CHLOROFORM-d) δ=8.59 (s, 1H), 8.10 (s, 1H), 8.03-7.99 (m, 1H), 7.91 (s, 1H), 7.56-7.53 (m, 2H), 7.49-7.40 (m, 5H), 7.35-7.28 (m, 2H), 7.24-7.16 (m, 4H), 6.92 (s, 1H), 6.29 (d, J=14.9 Hz, 1H), 6.08 (d, J=20.7 Hz, 1H), 5.97-5.83 (m, 1H), 5.76 (td, J=4.7, 15.6 Hz, 1H), 5.61-5.51 (m, 2H), 5.40 (d, J=4.3 Hz, 1H), 5.29-5.17 (m, 1H), 4.91 (dd, J=7.4, 14.9 Hz, 1H), 4.86-4.75 (m, 3H), 4.63 (dd, J=3.7, 9.2 Hz, 1H), 4.58-4.43 (m, 5H), 4.34-4.19 (m, 4H), 2.79 (td, J=5.9, 16.8 Hz, 1H), 2.66 (td, J=6.3, 16.8 Hz, 1H).

Compound 241 (SpSp) $^1$H NMR (400 MHz, CHLOROFORM-d) δ=8.11 (s, 1H), 8.03 (d, J=8.2 Hz, 1H), 7.94 (s, 1H), 7.90 (s, 1H), 7.61 (s, 1H), 7.56-7.40 (m, 7H), 7.33-7.28 (m, 2H), 7.23-7.17 (m, 4H), 6.22 (d, J=17.6 Hz, 1H), 6.15 (d, J=18.8 Hz, 1H), 5.85 (dd, J=3.5, 51.2 Hz, 1H), 5.75-5.45 (m, 5H), 4.95-4.23 (m, 14H), 2.82 (t, J=6.1 Hz, 2H).

Stage 12

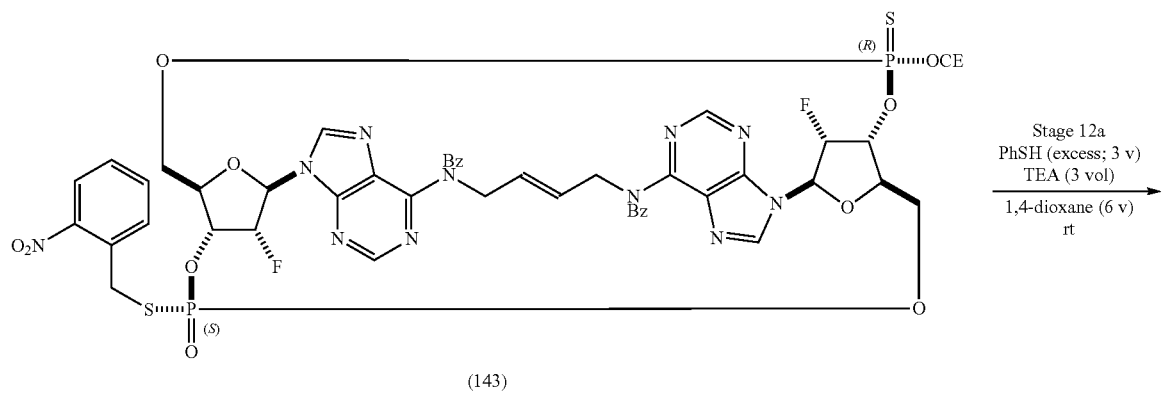

(143)

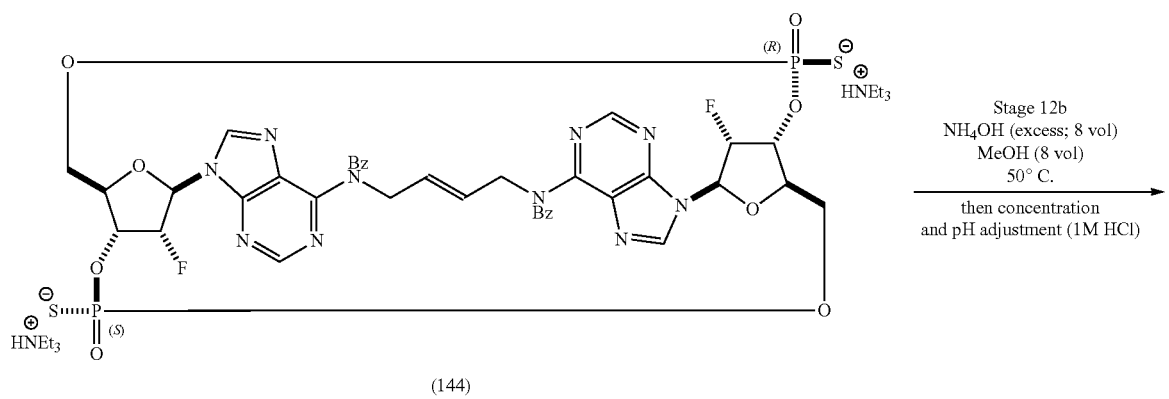

(144)

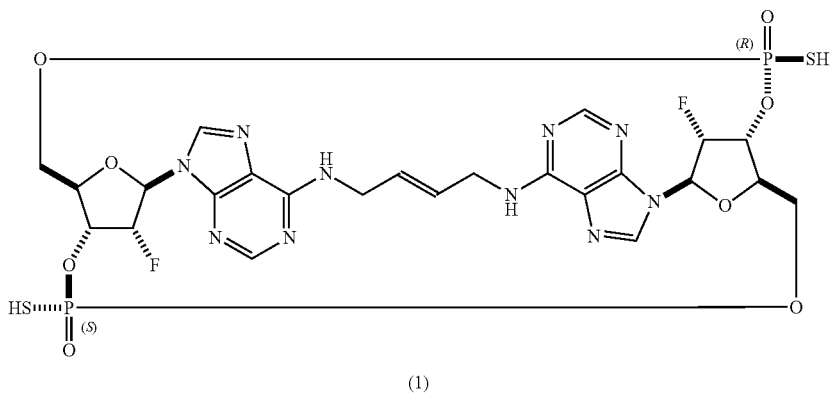

(1)

Compound 143 (71.6 g, 62.6 mmol, 1 wt, 1 vol, 1 eq) was dissolved in 1,4-dioxane (0.43 L, 6 vol). Thiophenol (215 ml, 2.09 mol, 230 g, 3.2 wt, 3 vol, >30 eq) was added followed by triethylamine (215 ml, 1.54 mol, 156 g, 2.2 wt, 3 vol). Some exotherm was observed (T-internal increased by ~7° C.), therefore, water/ice bath was used to cool and control T-internal below 27° C. The reaction was monitored by LCMS. After 2 h, MeOH (0.57 L, 8 vol) and NH$_4$OH (28 wt %; 15 mol, 0.57 L, 8 vol, >200 eq) were added. The resulting mixture was heated at 50° C. for 5 h, cooled to rt and stirred overnight. After 14 h, water (0.72 L, 10 vol) was added (no solid observed) and the mixture was extracted three times with 1:1 (v/v) mixture of n-heptane and toluene (3×0.86 L, 3×12 vol), followed by with toluene (0.57 L, 8 vol). The aqueous layer was concentrated in vacuo at 40-50° C. and diluted with water (1.07 L, 15 vol). The resulting slurry was kept overnight at rt. The resulting solid was filtered off, rinsing with water (0.36 L, 5 vol). The filtrate was still cloudy and filtered through celite and a Kuno filter. Cloudiness was still present. HCl (1.0 M solution in water; 132 ml, 132 mmol, 2.1 eq) was added over 1 h and pH was checked (pH <2). Stirring was continued at rt for 1 h and the mixture was filtered. The filter cake was rinsed with water (8×0.20 L), dried in a vacuum oven at 35° C. for 2 days and with no heat for 1 day to give Compound 1 as pale orange solid (44.88 g, 60.1 mmol, 0.63 wt, 96% yield).

Stage 13

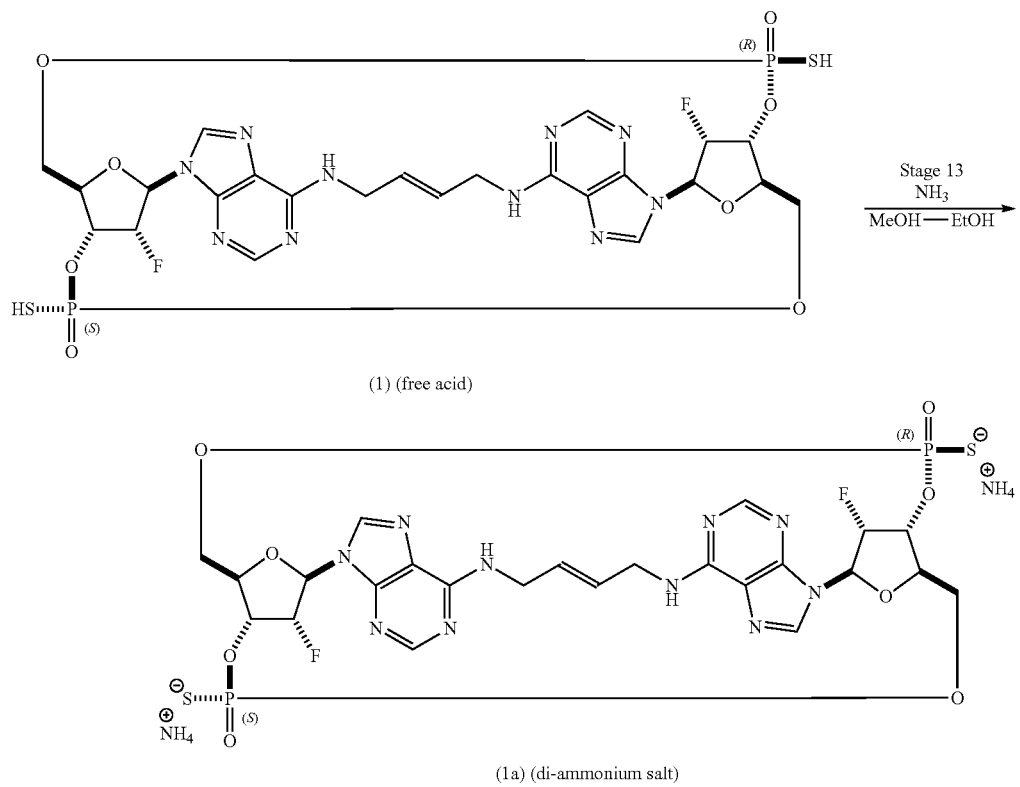

(1) (free acid)

(1a) (di-ammonium salt)

To the free acid Compound 1 (22.42 g, 30.03 mmol, 1 wt, 1 vol, 1 eq) was added ammonia (2.0M solution in MeOH; 220 ml, 440 mmol, 10 vol, 15 eq). EtOH (55 ml, 2.5 vol) was added and the resulting solution was filtered through a Kuno filter (0.45 micron; PTFE), rising with 1:1 (v/v) mixture of MeOH and EtOH (90 mL, 4 vol). The filtrate was concentrate in vacuo at 30° C. yielding an off white solid, which was dried at rt overnight, grinded with a spatular (easy to break) and dried further in vacuum at rt. The isolated solid was then suspended in toluene (250 ml) and stirred at rt for 30 minutes. The solid was then collected by vacuum filtration and rinsed with toluene twice (2×50 ml). The solid was then dried under vacuum in a vacuum oven to give 22.4 g of Compound 1a (the di-ammonium salt of Compound 1).

Recrystallization:

Compound 1a (22.14 g, 28.36 mmol, 1 wt, 1 vol, 1 eq) was dissolved in a mixture of water (664 ml, 30 vol) and ammonium hydroxide (28 wt %; 2.5 ml, 18 mmol, 0.63 eq) (pH=9-10) and extracted with toluene three times (3×300 ml, 3×14 vol), EtOAc three times (3×200 ml, 3×9 vol) and toluene three times (3×300 ml, 3×14 vol). The resulting aqueous layer was treated with HCl (1.0 M solution in water; 90 ml, 90 mmol, 3.2 eq) over a period of 3.5 hours (pH ≤2). The mixture stirred for 30 minutes and then the solid precipitate was collected by vacuum filtration. The filter cake was washed with water three times (3×200 ml, 3×9 vol) and dried in vacuo overnight. Ammonia (2.0 M solution in MeOH; 250 ml, 500 mmol, 17.6 eq) and ethanol (100 ml) were added to the solid and the resulting mixture was concentrated in vacuo until crystals appeared (~100 ml), at which time concentration was stopped and the mixture was stirred for 20 minutes. Ethanol (45 mL) was added and the mixture was partially concentrated (45 mL removed). The same operation was repeated two more times, and then the mixture was cooled to 0° C. and stirred for 3.5 h. The white solid was collected by vacuum filtration and washed with cold ethanol (20 ml) followed by ethyl acetate (2×50 mL). The white solid was dried under vacuum at rt for 3 days to give Compound 1a as white solid (16.6 g, 21.3 mmol, 0.75 wt, 75% yield). The filtrate was concentrated under vacuum and dried under vacuum at rt for 3 days to give Compound 1a as off white solid (4.16 g, 5.3 mmol, 18% yield).

Example 1.2—$^1$H NMR Analysis of Compound 1

Figure 3:
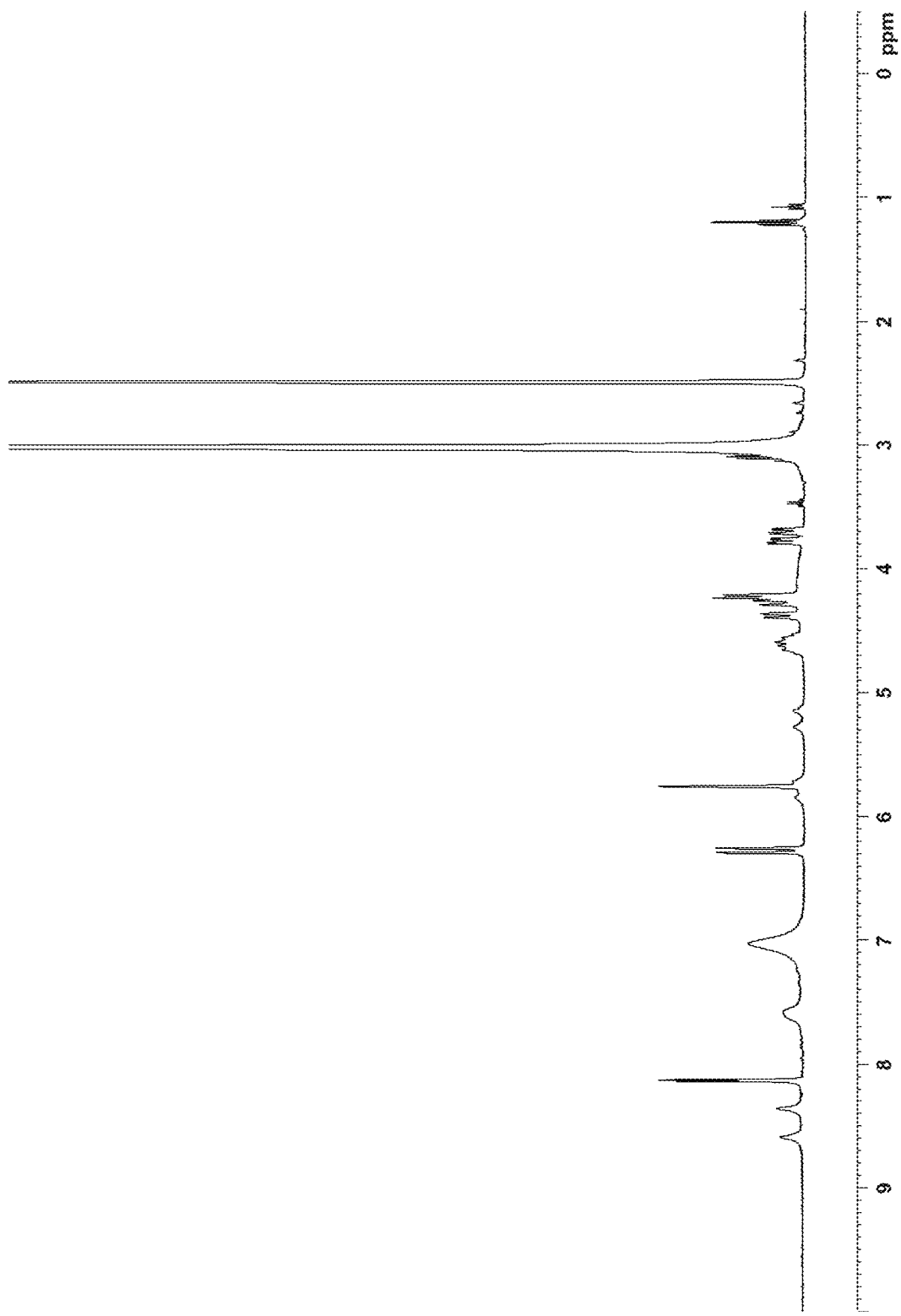
FIG. 3 shows an $^1$H NMR spectrograph for Compound 1.

A $^1$H NMR spectrograph of Compound 1a is shown in FIG. 3. The resulting spectrum was: $^1$H-NMR Spectrum (400 MHz, DMSO-d$_6$, $\delta_H$ 2.49 ppm, 80° C.)

δ (ppm): 3.05-3.13 (4H, m), 3.70 (1H, dd, J=13, 5 Hz), 3.78 (1H, dd, J=12, 4 Hz), 4.21-4.24 (2H, m), 4.28 (1H, m), 4.38 (1H, m), 4.53-4.68 (2H, m), 5.22 (1H, m), 5.76 (2H, s), 5.78 (1H, m), 6.26 (1H, m), 6.29 (1H, m), 8.13 (1H, s), 8.14 (1H, s), 8.36 (1H, brs), 8.59 (1H, brs).

Example 1.3—X-Ray Analysis of Compound 1

About 2 mg of Compound 1 was dissolved in 600 uL of water. 120 uL of this solution was put in another glass vial and then this vial was stored in fixed container with 3 mL of MeCN at room temperature for 1 week. This is the H$_2$O/MeCN vapor diffusion method of sample preparation.

A colorless block single crystal (0.1×0.1×0.1 mm) found in crystallization solution was dispersed in liquid Parabar 10312 and was mounted on a Dual-Thickness Micro-Mounts™ (MiTeGen). Diffraction data was collected at −160° C. on XtaLAB PRO P200 MM007HF (Rigaku) with co axis oscillation method using multi-layer mirror monochromated Cu-Kα radiation.

Figure 4A:
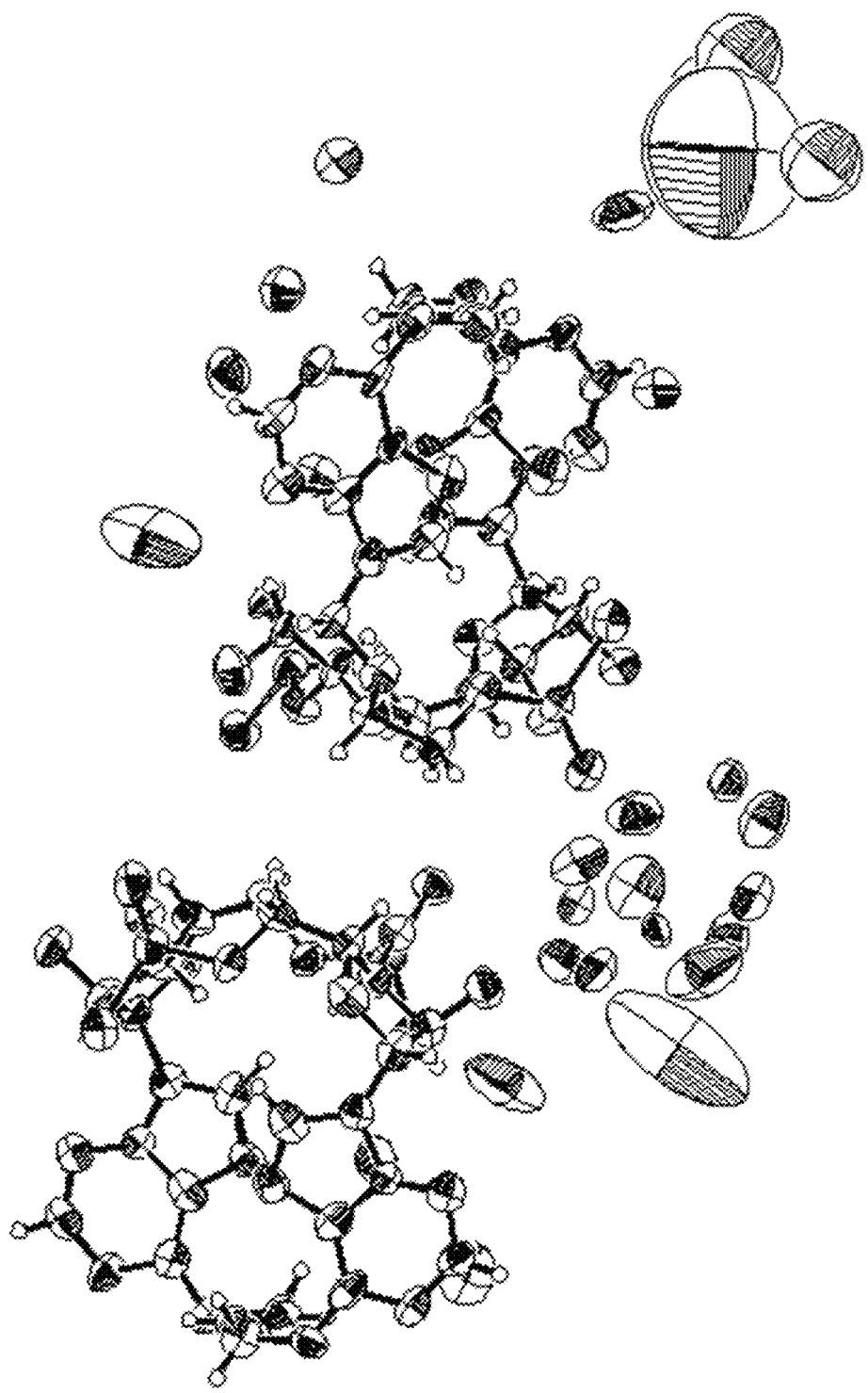
FIG. 4A, FIG. 4B, and FIG. 4C, show X-ray crystallography results (ORTEP drawings) for, respectively, an asymmetric crystal of Compound 1, a first molecule from the asymmetric crystal, and a second molecule from the asymmetric crystal.
Figure 4B:
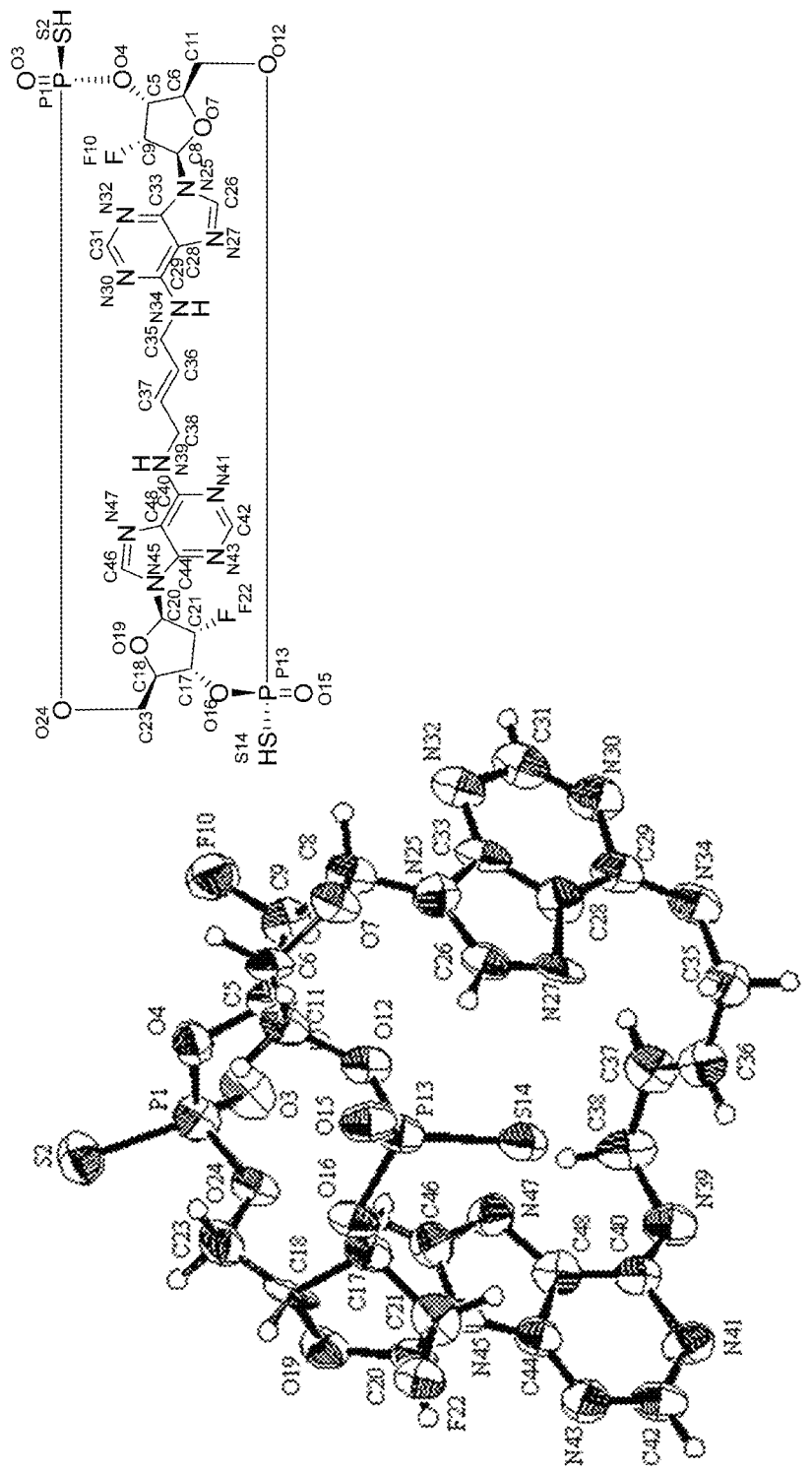
Figure 4C:
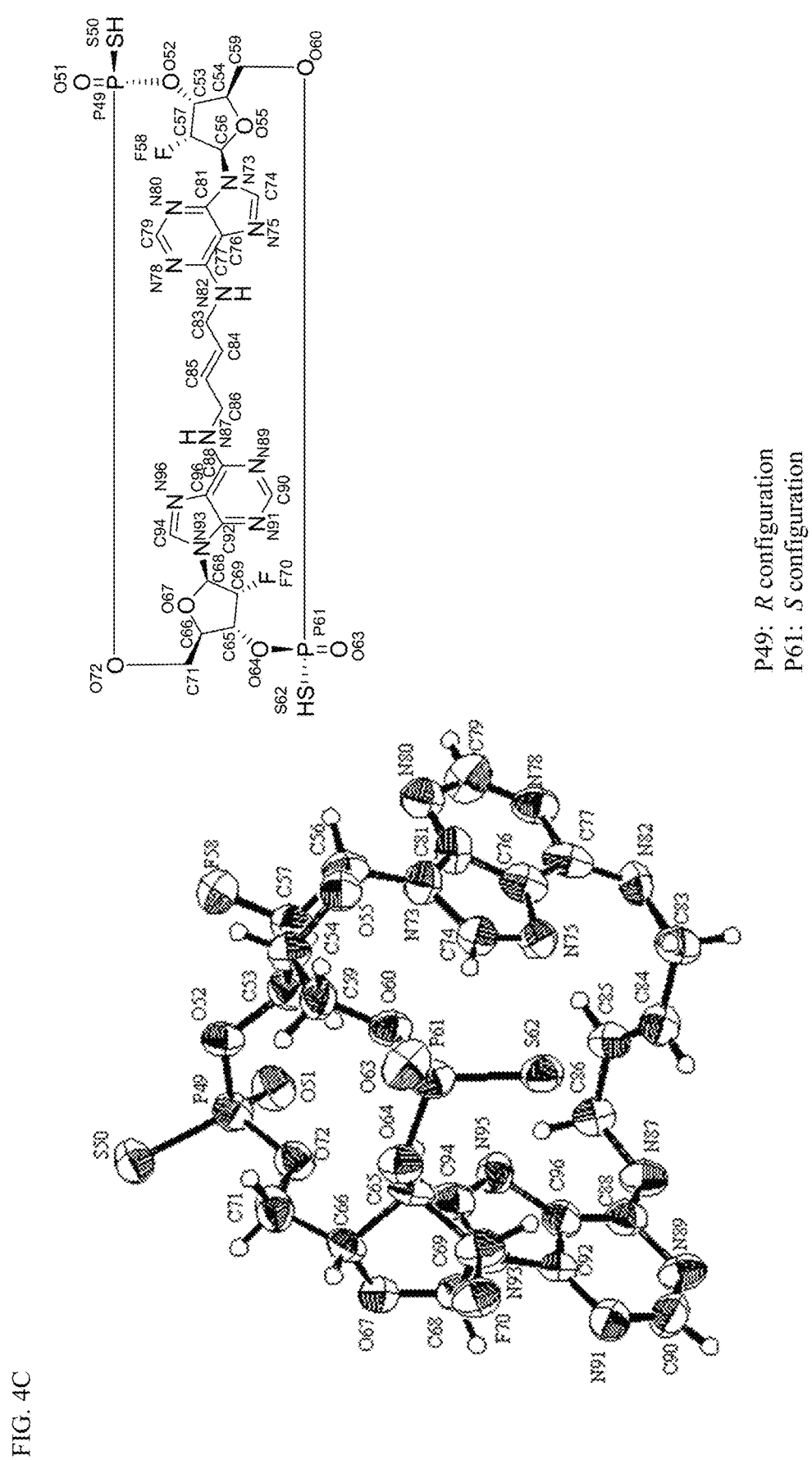

FIG. 4A shows an ORTEP figure of Compound 1 molecules in an asymmetric unit, along with a number of disordered water molecules. FIG. 4B shows the crystal structure of one of the Compound 1 molecules from FIG. 4A. FIG. 4C shows the crystal structure of the other molecule of Compound 1 shown in FIG. 4A.

The crystal structure of Compound 1 was solved with a final R-factor of 0.1354. The Flack parameter was nearly zero (0.083(17)), indicating that the absolute configuration of Compound 1 is (R, S). The crystal structure analysis also indicated that many water molecules were present in the large channel of Compound 1, which indicated that water molecules were able to easily slip out from the channel. The analysis also confirmed that the conformations of both crystallographically independent molecules the asymmetric unit were almost the same.

Further parameters of the X-ray analysis are shown below:

| | |
|---|---|
| Temperature | 113 K |
| Wavelength | 1.54184 Å |
| Crystal system, Space group | Monoclinic, P2$_1$ |
| Lattice parameter | a = 8.1584(3) Å |
| | b = 35.451(2) Å |
| | c = 15.9146(6) Å |
| | β = 91.313(3)° |
| Volume | 4601.7(4) Å$^3$ |
| Z value, calculated density | 4, 1.127 g/cm$^3$ |
| Crystal size | 0.1 × 0.1 × 0.1 mm |
| Total number of reflections/ number of unique reflections | 52006/17198 [R(intensity) = 0.0876] |
| Completeness | 92.2% |
| Phase determination | Direct methods (SHELXT Version 2014/5) |
| Refinement method | Full-matrix least-squares on F$^2$ (SHELXL Version 2014/7) |
| Data/parameter | 17198/1116 |
| Goodness of fit indicator | 1.545 |
| Residuals: R(I > 2σ(I)) | 0.1354 |
| Residuals: Rw | 0.3886 |
| Flack parameter | 0.083(17) |
| Maximum and Minimum peak difference | 1.17 and −0.88 e$^-$/Å$^3$ |

Example 2—Synthesis of Compound 2

Compound 106 (RpRp isomer of Compound 105) obtained from Example 1, Step E was processed separately through Example 1, Step F and Example 1, Step G to give Compound 2a (RR isomer of Compound 1a):

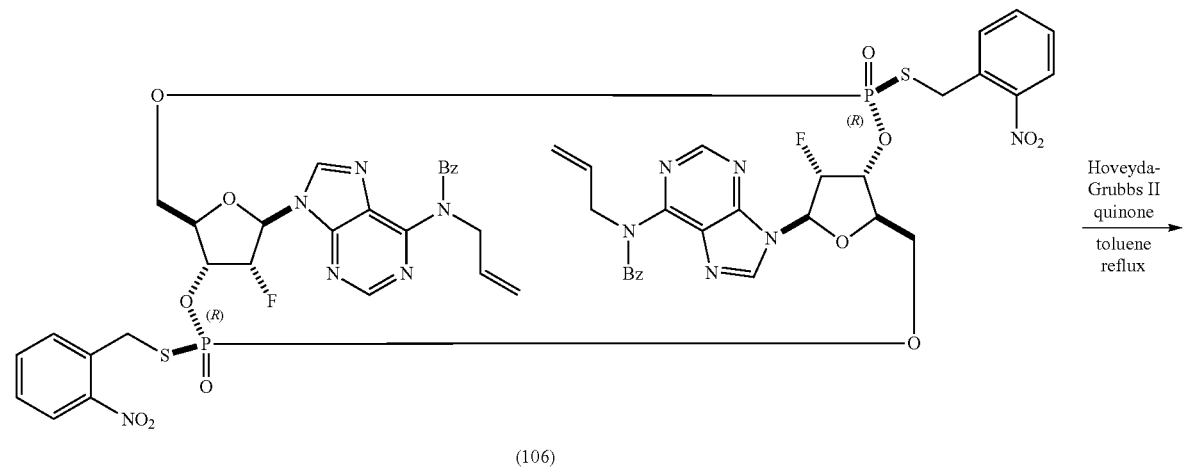

(106)

Hoveyda-Grubbs II quinone
toluene
reflux

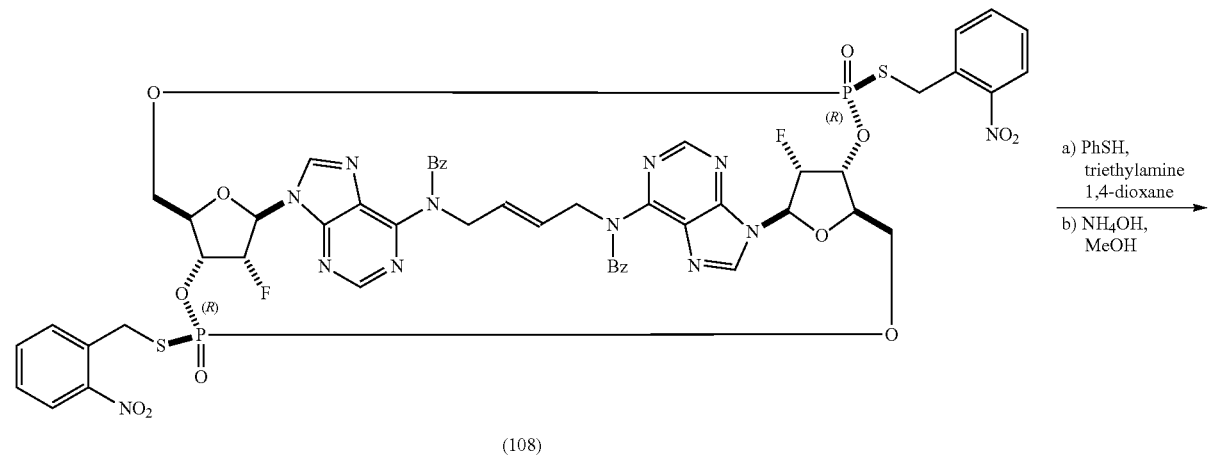

(108)

a) PhSH, triethylamine 1,4-dioxane b) NH$_4$OH, MeOH

-continued

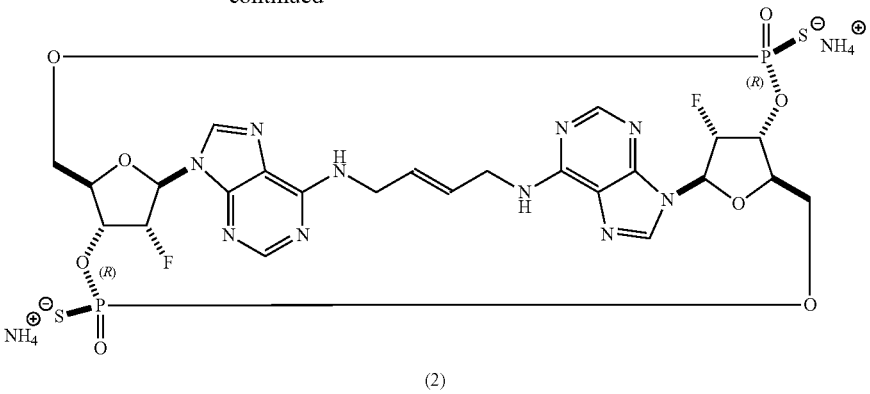

(2)

Compound 108 (RpRp) ¹H NMR (400 MHz, CDCl₃) δ=8.12 (dd, J=8.2, 0.8 Hz, 2H), 7.99 (s, 2H), 7.96 (s, 2H), 7.65-7.48 (m, 10H), 7.38-7.33 (m, 2H), 7.26-7.24 (m, 4H), 6.22 (d, J=17.6 Hz, 2H), 5.95-5.84 (m, 2H), 5.71 (dd, J=50.8, 3.9 Hz, 2H) 5.73-5.71 (m, 2H), 4.88-4.77 (m, 4H), 4.59-4.38 (m, 8H), 4.19 (m, 2H).

Compound 2a (RpRp, trans) ¹H NMR (400 MHz, CD₃OD) δ=8.70 (s, 1H), 8.49 (s, 1H), 8.23 (s, 1H), 8.09 (s, 1H), 6.34 (br s, 2H), 5.83 (br s, 2H), 5.73-5.53 (m, 2H), 5.38-5.01 (m, 2H), 4.76-4.32 (m, 6H), 3.95 (br s, 2H), 3.69-3.64 (m, 2H); ³¹P NMR (162 MHz, CD₃OD) δ=55.57 (s, 1P), 55.32 (s, 1P).

Example 2.1—X-Ray Analysis of Compound 2

Compound 2 (0.5 mg) was weighed and dissolved in acetonitrile/28% ammonia solution. Then, this solution was stored under room temperature with loosely fixed cap. After 2 weeks rod shape crystal appeared.

A colorless block single crystal (0.1×0.1×0.5 mm) found in crystallization solution was dispersed in liquid Parabar 10312 and was mounted on a Dual-Thickness Micro-Mounts™ (MiTeGen). Diffraction data was collected at −160° C. on XtaLAB PRO P200 MM007HF (Rigaku) with ω axis oscillation method using multi-layer mirror monochromated Cu-Kα radiation.

Figure 4D:
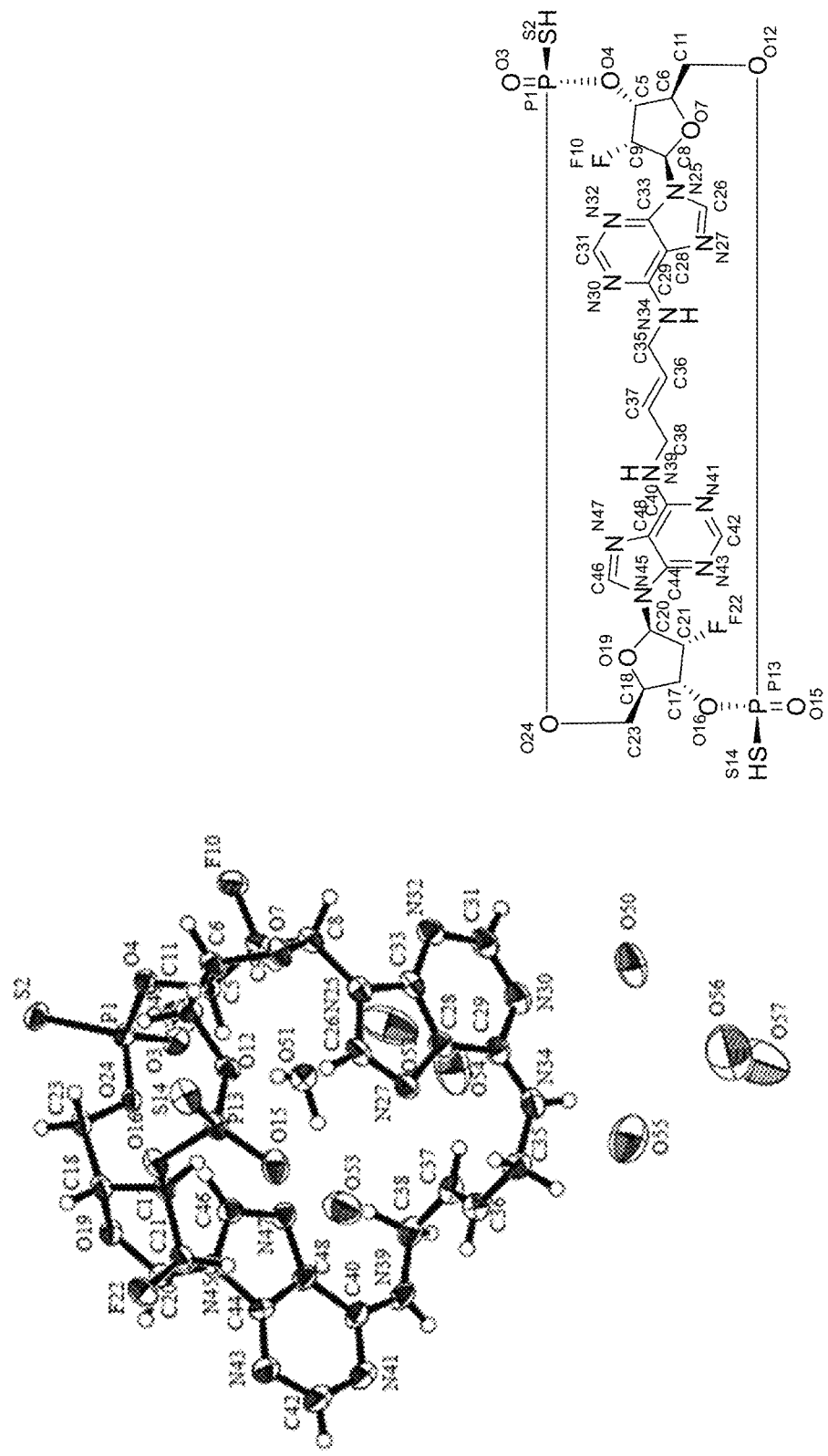
FIG. 4D shows X-Ray crystallography results (ORTEP drawing) for a crystal of Compound 2.
Figure 5A:
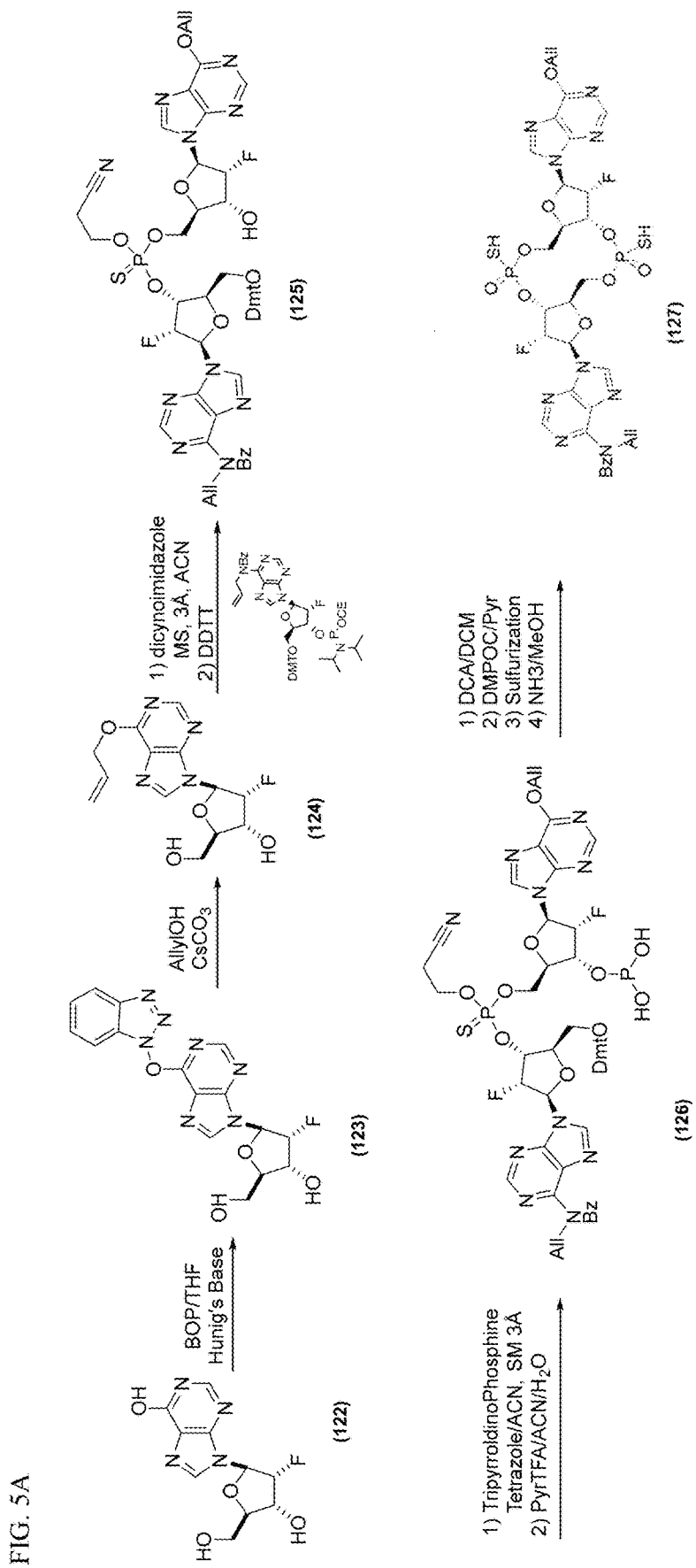
FIG. 5A and FIG. 5B shows a synthesis route for Compounds 18, 19, and 20.
Figure 5B:
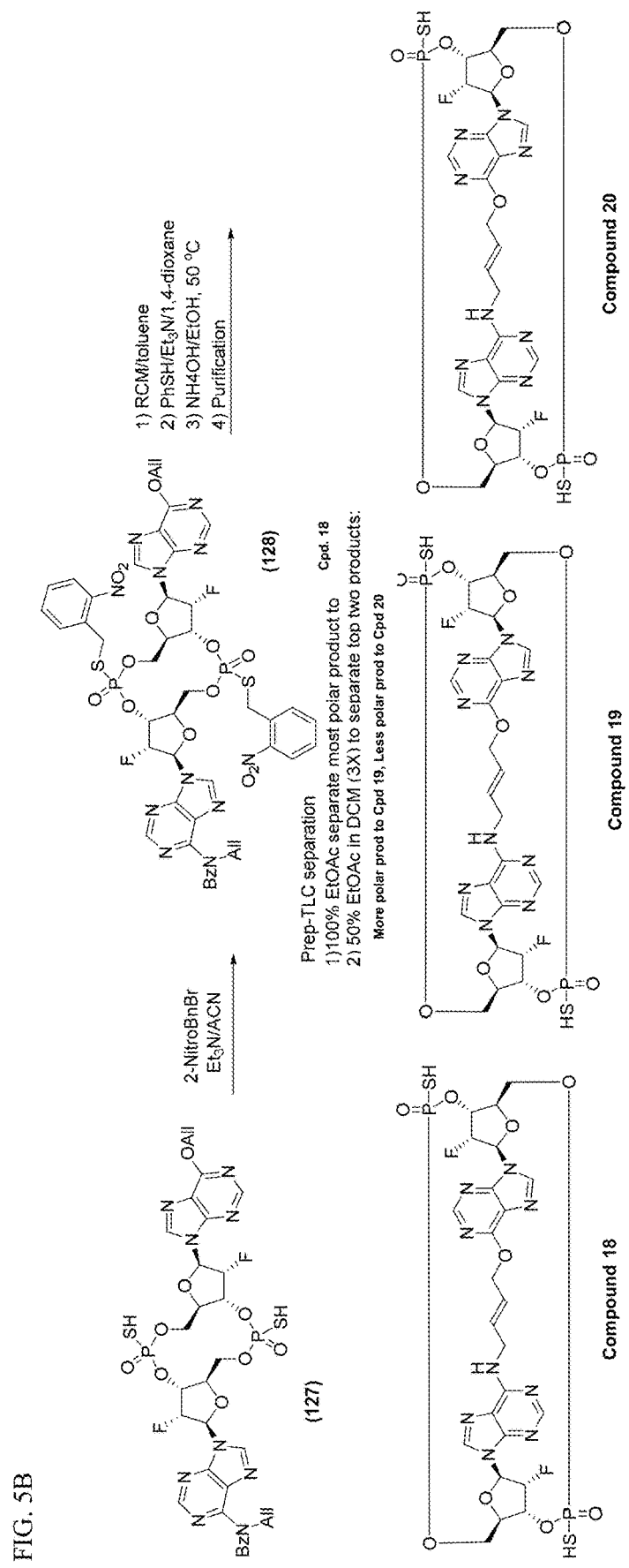

FIG. 4D shows an ORTEP figure of a Compound 2 molecule.

Further parameters of this X-ray analysis are shown, below:

| | |
|---|---|
| Temperature | 113 K |
| Wavelength | 1.54187 Å |
| Crystal system, Space group | Monoclinic, P2 |
| Lattice parameter | a = 14.20210(11) Å |
| | b = 7.99219(7) Å |
| | c = 19.03500(14) Å |
| | β = 94.2005(7)° |
| Volume | 2154.78(3) Å³ |
| Z value | 2 |
| Crystal size | 0.1 × 0.1 × 0.5 mm |
| Total number of reflections/ number of unique reflections | 29195/8152 [R(intensity) = 0.0216] |
| Completeness | 94.8% |
| Phase determination | Direct methods (SHELXT Version 2014/5) |
| Refinement method | Full-matrix least-squares on F² (SHELXL Version 2014/7) |
| Data/parameter | 8152/518 |
| Goodness of fit indicator | 1.099 |
| Residuals: R(I > 2σ(I)) | 0.0711 |
| Residuals: Rw | 0.2133 |
| Flack parameter | 0.020(8) |
| Maximum and Minimum peak difference | 1.95 and −0.64 e⁻/Å³ |

Example 3—Synthesis of Compound 3

Compound 109 (SpSp isomer of Compound 105) obtained from Example 1, Step E was processed separately through Example 1, Step F and Example 1, Step G to give Compound 3a (SS isomer of Compound 1a):

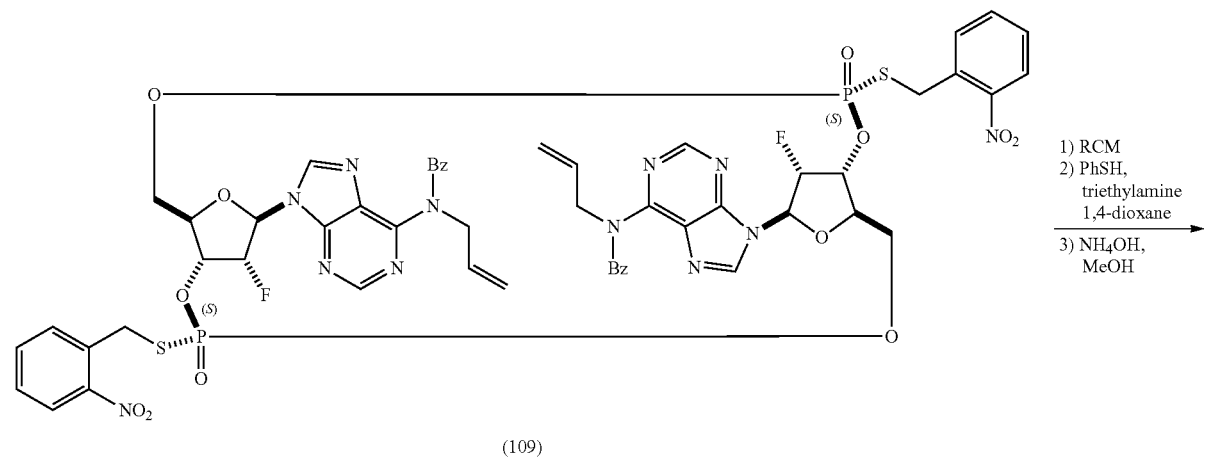

-continued

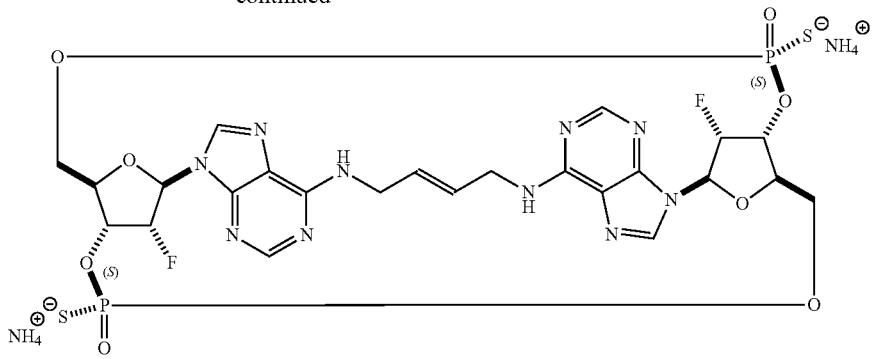

compound 3a

Compound 109

(SpSp isomer of Compound 105): $^1$H NMR (400 MHz, CHLOROFORM-d) δ=8.52 (s, 2H), 7.99 (d, J=8.2 Hz, 2H), 7.91 (s, 2H), 7.63-7.40 (m, 10H), 7.35-7.28 (m, 2H), 7.23-7.16 (m, 4H), 6.10-5.93 (m, 4H), 5.92-5.75 (m, 2H), 5.62-5.50 (m, 2H), 5.26-5.16 (m, 2H), 5.09-5.03 (m, 2H), 4.98-4.91 (m, 4H), 4.61-4.25 (m, 10H)

Compound 3a (SpSp, trans): $^1$H NMR (400 MHz, CD$_3$OD) δ=8.97 (br s, 1H), 8.84 (br s, 1H), 8.21 (br s, 2H), 6.31 (br s, 2H), 6.08 (br d, J=53.5 Hz, 1H), 5.89 (br s, 2H), 5.63 (br d, J=52.4 Hz, 1H), 5.13-4.96 (m, 2H), 4.72-4.32 (m, 6H), 4.01 (br d, J=9.8 Hz, 2H), 3.67 (br s, 2H).

Example 4—Synthesis of Compound 4a

Compound 107 obtained from Example 2, Step F, isolated as the only cis isomer via silica gel chromatography, was processed separately through Example 1, Step G to give Compound 4a.

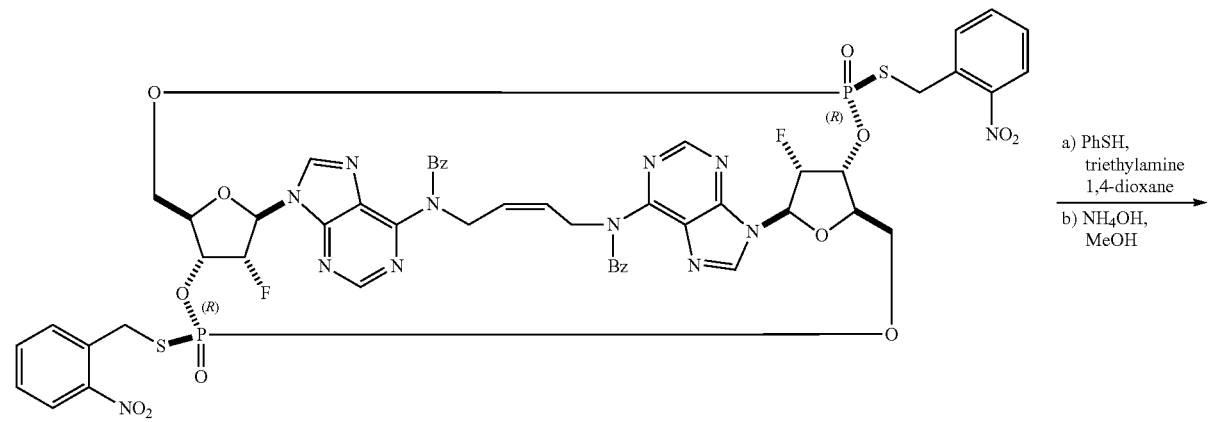

(107)

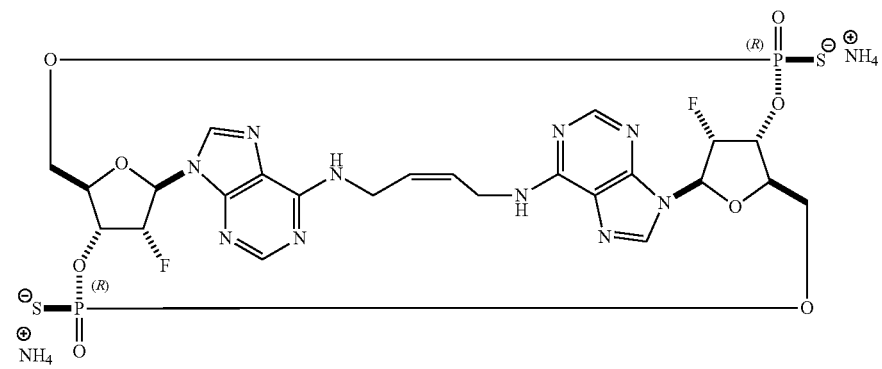

compound 4a

Compound 107:

$^1$H NMR (400 MHz, CHLOROFORM-d) δ=8.13 (s, 2H), 8.12-8.08 (m, 2H), 7.91 (s, 2H), 7.65-7.55 (m, 4H), 7.54-7.45 (m, 6H), 7.33-7.27 (m, 2H), 7.23-7.16 (m, 4H), 6.14 (d, J=17.6 Hz, 2H), 5.88 (dd, J=3.9, 50.8 Hz, 2H), 5.76-5.61 (m, 4H), 5.21-4.99 (m, 4H), 4.60-4.46 (m, 4H), 4.45-4.37 (m, 2H), 4.30-4.13 (m, 4H), 3.49 (d, J=5.1 Hz, 2H)

Compound 4a (RpRp, cis of 1a, Compound 4a): $^1$H NMR (400 MHz, METHANOL-d$_4$) δ=8.48 (br s, 2H), 8.02 (br s, 2H), 6.29 (d, J=14.8 Hz, 2H), 5.99 (br s, 2H), 5.43 (d, J=51.2 Hz, 2H), 5.03-4.88 (m, 2H), 4.43 (br d, J=11.7 Hz, 2H), 4.32 (br d, J=9.4 Hz, 2H), 4.27-4.17 (m, 2H), 4.21-4.02 (m, 2H), 3.97 (br dd, J=6.1, 12.3 Hz, 2H).

Example 5—Synthesis of Compound 5

The cis isomer obtained from Example 1, Step F was processed separately through Example 1, Step G to give Compound 5a.

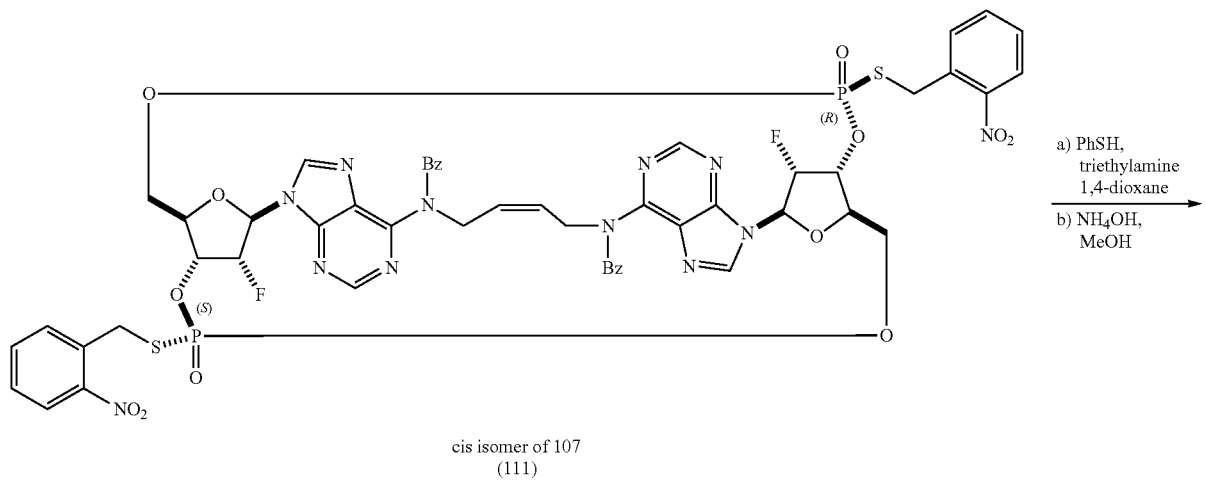

cis isomer of 107
(111)

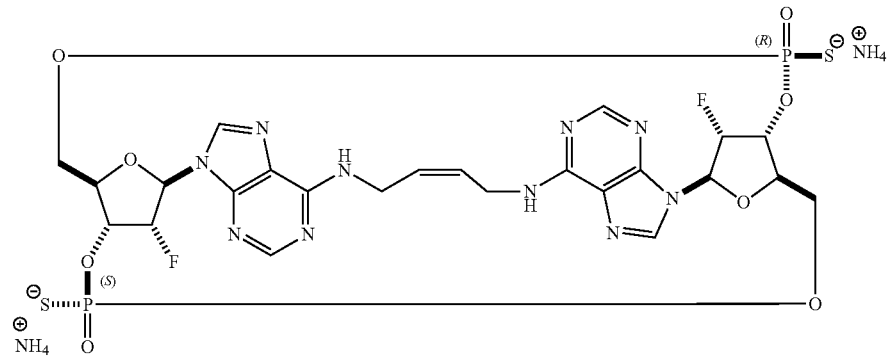

compound 5a

Compound 111 (Cis Isomer of Compound 107):

$^1$H NMR (400 MHz, CHLOROFORM-d) δ=8.48 (s, 1H), 8.15-8.09 (m, 1H), 8.03 (d, J=8.2 Hz, 1H), 7.94 (s, 1H), 7.75 (s, 1H), 7.65-7.06 (m, 11H), 6.07 (d, J=17.2 Hz, 1H), 5.98 (d, J=20.3 Hz, 1H), 5.97-5.79 (m, 1H), 5.84 (dd, J=3.5, 51.2 Hz, 1H), 5.54-5.47 (m, 1H), 5.50 (dd, J=3.9, 52.0 Hz, 1H), 5.38-5.21 (m, 2H), 5.18-5.02 (m, 2H), 5.02-4.95 (m, 1H), 4.78-4.69 (m, 1H), 4.60-4.16 (m, 10H)

Compound 5a (SpRp, cis of 1a): $^1$H NMR (400 MHz, METHANOL-d$_4$) δ=8.88 (br s, 1H), 8.51 (br s, 1H), 8.16 (s, 1H), 8.05 (s, 1H), 6.38 (d, J=15.6 Hz, 1H), 6.33 (d, J=14.1 Hz, 1H), 6.14-6.09 (m, 2H), 6.01 (d, J=49.2 Hz, 1H), 5.42 (d, J=49.6 Hz, 1H), 5.02-4.87 (m, 2H), 4.76-3.92 (m, 8H), 3.75-3.56 (m, 2H)

Example 6—Synthesis of Compound 6a (SpRp)

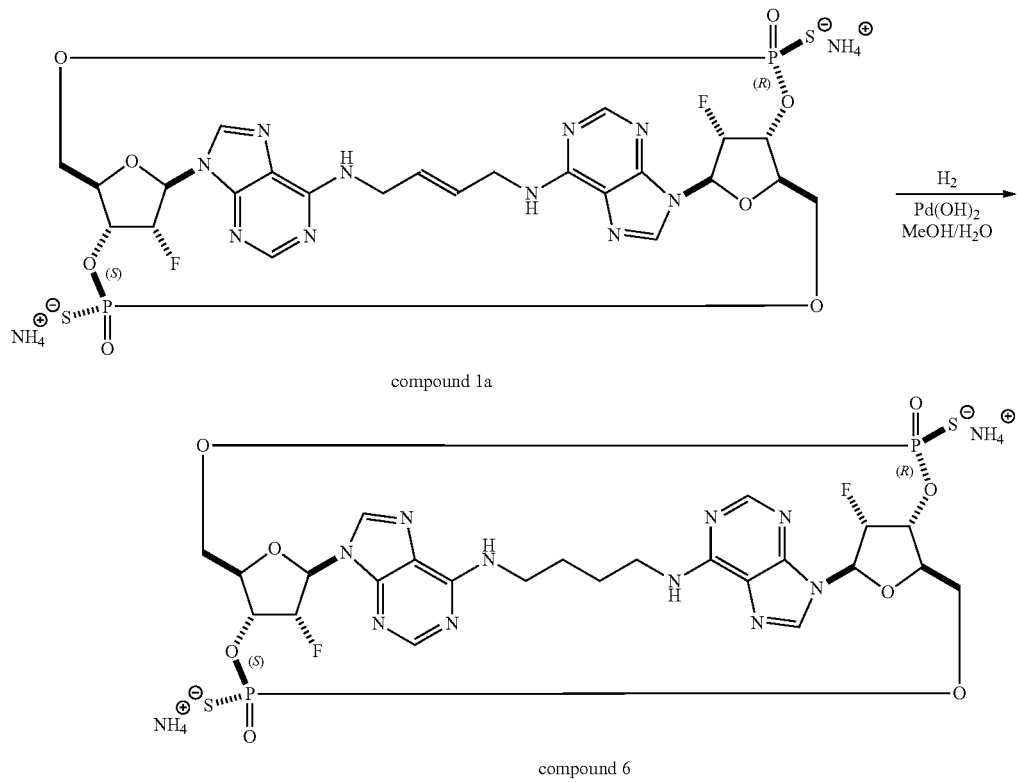

compound 1a compound 6

To a solution of compound 1a (1.5 mg, 2.0 µmol) in MeOH/H₂O (0.6/0.5 ml) at ambient temperature was added palladium hydroxide on carbon (20 wt. % dry basis, 2 mg). The resulting mixture was treated with hydrogen (balloon) while the reaction was monitored by LCMS. Upon complete consumption of the starting material, the mixture was filtered and rinsed with methanol until all product cleared out. The filtrate was concentrated in vacuo and the residue was dissolved water (1 ml). RHPLC purification provided compound 6a (0.9 mg).

LCMS (MS m/z 749.2 [M+H]⁺)

Example 7—Synthesis of Compound 9

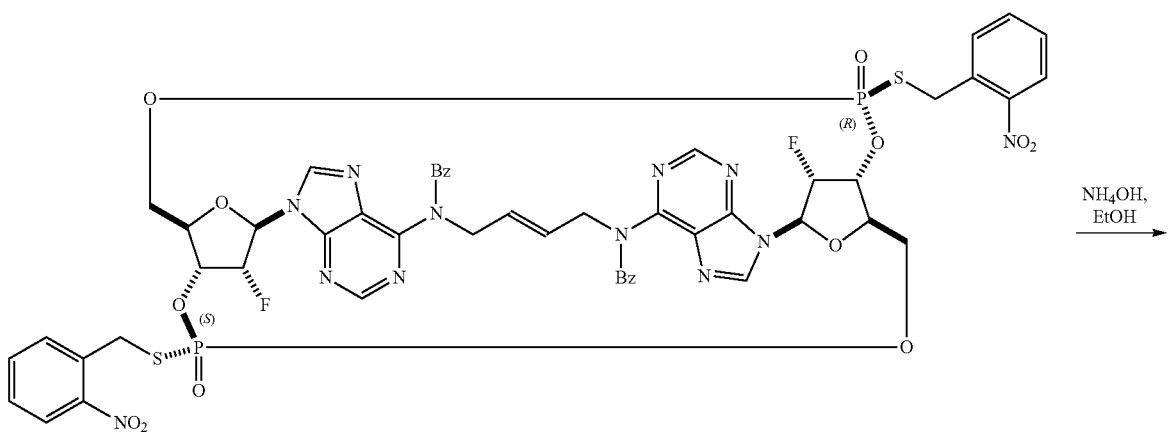

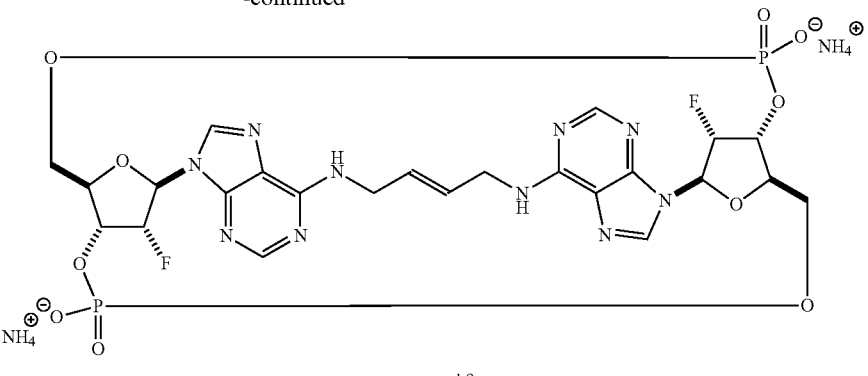

compound 9a

To a solution of 107 (3.7 mg, 3.02 µmol) in EtOH (1.5 mL) was added ammonium hydroxide (1 mL). The resulting mixture was heated at 50° C. for 8 h and cooled to ambient temperature. The solvent was removed under reduced pressure. The residue was treated with 2 mL water and the resulting solid was filtered off. The filtrate was subjected to preparative HPLC to give compound 9a (2.5 mg).

Compound 9a:

$^1$H NMR (400 MHz, METHANOL-$d_4$) δ=8.67 (br s, 1H), 8.50 (br s, 1H), 8.25 (br s, 1H), 8.12 (br s, 1H), 6.47-6.28 (m, 2H), 5.92-5.79 (m, 2H), 5.74 (d, J=50.8 Hz, 1H), 5.32 (d, J=52.4 Hz, 1H), 5.16-4.95 (m, 2H), 4.71-4.25 (m, 6H), 4.17-3.97 (m, 2H), 3.83-3.61 (m, 2H).

LCMS: MS m/z 715.2 [M+H]$^+$.

Example 8—Synthetic Routes for Compounds 8a, 11a and 12a

With Compound 112 and compound 102 as starting materials, compounds 8, 11 and 12 were prepared via the same reaction sequences as described in Example 1.

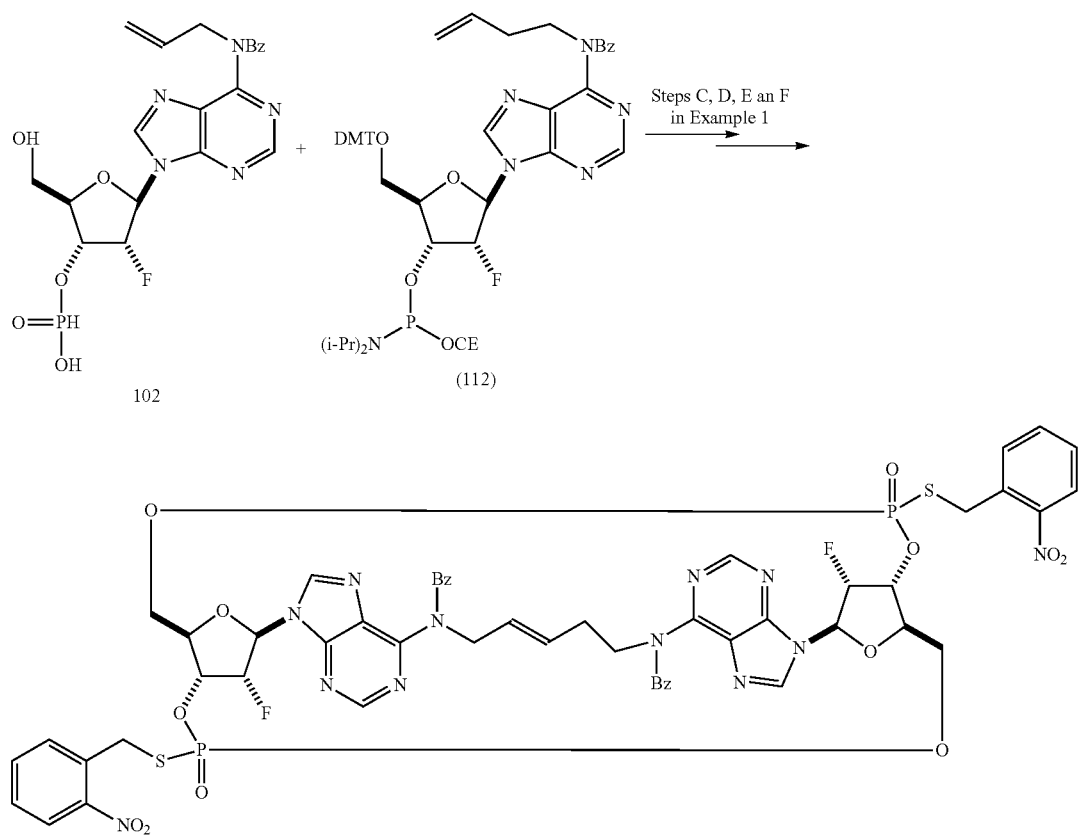

Mixture of four major isomers
Separated by preHPLC

-continued

Fraction A: retention time: 5.3 min
(1:1 mixture of two isomers)

a) PhSH, triethylamine
1,4-dioxane
⟶
b) NH₄OH, MeOH

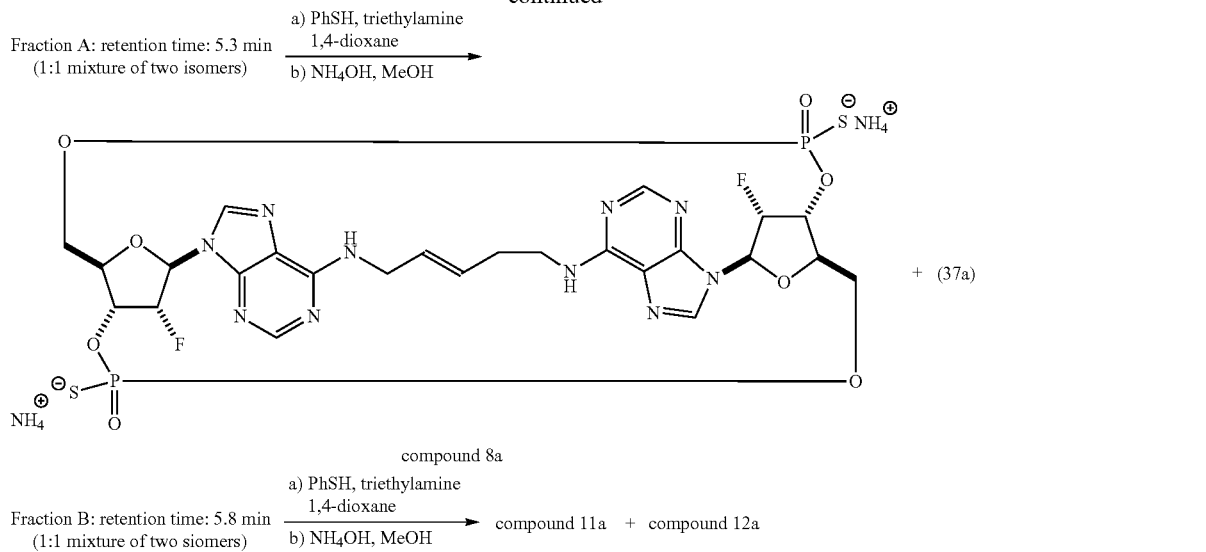

+ (37a)

compound 8a

Fraction B: retention time: 5.8 min
(1:1 mixture of two siomers)

a) PhSH, triethylamine
1,4-dioxane
⟶
b) NH₄OH, MeOH compound 11a + compound 12a

Preparative HPLC Conditions for Fractions A and B

| Instrument | Agilent 1200 |
|---|---|
| HPLC column | Waters Sunfire Prep C18 OBD column, 5 um, 19 × 100 mm, #186002567 |
| Flow rate | 20 ml/min |
| mobile phase | A: water, B: acetonitrile |
| Gradient Time (min) | 0   8   9.9   10   11 |
| B % | 40   99   99   40   40 |
| Run time | 12 min |
| Injection volume | 250 ul (0.03 g/ml in acetonitrile) |
| detection | UV 254 nm |
| Retention   Fraction A | 5.3 min |
| time          Fraction B | 5.8 min |

Compound 8a:

Fraction A was proceeded through Step G, Example 1 to give two isomers which were separated by HPLC. Compound 8a was a faster running isomer (retention time: 4.1 min) and Compound 37a (retention time: 4.5 min) was a slower-running isomer.

$^1$H NMR (400 MHz, METHANOL-$d_4$) δ=9.01 (s, 1H), 8.61 (s, 1H), 8.22 (s, 1H), 8.20 (s, 1H), 6.34 (d, J=10.2 Hz, 1H), 6.31 (d, J=10.9 Hz, 1H), 5.92 (dd, J=2.7, 51.2 Hz, 1H), 5.85-5.71 (m, 2H), 5.37 (d, J=51.6 Hz, 1H), 4.81-4.56 (m, 6H), 4.52 (br d, J=12.1 Hz, 1H), 4.42 (br d, J=9.4 Hz, 3H), 4.05 (dd, J=4.1, 11.9 Hz, 1H), 3.95 (br dd, J=4.3, 12.1 Hz, 1H), 3.94-3.84 (m, 1H), 3.62 (br dd, J=4.9, 15.4 Hz, 1H), 2.71-2.58 (m, 1H), 2.46-2.33 (m, 1H)

$^{31}$P NMR (162 MHz, METHANOL-$d_4$) δ=55.36 (s, 1P), 55.18 (s, 1P)

LCMS: MS m/z 761.2 [M+H]$^+$

Compound 37a:

$^1$H NMR (400 MHz, METHANOL-$d_4$) δ=8.95 (s, 1H), 8.40 (s, 1H), 8.18 (s, 1H), 8.15 (br s, 1H), 6.34 (d, J=5.5 Hz, 1H), 6.31 (d, J=6.6 Hz, 1H), 5.96-5.68 (m, 3H), 5.40 (dd, J=2.7, 51.6 Hz, 1H), 4.85 (s, 3H), 4.58 (br d, J=12.1 Hz, 1H), 4.49 (br d, J=12.1 Hz, 1H), 4.43-4.33 (m, 3H), 4.29 (dd, J=8.6, 14.1 Hz, 1H), 4.05 (dd, J=4.5, 11.9 Hz, 1H), 3.95 (dd, J=4.9, 12.3 Hz, 1H), 3.94-3.86 (m, 1H), 2.67-2.55 (m, 1H), 2.52-2.40 (m, 1H).

Compound 8a/37a Preparative HPLC Conditions:

| Instrument | Agilent 1200/1260 AS/FC |
|---|---|
| HPLC column | Waters XBridge C18, 10 × 100 mm, # 1413 |
| Flow rate | 4.0 ml/min |
| Column temperature | 35° C. |
| mobile phase | A: 0.1% NH₄OH in water, B: 0.1% NH₄OH in acetonitrile |
| Gradient (B %) | 0 → 50 |
| Run time | 20 min |
| Injection volume | 50 ul (4 mg/ml in water) |
| detection | UV 260 nm |
| Retention   Compound 8a | 4.1 min |
| time          Compound 37a | 4.5 min |

Fraction B was proceeded through Step G, Example 1 to give two isomers which were separated by prep-HPLC described below. Compound 11a is a faster running isomer (retention time: 11.2 min) and compound 12a is a slower running isomer (retention time: 12.1 min)

Compound 11a:

$^1$H NMR (400 MHz, METHANOL-$d_4$) δ=8.63 (br s, 2H), 8.18 (br s, 1H), 8.17 (br s, 1H), 6.34 (d, J=13.3 Hz, 1H), 6.32 (d, J=12.9 Hz, 1H), 5.86-5.65 (m, 2H), 5.48 (d, J=48.5 Hz, 1H), 5.35 (d, J=43.8 Hz, 1H), 4.84-4.53 (m, 6H), 4.47-4.36 (m, 2H), 4.05-3.91 (m, 2H), 3.96-3.85 (m, 1H), 3.70-3.54 (m, 1H), 2.66-2.54 (m, 1H), 2.43-2.30 (m, 1H)

Compound 12a:

$^1$H NMR (400 MHz, METHANOL-$d_4$) δ=8.56 (br s, 1H), 8.41 (s, 1H), 8.17 (s, 1H), 7.95 (br s, 1H), 6.35 (d, J=14.8 Hz, 1H), 6.31 (d, J=15.2 Hz, 1H), 5.82-5.65 (m, 2H), 5.50 (d, J=51.2 Hz, 1H), 5.36 (d, J=53.9 Hz, 1H), 4.74-4.33 (m, 8H), 4.26-4.16 (m, 1H), 4.07-3.93 (m, 3H), 2.64-2.44 (m, 2H).

Compound 11a/12a Preparative HPLC Conditions:

| Instrument | Agilent 1200/1260 AS/FC |
|---|---|
| HPLC column | Waters Xterra C18, 10 × 100 mm # 3128 |
| Flow rate | 3.0 ml/min |
| Column temperature | 35° C. |
| mobile phase | A: 0.1% formic acid in water, B: 0.1% formic acid in acetonitrile |

| | | |
|---|---|---|
| Gradient (B %) | | 0 → 30 |
| Run time | | 20 min |
| Injection volume | | 50 ul (2.5 mg/ml in water) |
| detection | | UV 260 nm |
| Retention | Compound 11a | 11.2 min |
| times | Compound 12a | 12.1 min |
Example 9—Synthetic Routes for Compound 13 and 14
With Compound 114 and Compound 115 as starting materials, Compounds 13 and 14 were prepared via the same reaction sequences as described in Example 1 plus TBS deprotection step.
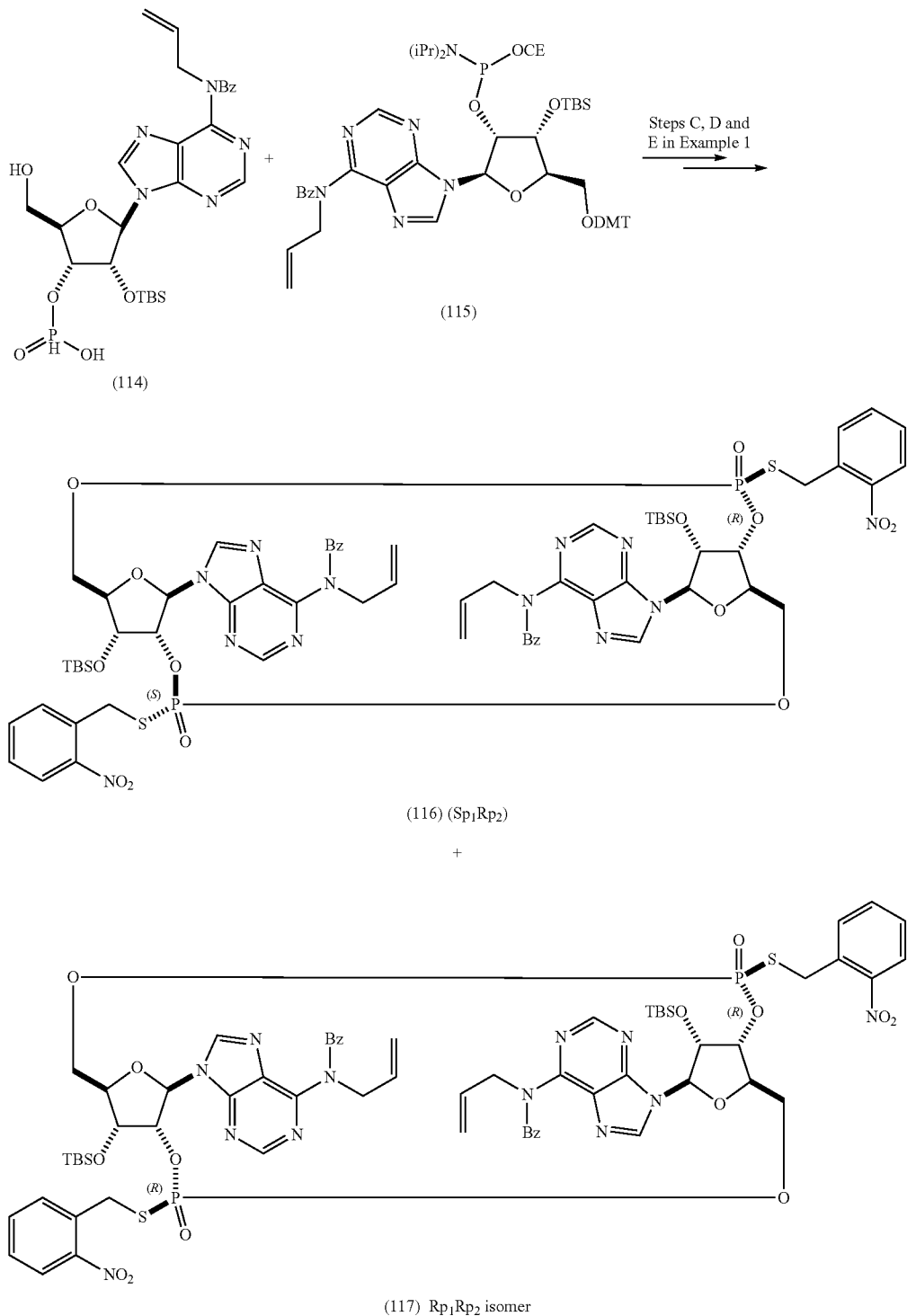

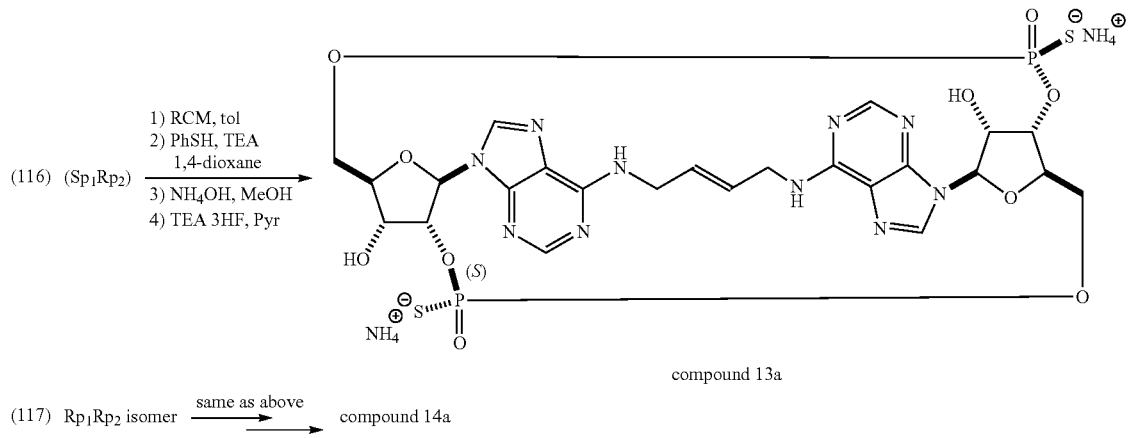

compound 13a (117) Rp₁Rp₂ isomer —same as above→ compound 14a

Compound 116:

$^1$H NMR (400 MHz, CHLOROFORM-d) δ=9.36 (s, 1H), 9.18 (s, 1H), 8.77 (s, 1H), 8.76 (s, 2H), 8.07 (br dd, J=1.8, 7.6 Hz, 3H), 8.05-8.00 (m, 2H), 7.99 (s, 1H), 7.87-7.82 (m, 1H), 7.70-7.65 (m, 1H), 7.63-7.55 (m, 3H), 7.55-7.41 (m, 6H), 7.39-7.35 (m, 1H), 7.30-7.26 (m, 1H), 6.37 (d, J=8.6 Hz, 1H), 5.89 (d, J=4.7 Hz, 1H), 5.36-5.27 (m, 2H), 5.15 (ddd, J=3.7, 8.4, 11.7 Hz, 1H), 4.64-4.43 (m, 4H), 4.43-4.38 (m, 1H), 4.37-4.30 (m, 1H), 4.23-4.13 (m, 2H), 4.11-3.98 (m, 2H), 3.97-3.86 (m, 1H), 0.97 (s, 9H), 0.83 (s, 9H), 0.25 (s, 3H), 0.18 (s, 3H), 0.16 (s, 3H), −0.13 (s, 3H).

Compound 13a:

$^1$H NMR (400 MHz, METHANOL-d₄) δ=8.78 (br s, 1H), 8.47 (br s, 1H), 8.21 (br s, 1H), 8.08 (br s, 1H), 6.44-6.21 (m, 1H), 6.19-6.03 (m, 1H), 6.01-5.78 (m, 2H), 5.38-4.95 (m, 2H), 4.67-4.45 (m, 5H), 4.45-4.35 (m, 1H), 4.34-4.29 (m, 1H), 4.25 (br d, J=11.3 Hz, 1H), 4.18-3.89 (m, 2H), 3.88-3.54 (m, 2H).

$^{31}$P NMR (162 MHz, METHANOL-d₄) δ=56.89 (br s, 1P), 56.37 (br s, 1P)

Compound 117 (Rp₁Rp₂ Isomer of Compound 116):

$^1$H NMR (400 MHz, CHLOROFORM-d) δ=9.36 (br s, 1H), 9.11 (br s, 1H), 8.98 (s, 1H), 8.87 (s, 1H), 8.78 (s, 1H), 8.14-7.96 (m, 6H), 7.72-7.27 (m, 13H), 6.44 (d, J=8.6 Hz, 1H), 5.84 (d, J=6.6 Hz, 1H), 5.59-5.50 (m, 1H), 5.48-5.44 (m, 1H), 5.33-5.24 (m, 1H), 4.75-3.85 (m, 11H), 0.90 (s, 9H), 0.79 (s, 9H), 0.20 (s, 3H), 0.11 (s, 3H), 0.07 (s, 3H), −0.21 (s, 3H)

Compound 14a (Rp₁Rp₂ Isomer of Compound 13a)

LCMS: MS m/z 743.17 [M+H]⁺

Example 10—Synthetic Routes for Compound 15 and 16

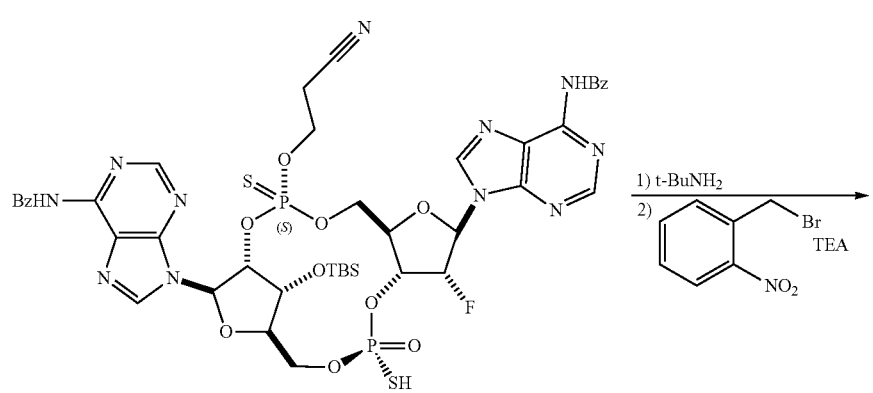

compound A (SR isomer)

-continued
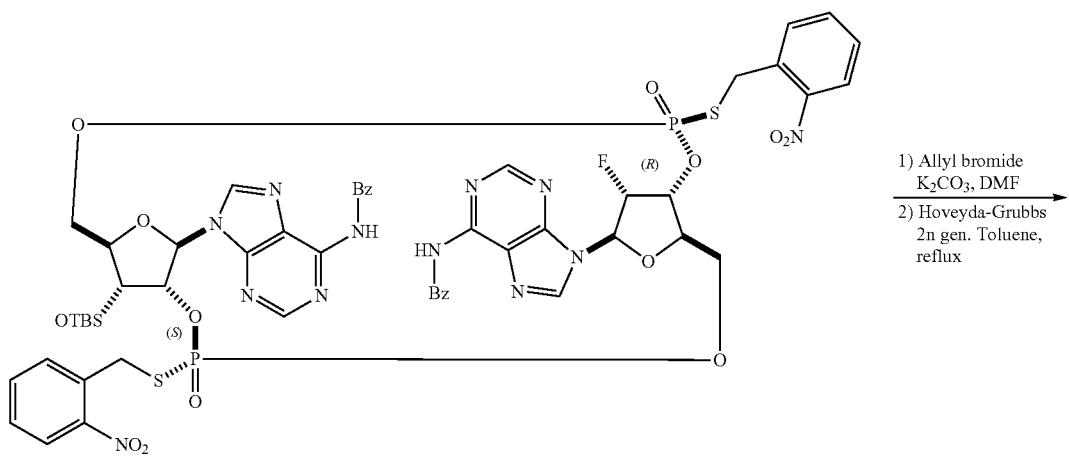
(118)
1) Allyl bromide K$_2$CO$_3$, DMF
2) Hoveyda-Grubbs 2n gen. Toluene, reflux
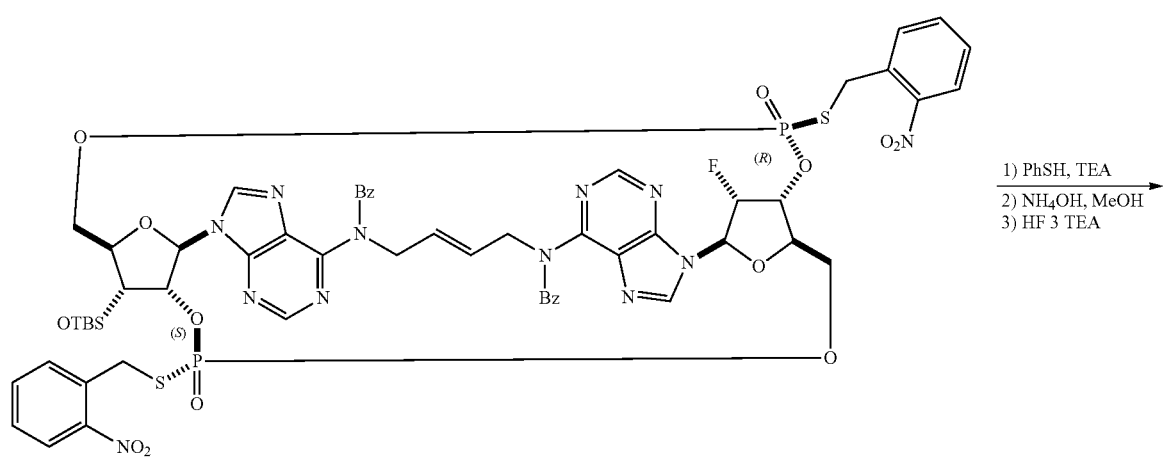
(119)
1) PhSH, TEA
2) NH$_4$OH, MeOH
3) HF 3 TEA
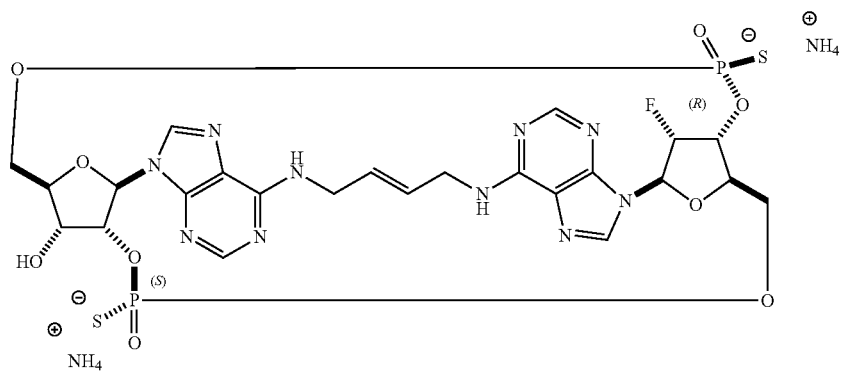
compound 15

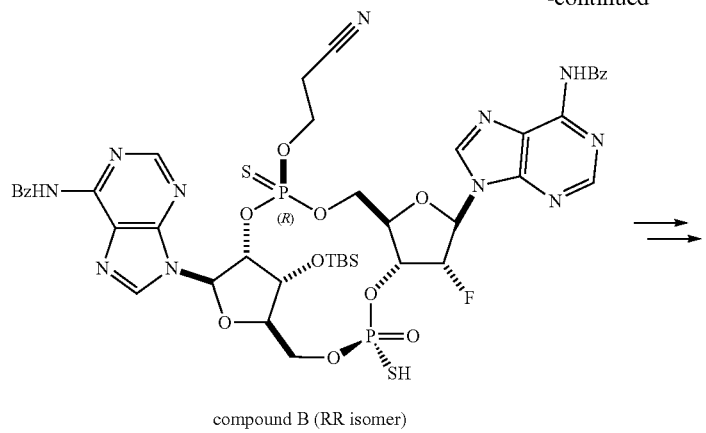

compound B (RR isomer)

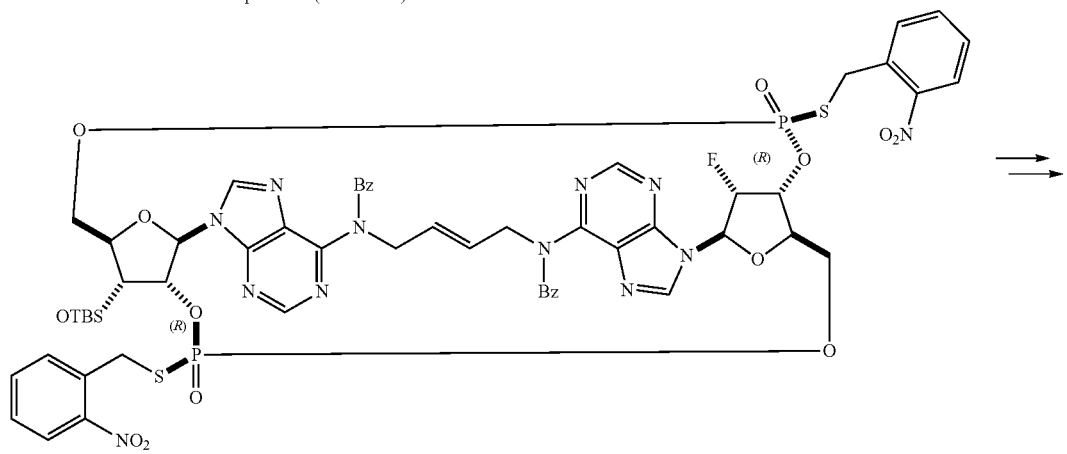

(120)

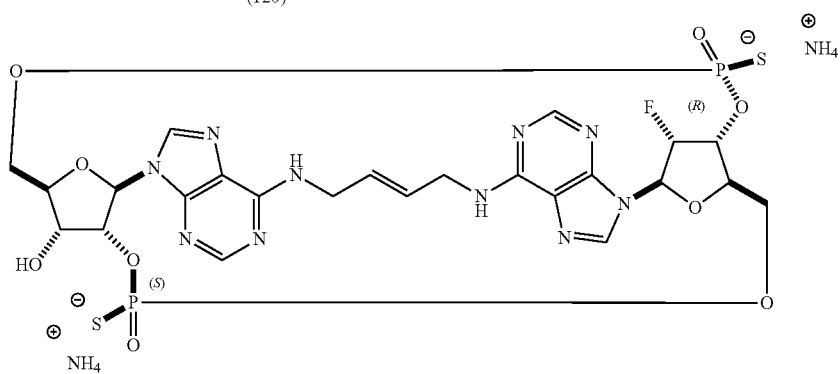

compound 16

To a solution of compound A (2.63 g, 2.46 mmol) in MeCN (26.3 ml) was added tert-butylamine (13.15 ml, 124.1 mmol). After stirred for 1 h at ambient temperature, the reaction mixture was concentrated in vacuo and azeotroped with MeCN. The residue was dissolved in MeCN (52.6 ml) and treated with 1-(bromomethyl)-2-nitrobenzene (1.064 g, 4.925 mmol) and triethylamine (0.755 ml, 5.42 mmol). Upon complete reaction (monitored by LC/MS), the reaction mixture was concentrated in vacuo and purified by silica gel column chromatography (66% ethyl acetate/n-heptane to 100% ethyl acetate) to give 0.226 g of Compound 118. The isolated product was dissolved in DMF (5 mL) and allyl bromide (0.046 ml, 0.528 mmol) and potassium carbonate (0.073 g, 0.528 mmol) were added. The resulting mixture was stirred at ambient temperature while the progress was monitored by LCMS. After 19 h, 1/1 mixture of MTBE/EtOAc (12/12 mL), a saturated aqueous NH$_4$Cl solution (15 ml), and water (10 mL) were added. The organic layer was separated out, washed with brine (5 mL) twice, dried over MgSO$_4$ and concentrated in vacuo. The residue was purified by silica gel column chromatography (50% ethyl acetate/n-heptane to 100% ethyl acetate) to give 37 mg of bis-allylated product. The isolated product (37 mg, 0.027 mmol) was dissolved in toluene (55 mL) and heated to mild reflux (120-125° C. oil bath). A solution of Hoveyda-Grubbs Catalyst 2nd Generation ((1,3-Bis-(2,4,6-trimethylphenyl)-2-imidazolidinylidene)dichloro(o-isopropoxy-phenylmethylene)ruthenium; available at SIGMA-ALDRITCH® Catalog No. 569755; CAS 301224-40-8; 8.5 mg, 0.014 mmol) and quinone (5.9 mg, 0.054 mmol) in toluene (10 mL) was added. The mixture was heated to reflux and reaction progress was monitored by LC/MS. Upon complete consumption of the starting material, the mixture was cooled down to ambient temperature and treated with DMSO (0.059 ml, 0.81 mmol) for 15 hours. The resulting mixture was concentrated in vacuo and purified by silica gel column chromatography (SiO$_2$ 10 g, 66% ethyl acetate in n-heptane to 100% ethyl acetate) to give Compound 119 (2.2 mg).

Compound 119:
$^1$H NMR (400 MHz, CHLOROFORM-d) δ=8.49 (s, 1H), 8.12 (d, J=7.8 Hz, 1H), 8.05-8.02 (m, 1H), 8.02 (s, 1H), 7.82 (s, 1H), 7.70-7.10 (m, 17H), 6.27 (d, J=16.8 Hz, 1H), 6.15-6.05 (m, 1H), 5.97 (d, J=8.2 Hz, 1H), 5.94-5.72 (m, 3H), 4.94 (br s, 2H), 4.86-4.69 (m, 2H), 4.67-4.60 (m, 1H), 4.60-4.44 (m, 4H), 4.39-4.33 (m, 1H), 4.31-4.10 (m, 6H), 0.96 (s, 9H), 0.25 (s, 3H), 0.19 (s, 3H)

Compound 119 was proceeded through Step G in Example 1 followed by TBS deprotection with TEA 3HF to give compound 15a.

Compound 15a:
$^1$H NMR (400 MHz, METHANOL-d$_4$) δ=8.76 (br s, 1H), 8.44 (br s, 1H), 8.24 (br s, 1H), 8.07 (br s, 1H), 6.45-6.19 (m, 2H), 6.12-5.75 (m, 2H), 5.54 (br d, J=51.6 Hz, 1H), 5.67-5.06 (m, 2H), 4.66-4.37 (m, 3H), 4.47-4.37 (m, 1H), 4.36-4.22 (m, 2H), 4.17-3.94 (m, 2H), 3.94-3.80 (m, 1H) 3.80-3.59 (m, 2H)

Compound 16 was obtained from compound B (RR isomer of compound A) via the same sequences as described in compound 15.

Compound 120 (Rp$_1$Rp$_2$ Isomer of Compound 119):
$^1$H NMR (400 MHz, CHLOROFORM-d) δ=8.89 (s, 1H), 8.10 (d, J=8.2 Hz, 1H), 8.01 (d, J=8.2 Hz, 1H), 7.85-7.74 (m, 4H), 7.69-7.61 (m, 2H), 7.58 (s, 1H), 7.55-7.48 (m, 1H), 7.45-7.30 (m, 6H), 7.22-7.15 (m, 1H), 7.13-7.04 (m, 3H), 6.76-6.68 (m, 1H), 6.31-6.22 (m, 1H), 6.22 (d, J=16.0 Hz, 1H), 6.12-5.99 (m, 2H), 5.94 (d, J=8.2 Hz, 1H), 5.92-5.81 (m, 1H), 5.67 (dd, J=3.5, 51.2 Hz, 1H), 5.08-4.93 (m, 2H), 4.87-4.77 (m, 1H), 4.60-4.22 (m, 8H), 4.21-4.16 (m, 1H), 4.11-4.02 (m, 1H), 3.94 (br d, J=11.7 Hz, 1H), 3.66 (dd, J=4.7, 11.3 Hz, 1H), 0.90 (s, 9H), 0.09 (s, 3H), 0.08 (s, 3H)

Compound 16a:
$^1$H NMR (400 MHz, METHANOL-d$_4$) δ=8.54 (br s, 1H), 8.24 (br s, 1H), 8.17 (br s, 1H), 8.08 (br s, 1H), 6.44-6.23 (m, 2H), 6.07-5.68 (m, 2H), 5.43 (d, J=50.4 Hz, 1H), 5.31-5.05 (m, 2H), 4.69-4.26 (m, 6H), 4.19-3.90 (m, 2H), 3.90-3.57 (m, 3H)

Example 11—Synthetic Routes of Compounds Adenine/Guanine (A/G) Analogs—Compound 21, Compound 22, and Compound 23

With Compound 121 and Compound 101 as starting materials, adenine/guanine analogs were prepared via the same reaction sequences as described in Example 1.

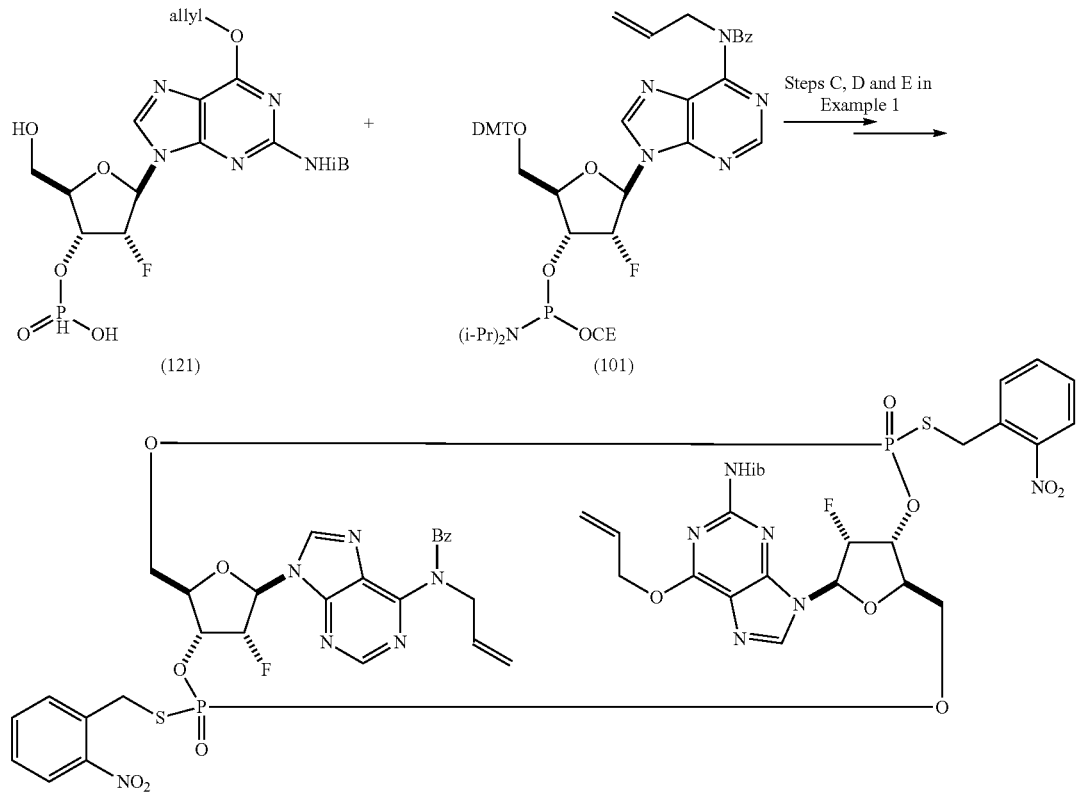

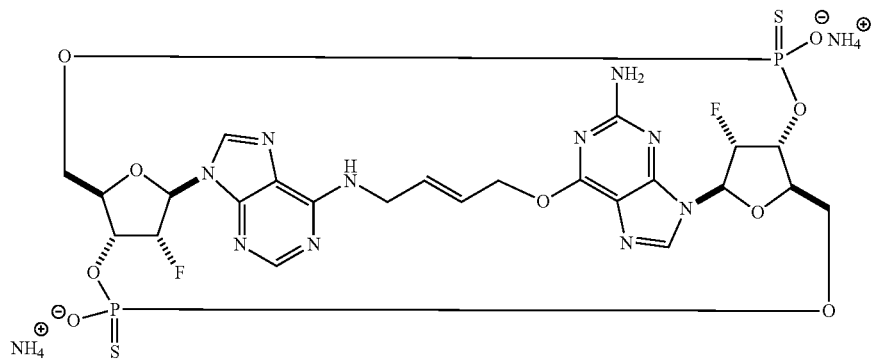

21a

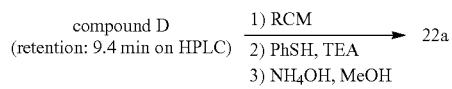

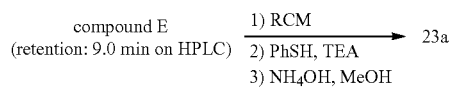

Preparative HPLC Conditions for Separation of Compounds C, D and E

| | | | | | | |
|---|---|---|---|---|---|---|
| Instrument | | Agilent 1100 | | | | |
| HPLC column | | Waters Sunfire Prep C18 OBD column, 5 um, 19 × 100 mm, #186002567 | | | | |
| Flow rate | | 12 ml/min | | | | |
| mobile phase | | A: water, B: acetonitrile | | | | |
| Gradient | Time (min) | 0 | 13 | 14.5 | 14.51 | 16 |
| | B % | 40 | 99 | 99 | 40 | 40 |
| Run time | | 16 min | | | | |
| Injection volume | | 150 ul (0.027 g/ml in acetonitrile) | | | | |
| detection | | UV 254 nm | | | | |
| Retention time | Compound C | 9.9 min | | | | |
| | Compound D | 9.4 min | | | | |
| | Compound E | 9.0 min | | | | |

Compound D: $^1$H NMR (400 MHz, CHLOROFORM-d) δ=8.60 (s, 1H), 8.27 (s, 1H), 8.04-8.01 (m, 1H), 8.01 (s, 1H), 7.99-7.95 (m, 1H), 7.80 (s, 1H), 7.63-7.51 (m, 5H), 7.46-7.41 (m, 1H), 7.39-7.30 (m, 3H), 7.25-7.20 (m, 2H), 6.96-6.84 (m, 1H), 6.19-5.99 (m, 4H), 5.67 (dd, J=4.3, 52.3 Hz, 1H), 5.47 (dd, J=1.4, 17.4 Hz, 1H), 5.36-5.24 (m, 4H), 5.14-5.09 (m, 1H), 5.08 (d, J=5.5 Hz, 2H), 5.04-4.98 (m, 2H), 4.51-4.30 (m, 10H), 4.21-4.13 (m, 1H), 2.83-2.67 (m, 1H), 1.16 (d, J=7.0 Hz, 3H), 1.14 (d, J=6.6 Hz, 3H)

Compound D was proceeded through Steps F and G, Example 1 to give Compound 22.

Compound 22:

LCMS: MS m/z 763.07 [M+H]$^+$

Compound C: $^1$H NMR (400 MHz, CHLOROFORM-d) δ=9.08 (s, 1H), 8.60 (s, 1H), 8.07-8.02 (m, 2H), 8.02 (s, 1H), 7.80 (s, 1H), 7.55-7.30 (m, 9H), 7.24-7.19 (m, 2H), 6.58-6.45 (m, 1H), 6.23-5.97 (m, 4H), 5.97-5.86 (m, 1H), 5.63-5.57 (m, 1H), 5.54-5.47 (m, 1H), 5.48-5.44 (m, 1H), 5.35-5.30 (m, 1H), 5.29-5.22 (m, 1H), 5.18-5.13 (m, 2H), 5.11-5.07 (m, 1H), 5.02-4.97 (m, 2H), 4.51-4.22 (m, 9H), 4.14-4.07 (m, 1H), 2.99-2.85 (m, 1H), 1.20 (d, J=6.6 Hz, 3H), 1.17 (d, J=7.0 Hz, 3H)

Compound C was proceeded through Steps F and G in Example 1 to give Compound 21

Compound 21:

LCMS: MS m/z 763.13 [M+H]$^+$

Compound E: $^1$H NMR (400 MHz, CHLOROFORM-d) δ=8.99 (s, 1H), 8.57 (s, 1H), 8.02-7.94 (m, 2H), 7.93 (s, 1H), 7.82 (s, 1H), 7.68-7.63 (m, 1H), 7.60-7.55 (m, 1H), 7.54-7.49 (m, 2H), 7.45-7.31 (m, 5H), 7.25-7.21 (m, 2H), 6.22-5.94 (m, 6H), 5.56 (br dd, J=5.1, 51.5 Hz, 1H), 5.54-5.46 (m, 1H), 5.34-5.29 (m, 1H), 5.29-5.22 (m, 2H), 5.16-5.08 (m, 3H), 5.02-4.96 (m, 2H), 4.62-4.54 (m, 1H), 4.52-4.26 (m, 9H), 2.93-2.81 (m, 1H), 1.21 (d, J=2.3 Hz, 3H), 1.20 (d, J=2.0 Hz, 3H)

Compound E was proceeded through Steps F and G in Example 1 to give Compound 23

Compound 23:

LCMS: MS m/z 763.18 [M+H]$^+$

Example 12—Synthesis of Compound 24

With compound F, Compound 24a was prepared via the same reaction sequences as described in Example 1.

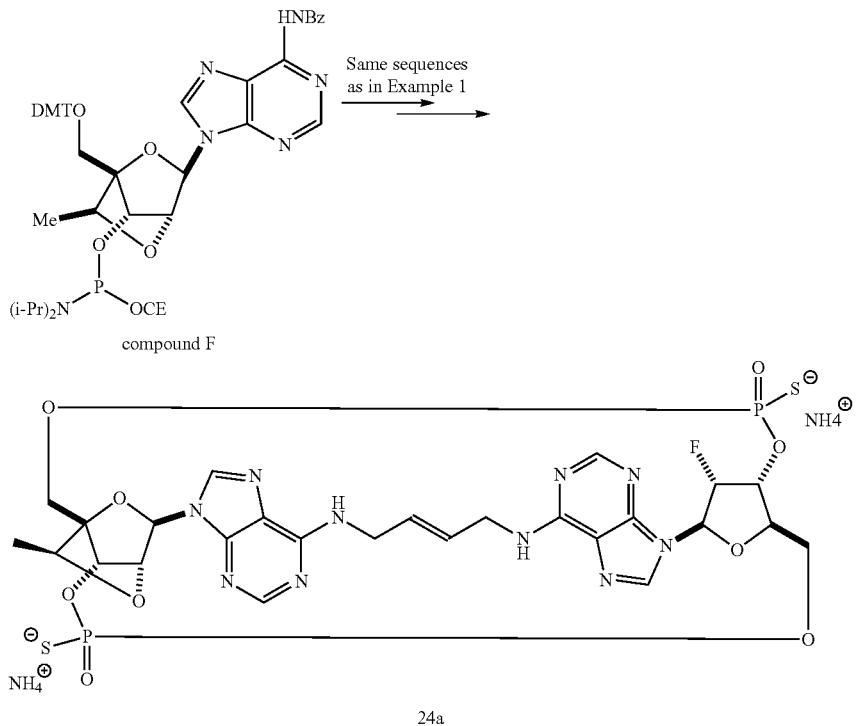

Compound 24:

$^1$H NMR (400 MHz, METHANOL-$d_4$) δ=8.95 (br s, 1H), 8.29 (br s, 1H), 8.23 (br s, 1H), 8.08 (br s, 1H), 6.31 (br d, J=12.9 Hz, 2H), 6.23-6.07 (m, 1H), 6.04-5.84 (m, 2H), 5.71 (br d, J=50.8 Hz, 1H), 5.27-4.32 (m, 7H), 4.27-4.16 (m, 1H), 4.12 (dd, J=5.7, 11.9 Hz, 1H), 4.07-3.98 (m, 1H), 3.78-3.62 (m, 2H), 1.40 (d, J=7.0 Hz, 3H)

Example 13—Synthesis of Compound 18, Compound 19, and Compound 20

A route for this synthesis is shown in FIG. 3.

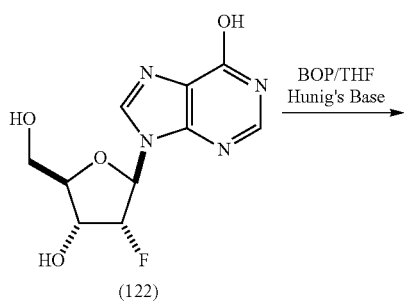

(122)

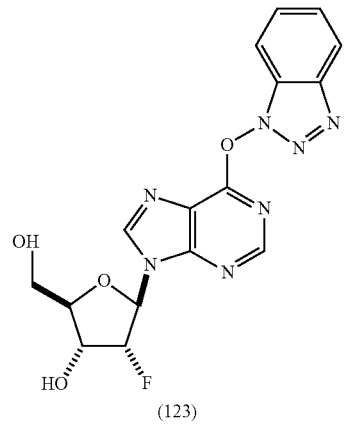

(123)

To a solution of 9-((2R,3R,4R,5R)-3-fluoro-4-hydroxy-5-(hydroxymethyl)tetrahydrofuran-2-yl)-9H-purin-6-ol (100 mg, 0.37 mmol) and Hunig's Base (0.129 ml, 0.74 mmol) in DMF (1 ml) was added BOP (327 mg, 0.74 mmol) at 20° C. The mixture was stirred at 20° C. overnight. UPLC-MS indicated that the reaction was completed. Solvent was removed on highvac rotavapor. The residue was dissolved in DCM and purified using Biotage (24 g Si-gel column, EtOAc in Heptane=0 to 100%, 10 vol, 100%, 10 vol) to afford 105 mg of the BOP adduct at 73% of yield. $^1$H NMR (400 MHz, METHANOL-d$_4$) δ ppm 3.74-3.84 (m, 1H) 3.92-4.00 (m, 1H) 4.12-4.19 (m, 1H) 4.62-4.74 (m, 1H) 5.37-5.57 (m, 1H) 6.41-6.52 (m, 1H) 7.47-7.55 (m, 1H) 7.57-7.64 (m, 2H) 8.03-8.14 (m, 1H) 8.36-8.46 (m, 1H) 8.86 (s, 1H)

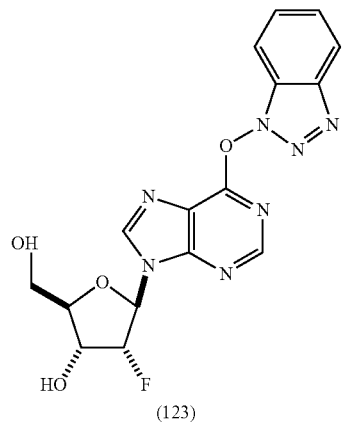

(123)

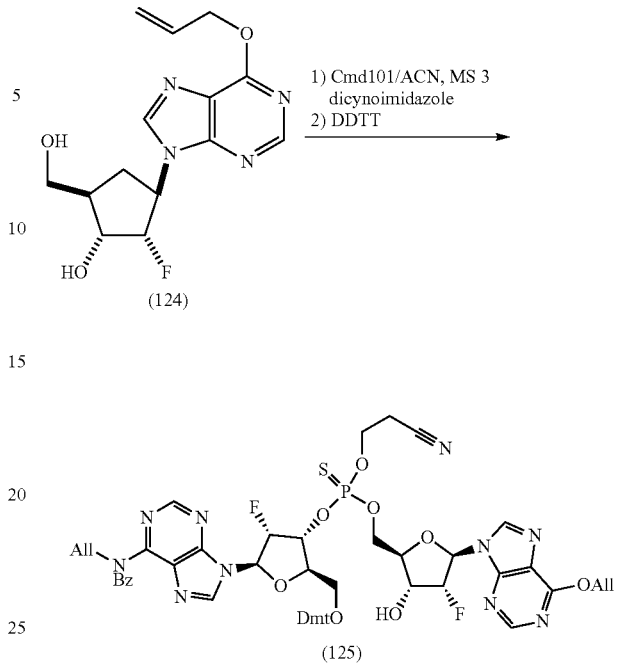

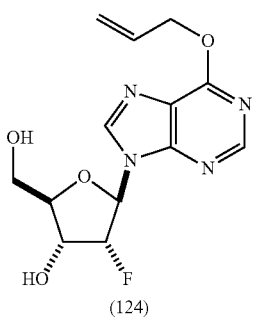

(124)

To a solution of (2R,3R,4R,5R)-5-(6-((1H-benzo[d][1,2,3]triazol-1-yl)oxy)-9H-purin-9-yl)-4-fluoro-2-(hydroxymethyl)tetrahydrofuran-3-ol (135 mg, 0.349 mmol) in allyl alcohol (3 ml) was added cesium carbonate (500 mg, 1.535 mmol) at 20° C. The mixture was stirred at 20° C. for 1 hr. UPLC-MS indicated that the reaction was completed. The reaction was worked up with sat. NaHCO$_3$/brine and extracted with EtOAc/Hept. The organic layer was dried over Na$_2$SO$_4$ and filtered. The solvent and volatile organics in the filtrate were removed on rotavapor. The residue was purified using Biotage (12 g Si-gel column, EtOAc in Heptane=0 to 100%, 10 vol, 100%, 10 vol) to afford 100 mg of desired allyl adduct at 92% of yield.

$^1$H NMR (400 MHz, METHANOL-d$_4$) δ ppm 8.56 (s, 1H) 8.47 (s, 1H) 6.29-6.41 (m, 1H) 6.06-6.21 (m, 1H) 5.33-5.53 (m, 2H) 5.22-5.31 (m, 1H) 5.02-5.14 (m, 2H) 4.56-4.71 (m, 1H) 4.10-4.18 (m, 1H) 3.88-3.96 (m, 1H) 3.70-3.79 (m, 1H)

To a solution of diisopropylphosphoramidite (150 mg, 0.164 mmol) and (2R,3R,4R,5R)-5-(6-(allyloxy)-9H-purin-9-yl)-4-fluoro-2-(hydroxymethyl)tetrahydrofuran-3-ol (76 mg, 0.246 mmol) in acetonitrile (1069 μl, 20.47 mmol) was added—molecular sieves (3 A, 150 mg) at 20° C. The mixture was stirred at 20° C. for 1 hr before 1H-Imidazole-4,5-dicarbonitrile (38.7 mg, 0.328 mmol) was added. at RT. The mixture was stirred at RT for 1 hr. UPLC-MS indicated that the reaction was completed. (E)-N,N-dimethyl-N'-(3-thioxo-3H-1,2,4-dithiazol-5-yl)formimidamide (37.0 mg, 0.18 mmol) was added. UPLC-MS indicated that sulfurization was completed in 30 min. The reaction was worked up with sat. NaHCO$_3$/brine and extracted with EtOAc/Hept. The organic layer was dried over Na$_2$SO$_4$ and filtered. The solvent and volatile organics in the filtrate were removed on rotavapor. The residue was purified using Biotage (25 g Si-gel column, EtOAc in Heptane=0 to 100%, 15 vol, 100%, 10 vol).

$^1$H NMR (500 MHz, METHANOL-d$_4$, two diastereomers ~1:1) δ ppm 8.62-8.63 (m, 1H) 8.57-8.58 (m, 1H) 8.48-8.50 (m, 1H) 8.44-8.46 (m, 1H) 8.40-8.41 (m, 1H) 8.38-8.39 (m, 1H) 8.33-8.35 (m, 1H) 8.25-8.27 (m, 1H) 7.22-7.33 (m, 11H) 7.11-7.20 (m, 17H) 7.05-7.11 (m, 4H) 6.83-6.92 (m, 6H) 6.65-6.77 (m, 11H) 6.28-6.41 (m, 5H) 6.23-6.28 (m, 2H) 6.10-6.22 (m, 5H) 6.00-6.10 (m, 4H) 5.89-6.00 (m, 5H) 5.52-5.57 (m, 2H) 5.45-5.52 (m, 3H) 5.41-5.45 (m, 1H) 5.24-5.34 (m, 4H) 5.13-5.17 (m, 3H) 5.07-5.12 (m, 5H) 4.93-4.98 (m, 4H) 4.88-4.93 (m, 5H) 4.73-4.82 (m, 3H) 4.50-4.59 (m, 2H) 4.36-4.48 (m, 4H) 4.27-4.36 (m, 5H) 4.16-4.27 (m, 5H) 3.83-4.04 (m, 5H) 3.73-3.78 (m, 13H) 3.64-3.73 (m, 4H) 3.52-3.58 (m, 1H) 3.45-3.51 (m, 2H) 3.35-3.41 (m, 2H) 3.16-3.23 (m, 2H) 3.08-3.15 (m, 2H) 2.84-2.93 (m, 2H) 2.79-2.83 (m, 2H) 2.70-2.77 (m, 2H) 2.61-2.69 (m, 3H)

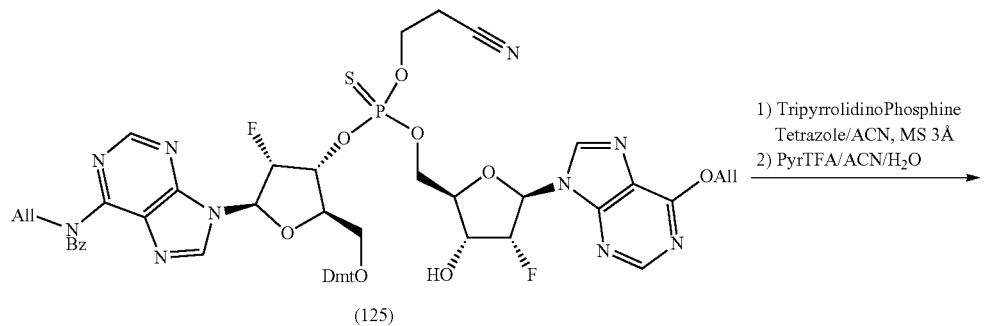

(125)

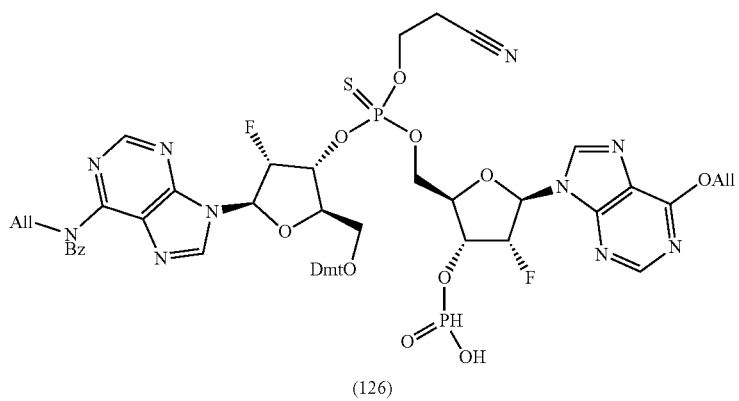

(126)

To a solution of O-((2R,3R,4R,5R)-5-(6-(N-allylbenzamido)-9H-purin-9-yl)-2-((bis(4-methoxyphenyl)(phenyl)methoxy)methyl)-4-fluorotetrahydrofuran-3-yl) O-(((2R,3R,4R,5R)-5-(6-(allyloxy)-9H-purin-9-yl)-4-fluoro-3-hydroxytetrahydrofuran-2-yl)methyl) O-(2-cyanoethyl) phosphorothioate (120 mg, 0.104 mmol) in acetonitrile (4171 µl, 79.852 mmol) was added molecular sieves (3A, 1 wt) at 20° C. The mixture was stirred at 20° C. for 1 hr before Tripyrrolidinophosphine (71.6 µl, 0.311 mmol) was added. 0.45 M Tetrazole in ACN (253 µl, 0.114 mmol) was then added in 7 portions, at 2 min interval. TLC (EtOAc/Hept=2:1, RfSM=0.7, RfProd=0.0 to 0.6) was incomplete. 2× of the phosphorylationg reagent and terazole were added. The reaction mixture was stirred at RT for 10 min. Neither UPLC-MS nor TLC indicated any SM left. The reaction mixture was transferred into a flask containing acetonitrile (20.8 ml), water (104 µl, 5.776 mmol) and pyridine trifluoroacetate salt (421 mg, 2.178 mmol). The mixture was stirred for 10 min. UPLC-MS indicated the desired product was formed. The reaction mixture was mixed with EtOAc and washed with HCl [0.1N]/brine and then sat. NaHCO₃/Brine to prevent DMT deprotection. The aqueous layer was back extracted with EtOAc (1×). The combined organic layer was dried over Na₂SO₄ and then filtered. Solvents and volatiles in the filtrate were removed on rotavapor to afford the crude product which was used for the next step without further purification.

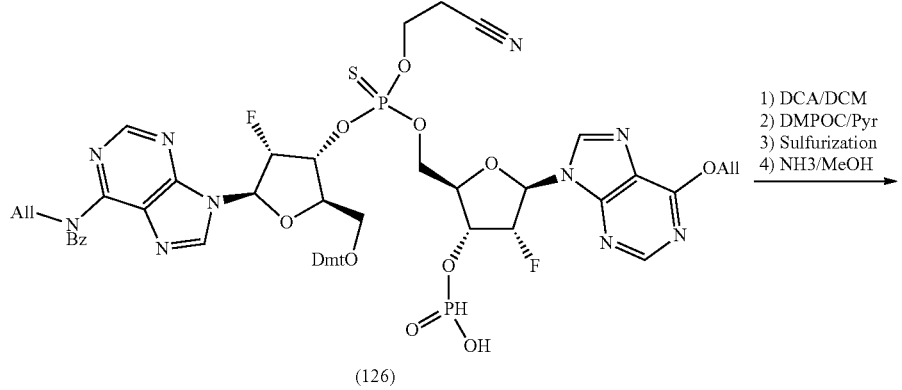

(126)

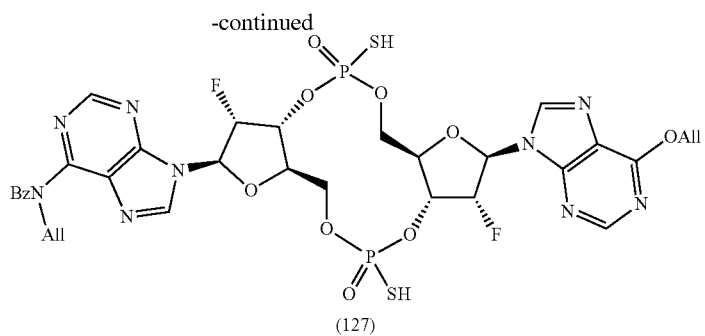
(127)

The crude hydrogen phosphonate intermediate was dissolved in DCM (2635 μl, 40.946 mmol) and water (29.5 μl, 1.638 mmol) before Dichloroacetic acid (135 μl, 1.638 mmol) in DCM (2635 μl, 40.946 mmol) was added at 20° C. The mixture was stirred at 20° C. for 5 min. UPLC-MS indicated that the reaction was completed. The reaction was neutralized with pyridine (510 μl, 6.308 mmol). The volatiles were removed on rotavapor and then highvac rotavapor. The residue was azeotroped with pyridine one more time before used for cyclization.

The crude DMT deprotected hydrogen phosphonate (80 mg, 0.087 mmol) was dissolved in pyridine (1831 μl, 22.639 mmol) before 2-chloro-5,5-dimethyl-1,3,2-dioxaphosphinane 2-oxide (48.2 mg, 0.261 mmol) was added at RT. The mixture was stirred at RT for 10 min. UPLC showed no SM peak at 2.1 min. The reaction was quenched by addition of water (47.1 μl, 2.612 mmol) followed by the immediate addition of 3H-benzo[c][1,2]dithiol-3-one (21.97 mg, 0.131 mmol). After 10 min, UPLC showed no starting material left. The reaction was stirred at RT for 1 hr. No change was found on UPLC-MS. The reaction mixture was diluted with EtOAc and washed with sat. NaHCO₃ and brine. The organic layer was dried over Na₂SO before filtered. The residue after solvent evaporation was dissolved in MeOH before NH₃—H₂O was added. The mixture was stirred for 5 min before all the solvent and volatiles were removed on rotavapor and highvac rotavapor.

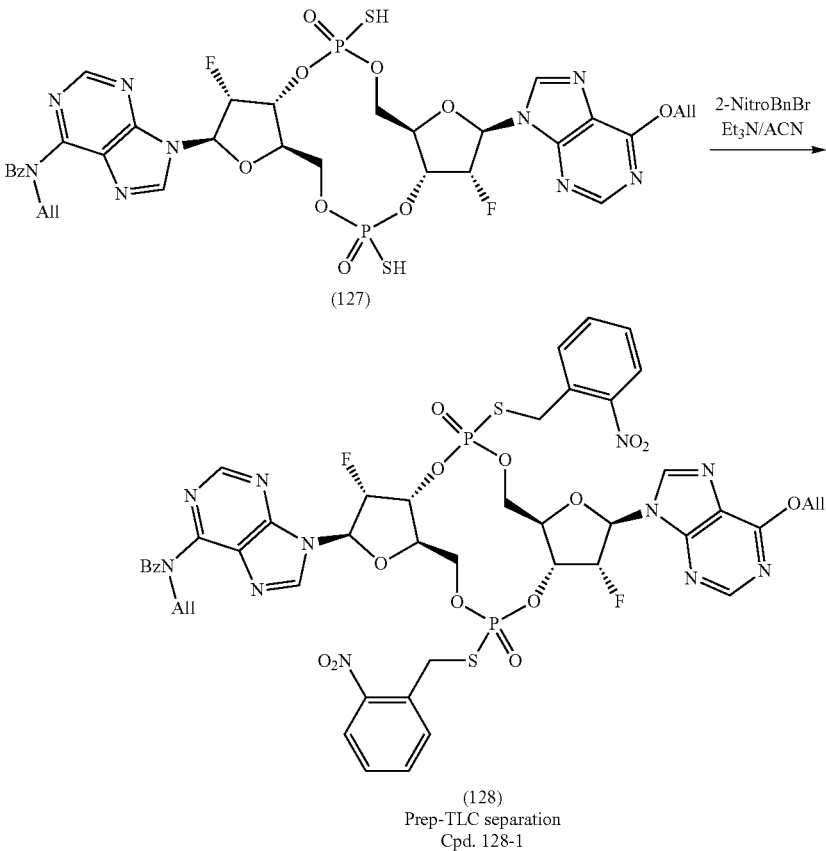

(128)
Prep-TLC separation
Cpd. 128-1

1) 100% EtOAc separate most polar product to
2) 50% EtOAc in DCM (3X) to separate top two products:
   More polar product to Cpd. 128-2, Less polar product to Cpd. 128-3

The CDN intermediate was dissolved in in acetonitrile (1484 μl, 28.417 mmol) and 1,4-dioxane (496 μl, 5.797 mmol) before TEA (39.6 μl, 0.284 mmol) and 1-(bromomethyl)-2-nitrobenzene (49.1 mg, 0.227 mmol) was added at 20° C. The mixture was stirred at 20° C. for 16 hr. UPLC-MS indicated that the reaction was incomplete. Neither TLC (EtOAc) nor HPLC indicated any o-nitrobenzyl bromide left. 1-(bromomethyl)-2-nitrobenzene (49.1 mg, 0.227 mmol) and TEA (39.6 μl, 0.284 mmol) was added. The reaction was stirred for 5 hrs. The reaction was worked up with sat. $NaHCO_3$/brine and extracted with EtOAc/Hept. The organic layer was dried over $Na_2SO_4$ and filtered. The solvent and volatile organics in the filtrate were removed on rotavapor. The residue was purified using Biotage (12 g Si-gel column, EtOAc in Heptane=0 to 100%, 15 vol, 100%, 10 vol, 10% MeOH in EtOAc, 6 vol). The fractions contained the desired product were combined. Solvent evaporation afforded the desired product. Prep-TLC (EtOAc) was used to isolate the most polar isomer which leads to the final product Compound 18. Other two isomers were separated using prep-TLC (EtOAc/DCM=1:1, running for 3 times). The more polar isomer was converted to Compound 19 and the less polar isomer was converted to Compound 20.

The most polar product from the first p-TLC (EtOAc), designated Compound 128-1: $^1$H NMR (500 MHz, chloroform-d) δ ppm 8.62 (s, 1H) 8.55 (s, 1H) 8.00-8.07 (m, 2H) 7.99 (s, 1H) 7.96 (s, 1H) 7.56-7.64 (m, 2H) 7.48-7.56 (m, 3H) 7.42-7.48 (m, 1H) 7.34-7.42 (m, 2H) 7.29-7.34 (m, 1H) 7.18-7.25 (m, 2H) 6.09-6.21 (m, 3H) 5.98-6.09 (m, 2H) 5.63-5.75 (m, 1H) 5.52-5.63 (m, 1H) 5.42-5.51 (m, 2H) 5.32 (dd, J=10.27, 0.98 Hz, 1H) 5.27 (dd, J=17.12, 1.47 Hz, 1H) 5.13 (d, J=5.87 Hz, 2H) 5.09-5.12 (m, 1H) 4.95-5.05 (m, 2H) 4.36-4.54 (m, 7H) 4.23-4.31 (m, 2H) 4.15-4.21 (m, 1H)

More polar Product from the second time p-TLC, designated Compound 128-2 (EtOAc/DCM=1:1, 3×) $^1$H NMR (400 MHz, methanol-$d_4$) δ ppm 8.75 (s, 1H) 8.59 (s, 1H) 8.43 (s, 1H) 8.39 (s, 1H) 8.01-8.07 (m, 2H) 7.38-7.56 (m, 7H) 7.27-7.35 (m, 1H) 7.15-7.26 (m, 3H) 6.45 (d, J=19.91 Hz, 1H) 6.38 (d, J=19.52 Hz, 1H) 5.95-6.26 (m, 4H) 5.83 (dd, J=51.54, 4.69 Hz, 1H) 5.73 (dd, J=51.54, 4.69 Hz, 1H) 5.46-5.57 (m, 1H) 5.28-5.36 (m, 1H) 5.19-5.28 (m, 1H) 5.16 (dt, J=5.56, 1.51 Hz, 2H) 5.03-5.10 (m, 1H) 4.95 (br d, J=5.50 Hz, 2H) 4.41-4.62 (m, 4H) 4.28-4.40 (m, 2H) 4.12-4.27 (m, 4H)

Less polar Product from the second time p-TLC, designated Compound 128-3 (EtOAc/DCM=1:1, 3×) $^1$H NMR (400 MHz, chloroform-d) δ ppm 8.53 (s, 1H) 8.36 (s, 1H) 7.95-8.02 (m, 2H) 7.95 (s, 1H) 7.89 (s, 1H) 7.53-7.61 (m, 2H) 7.44-7.53 (m, 4H) 7.36-7.44 (m, 2H) 7.25-7.31 (m, 1H) 7.12-7.20 (m, 2H) 5.91-6.18 (m, 4H) 5.85-5.91 (m, 1H) 5.72-5.79 (m, 1H) 5.61-5.72 (m, 1H) 5.47-5.57 (m, 1H) 5.40-5.47 (m, 1H) 5.25-5.32 (m, 1H) 5.15-5.23 (m, 1H) 4.99-5.14 (m, 3H) 4.92 (d, J=5.47 Hz, 2H) 4.52-4.60 (m, 2H) 4.37-4.52 (m, 4H) 4.35 (d, J=3.13 Hz, 1H) 4.30 (d, J=5.47 Hz, 1H) 4.25 (d, J=2.74 Hz, 1H) 4.20 (d, J=4.69 Hz, 1H)

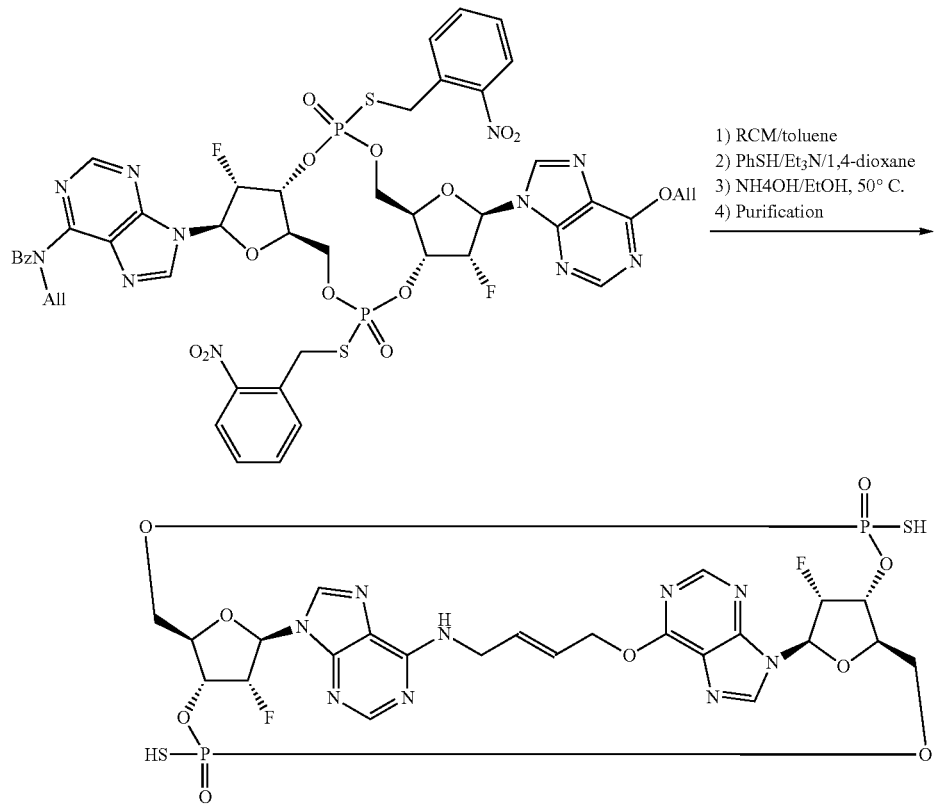

128-1 (Most polar Product from 100% EtOAc pTLC separation) ⟶ Compound 18

128-2 (More polar prod from 50% EtOAc in DCM (3X) pTLC separation) ⟶ Compound 19

128-3 (Less polar prod from 50% EtOAc in DCM (3X) pTLC separation) ⟶ Compound 20

To the reflux solution of 2-nitrobenzyl protected CDN (10 mg, 8.696 μmol) in toluene (20 ml, 187.761 mmol) was added the solution of Hoveyda-Grubbs Catalyst 2nd Generation ((1,3-Bis-(2,4,6-trimethylphenyl)-2-imidazolidinylidene)dichloro(o-isopropoxyphenylmethylene)ruthenium; available at SIGMA-ALDRITCH® Catalog No. 569755; CAS 301224-40-8; 2.73 mg, 4.348 μmol) and benzoquinone (2.350 mg, 0.022 mmol) in TOLUENE (2 ml). The resulting solution was refluxed for 4 hrs (oil bath temp 120-125° C.). TLC (EtOAc, $Rf_{sm}$=0.8, $Rf_{Prod}$=0.3) and UPLC-MS indicated that the reaction was incomplete. 1 ml of the Ru catalyst solution was added. The reaction was refluxed for 2 more hrs. Still lots of non-reacted SM left. Another 1 ml of the Ru catalyst solution was added. The reaction was refluxed for 2 more hrs. No SM was detected on reverse phase HPLC. The reaction mixture was cooled to RT and quenched with DMSO (0.019 ml, 0.261 mmol). Solvent evaporation afforded the crude product which was purified on Si-gel column (10 g Si-gel column, eluent from 50 to 100%, 15 vol, 100%, 10 vol). Fractions contained the products with desired MS were combined and rotavaped. The residue was purified one more time on Prep-TLC (EtOAc).

To the pTLC purified bridge-locked CDN (2.5 mg, 2.228 μmol) (the trans isomer) in 1,4-dioxane (0.5 ml, 5.845 mmol) was added Thiophenol (0.25 ml, 2.428 mmol) and TEA (0.25 ml, 1.794 mmol) at 20° C. The mixture was stirred at RT for 3 hrs. UPLC indicated that the conversion was completed.

Methanol (1.5 ml) was added which was followed by the addition of 29% $NH_3$ in $H_2O$ (1.0 ml). The resulting mixture was heated at 50° C. for 6 h and cooled to RT.

The suspension of the reaction mixture was filtered and rinsed with water (25 mL). Precipitations were formed in the filtrate after water rinse. The filtrate was filtered again to remove some solid.

The resulting filtrate was extracted with mixture of tol/Hep (3×, 1/1, 25 ml each). The aqueous layer was concentrated in vacuo and then dissolved in water (6 mL). The precipitates were filtered one more time. UPLC indicated the desired product was formed. The product was purified with reverse phase HPLC using the same method to purify other based locked CDN analogs.

For Compound 18, LCMS: MS m/z 748.11 $[M+H]^+$ 746.15 $[M-H]^-$

For Compound 19, LCMS: MS m/z 748.06 $[M+H]^+$ 746.17 $[M-H]^-$

For Compound 20, LCMS: MS m/z 748.09 $[M+H]^+$ 746.21 $[M-H]^-$

Example 13—Synthesis of Compound 26

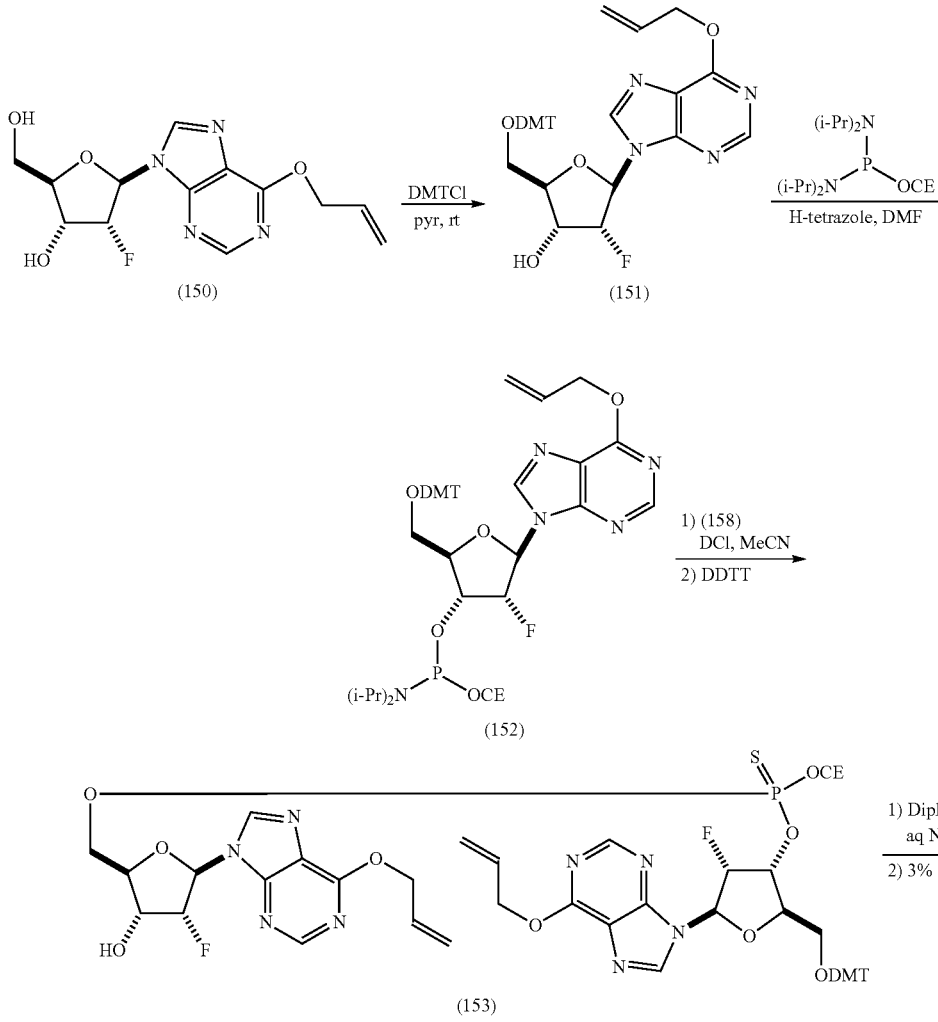

-continued
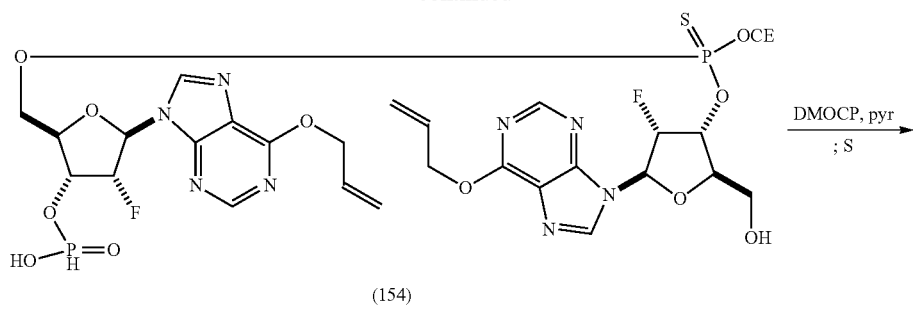
(154)
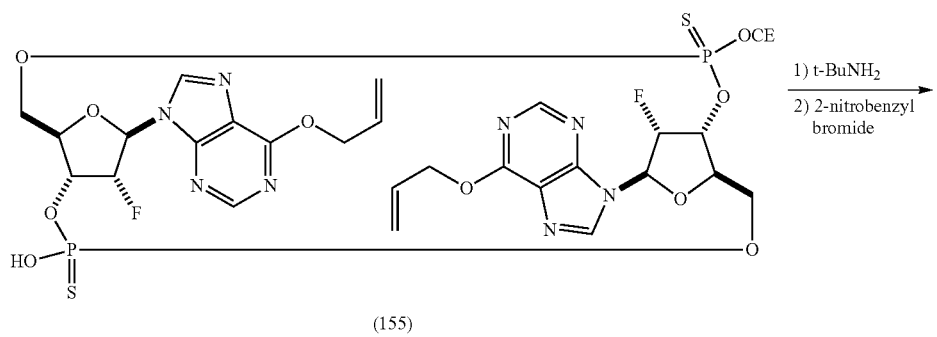
(155)
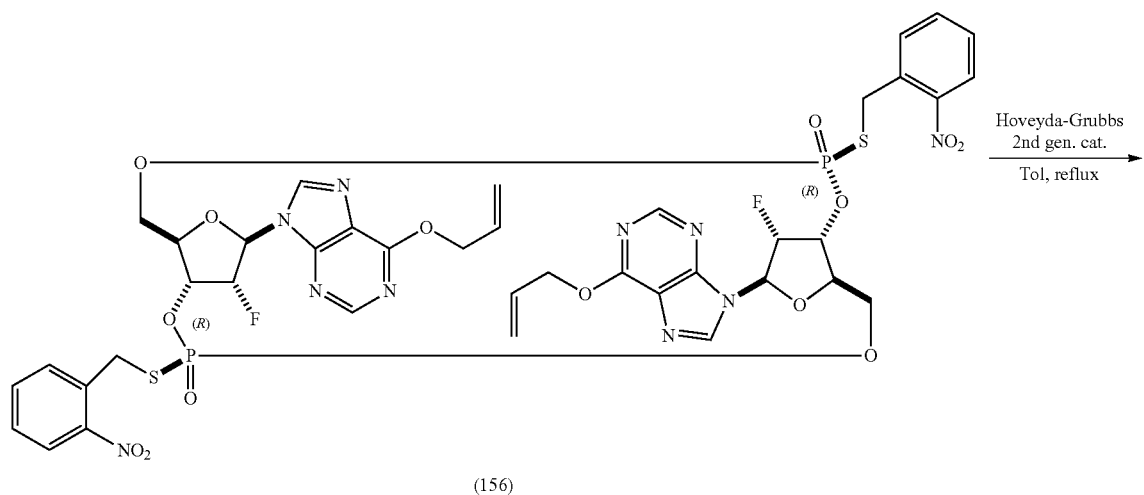
(156)
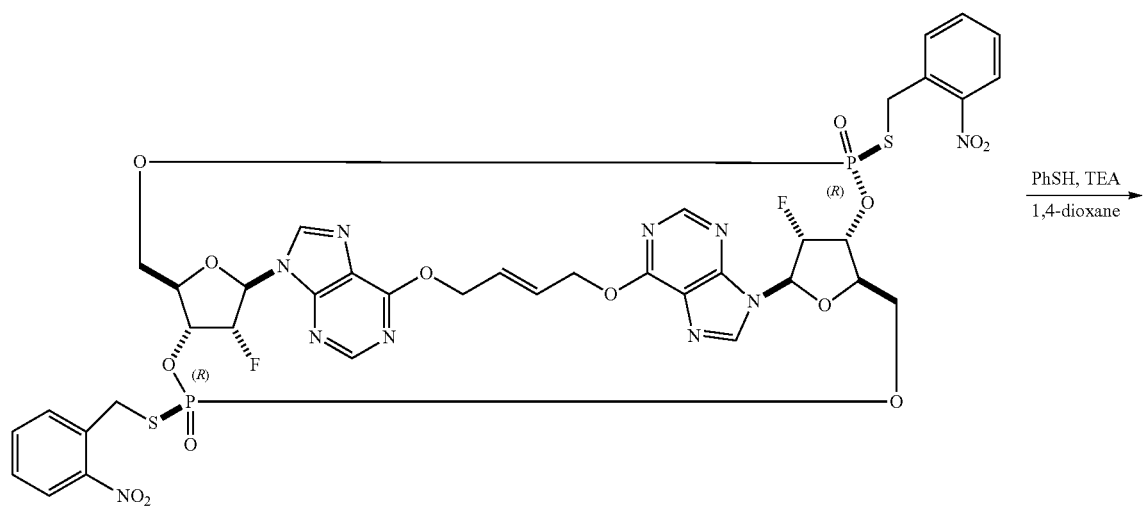
(157)

-continued

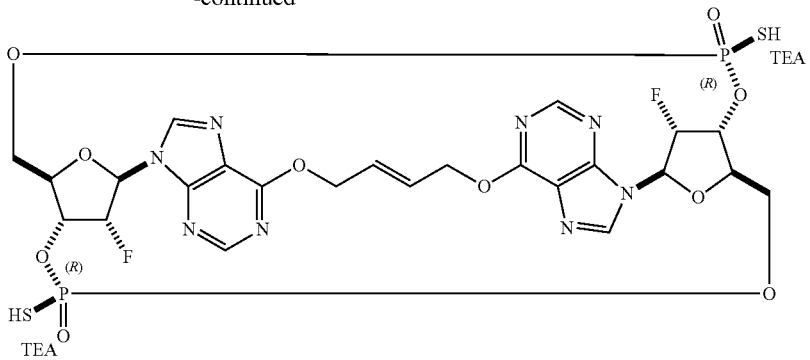

(26)

Compound 151

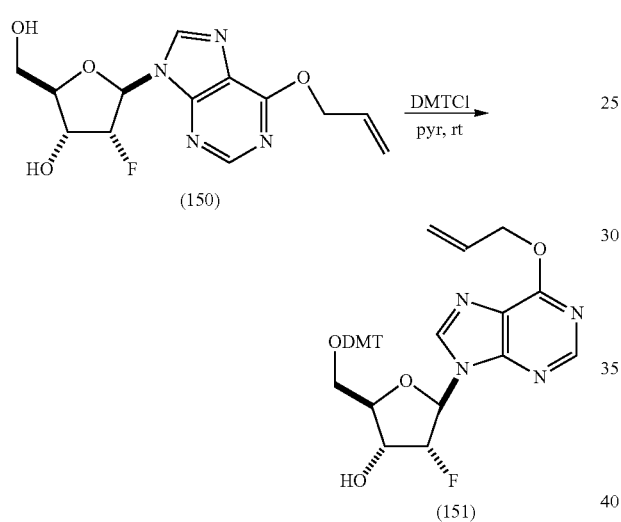

Compound 152

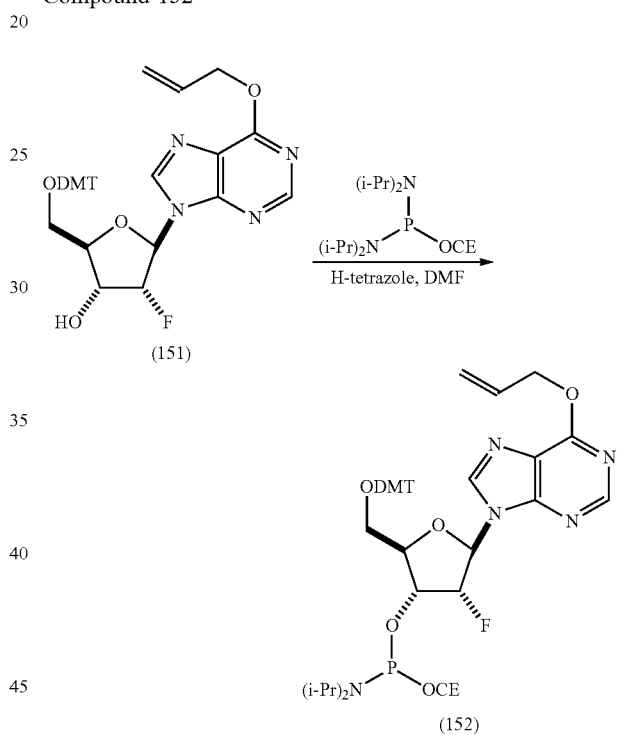

To a solution of Compound 150 (0.70 g, 2.256 mmol) in pyridine (10.5 ml) 0° C. was added 4,4'-dimethoxytrityl chloride (0.803 g, 2.369 mmol). The resulting solution was stirred overnight while warmed to ambient temperature. Upon completion (monitored by LCMS), a sat'd NH$_4$Cl solution (10 ml) and MTBE (20 mL) were added. The layers were separated and the aqueous layer was extracted with MTBE/EtOAc (3/1, 12 mL). The combined organic layers were washed with 30% aqueous NaCl solution (5 ml), dried over MgSO$_4$, filtered and concentrated in vacuo. Purification of the crude product by silicagel column chromatography (SiO$_2$ 25 g, 50% to 70% EtOAc in n-heptane) gave 0.942 g of Compound 151.

$^1$H NMR (400 MHz, CHLOROFORM-d) δ=8.47 (s, 1H), 8.11 (s, 1H), 7.43-7.35 (m, 2H), 7.30-7.26 (m, 4H), 7.25-7.17 (m, 3H), 6.82-6.75 (m, 4H), 6.28 (dd, J=2.3, 17.6 Hz, 1H), 6.22-6.10 (m, 1H), 5.63 (ddd, J=2.7, 4.7, 53.1 Hz, 1H), 5.47 (qd, J=1.4, 17.3 Hz, 1H), 5.31 (dd, J=1.2, 10.6 Hz, 1H), 5.13 (t, J=1.4 Hz, 1H), 5.12 (t, J=1.2 Hz, 1H), 4.89-4.76 (m, 1H), 4.21 (td, J=3.2, 6.8 Hz, 1H), 3.78 (s, 6H), 3.55 (dd, J=2.7, 10.9 Hz, 1H), 3.44 (dd, J=4.3, 10.9 Hz, 1H), 2.29-2.21 (m, 1H).

To a solution of Compound 151 (0.942 g, 1.538 mmol) in DMF (7.5 mL) at ambient temperature were added 3-((bis(diisopropylamino)phosphino)oxy)propanenitrile (0.927 g, 3.075 mmol), 0.45 M 1,2,3,4-tetrazole (2.8 mL, 1.2 mmol) and 1-Methylimidazole (30 μl, 0.38 mmol). The resulting solution was stirred at ambient temperature for 4 h. Upon completion (monitored by LCMS), TEA (0.50 ml, 3.6 mmol), DMF (11.3 mL,) and water (1.9 mL) were added. The resulting mixture was extracted with n-heptane (3 mL each time) three times. The DMF layer was diluted with water (4 ml) and extracted with a mixture of toluene/n-heptane (1/1, 10 mL). The combined organic layers were washed with 30% aqueous NaCl solution twice (3 mL each time), dried with MgSO$_4$, filtered and concentrated in vacuo. Purification of the residue by silicagel column chromatography (SiO$_2$ 50 g, 33% to 40% EtOAc in n-heptane with 1% TEA) gave 1.115 g of Compound 152 (3:2 diastereomeric mixture) as a white foam solid.

Compound 153

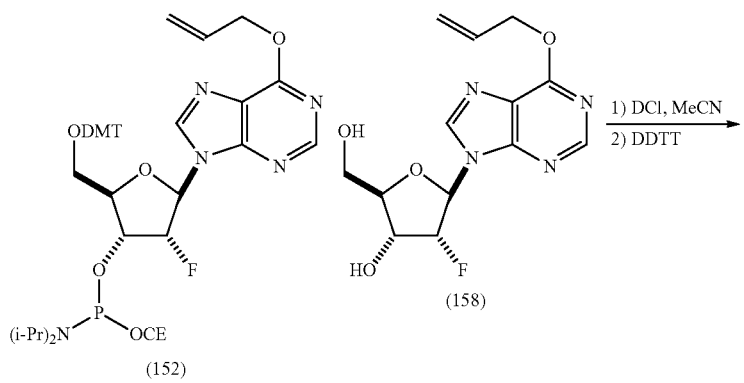

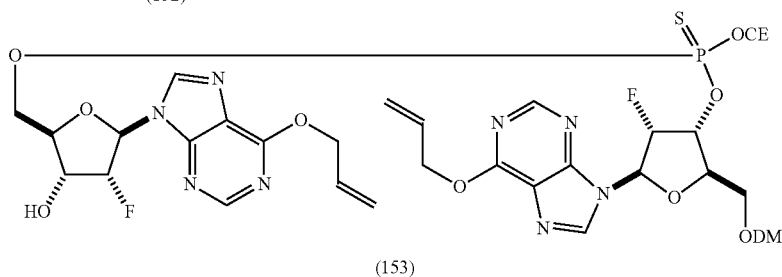

A mixture of Compound 152 (1.115 g, 1.372 mmol) and Compound 158 (0.650 g, 2.095 mmol) was azeotroped with MeCN (20 mL each time) twice. To the resulting residue were added MeCN (20.0 ml) and 1H-imidazole-4,5-dicarbonitrile (0.243 g, 2.058 mmol). Upon complete reaction (monitored by LCMS), the reaction mixture was treated with (E)-N,N-dimethyl-N'-(3-thioxo-3H-1,2,4-dithiazol-5-yl)formimidamide (0.422 g, 2.058 mmol). Upon complete sulfurization, a sat'd NaHCO$_3$ solution (20 mL) and MTBE (30 mL) were added. The layers were separated and the aqueous layer was extracted with a mixture of MTBE/EtOAc (15/15 mL). The combined organic layers were washed with 30% aqueous NaCl solution (10 mL), dried over MgSO$_4$, filtered and concentrated in vacuo. Purification of the residue by silicagel column chromatography (SiO$_2$ 50 g, 33% to 100% EtOAc in n-heptane with 1% TEA) gave 0.88 g of Compound 153.

LC/MS (ESI) m/z 1076.48 [M+Na]$^+$.

Compound 154

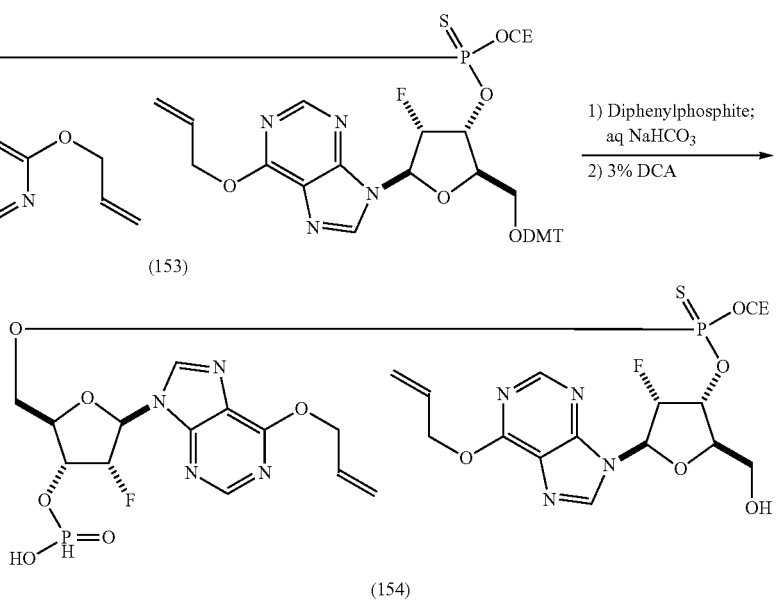

To a solution of Compound 153 (0.880 g, 0.835 mmol) in pyridine (8.8 ml) at ambient temperature was added diphenyl phosphite (0.323 ml, 1.67 mmol). The reaction mixture was stirred for 1 h and monitored by LCMS. Upon completion, the mixture was added into a mixture of a sat'd aqueous NaHCO$_3$ solution (13.2 ml) and water (4.4 ml) while keeping the internal T below 30° C., rinsing with EtOAc (8.8 ml). The resulting mixture was stirred at ambient temperature and the hydrolysis was monitored by LCMS. Upon completion, the mixture was extracted twice with a mixture of EtOAc/MTBE (1/1, 26 mL). The combined organic layers were washed with 30% aqueous NaCl solution (3 ml), dried over MgSO$_4$, filtered and concentrated in vacuo. The residue was azeotroped with toluene (7 mL each time) twice. The crude product was dissolved in dichloromethane (6.6 ml), and treated with water (0.15 ml, 8.35 mmol) and 6% dichloroacetic acid (0.41 ml, 5.0 mmol) in dichloromethane (6.6 ml) at ambient temperature. Upon complete DMT deprotection (monitored by LCMS), triethylsilane (2.7 ml, 17 mmol) was added. After 10 min stirring, the resulting mixture was treated with pyridine (4.4 ml) and TEA (1 ml) and concentrated in vacuo. The residue was triturated with n-heptane (8.8 ml each time) three times and azeotroped with MeCN twice. The crude product (Compound 154) was used in next step without further purification.

LC/MS (ESI) m/z 814.29 [M−H]$^-$.

Compound 155

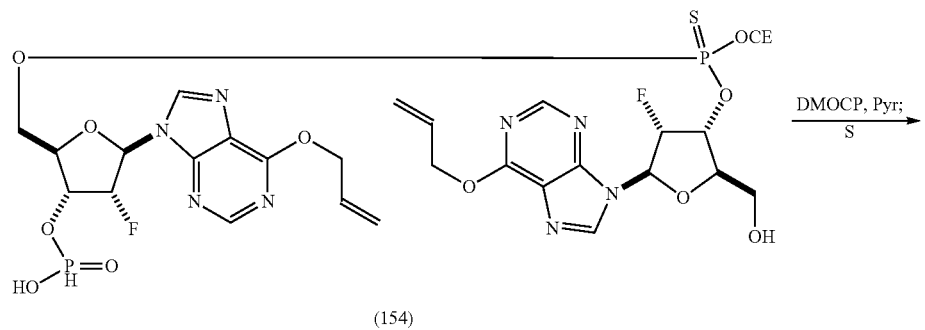

(154)

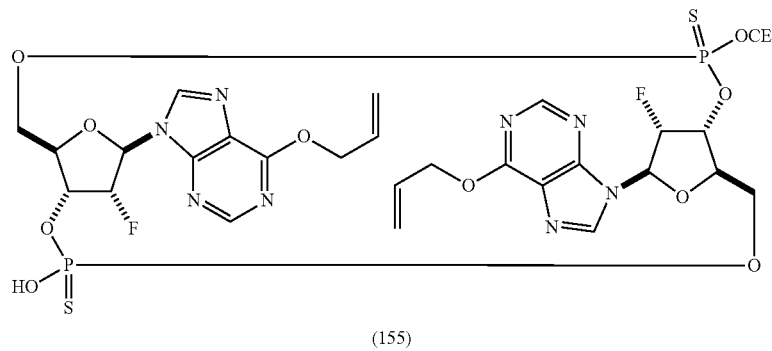

(155)

To a solution of Compound 154 (0.681 g, 0.835 mmol) in pyridine (68 ml) at ambient temperature was added 2-Chloro-5,5-dimethyl-1,3,2-dioxaphophorinane-2-oxide (0.462 g, 2.505 mmol). The resulting solution was stirred for 1 h at ambient temperature and monitored by LCMS. Upon completion, water (0.45 ml, 25 mmol) (10 eq of DMOCP) and sulfur (0.134 g, 4.175 mmol) were added. Upon complete sulfurization (monitored by LCMS), the reaction mixture was treated with a sat'd aqueous solution NaHCO$_3$ (13.6 ml) and concentrated in vacuo. The residue was treated with EtOAc (27 ml) and water (13.6 ml). The layers were separated and the aqueous layer was extracted with a mixture of EtOAc/MTBE (1/1, 27 mL). The combined organic layers were washed with 30% aqueous NaCl solution (13.6 ml), dried over MgSO$_4$, filtered and concentrated in vacuo. Purification of the residue by silicagel column chromatography (SiO$_2$ 25 g, 0% to 10% MeOH in EtOAc) gave 0.693 g (theoretical yield) of Compound 155.

LC/MS (ESI) m/z 830.23 [M+H]$^+$.

Compound 156

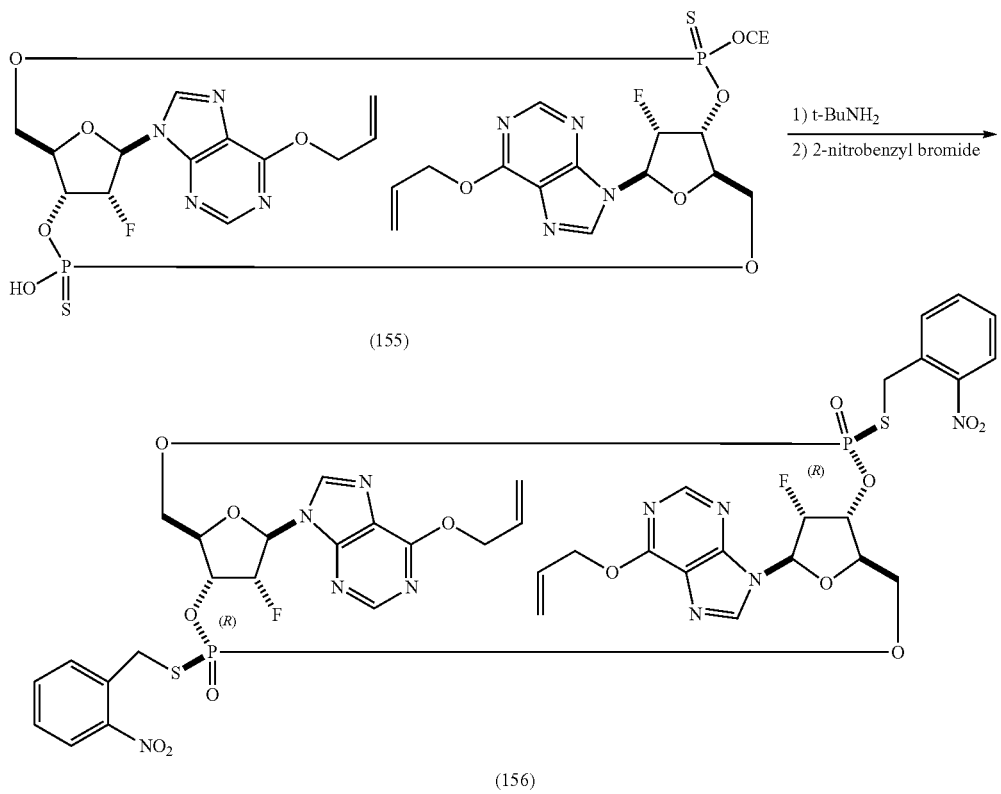

(155)

(156)

To a solution of Compound 155 (0.693 g, 0.835 mmol) in acetonitrile (14 ml) at ambient temperature was added tert-butylamine (14 ml, 131 mmol). The resulting solution was stirred for 10 min and monitored by LCMS. Upon completion, the reaction mixture was concentrated in vacuo and azeotroped with MeCN twice. To the residue were added acetonitrile (14 ml) and 2-nitrobenzyl bromide (0.541 g, 2.51 mmol). After being stirred overnight, the reaction mixture was concentrated in vacuo and purified by silicagel column chromatography (SiO$_2$ 100 g, 75% to 100% EtOAc in n-heptane and 0% to 10% MeOH in EtOAc) to give 0.103 g of Compound 156.

$^1$H NMR (400 MHz, CHLOROFORM-d) δ=8.59 (s, 2H), 8.05 (br d, J=8.2 Hz, 2H), 8.03 (s, 2H), 7.58 (d, J=7.4 Hz, 2H), 7.48 (t, J=7.4 Hz, 2H), 7.45-7.37 (m, 2H), 6.20 (br d, J=18.8 Hz, 2H), 6.21-6.08 (m, 2H), 5.98-5.83 (m, 2H), 5.69 (dd, J=4.7, 52.0 Hz, 1H), 5.47 (br d, J=17.2 Hz, 2H), 5.31 (br d, J=10.6 Hz, 2H), 5.14 (br d, J=5.5 Hz, 4H), 4.54-4.46 (m, 2H), 4.45-4.40 (m, 2H), 4.37-4.26 (m, 4H), 4.21-4.11 (m, 2H).

Based upon synthetic methodology, NMR data (symmetric) and HPLC retention time (slowest eluting isomer), applicants believe that compound 156 has RR phosphorous stereochemistry. This stereochemical assignment would be subject to confirmation by X-ray crystallography.

Compound 157

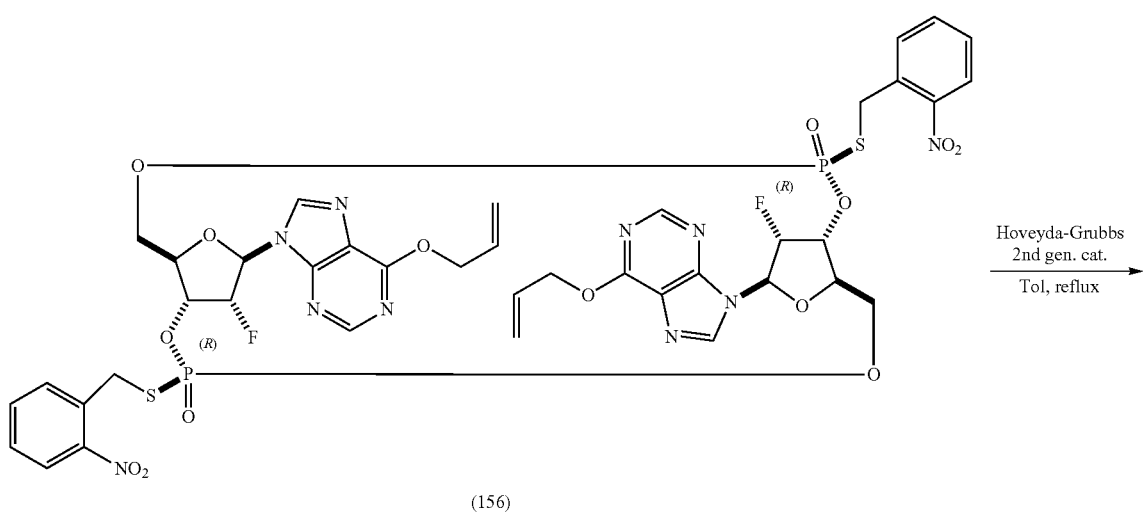

(156)

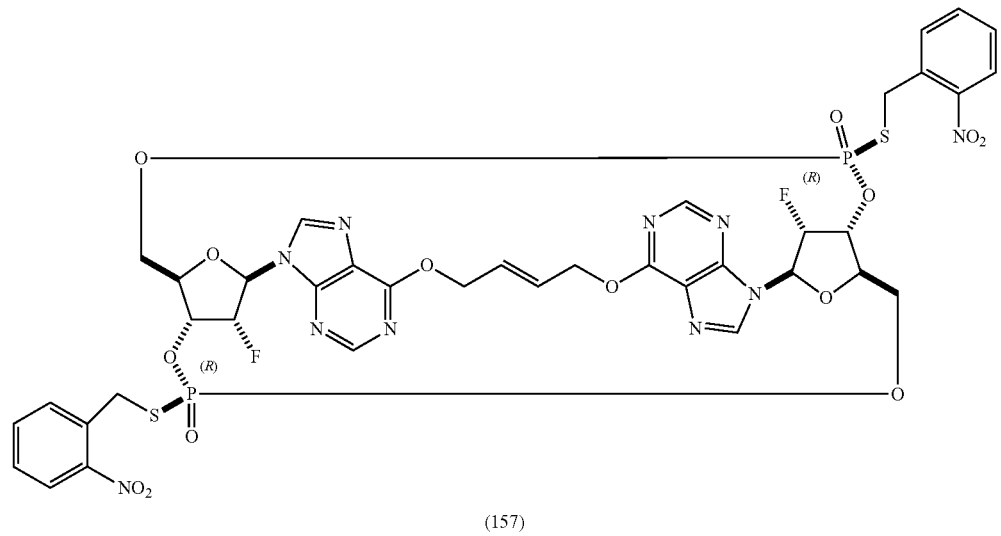

(157)

To a solution of Compound 156 (0.103 g, 0.098 mmol) in toluene (103 ml) at reflux was added a solution of Hoveyda-Grubbs Catalyst 2nd Generation ((1,3-Bis-(2,4,6-trimethylphenyl)-2-imidazolidinylidene)dichloro(o-isopropoxyphenylmethylene)ruthenium; available at SIGMA-ALDRITCH® Catalog No. 569755; CAS 301224-40-8; 31 mg, 0.049 mmol) and quinone (32 mg, 0.295 mmol) in toluene (10 mL). The mixture was stirred at reflux for 2 h and additional catalyst (16 mg, 0.025 mmol) was added. Upon completion, the reaction mixture was cooled down to ambient temperature and treated with DMSO (0.14 ml, 2.0 mmol) overnight. The resulting mixture was concentrated in vacuo and purified by silicagel column chromatography (SiO$_2$ 10 g, 0% to 10% methanol in EtOAc) to give the desired product, which was further purified by pre TLC (EtOAc) to give 3.6 mg of compound 157.

$^1$H NMR (400 MHz, CHLOROFORM-d) δ=8.11 (dd, J=1.2, 8.2 Hz, 2H), 8.09 (s, 2H), 7.68 (s, 2H), 7.67-7.58 (m, 4H), 7.52-7.48 (m, 2H), 6.26 (d, J=17.6 Hz, 2H), 6.02-5.97 (m, 2H), 5.97-5.88 (m, 2H), 5.68 (dd, J=3.9, 50.8 Hz, 2H), 5.15 (br d, J=10.9 Hz, 2H), 4.99 (br d, J=10.9 Hz, 2H), 4.56-4.44 (m, 8H), 4.25 (br t, J=6.1 Hz, 2H).

Compound 26

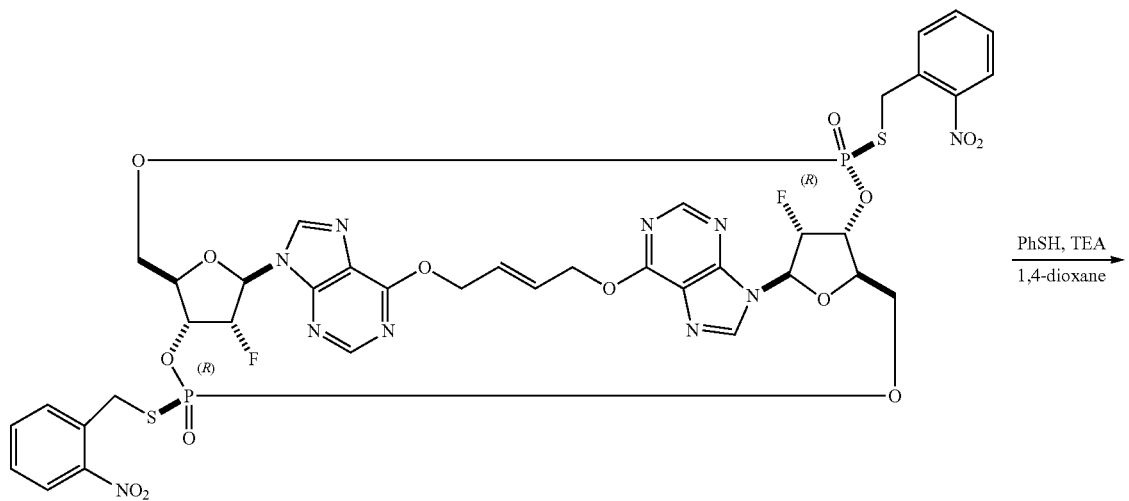

(157)

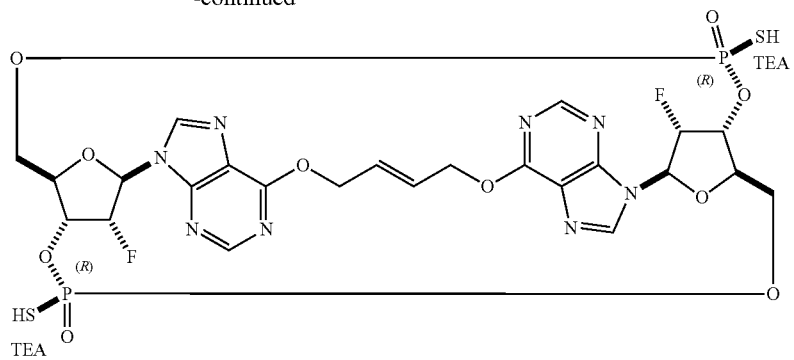

(26)

To Compound 157 (3.6 mg, 3.5 μmol) were added 1,4-dioxane (0.11 mL), thiophenol (0.045 mL, 0.44 mmol) and TEA (0.054 mL, 0.39 mmol). The resulting mixture was stirred at ambient temperature while the reaction was monitored by LCMS. Upon complete conversion, water (0.5 mL) was added. The resulting mixture was extracted three times with a mixture of n-heptane/toluene (1/1, 0.4 mL each time) and then toluene (0.3 mL). The aqueous layer was concentrated in vacuo and treated with water (0.5 mL). The resulting solid was filtered off, rinsing with water (0.5 mL). Freeze-drying of the combined filtrates gave 2.0 mg of bis-TEA salt Compound 26 as a white foam solid.

$^1$H NMR (400 MHz, METHANOL-d$_4$) δ=8.67 (s, 2H), 8.18 (s, 2H), 6.41 (d, J=14.8 Hz, 2H), 6.07-6.01 (m, 2H), 5.56 (dd, J=3.1, 51.2 Hz, 2H), 5.48-5.41 (m, 2H), 5.08 (br d, J=12.1 Hz, 2H), 4.99-4.88 (m, 2H), 4.52 (br d, J=12.5 Hz, 2H), 4.40 (br d, J=9.8 Hz, 2H), 3.98 (dd, J=5.7, 12.3 Hz, 2H), 3.14 (q, J=7.4 Hz, 12H), 1.27 (t, J=7.4 Hz, 18H).

Example 15—Synthesis of Compound 27

Figure 2B:
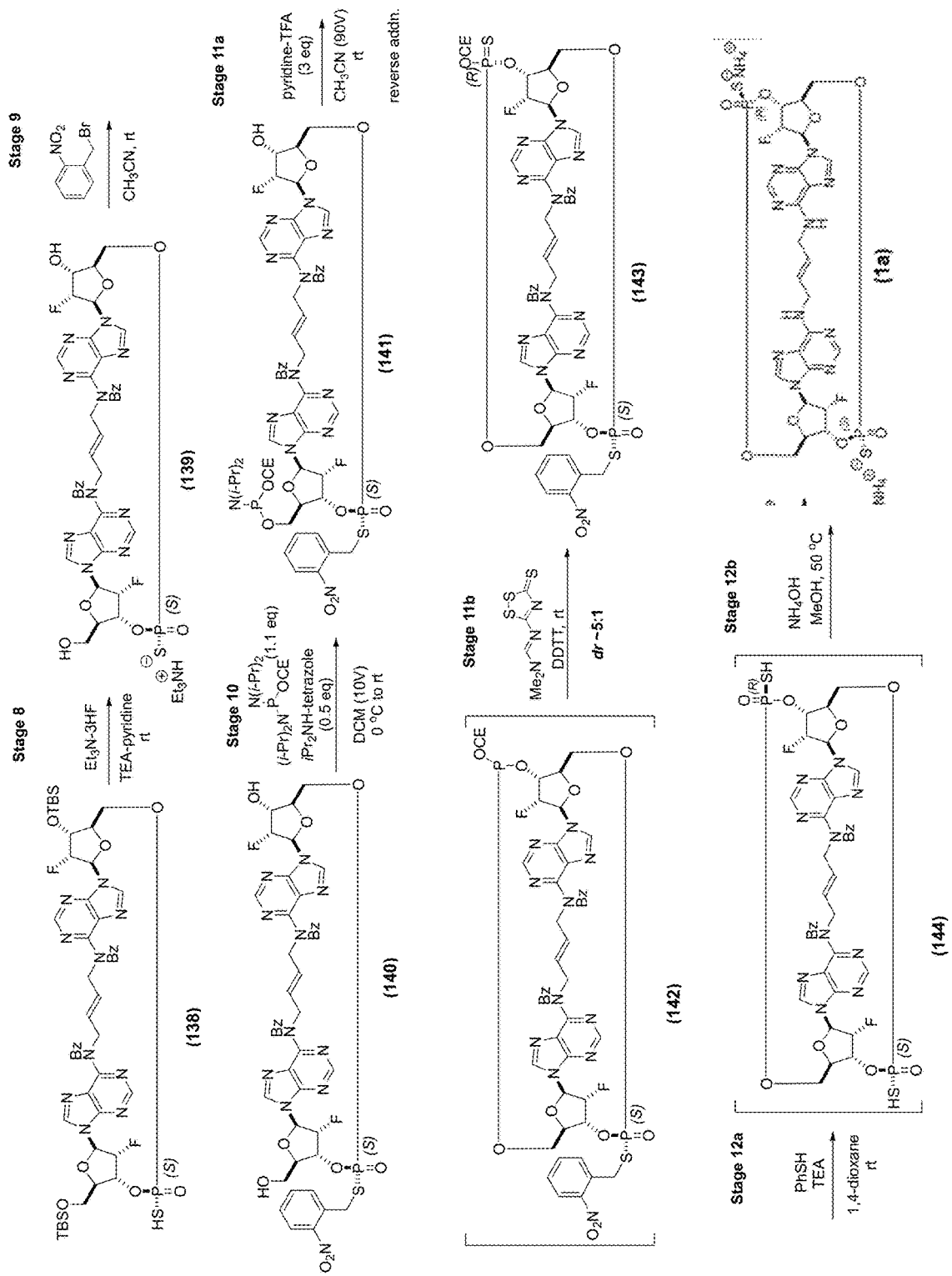
Figure 2C:
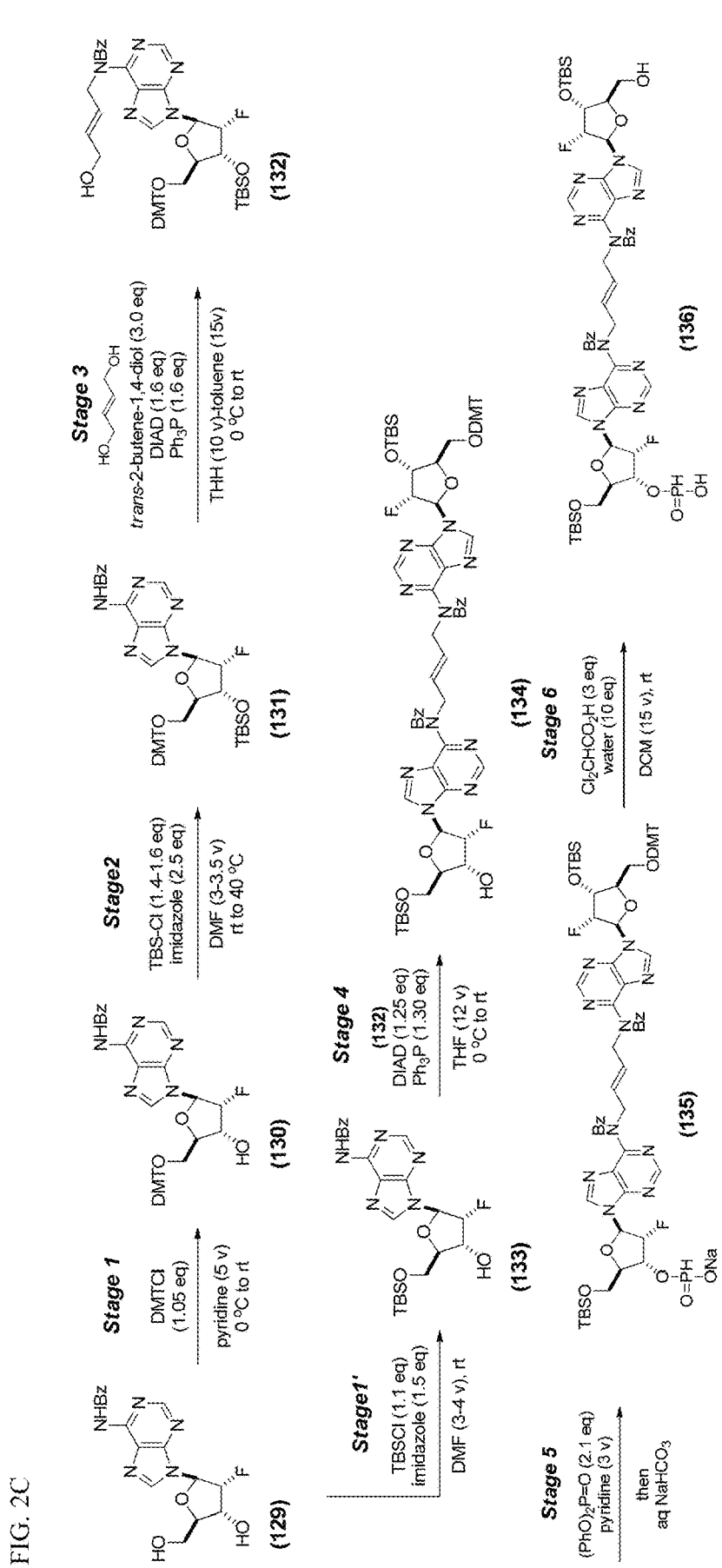
Figure 2D:
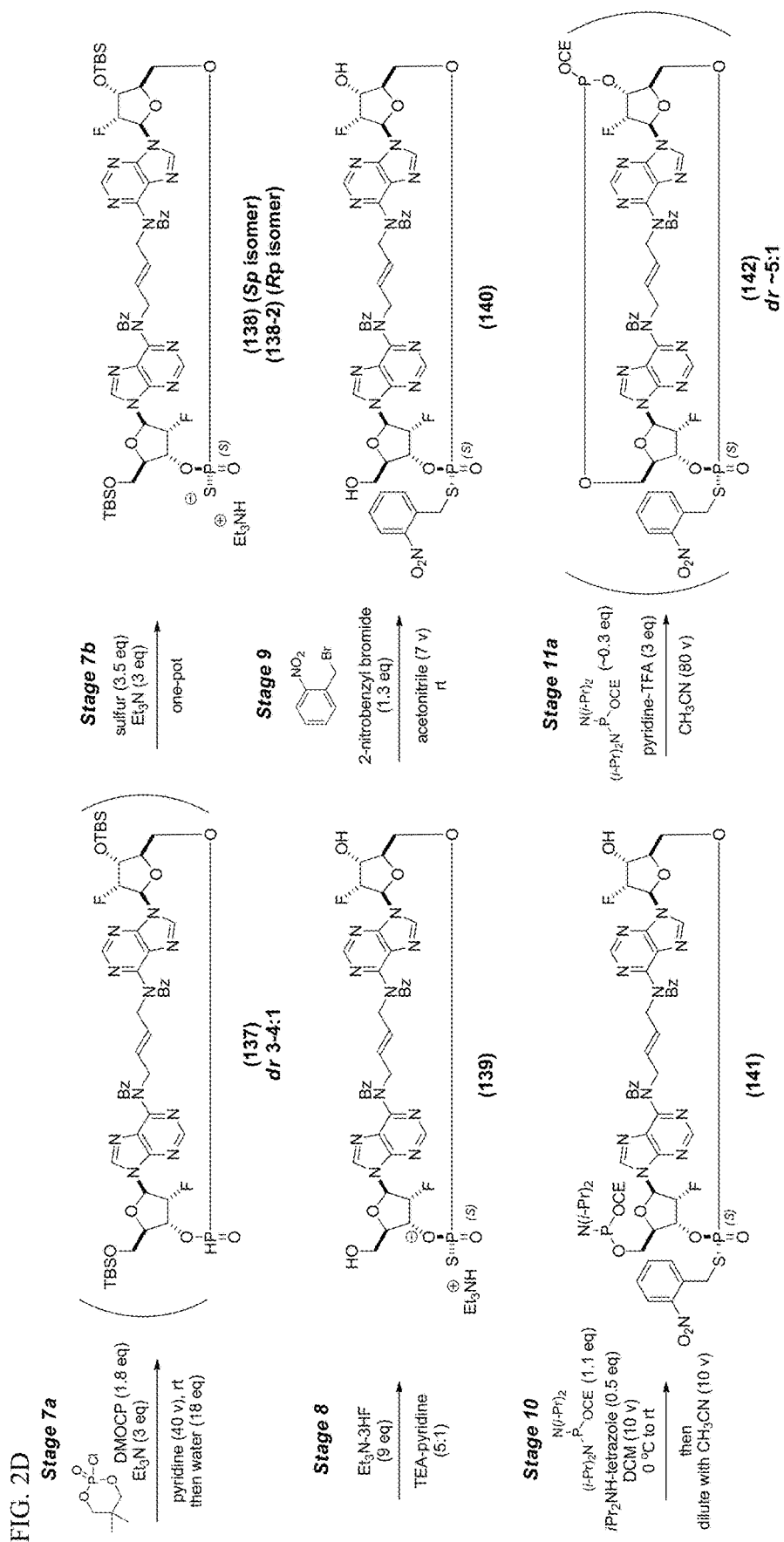
Figure 2E:
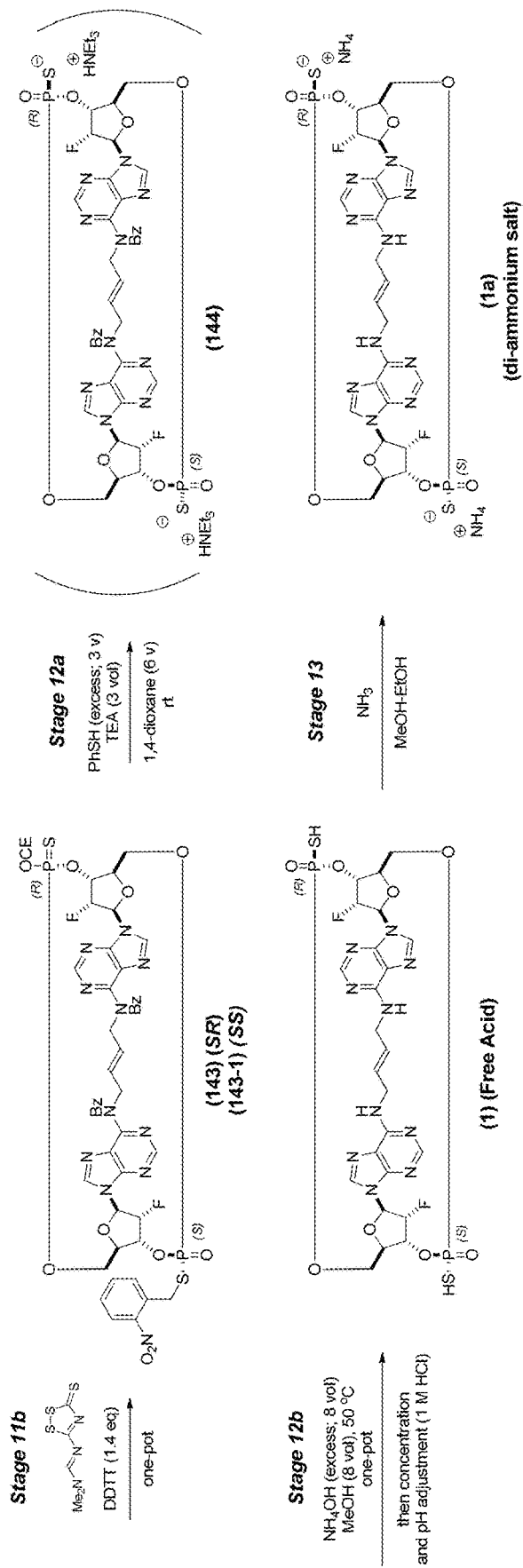

Compound 27 was prepared from Compound 159, a byproduct in Stage 11b of a route for Compound 1 shown in FIG. 2B.

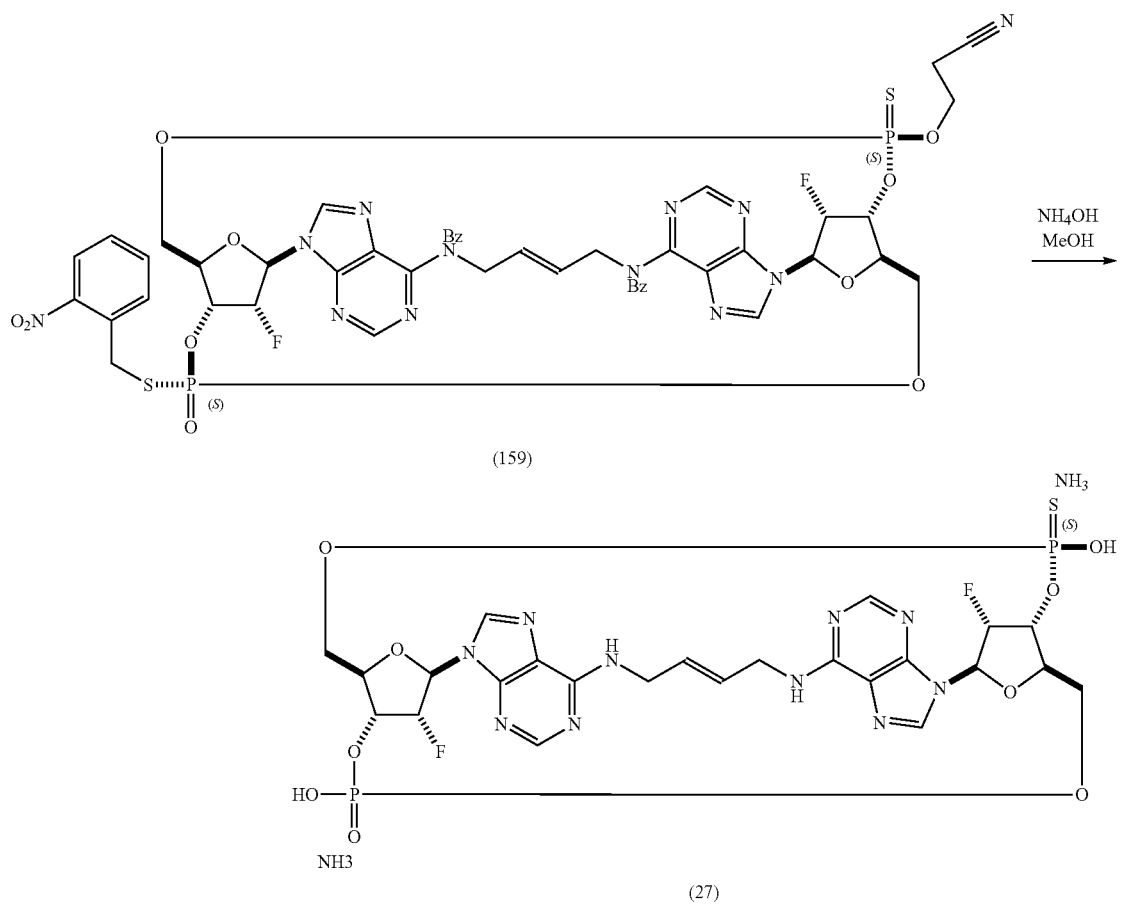

(159)

(27)

To a solution of Compound 159 (2.0 g, 1.75 mmol) in methanol (24 ml) was added 28% ammonium hydroxide (12 ml). The resulting mixture was stirred at 50° C. for 5 h and cooled to ambient temperature. Upon completion (monitored by LCMS), the reaction mixture was cooled to ambient temperature, treated with water (20 ml) and extracted three times with a mixture of toluene/EtOAc (1/1, 24 mL each time). The aqueous layer was acidified with 1.0 M hydrochloric acid (3.5 ml, 3.5 mmol), stirred at ambient temperature for 30 min and 0° C. for 30 min. The resulting slurry was filtered, rinsing with water (20 mL). The cake was dried in a vacuum oven at 35° C. overnight and dissolved with a mixture of 28% NH₄OH (2 mL) and MeOH (20 mL). The resulting solution was concentrated in vacuo and treated with EtOH (4 ml) to make a slurry. The resulting solid was collected by filtration and dried in vacuo. 70 mg of Compound 27 as a white solid was obtained.

¹H NMR (400 MHz, METHANOL-d₄) δ=9.03 (br s, 1H), 8.31 (br s, 1H), 8.26 (br s, 1H), 8.13 (br s, 1H), 6.43-6.24 (m, 2H), 5.97-5.83 (m, 2H), 5.71 (br d, J=51.6 Hz, 1H), 5.64 (br d, J=50.0 Hz, 1H), 5.12-4.99 (m, 1H), 4.96-4.90 (m, 1H), 4.68-4.32 (m, 6H), 4.14-3.97 (m, 2H), 3.77-3.62 (m, 2H).

Example 16—Synthesis of Compound 28

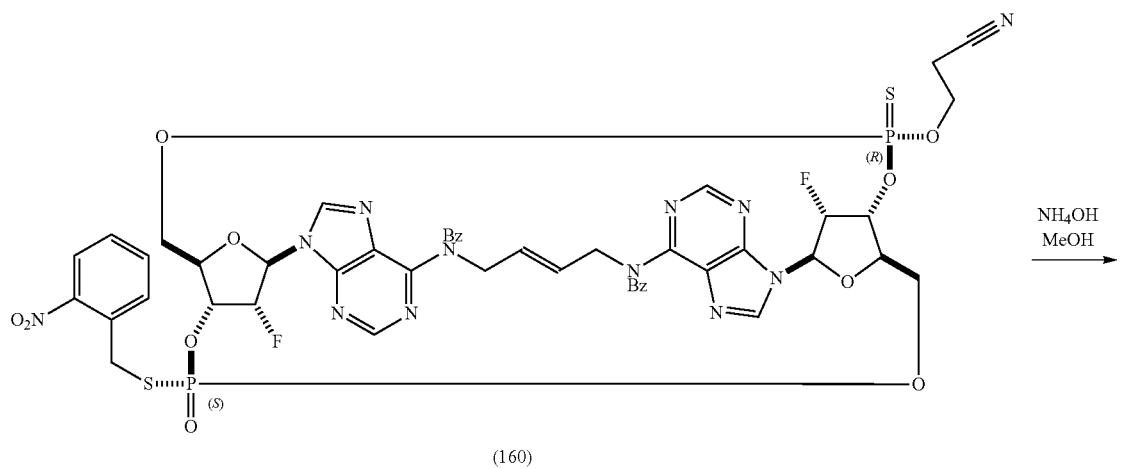

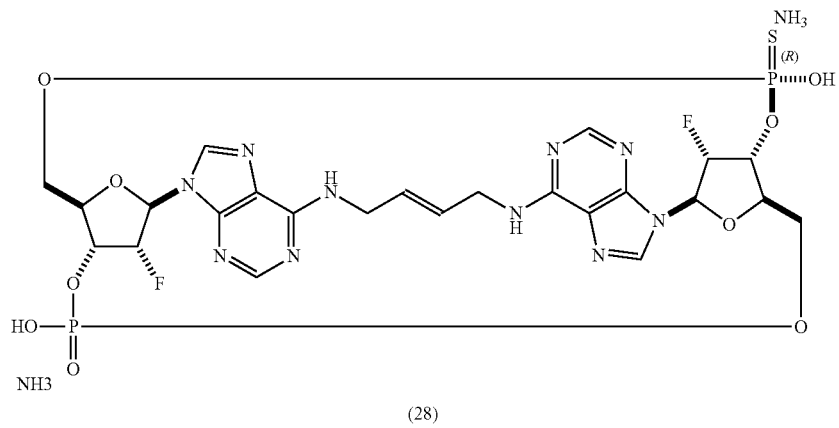

Compound 28 was prepared from Compound 160, a product in Stage 11 of the route for Compound 1 shown in FIG. 2B, using the same method for Compound 27.
$^1$H NMR (400 MHz, METHANOL-$d_4$) δ=8.70 (br s, 1H), 8.49 (br s, 1H), 8.24 (br s, 1H), 8.10 (br s, 1H), 6.52-6.26 (m, 2H), 5.94-5.78 (m, 2H), 5.69 (br d, J=54.7 Hz, 1H), 5.48-5.26 (m, 1H), 5.14 (br d, J=53.1 Hz, 2H), 5.06-4.94 (m, 1H), 4.74-4.19 (m, 4H), 4.10-3.93 (m, 2H), 3.76-3.58 (m, 2H)
Example 17—Synthesis of Compound 29
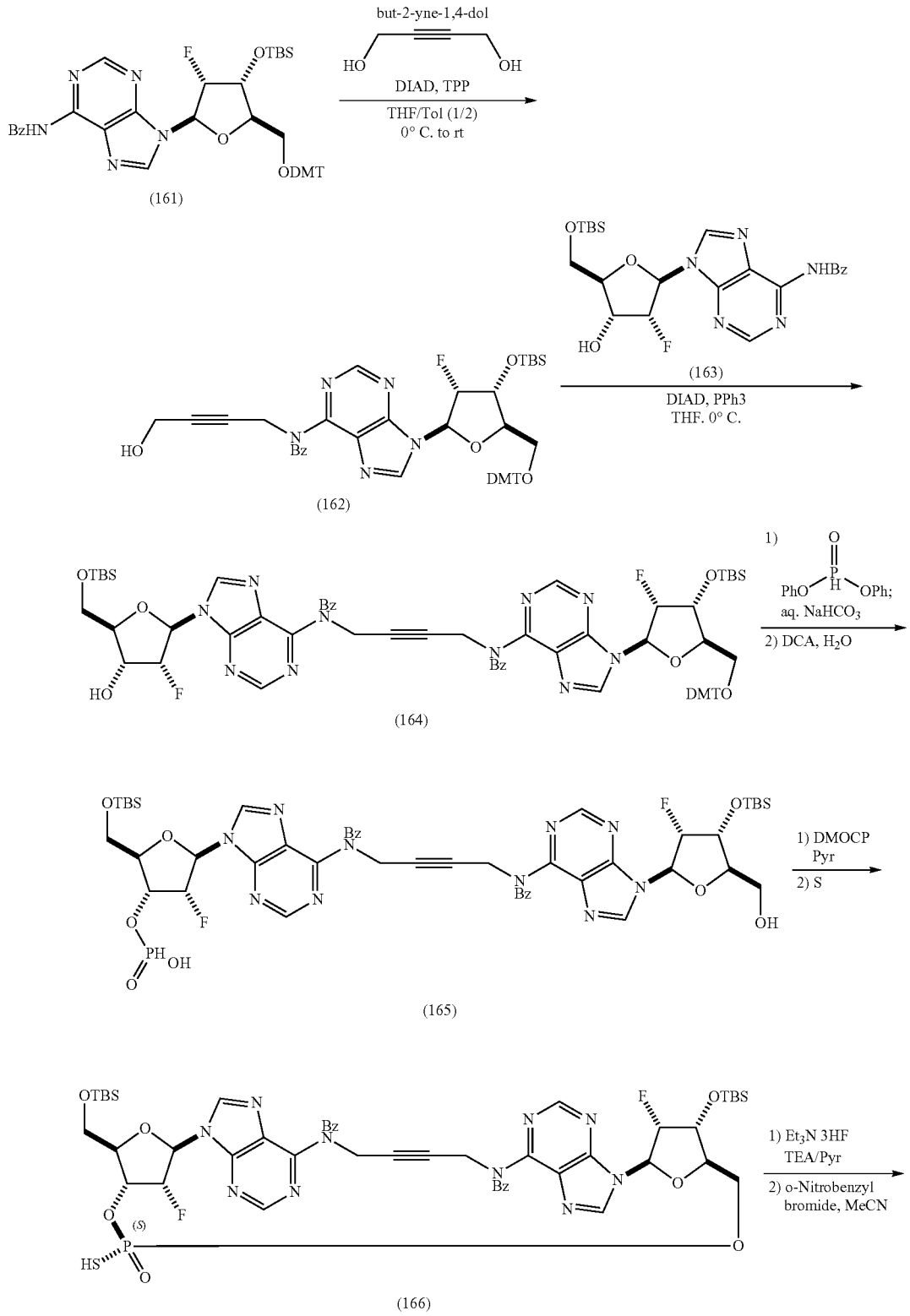

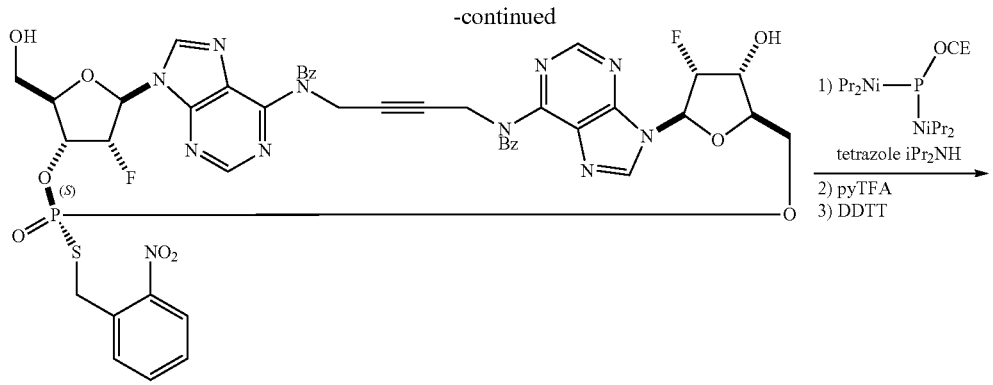

(167)

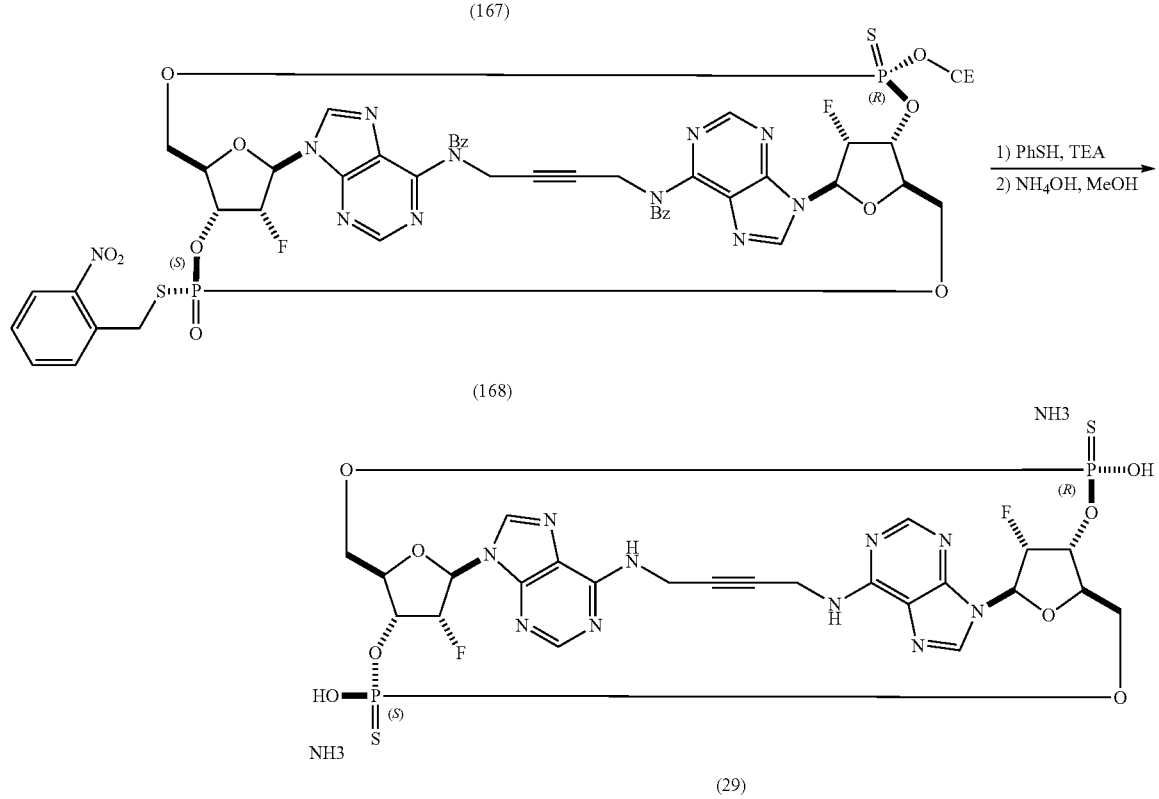

(168)

(29)

Compound 162

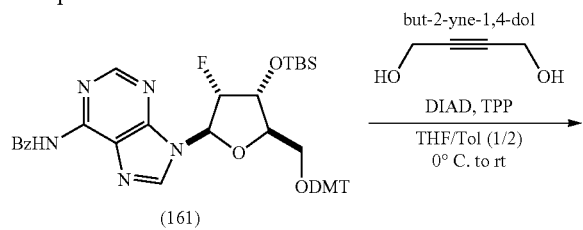

Compound 161 (5.0 g, 6.329 mmol) and but-2-yne-1,4-diol (1.907 g, 22.153 mmol) were azeotroped with THF twice. The residue was dissolved in THF (50.0 ml) and toluene (75 ml). Triphenylphosphine (2.158 g, 8.228 mmol) was added and the resulting solution was cooled down below 5° C. DIAD (1.60 ml, 8.23 mmol) was added dropwise while keeping internal T below 10° C. The resulting solution was stirred at 0-5° C. while the progress was monitored by LCMS. Upon complete, the reaction mixture was concentrated in vacuo to remove most of THF. The residue was diluted with MTBE (50.0 ml) and washed twice with 30% aqueous NaCl solution (40.0 ml each time) and twice with water (25 ml each time). The organic solution was concentrated in vacuo and purified by silica gel column chromatography ($SiO_2$ 100 g, 50% to 70% EtOAc in n-heptane buffered with 1% TEA) to give 4.671 g of Compound 162.

$^1$H NMR (400 MHz, CHLOROFORM-d) δ=8.61 (s, 1H), 8.14 (s, 1H), 7.43 (d, J=7.2 Hz, 2H), 7.33-7.27 (m, 3H), 7.24-7.18 (m, 8H), 7.05-7.01 (m, 2H), 6.76 (d, J=8.6 Hz, 4H), 6.20 (dd, J=2.7, 17.2 Hz, 1H), 5.59 (td, J=3.1, 53.1 Hz, 1H), 5.19 (br d, J=2.3 Hz, 2H), 4.93-4.83 (m, 1H), 4.18-4.15 (m, 1H), 4.01 (br d, J=6.3 Hz, 2H), 3.78 (s, 6H), 3.53 (dd, J=2.7, 10.9 Hz, 1H), 3.17 (dd, J=3.7, 11.1 Hz, 1H), 0.85 (s, 9H), 0.10 (s, 3H), 0.02 (s, 3H).

Compound 164

$^1$H NMR (400 MHz, CHLOROFORM-d) δ=8.51 (s, 1H), 8.45 (s, 1H), 8.20 (s, 1H), 8.05 (s, 1H), 7.41 (d, J=7.1 Hz, 2H), 7.36-7.32 (m, 4H), 7.28-7.13 (m, 8H), 6.98 (t, J=7.8 Hz, 2H), 6.79-6.74 (m, 4H), 6.29 (dd, J=2.0, 16.4 Hz, 1H), 6.19 (dd, J=2.7, 17.2 Hz, 1H), 5.53 (ddd, J=2.7, 4.7, 53.1 Hz, 1H), 5.33 (ddd, J=2.0, 3.9, 53.1 Hz, 1H), 5.23-5.21 (m, 1H), 5.05-5.01 (m, 2H), 4.99-4.94 (m, 2H), 4.81 (ddd, J=4.3, 6.7,

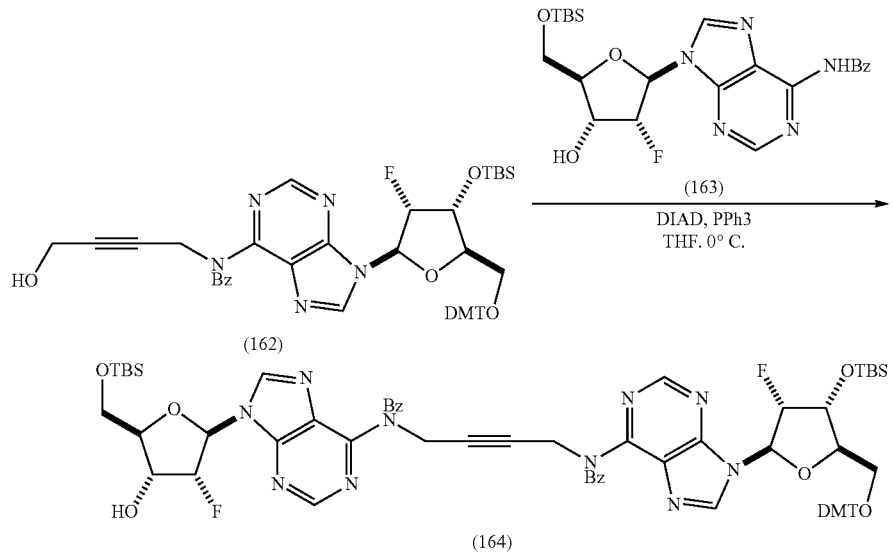

16.7 Hz, 1H), 4.71-4.60 (m, 1H), 4.21-4.14 (m, 2H), 4.08-4.03 (m, 1H), 3.89 (dd, J=3.1, 11.7 Hz, 1H), 3.77 (s, 6H), 0.91 (s, 9H), 0.84 (s, 9H), 0.09 (s, 3H), 0.08 (s, 6H), 0.00 (s, 3H).

Compound 165

Compound 162 (4.671 g, 5.444 mmol), Compound 163 (3.32 g, 6.805 mmol) and triphenyl phosphine (1.856 g, 7.077 mmol) were dissolved in THF (56.1 ml) and cooled below 5° C. To the resulting solution was added DIAD (1.3 ml, 6.8 mmol)) while keeping the internal T below 10° C.

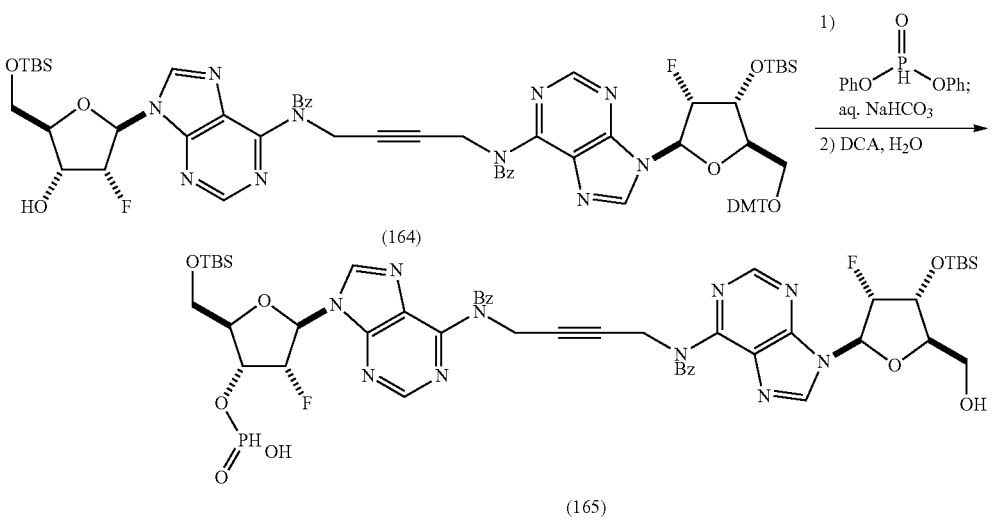

After complete consumption of Compound 162 (monitored by LCMS), the reaction mixture was concentrated in vacuo and purified by silica gel column chromatography (SiO$_2$ 340 g, 55% to 70% EtOAc in n-heptane buffered with 1% TEA) to give 3.879 g of Compound 164 as a white foam solid.

To a solution of Compound 164 (1.5 g, 1.13 mmol) in pyridine (12.0 ml) was added diphenyl phosphite (0.35 ml, 1.8 mmol) at ambient temperature. The resulting solution was stirred at ambient temperature while monitored by LCMS. Upon complete, the reaction mixture was added into a mixture of saturated aqueous NaHCO₃ (22.5 ml) and water (7.5 ml) while keeping the internal T below 30° C. After hydrolysis was complete (monitored by LCMS), the resulting mixture was extracted twice with a mixture of EtOAc/MTBE (30.0/30.0 ml). The combined organic layers were washed with 30% aq NaCl (15.0 ml), dried over MgSO₄, filtered and concentrated in vacuo. The residue was azeotroped with toluene three times and dissolved in dichloromethane (11 ml). water (0.20 ml, 11 mmol) and 6% dichloroacetic acid (0.57 ml, 6.9 mmol) in dichloromethane (11 ml) at ambient temperature. Upon complete removal of DMT group (monitored by LCMS), triethylsilane (1.8 ml, 11 mmol) was added. After 10 min stirring, TEA (1.6 ml, 11 mmol)) was added and the resulting mixture was concentrated in vacuo. The residue was dissolved in EtOAc (22.5 ml), washed with water (3.8 ml) and saturated aqueous NaHCO₃ (8%) (3.0 ml), dried over MgSO₄, filtered, and concentrated in vacuo. The crude product was triturated twice with n-heptane (33.8 ml) and a mixture of n-heptane (9.0 ml) and toluene (3.0 ml). The supernatant was decanted off and the solid remained at the bottom was dissolved in acetonitrile. The resulting solution was concentrated in vacuo and azeotroped with acetonitrile twice. The crude product, Compound 165, was used for the next stage without purification (theoretical 100% yield assumed).

LC/MS (ESI) m/z 1089.74 [M+H]⁺.

Compound 166

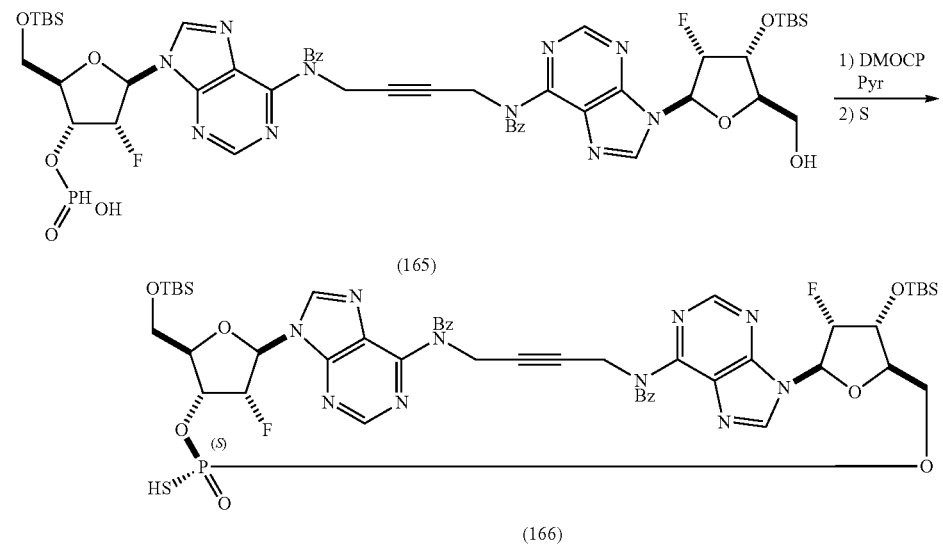

To a solution of Compound 165 (1.231 g, 1.13 mmol) in pyridine (100 mL) at ambient temperature were added TEA (0.47 ml, 3.4 mmol) and DMOCP (0.375 mg, 2.03 mm). The resulting solution was stirred at ambient temperature while monitored by LCMS. Upon completion, water (0.41 mL, 22.6 mmol) and then sulfur (0.181 g, 5.651 mmol) were added. Upon complete sulfurization (monitored by LCMS), saturated aqueous NaHCO₃ (8%) (24.6 ml) and water (10 mL) were added. The resulting mixture was concentrated in vacuo to ~50 mL and extracted twice with a mixture of MTBE/EtOAc (31/31 ml) each time. The combined organic layers were washed with 30% aq NaCl (25 ml), dried over MgSO₄, filtered, concentrated in vacuo, and purified by silica gel column chromatography (SiO₂ 100 g, 0 to 10% methanol in ethyl acetate buffered with 1% TEA) to give Compound 166 (0.484 g).

LC/MS (ESI) m/z 1103.65 [M+H]⁺.

Compound 167

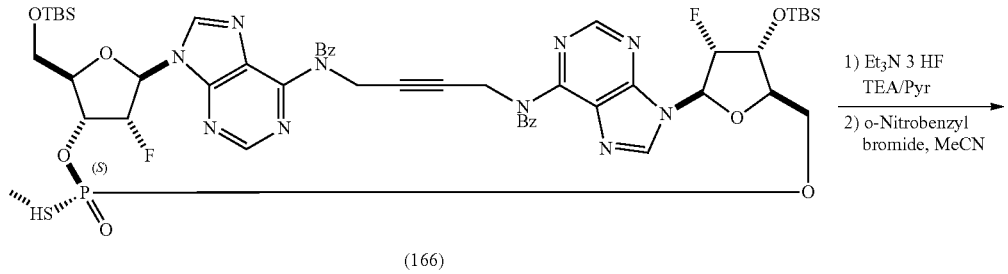

-continued

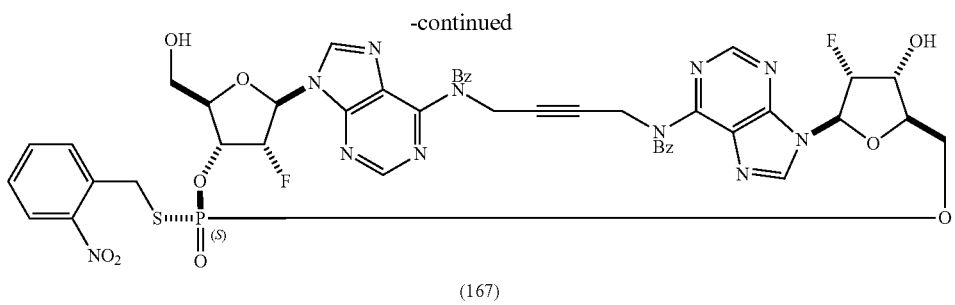

(167)

To a solution of Compound 166 (0.484 g, 0.402 mmol) in pyridine (1.2 ml) and TEA (5.8 ml) at ambient temperature was added Et$_3$N 3HF (0.581 ml, 3.563 mmol). The resulting mixture was stirred at ambient temperature while monitored by LCMS. Upon complete conversion, methoxytrimethylsilane (3.9 ml, 28 mmol) was added. After 20 min stirring at ambient temperature, the supernatant was decanted. To the residue was added toluene (5 mL) and after 10 min stirring, the tolune layer was decanted. The same operation was repeated one more time. The resulting crude product was dissolved in dichloromethane (10 mL), washed with a saturated aqueous NH$_4$Cl (27 wt %) (5 ml) and 30% aq NaCl (2.4 ml), and dried over MgSO$_4$. Filtration followed by concentration of the resulting organic layer gave 0.386 g of pale brown solid which was azeotroped with MeCN twice. The resulting crude product was dissolved in MeCN (4.6 ml) and treated with 2-nitrobenzyl bromide (0.103 g, 0.475 mmol) at ambient temperature. After the alklation was complete (monitored by LCMS), the reaction mixture was concentrated in vacuo and purified by silica-gel column chromtogray (SiO$_2$ 25 g, 0 to 5% MeOH in EtOAc) to give 0.251 g of Compound 167 as a white solid.

$^1$H NMR (400 MHz, CHLOROFORM-d) δ=8.42 (br s, 1H), 8.31 (br s, 1H), 8.22 (br s, 1H), 8.10-8.04 (m, 1H), 7.93 (s, 1H), 7.53-7.37 (m, 8H), 7.32-7.27 (m, 3H), 7.24-7.16 (m, 2H), 6.18 (br d, J=16.8 Hz, 1H), 6.26-6.14 (m, 1H), 5.56 (d, J=53.1 Hz, 1H), 5.48-5.37 (m, 1H), 5.31 (br s, 1H), 5.15 (br d, J=17.6 Hz, 1H), 4.92 (d, J=17.6 Hz, 1H), 4.82 (d, J=17.2 Hz, 1H), 4.88-4.77 (m, 1H), 4.76-4.66 (m, 1H), 4.58-4.33 (m, 3H), 4.29 (br d, J=5.9 Hz, 1H), 4.21 (br s, 1H), 4.13-4.06 (m, 1H), 3.93-3.79 (m, 2H).

Compound 168

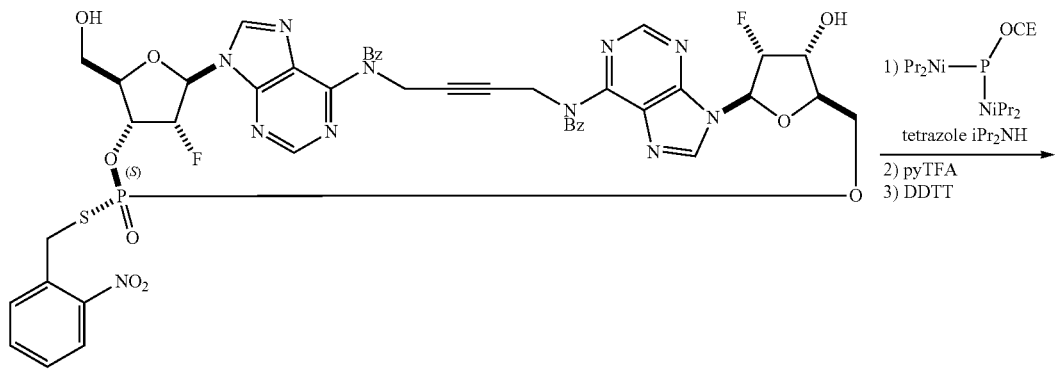

(167)

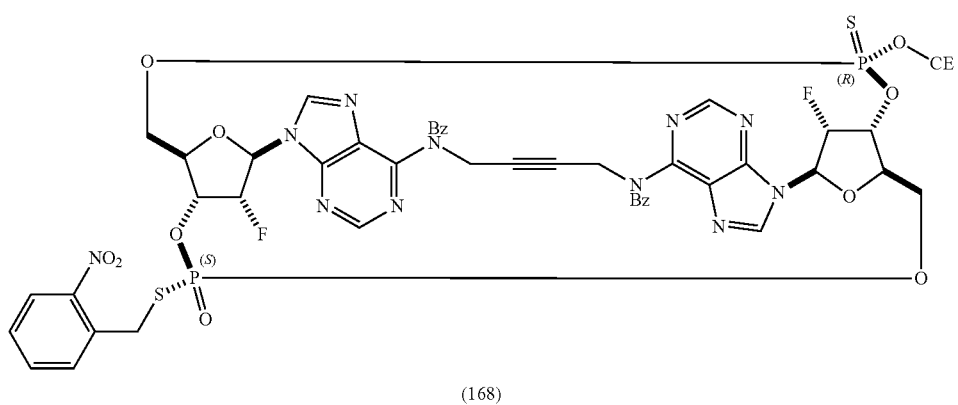

(168)

Compound 167 (0.224 g, 0.222 mmol) and 3-(Bis(diisopropylamino)phosphinooxy)propanenitrile (0.081 ml, 0.255 mmol) were dissolve in MeCN (5 mL) and concentrated. The same operation was repeated two more times. The resulting mixture was dissolved in dichloromethane (2.2 ml), cooled to 0° C., and treated with diisopropylammonium tetrazolide (0.019 g, 0.111 mmol). The reaction mixture was brought to ambient temperature over night and diluted with MeCN (2.2 mL). The resulting solution was added over 10 h via syringe pump into a solution of pyridine trifluoroacetate salt (0.129 g, 0.665 mmol) in MeCN (18 ml). After additional 1 h stirring, 3-(Bis(diisopropylamino)phosphinooxy)propanenitrile (0.04 mL, 0.12 mmol) in MeCN (1 mL) was added over 4 h. (E)-N,N-dimethyl-N'-(3-thioxo-3H-1,2,4-dithiazol-5-yl)formimidamide (0.064 g, 0.311 mmol) was added. Upon complete sulfurization (monitored by LCMS), the reaction mixture was concentrated in vacuo and the resulting residue was taken up with MTBE (4.5 ml). The resulting organic solution was washed with saturated aqueous $NaHCO_3$ (8%) (4 ml) and water (2 ml). The combined aqueous layers were backextracted with a mixture of MTBE/EtOAc (4/4 mL). The combined organic layers were washed twice with 30% aqueous NaCl (2 mL each time), dried over $MgSO_4$, filtered, concentrated in vacuo. The residue was purified by silicagel column chromatography ($SiO_2$ 25 g, 50% to 100% EtOAc in n-heptane) to give 64 mg of Compound 168.

$^1$H NMR (400 MHz, CHLOROFORM-d) δ=8.57 (s, 1H), 8.18 (s, 1H), 8.06-8.01 (m, 1H), 7.91 (s, 1H), 7.62-7.56 (m, 2H), 7.55-7.50 (m, 2H), 7.49-7.43 (m, 3H), 7.42-7.34 (m, 2H), 7.30-7.18 (m, 5H), 6.33 (d, J=15.2 Hz, 1H), 6.10 (d, J=20.7 Hz, 1H), 5.95-5.77 (m, 1H), 5.54 (dd, J=4.3, 52.8 Hz, 1H), 5.46 (dd, J=3.9, 50.8 Hz, 1H), 5.32-5.18 (m, 1H), 5.10 (d, J=17.6 Hz, 1H), 4.89 (d, J=17.6 Hz, 1H), 4.85-4.81 (m, 2H), 4.78 (br d, J=12.1 Hz, 1H), 4.64 (br dd, J=4.1, 9.2 Hz, 1H), 4.55 (dd, J=2.7, 12.1 Hz, 1H), 4.52-4.44 (m, 3H), 4.38-4.20 (m, 4H), 2.75 (td, J=6.3, 17.6 Hz, 1H), 2.58 (td, J=5.9, 17.2 Hz, 1H).

Compound 29

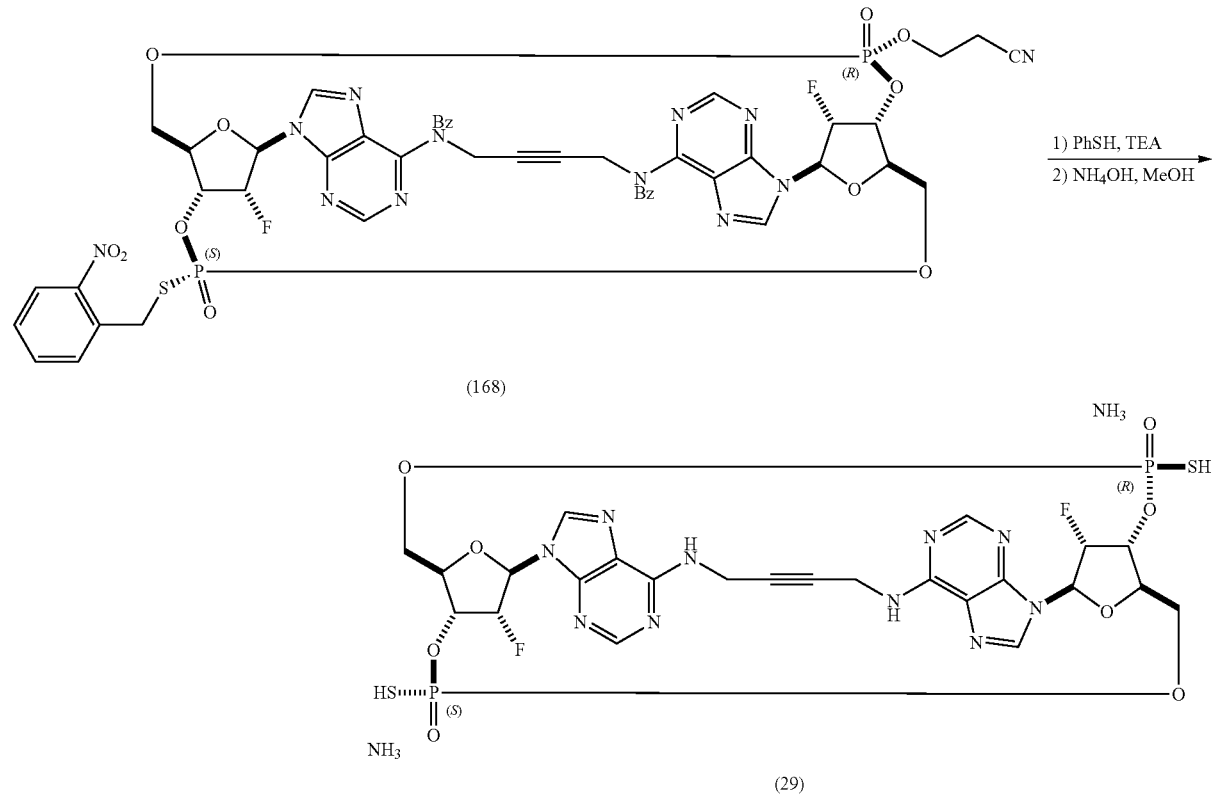

To a solution of Compound 168 (40 mg, 0.035 mmol) in 1,4-dioxane (0.5 mL) were added thiophenol (0.24 ml, 2.3 mmol) and TEA (0.24 ml, 1.7 mmol). The resulting mixture was stirred at ambient temperature while the reaction was monitored by LCMS. Upon completion, methanol (0.64 ml) and 28% ammonium hydroxide (0.64 ml) were added. The resulting mixture was heated to 50° C., stirred for 5 h and cooled to ambient temperature. Upon complete deprotection (monitored by LCMS), the resulting mixture was treated with water (0.80 ml) and extracted three times with a mixture of n-heptane/toluene (1/1, 0.5 mL each time) and then toluene (0.3 ml). The aqueous layer was concentrated in vacuo at 40-50° C. and treated with water (1 mL). The resulting solid was filtered off, rinsing with water (0.3 ml). The combined filtrates were treated with 1.0 M HCl (0.07 ml, 0.07 mmol). The resulting slurry was filtered and rinsed with water (1 mL). The filter cake was dissolved with a 2.0 M solution of ammonia (1.0 ml, 2.0 mmol) in MeOH. The resulting solution was concentrated in vacuo to 0.5 mL and treated with EtOH (0.5 ml). The same operation was repeated two more times. To the resulting solution was added EtOAc (0.9 mL) dropwise. Precipitation occurred. The resulting solid was collected by filtration, rinsed with a 4/1 mixture of EtOAc/EtOH (0.4 mL) and dried in vacuo overnight at ambient temperature. 12 mg of Compound 29 was obtained.

¹H NMR (400 MHz, METHANOL-d₄) δ=8.88 (br s, 1H), 8.50 (br s, 1H), 8.20 (br s, 1H), 8.12 (br s, 1H), 6.42-6.17 (m, 2H), 5.84-5.54 (m, 1H), 5.52 (d, J=51.6 Hz, 1H), 5.06-4.78 (m, 2H), 4.77-4.55 (m, 3H), 4.49 (br d, J=10.2 Hz, 1H), 4.42 (br s, 2H), 4.09-3.77 (m, 4H).

Example 18—Synthesis of Compound 25

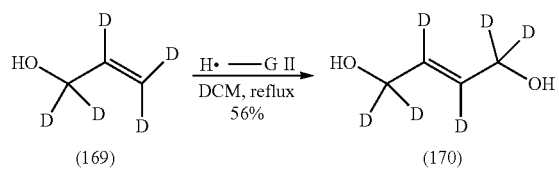

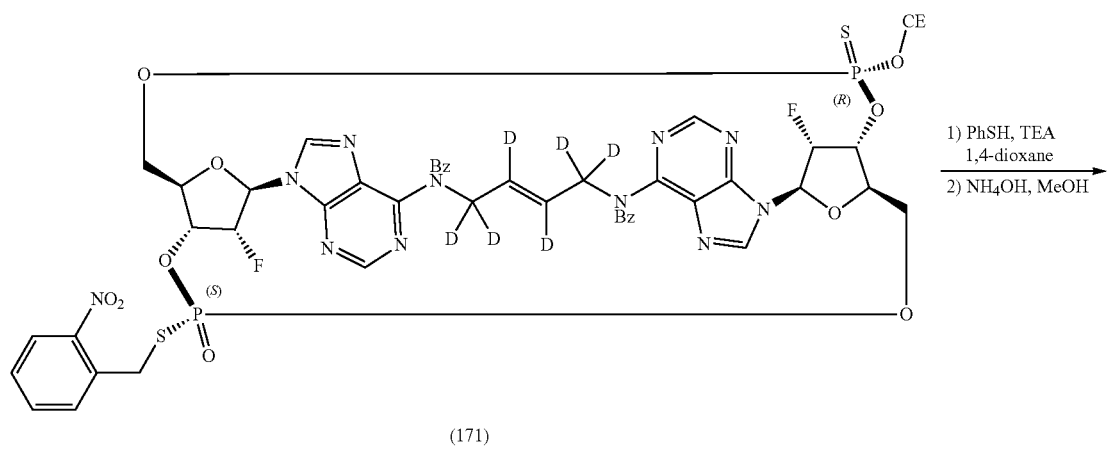

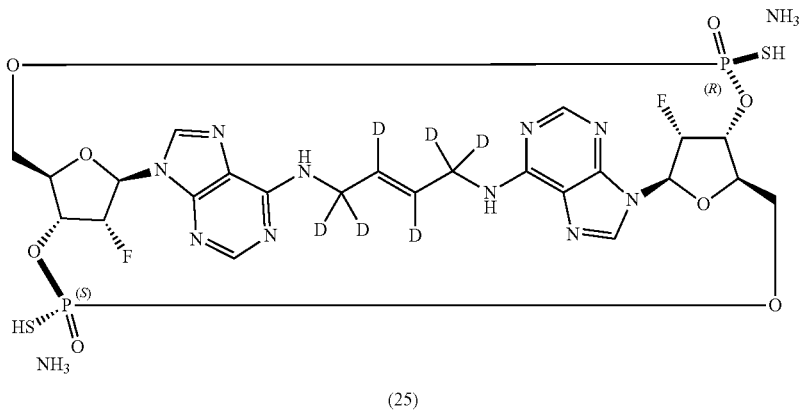

Compound 170

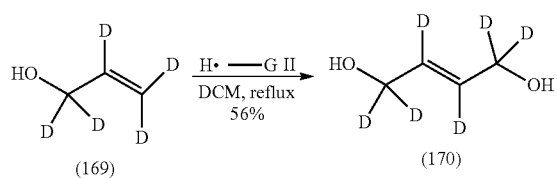

To a solution of Hoveyda-Grubbs Catalyst 2nd Generation (0.996 g, 1.585 mmol) in dichloromethane (40.0 ml) at reflux was added prop-2-en-d5-1-ol (10.0 g, 158 mmol). After 1 h, additional 1 mol % Hoveyda-Grubbs Catalyst 2nd Generation (0.996 g, 1.585 mmol) was added. The resulting solution was stirred at reflux overnight, cooled to ambient temperature, and concentrated in vacuo. The residue was purified by silicagel column chromatography (SiO₂ 340 g 0% to 10% MeOH in EtOAc) to give 4.2 g of Compound 170 as a brown oil.

¹³C NMR (101 MHz, METHANOL-d₄) δ=130.87 (t, J=23.8 Hz, 2C), 62.22 (quin, J=21.9 Hz, 2C).

Compound 171
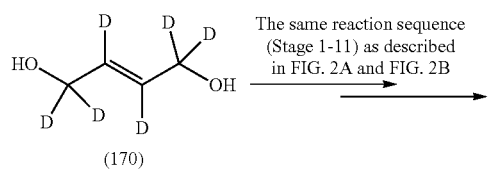
(170)
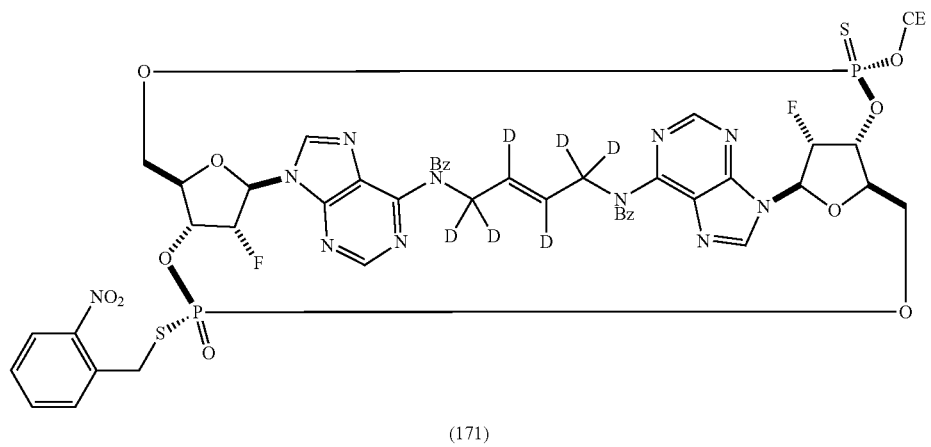
(171)
With Compound 170 as a starting material, compounds Compound 171 was prepared via the same reaction sequence (Stage 1 to 11) as described in the synthetic route for Compound 1 in FIG. 2A and FIG. 2B.
$^1$H NMR (400 MHz, CHLOROFORM-d) δ=8.59 (s, 1H), 8.10 (s, 1H), 8.02-7.96 (m, 1H), 7.93 (s, 1H), 7.58-7.50 (m, 2H), 7.48-7.37 (m, 5H), 7.34-7.27 (m, 2H), 7.24-7.14 (m, 4H), 6.90 (s, 1H), 6.28 (d, J=14.8 Hz, 1H), 6.14-6.03 (m, 1H), 5.97-5.81 (m, 1H), 5.49 (dd, J=4.7, 52.3 Hz, 2H), 5.43 (dd, J=3.9, 50.8 Hz, 1H), 5.30-5.15 (m, 1H), 4.75 (br d, J=12.1 Hz, 1H), 4.61 (br dd, J=4.3, 9.4 Hz, 1H), 4.53 (dd, J=2.9, 11.9 Hz, 1H), 4.47-4.41 (m, 3H), 4.32-4.18 (m, 4H), 2.79 (td, J=7.0, 17.2 Hz, 1H), 2.66 (td, J=6.3, 16.8 Hz, 1H)
Compound 25
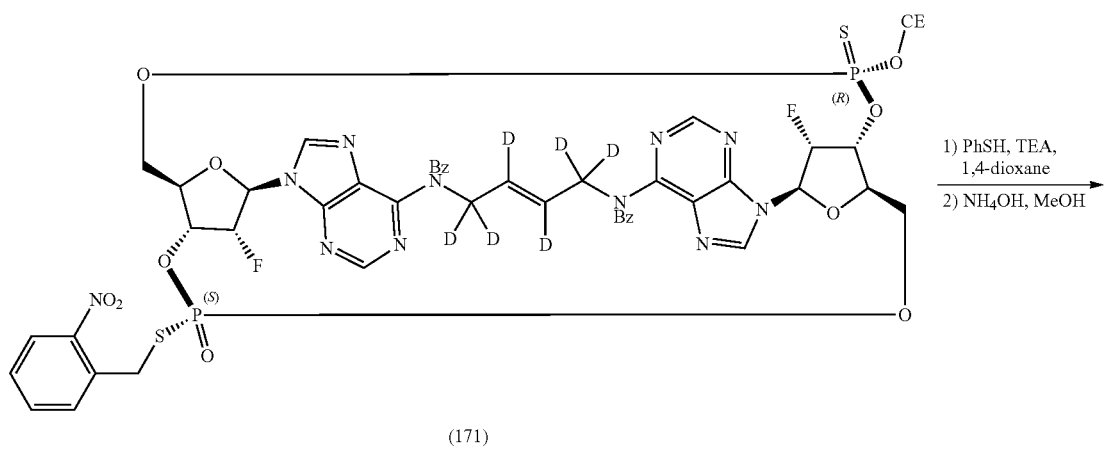
(171)
1) PhSH, TEA, 1,4-dioxane
2) NH$_4$OH, MeOH

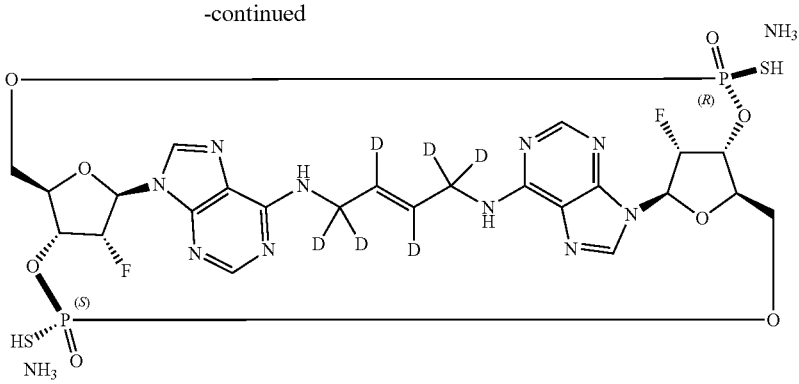
(25)
With Compound 171 as a starting material, Compound 25 was prepared via the same reaction sequence (Stage 12-13) as described in FIG. 2A and FIG. 2B.
¹H NMR (400 MHz, CD₃OD) δ=9.03 (br s, 1H), 8.30 (br s, 1H), 8.24 (br s, 1H), 8.10 (br s, 1H), 6.44-6.13 (m, 2H), 0.00 (d, J=52.4 Hz, 1H), 0.00 (d, J=51.2 Hz, 1H), 4.71-4.32 (m, 6H), 4.09-3.98 (m, 1H), 3.97-3.87 (m, 1H).
Example 19—Synthesis of Compound 31 (either RpRp or SpSp)
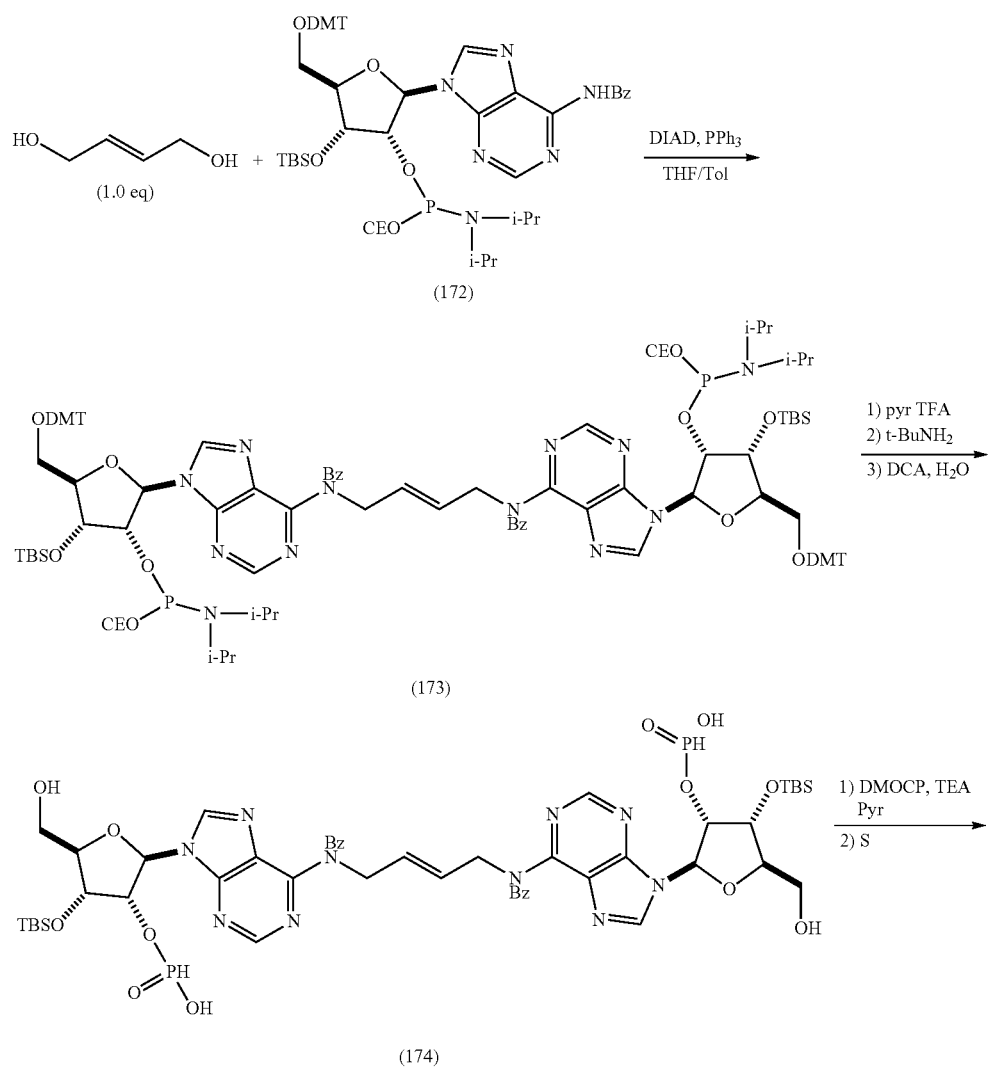

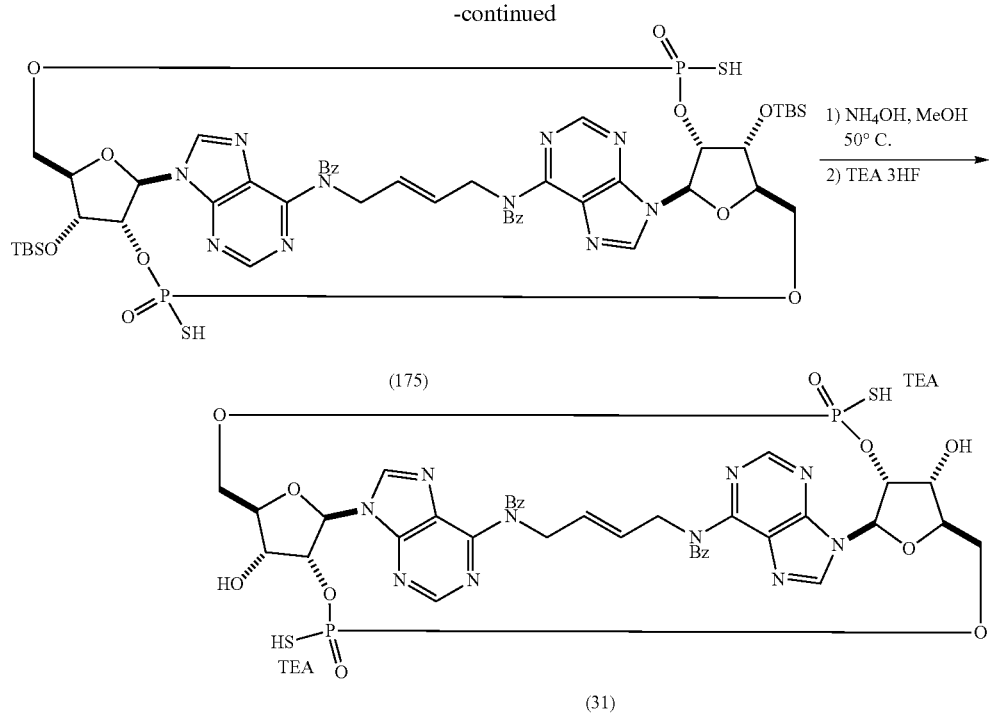

(175)

(31)

Compound 173

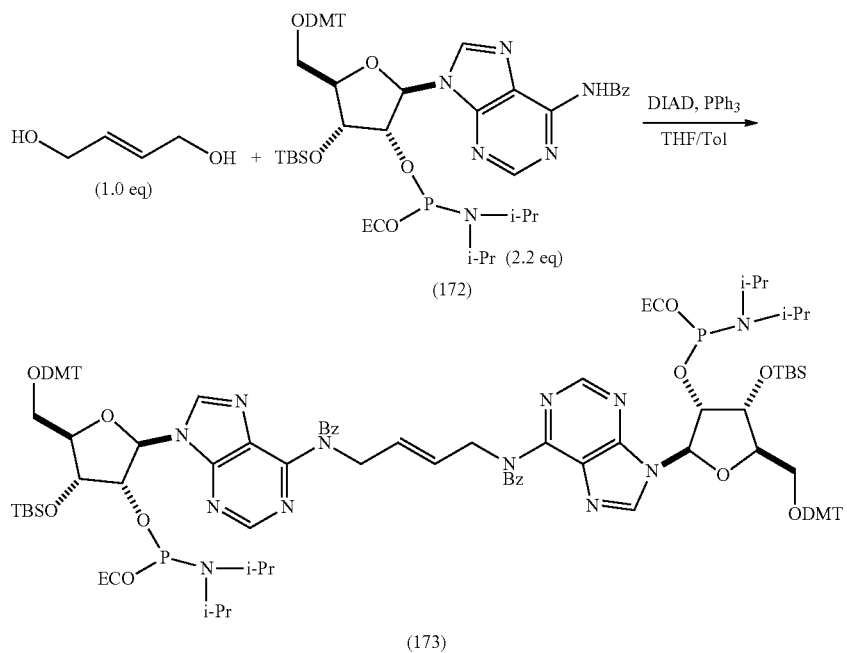

(172)

(173)

A mixture of (E)-but-2-ene-1,4-diol (0.10 g, 1.135 mmol) and Compound 172 (2.52 g, 2.55 mmol) was azeotroped with THF twice and dissolved in THF (5.0 ml) and toluene (7.5 ml). To the resulting solution was added triphenylphosphine (0.714 g, 2.724 mmol). The resulting solution was cooled down below 5° C. and treated with DIAD (0.53 ml, 2.72 mmol) while keeping internal T below 10° C. The resulting reaction mixture was stirred overnight while warmed to ambient temperature. Upon complete reaction (monitored by LCMS), the reaction mixture was concentrated in vacuo and purified by silicagel column chromatography (SiO$_2$ 50 g pretreated with 1% TEA in n-heptane/EtOAc (1/1), 50% to 66% EtOAc in n-heptane) to give 2.46 g of Compound 173 as a white foam solid. This material was used in next step without further purification.

Compound 174

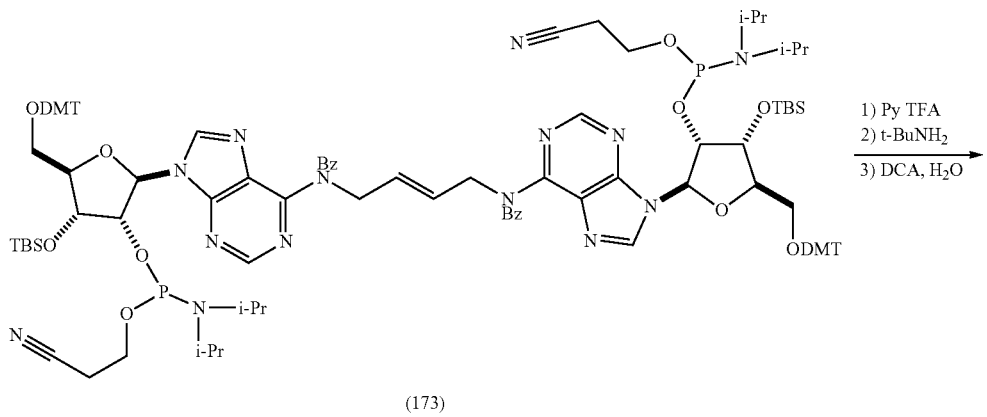

(173)

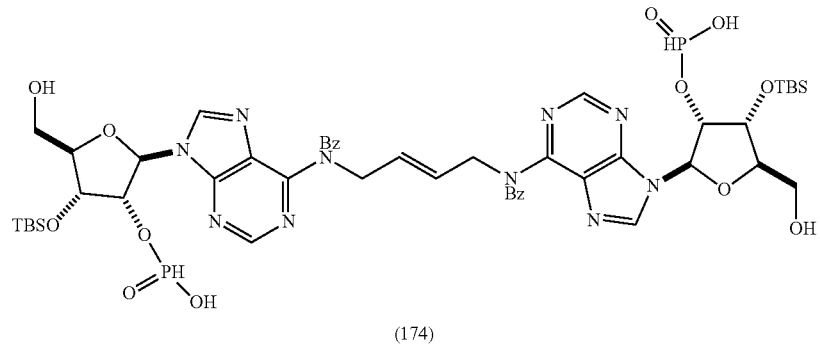

(174)

To a solution of Compound 173 (2.387 g, 1.177 mmol) in acetonitrile (28.6 ml) were added water (0.085 ml, 4.7 mmol), pyridine trifluoroacetate salt (0.500 g, 2.589 mmol) at ambient temperature. After 1 min, 2-amino-2-methylpropane (19.1 ml, 182 mmol) was added. The resulting mixture was stirred at ambient temperature while the reaction was monitored by LCMS. Upon completion, the reaction mixture was concentrated in vacuo and azeotroped with MeCN. The residue was dissolved in dichloromethane (24 mL) and treated with water (0.42 ml) and 6% dichloroacetic acid (1.2 ml, 14 mmol) in dichloromethane (24 ml). Upon complete DMT deprotection (monitored by LCMS), the reaction was quenched with pyridine (12 ml) and the reaction mixture concentrated in vacuo. The resulting residue was treated with a mixture of n-heptane/toluene (15/15 ml) and the top layer was decanted. The same operation was repeated one more time. Drying the remaining residue in vacuo gave Compound 174, which was used in next step without further purification.

LC/MS (ESI) m/z 1151.64 [M+H]+.

Compound 175

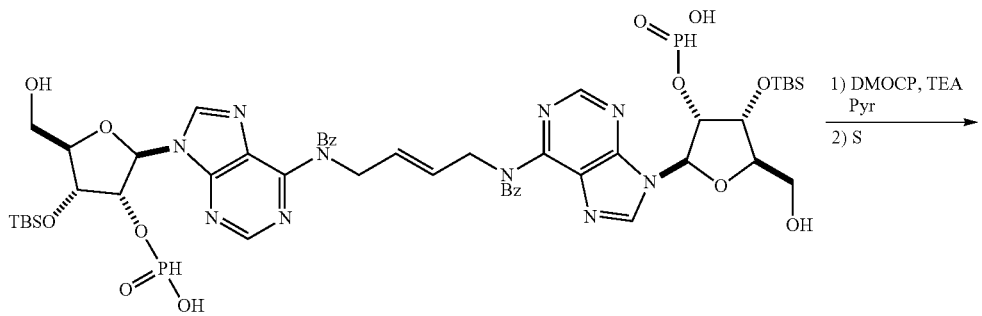

(174)

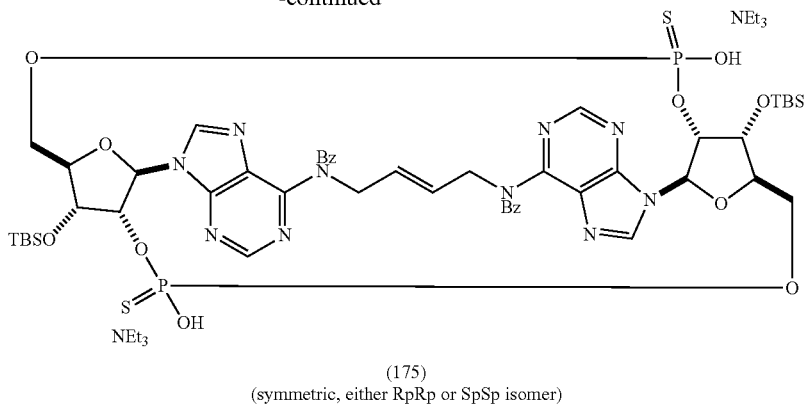

(175)
(symmetric, either RpRp or SpSp isomer)

To a solution of Compound 174 (1.355 g, 1.177 mmol) in pyridine (271 ml) at ambient temperature were added TEA (0.98 ml, 7.1 mmol) and 2-chloro-5,5-dimethyl-1,3,2-dioxaphosphinane 2-oxide (0.869 g, 4.708 mmol). The resulting solution was stirred at ambient temperature until all the starting material was consumed (monitored by LCMS). Upon complete reaction, water (0.85 ml, 47 mmol) (10 eq of DMOCP) and then sulfur (0.377 g, 11.77 mmol) were added. The resulting mixture was stirred at ambient temperature while the reaction was monitored by LCMS Upon complete sulfurization, the reaction mixture was treated with a sat'd aqueous NaHCO$_3$ (27 ml) and water (10 mL), and concentrated in vacuo. To the resulting residue were added a mixture of MTBE/EtOAc (34/34 ml), a sat'd aqueous NaHCO$_3$ solution (27 ml) and water (20 mL). The layers were separated and the aqueous layer was extracted with a mixture of EtOAc/MTBE (34/34 mL). The combined organic layers were washed with 30% aqueous NaCl solution (7 ml), dried over MgSO$_4$, filtered and concentrated in vacuo. The residue was purified by silicagel column chromatography (SiO$_2$ 50 g, 0% to 20% MeOH in EtOAc with 1% TEA) to give 56 mg of Compound 175 (symmetric based on NMR; either RpRp or SpSp isomer).

$^1$H NMR (400 MHz, CHLOROFORM-d) δ=9.09 (s, 2H), 8.46 (s, 2H), 7.56-7.05 (m, 10H), 6.37 (d, J=8.2 Hz, 2H), 6.28-6.22 (m, 2H), 5.29 (ddd, J=4.7, 7.8, 11.7 Hz, 2H), 5.00 (br d, J=13.7 Hz, 2H), 4.84 (d, J=4.3 Hz, 2H), 4.76 (br d, J=13.3 Hz, 2H), 4.31 (br s, 2H), 4.28-4.20 (m, 2H), 4.16-4.08 (m, 2H), 3.00-2.77 (m, 12H), 1.12-0.99 (m, 18H), 0.96 (s, 18H), 0.34 (s, 6H), 0.25 (s, 6H).

Compound 31

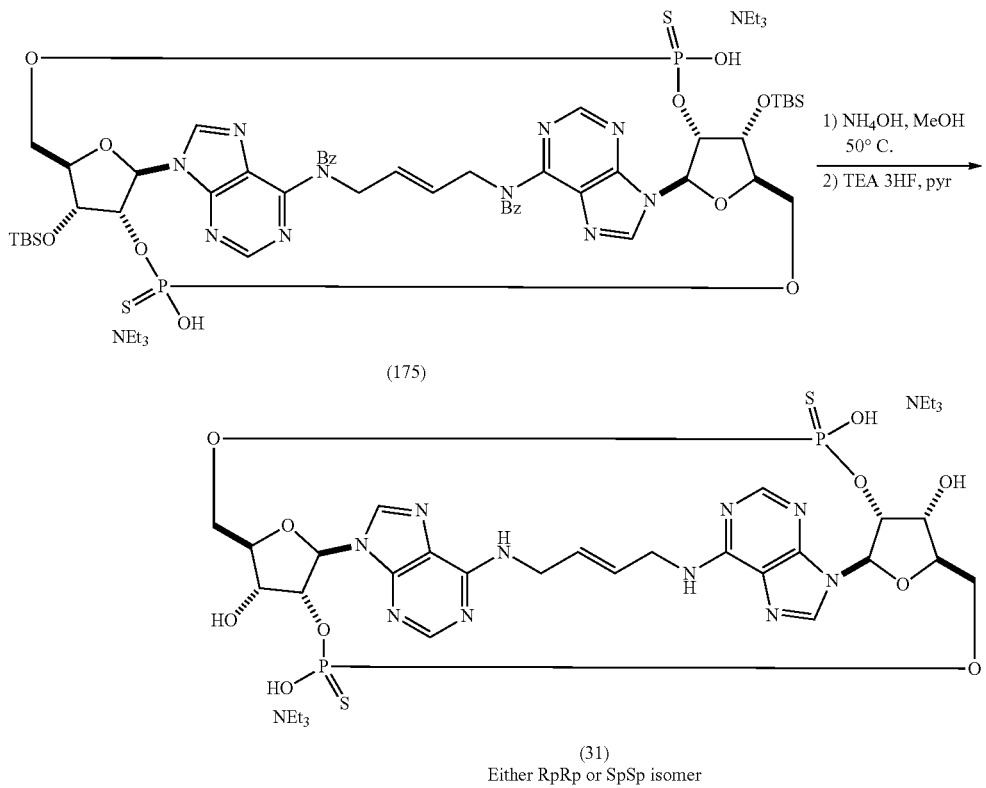

(31)
Either RpRp or SpSp isomer

To a solution of Compound 175 (56 mg, 0.0405 mmol) in methanol (1.1 mL) was added 28% ammonium hydroxide (0.22 mL). The resulting mixture was stirred at 50° C. for 5 h, cooled to ambient temperature, concentrated in vacuo and azeotroped with MeCN twice. To the resulting residue was added pyridine (0.22 mL), TEA (0.11 mL) and TEA 3HF (0.11 ml, 0.69 mmol). The resulting mixture was stirred at 500 for 5 h, cooled to ambient temperature, treated with methoxytrimethyl silane (0.90 mL, 6.50 mmol) for 30 min. The resulting mixture was concentrated in vacuo and dissolved in water (5 mL). The resulting aqueous solution was extracted three times with toluene (5 mL each time) and concentrated in vacuo. The crude product was dissolved in 1 mL water, filtered through a syringe filter and acidified 1N HCl to make pH <3. The resulting mixture was kept in a refreezer (5° C.) for 2 days and the resulting solid was collected by filtration. The solid was dissolved in 2M $NH_3$ in MeOH (1.5 ml) and concentrated in vacuo to give 2.8 mg of Compound 31 as a mixture of $NH_3$ and TEA salt. The product was dissolved in EtOH (1 mL), treated with 0.1 ml TEA, concentrated to 0.5 mL and kept in a freezer (−20° C.) overnight. The supernatant was removed and the remaining solid was further dried in a vacuum to give 0.8 mg of bis TEA salt Compound 31 (symmetric by NMR; either RpRp or SpSp isomer).

$^1$H NMR (400 MHz, METHANOL-$d_4$) δ=8.26-7.83 (m, 4H), 6.37 (br s, 2H), 5.89 (br s, 2H), 5.36-5.07 (m, 2H), 4.95 (br d, J=3.5 Hz, 2H), 4.58 (br dd, J=6.3, 10.6 Hz, 2H), 4.43 (br s, 2H), 4.12-4.00 (m, 4H), 3.89-3.70 (m, 2H), 3.19 (q, J=7.2 Hz, 12H), 1.30 (t, J=7.4 Hz, 18H)

Example 20—Synthesis of Compound 32

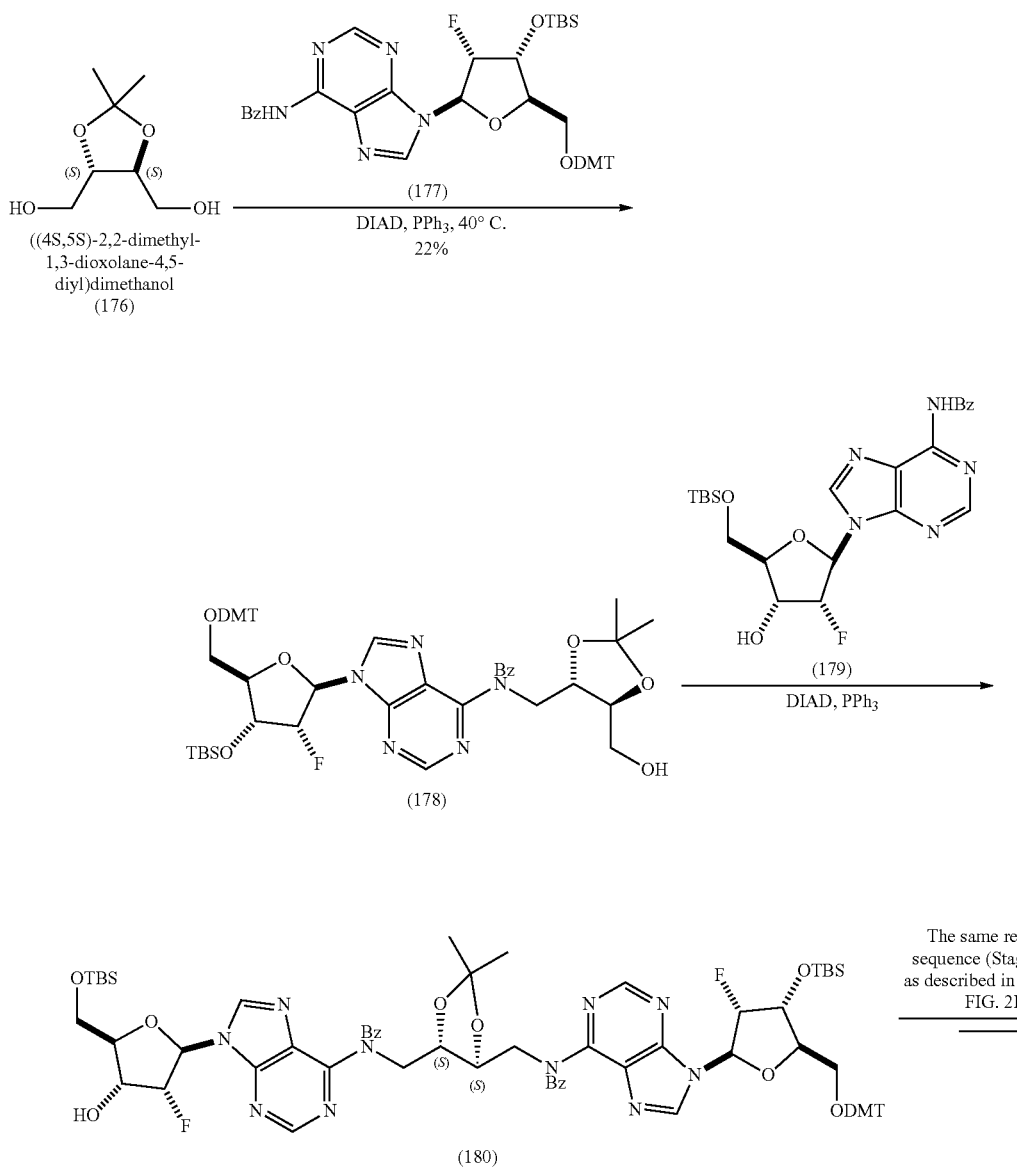

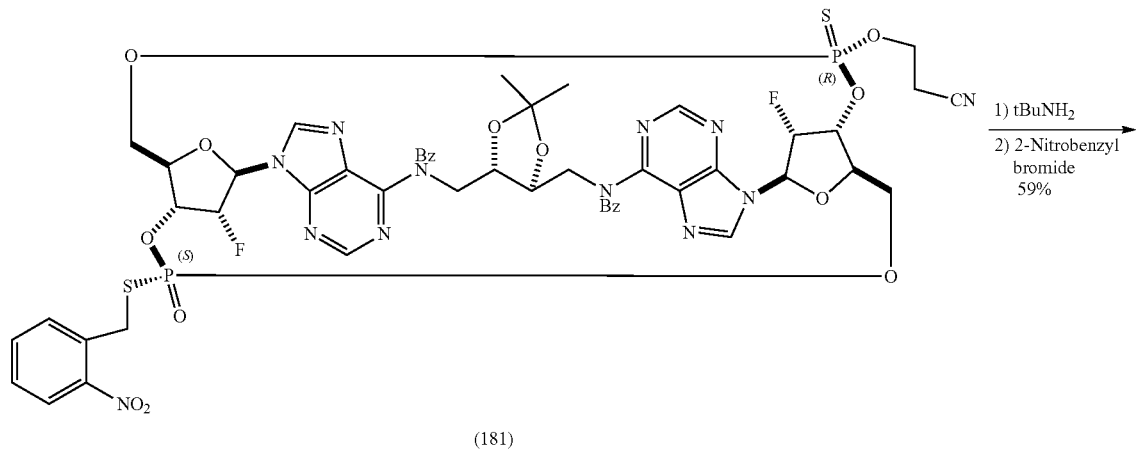
(181)
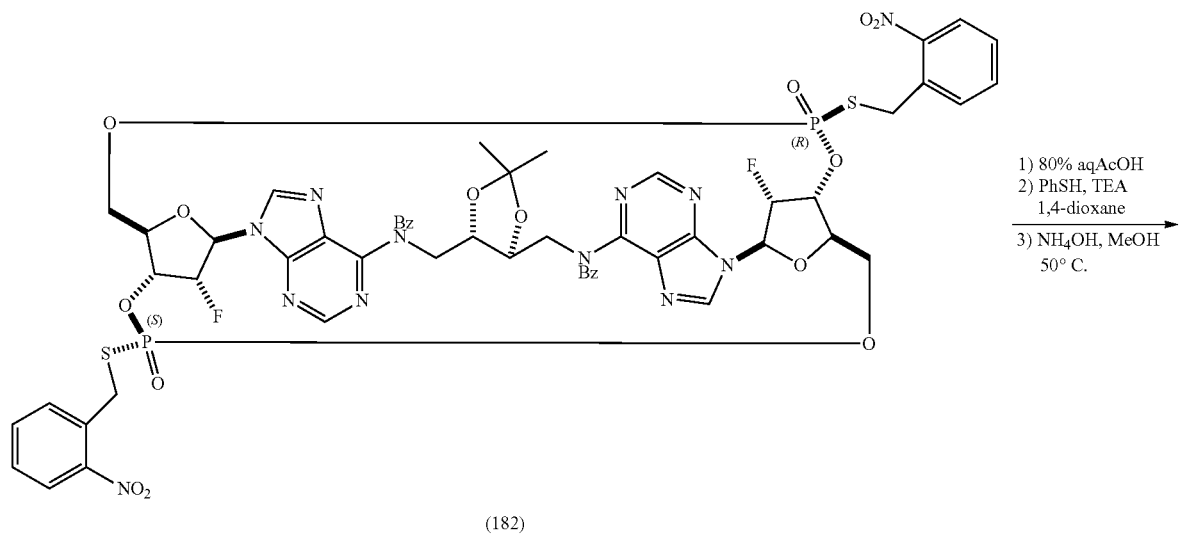
(182)
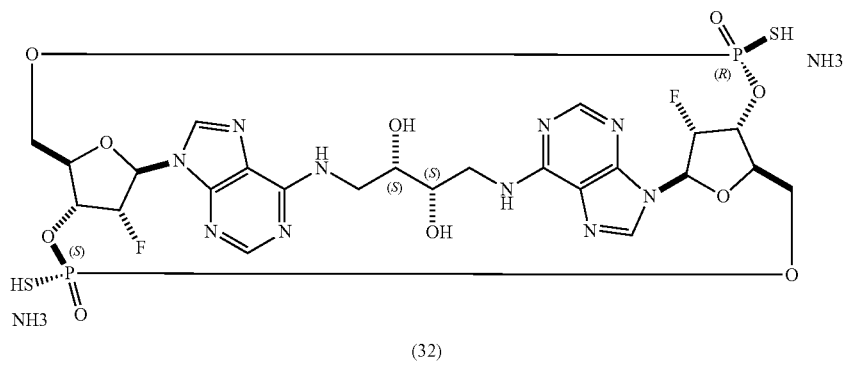
(32)

Compound 178

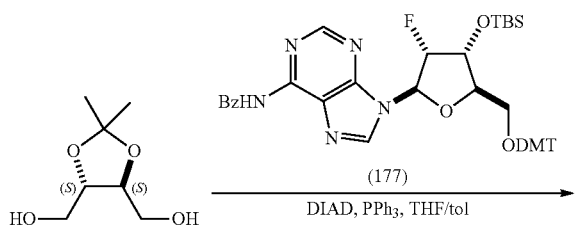

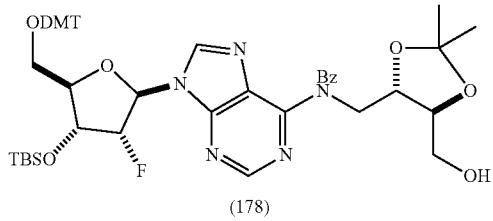

To a solution of Compound 177 (2.0 g, 2.532 mmol) and (+)-2,3-O-Isopropylidene-L-threitol (Compound 176) (1.232 g, 7.595 mmol) in THF (20.0 ml) and toluene (30.0 ml) was added triphenylphosphine (0.930 g, 3.544 mmol). The resulting solution was cooled down below 5° C. and treated with DIAD (0.64 ml, 3.3 mmol). The reaction mixture was warmed to ambient temperature. After 8 h stirring at ambient temperature, additional DIAD (0.64 mL) and PPh₃ (0.93 g) were added. After overnight stirring at ambient temperature, the reaction mixture was stirred at 40° C. for 2 days and concentrated in vacuo. Purification of the residue by silicagel column chromatography (SiO₂ 100 g pretreated with 1% TEA in n-heptane/EtOAc (1/1), 50% to 70% EtOAc in n-heptane) gave 0.524 g of Compound 178 as a white foam solid.

¹H NMR (400 MHz, CHLOROFORM-d) δ=8.62 (s, 1H), 8.09 (s, 1H), 7.40-7.09 (m, 12H), 7.01-6.92 (m, 2H), 6.80-6.73 (m, 4H), 6.16 (dd, J=2.7, 16.8 Hz, 1H), 5.49 (ddd, J=3.1, 4.3, 53.1 Hz, 1H), 4.85-4.75 (m, 2H), 4.63 (dd, J=3.9, 14.8 Hz, 1H), 4.30-4.19 (m, 2H), 4.18-4.12 (m, 1H), 3.94 (tt, J=3.5, 8.2 Hz, 1H), 3.84 (td, J=5.5, 12.1 Hz, 1H), 3.78 (s, 6H), 3.53 (dd, J=2.7, 10.9 Hz, 1H), 3.17 (dd, J=3.5, 10.9 Hz, 1H), 2.94 (brt, J=5.5 Hz, 1H), 0.89 (s, 6H), 0.83 (s, 9H), 0.08 (s, 3H), −0.01 (s, 3H)

Compound 180

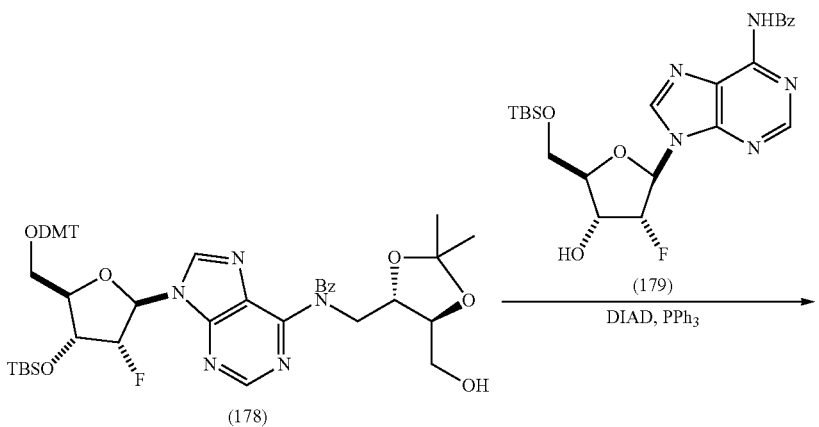

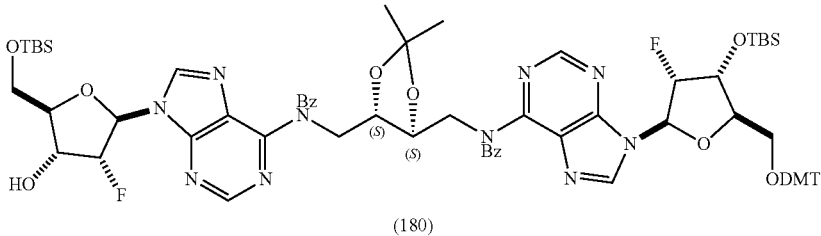

To a solution of Compound 178 (0.409 g, 0.84 mmol) in THF (6 mL) were added triphenylphosphine (0.191 g, 0.728 mmol) and DIAD (0.142 ml, 0.728 mmol). After 40 h stirring at ambient temperature, the reaction mixture was concentrated in vacuo and purified by column chromatography (SiO₂ 50 g pretreated with 1% TEA in n-heptane/EtOAc (1/1), 50% to 66% EtOAc in n-heptane) to give 0.533 g of Compound 180.
LC/MS: LRMS (ESI) m/z 1403.86 [M+H]⁺.
Compound 181

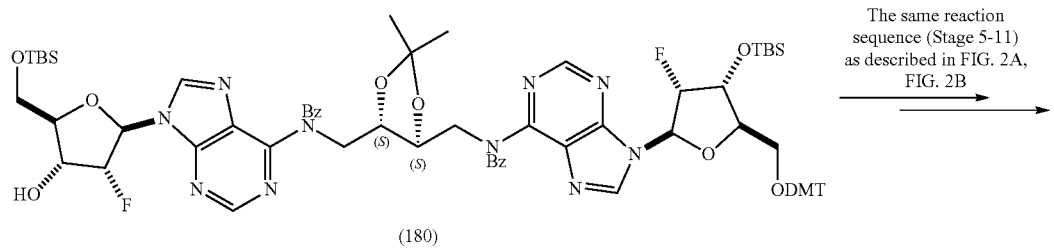

(180)

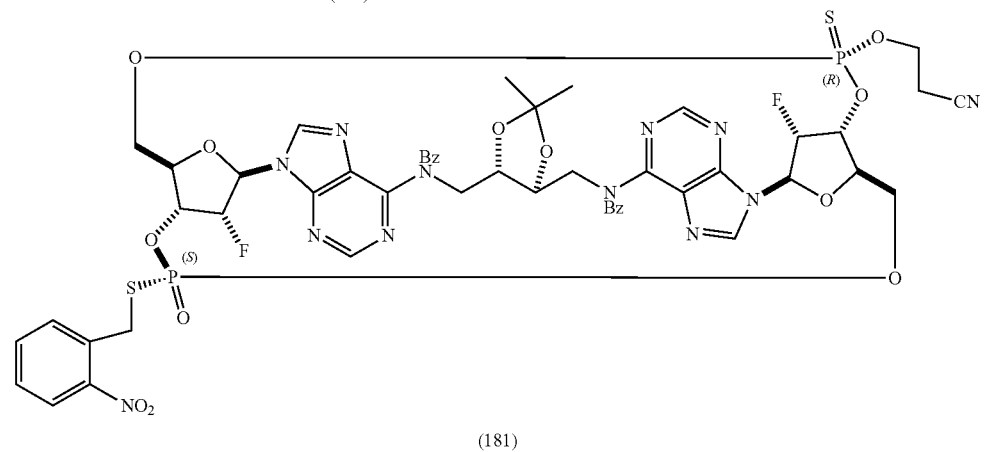

(181)

With Compound 180 as a starting material, Compound 181 was prepared via the same reaction sequence (Stage 5-11) as described in FIG. 2A and FIG. 2B.

¹H NMR (400 MHz, CHLOROFORM-d) δ=8.72 (s, 1H), 8.14-8.06 (m, 1H), 7.93 (s, 1H), 7.69 (s, 1H), 7.62-7.53 (m, 6H), 7.53-7.45 (m, 1H), 7.43-7.33 (m, 2H), 7.30-7.24 (m, 3H), 7.19-7.12 (m, 2H), 6.11 (d, J=16.8 Hz, 1H), 6.05 (d, J=19.5 Hz, 1H), 5.89 (dd, J=3.5, 52.3 Hz, 1H), 5.57-5.46 (m, 1H), 5.41 (dd, J=3.5, 53.1 Hz, 1H), 5.18-5.04 (m, 1H), 4.83 (dd, J=4.7, 14.4 Hz, 1H), 4.78-4.73 (m, 1H), 4.70 (br d, J=12.1 Hz, 1H), 4.64-4.48 (m, 4H), 4.46-4.35 (m, 4H), 4.33-4.27 (m, 2H), 4.16-4.06 (m, 2H), 4.05-3.96 (m, 1H), 2.55 (t, J=6.1 Hz, 2H), 1.26 (s, 6H).
Compound 182

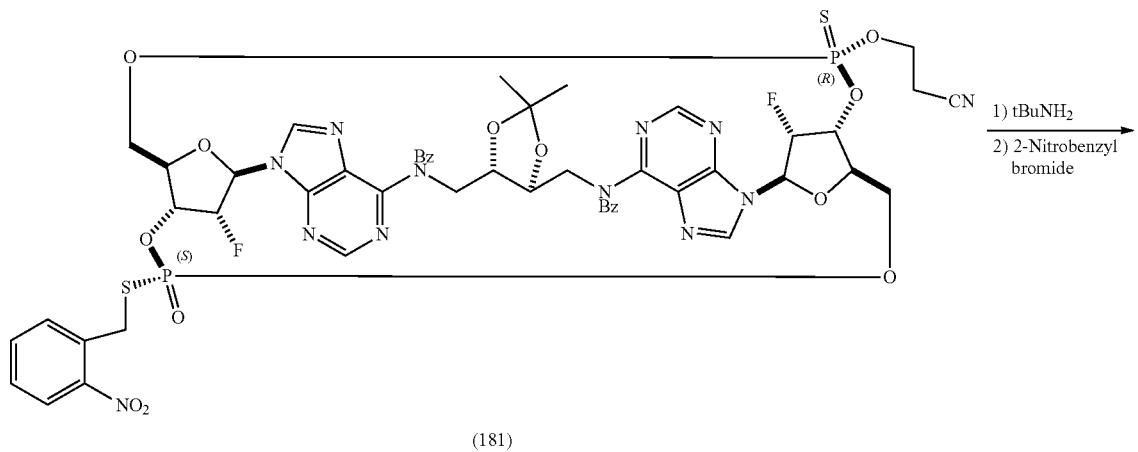

(181)

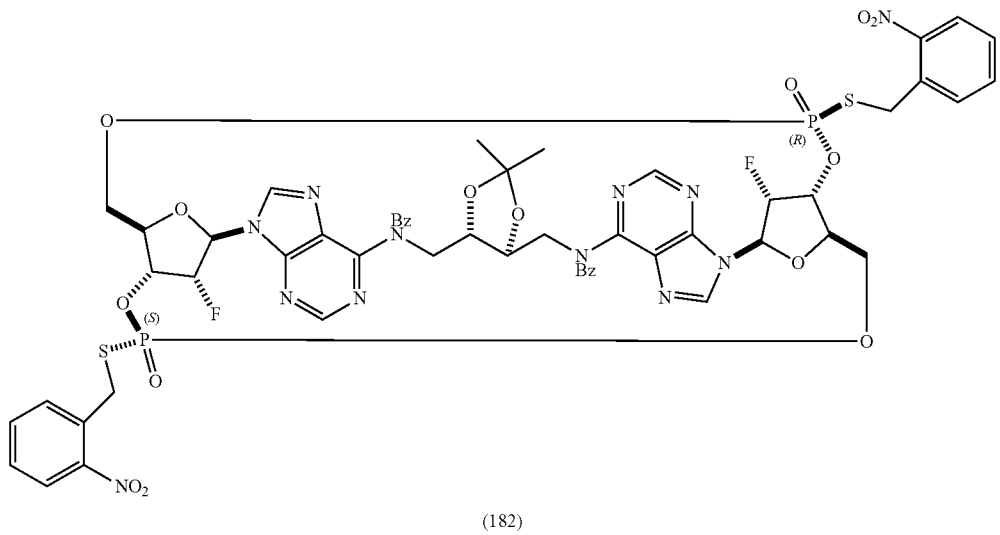

(182)

To a solution of Compound 181 (3.2 mg, 2.629 μmol) in dichloromethane (0.5 ml) was added tert-butylamine (0.5 ml, 4.7 mmol). After 30 min stirring, the reaction solution was concentrated in vacuo and azeotroped with MeCN twice. The residue was dissolved in acetonitrile (1 ml) and treated with 1-(bromomethyl)-2-nitrobenzene (1.7 mg, 7.9 μmol). Upon complete alkylation (monitored by LCMS), the reaction mixture was concentrated with nitrogen purge. Purification of the residue by silicagel column chromatography (SiO₂ 4 g, 80% to 100% EtOAc in n-heptane) gave 2 mg of Compound 182.

$^1$H NMR (400 MHz, CHLOROFORM-d) δ=8.12 (dd, J=1.4, 8.0 Hz, 1H), 8.03-8.00 (m, 1H), 8.00 (s, 1H), 7.93 (s, 1H), 7.70 (s, 1H), 7.70-7.29 (m, 13H), 7.21 (dt, J=2.7, 7.6 Hz, 4H), 6.07 (d, J=19.9 Hz, 1H), 5.94 (d, J=21.1 Hz, 1H), 5.91-5.77 (m, 1H), 5.81 (dd, J=4.3, 51.5 Hz, 1H), 5.62-5.49 (m, 1H), 5.54 (dd, J=3.1, 52.7 Hz, 2H), 4.83 (q, J=5.9 Hz, 1H), 4.72-4.63 (m, 2H), 4.61-4.28 (m, 13H), 1.42 (s, 3H), 1.28 (s, 3H).

Compound 32

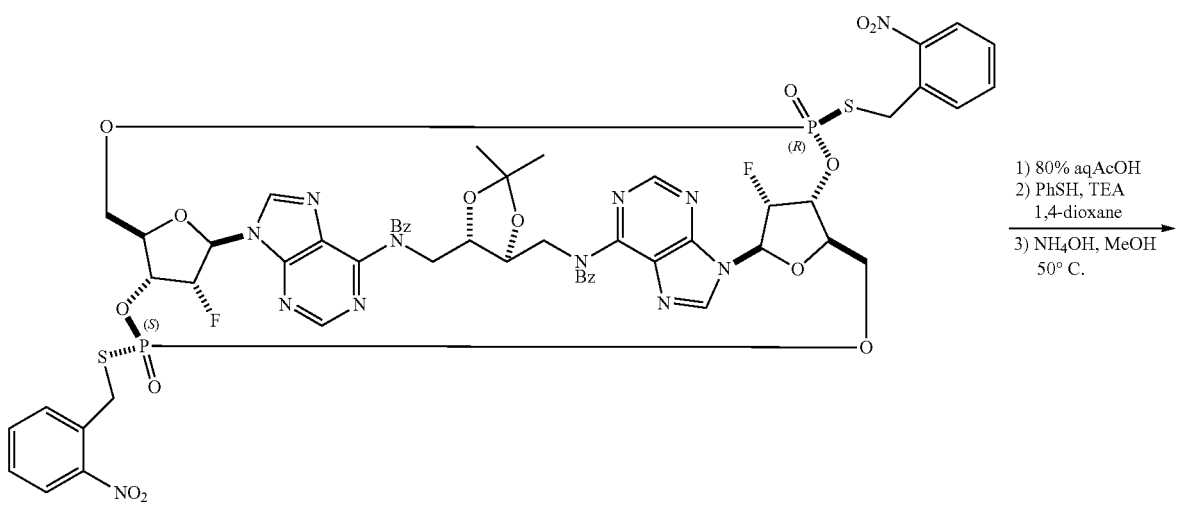

(182)

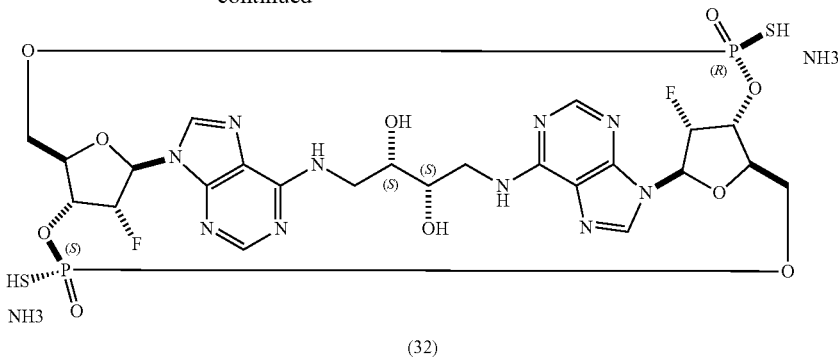

(32)

To Compound 182 (2.0 mg, 1.5 µmol) were added acetic acid (0.8 ml) and water (0.2 ml). The resulting mixture was stirred at ambient temperature for 14 h and at 45-50° C. for 24 h, concentrated in vacuo, and azeotroped with toluene twice. To the residue were added 1,4-dioxane (0.12 mL), thiophenol (60 µl) and then TEA (60 µl). The resulting mixture was stirred at ambient temperature while the reaction was monitored by LCMS. Upon completion, methanol (160 µl) and 28% ammonium hydroxide (160 µl) were added. The resulting mixture was stirred at 50° C. until debenzoylation was complete (monitored by LCMS). Upon completion, water (0.3 ml) was added. The resulting solid was filtered off, rinsing with water (0.2 mL). The filtrate was extracted twice with toluene (0.5 mL each time) and concentrated in vacuo at 40-50° C. The residue was treated with water (0.5 mL) and the resulting solid was filtered off, rinsing with water (0.1 mL). HPLC purification of the combined aqueous layers under the conditions described below gave 1.5 mg of Compound 32.

LC/MS: LRMS (ESI) m/z 781.23 [M+H]$^+$.

Preparative HPLC Conditions for Compound 32:

| | |
|---|---|
| Instrument | Agilent 1200/1260 AS/FC |
| HPLC column | Waters Xterra C18, 10 × 100 mm, # 1414 |
| Flow rate | 3.0 ml/min |
| Column temperature | 35° C. |
| mobile phase | A: 0.1% NH$_4$OH in water, B: 0.1% NH$_4$OH in acetonitrile |
| Gradient (B %) | 0 → 5 |
| Run time | 20 min |
| Injection volume | 50 ul (1 mg/ml in water) |
| detection | UV 260 nm |
| Retention times | 12.7 min |

Example 21—Synthesis of Compound 33 and Compound 34

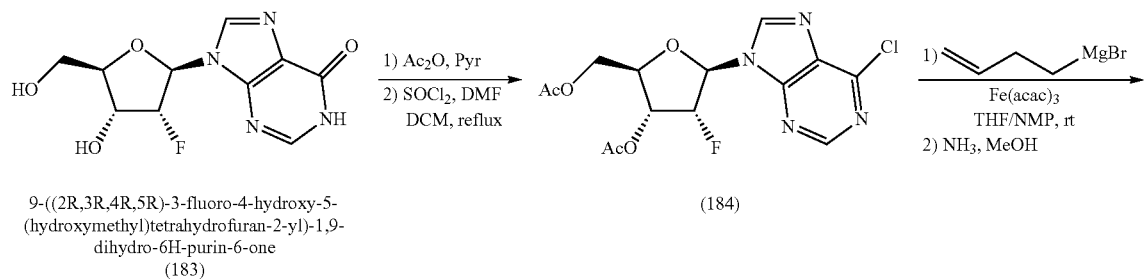

9-((2R,3R,4R,5R)-3-fluoro-4-hydroxy-5-(hydroxymethyl)tetrahydrofuran-2-yl)-1,9-dihydro-6H-purin-6-one
(183)

(184)

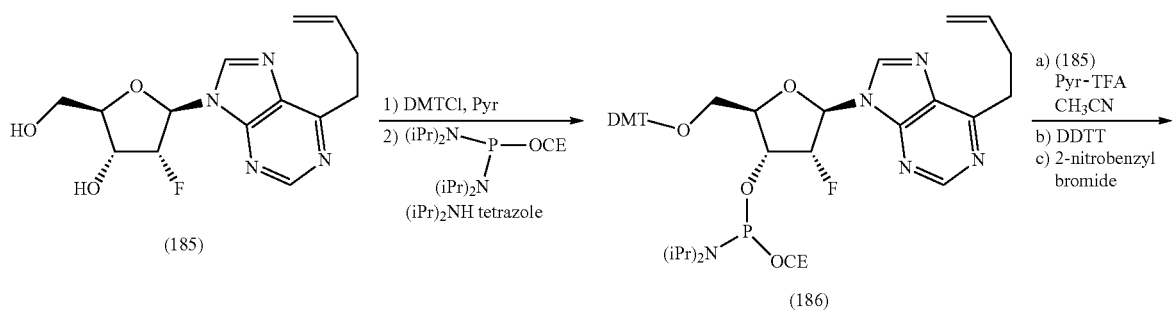

(185)

(186)

-continued
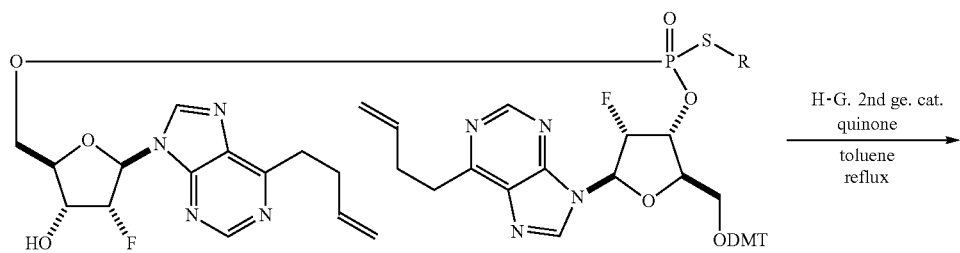
H-G. 2nd ge. cat.
quinone
———————→
toluene
reflux
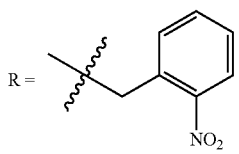
(188)
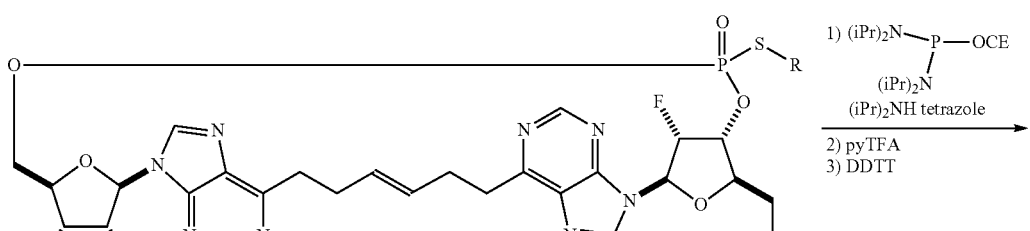
1) (iPr)₂N—P—OCE
       |
     (iPr)₂N
(iPr)₂NH tetrazole
————————→
2) pyTFA
3) DDTT
(189)
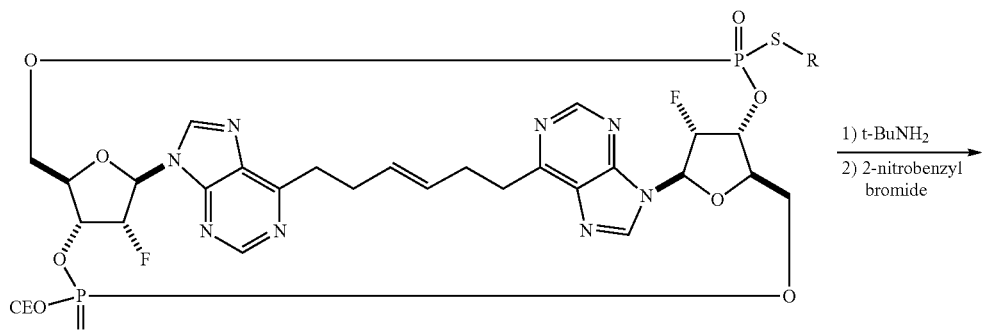
1) t-BuNH₂
————————→
2) 2-nitrobenzyl
   bromide
(190)
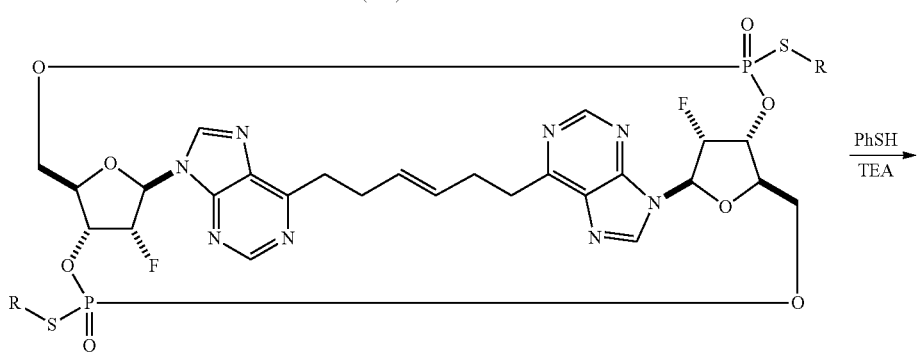
PhSH
———→
TEA
(191) (SpRp)
(192) (RpRp)

-continued

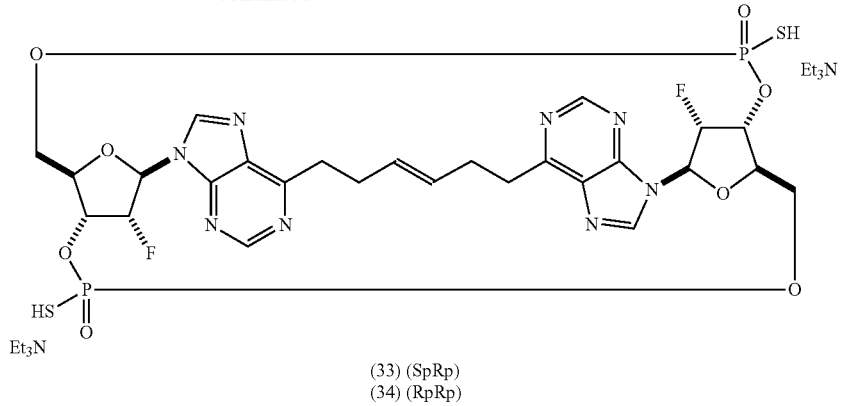

(33) (SpRp)
(34) (RpRp)

Compound 193

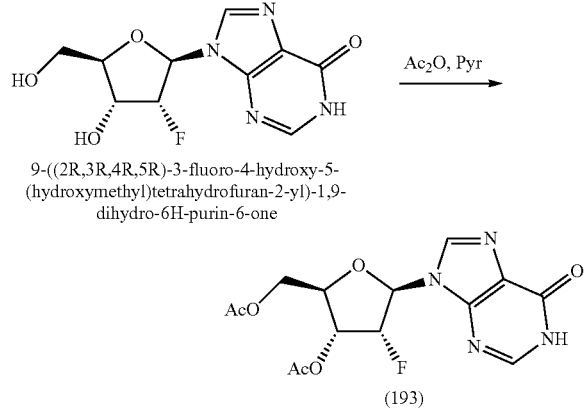

9-((2R,3R,4R,5R)-3-fluoro-4-hydroxy-5-(hydroxymethyl)tetrahydrofuran-2-yl)-1,9-dihydro-6H-purin-6-one To a solution of 9-((2R,3R,4R,5R)-3-fluoro-4-hydroxy-5-(hydroxymethyl)tetrahydrofuran-2-yl)-1,9-dihydro-6H-purin-6-one, Compound 183 (5.00 g, 18.5 mmol) in pyridine (75 ml) at 0° C. were added Ac$_2$O (7.0 ml, 74 mmol) and DMAP (0.565 g, 4.626 mmol). The resulting mixture was warmed to ambient temperature and stirred while the reaction was monitored by LCMS. Upon completion, the reaction mixture was concentrated in vacuo and treated with EtOAc (200 mL) and water (50 ml). Precipitation occurred. The resulting solid was collected by filtration and rinsed with MTBE. Drying in vacuo at 40° C. overnight gave 5.81 g of Compound 193 as a white solid.

$^1$H NMR (400 MHz, DMSO-d6) δ=12.53 (br s, 1H), 8.33 (s, 1H), 8.15 (d, J=4.3 Hz, 1H), 6.37 (dd, J=2.7, 19.1 Hz, 1H), 5.86 (ddd, J=2.7, 5.1, 51.6 Hz, 1H), 5.62 (ddd, J=5.5, 7.0, 16.0 Hz, 1H), 4.49-4.38 (m, 2H), 4.26 (dd, J=4.7, 12.1 Hz, 1H), 2.19 (s, 3H), 2.04 (s, 3H).

Compound 184

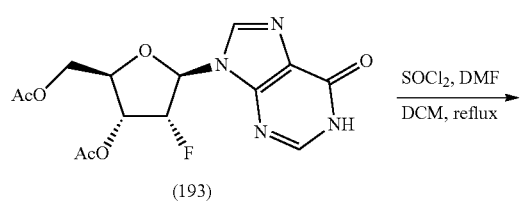

To a solution of Compound 193 in dichloromethane (40.0 ml) at 0° C. were added DMF (1.3 ml, 16.9 mmol) and thionyl chloride (1.28 ml, 17.5 mmol) slowly. The resulting mixture was heated to reflux and stirred until all the starting material was consumed (monitored by LCMS). Upon completion, the reaction mixture was cooled to ambient temperature and treated with a sat'd aqueous NaHCO$_3$ solution (40 mL). The layers were separated and the aqueous layer was extracted twice with dichloromethane (30 mL each). The combined organic layers were dried over MgSO$_4$, filtered and concentrated in vacuo to give 2.81 g of Compound 184 as pale brown oil.

$^1$H NMR (400 MHz, CHLOROFORM-d) δ=8.79 (s, 1H), 8.30 (s, 1H), 6.29 (dd, J=2.0, 18.0 Hz, 1H), 5.79 (ddd, J=1.6, 4.7, 51.6 Hz, 1H), 5.53 (ddd, J=5.1, 7.6, 17.8 Hz, 1H), 4.58-4.48 (m, 2H), 4.33 (dd, J=3.9, 12.5 Hz, 1H), 2.20 (s, 3H), 2.07 (s, 3H).

Compound 194

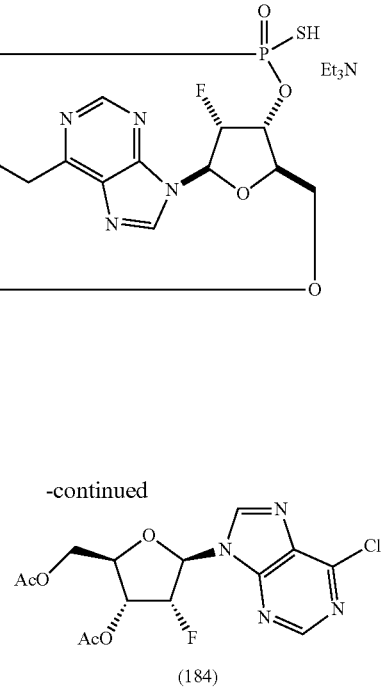

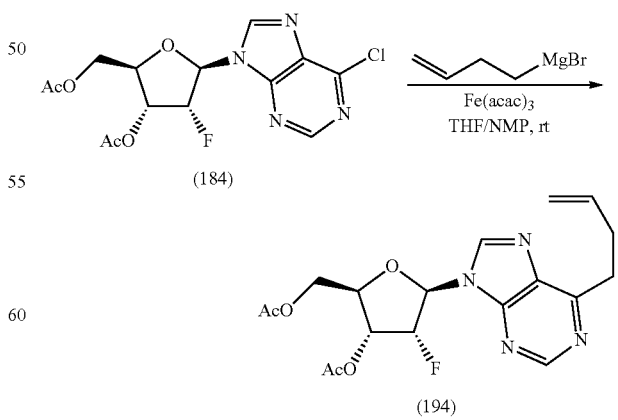

To a solution of Compound 184 (0.22 g, 0.59 mmol) in a mixture of THF (7.7 ml) and NMP (0.77 ml) at ambient temperature were added Iron(III) acetylacetonate (0.021 g, 0.059 mmol) and 0.5M 3-Butenylmagnesium bromide (1.77 ml, 0.885 mmol) in THF. Upon complete reaction (monitored by LCMS), MTBE (10 mL) and 0.1 N HCl (10 mL) were added. The resulting mixture was stirred at ambient temperature for 10 min. The layers were separated and the aqueous layer was extracted with a mixture of EtOAc/MTBE (1/1, 10 ml). The combine organic layers were washed with 30% aqueous NaCl solution (5 mL), dried over MgSO$_4$ and concentrated in vacuo. The crude product was used in next step without further purification.

$^1$H NMR (400 MHz, CHLOROFORM-d) δ=8.90 (s, 1H), 8.16 (s, 1H), 6.26 (dd, J=2.0, 18.4 Hz, 1H), 5.98-5.85 (m, 1H), 5.90-5.73 (m, 1H), 5.63 (ddd, J=4.9, 7.5, 17.7 Hz, 1H), 5.12-5.05 (m, 1H), 4.98 (dd, J=1.6, 10.2 Hz, 1H), 4.54-4.50 (m, 2H), 4.31 (dd, J=5.1, 12.9 Hz, 1H), 3.30 (t, J=7.4 Hz, 2H), 2.70-2.64 (m, 2H), 2.19 (s, 3H), 2.05 (s, 3H).

Compound 185

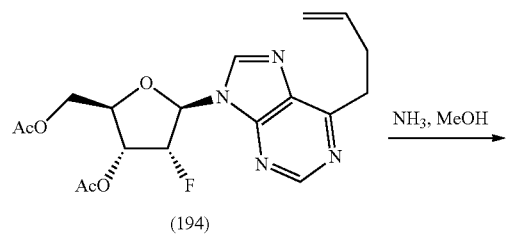

(194)

Crude product Compound 194 (0.232 g, 0.590 mmol in theory) was dissolved in methanol (1.5 ml) and treated with 2.0 M ammonia (1.5 ml, 3.0 mmol) in MeOH at ambient temperature. Upon complete deacetylation, the reaction mixture was concentrated in vacuo and purified by silicagel column chromatography (SiO$_2$ 10 g, 0% to 5% MeOH in EtOAc) to give 0.17 g of Compound 185.

LCMS: MS (ESI) m/z 309.20 [M+H]$^+$

Compound 195

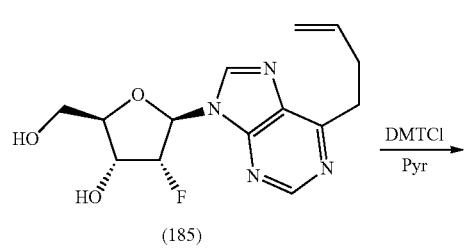

(185)

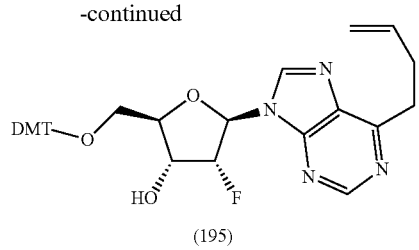

(195)

To a solution of Compound 185 (1.22 g, 2.928 mmol) in pyridine (9.0 ml) at 0° was added 4,4'-(chloro(phenyl)methylene)bis(methoxybenzene) (1.042 g, 3.075 mmol). The reaction mixture was allowed to warm to ambient temperature while the reaction was monitored by LCMS. Upon completion, MTBE (18 mL) and a sat'd aqueous NaHCO$_3$ (9.0 ml) were added. After 10 min stirring, the layers were separated and the aqueous layer was extracted with MTBE (18.0 ml). The combined organic layers were washed with 30% aqueous solution NaCl (10 ml), filtered and concentrated in vacuo. Purification by silicagel column chromatography (SiO$_2$ 50 g, 50% to 100% ethyl acetate in heptane with 1% TEA) to give 1.53 g of Compound 195 as an orange solid.

$^1$H NMR (400 MHz, CHLOROFORM-d) δ=8.86-8.78 (m, 1H), 8.21 (s, 1H), 7.40-7.36 (m, 2H), 7.31-7.18 (m, 7H), 6.79 (d, J=8.6 Hz, 4H), 6.29 (dd, J=2.3, 17.2 Hz, 1H), 5.92 (tdd, J=6.4, 10.4, 17.0 Hz, 1H), 5.70 (ddd, J=2.7, 4.7, 52.8 Hz, 1H), 5.09 (dd, J=1.6, 17.2 Hz, 1H), 4.97 (dd, J=1.6, 10.2 Hz, 1H), 4.90-4.77 (m, 1H), 4.26-4.19 (m, 1H), 3.78 (s, 6H), 3.56 (dd, J=3.1, 10.9 Hz, 1H), 3.43 (dd, J=4.3, 10.9 Hz, 1H), 3.33-3.28 (m, 2H), 2.70-2.64 (m, 2H), 2.20 (dd, J=2.5, 7.2 Hz, 1H).

Compound 186

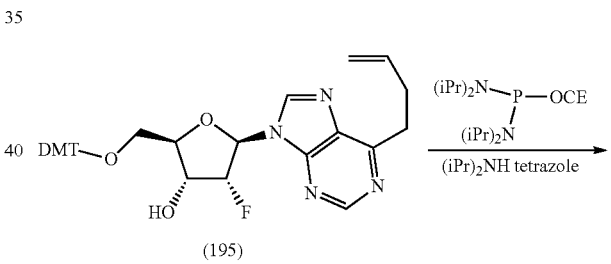

(195)

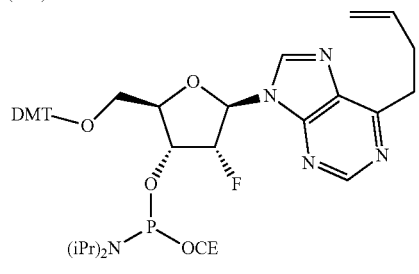

(186)

To a solution of Compound 195 (1.530 g, 2.505 mmol) in dichloromethane (23 ml) at ambient temperature were added 3-(Bis(diisopropylamino)phosphinooxy)propanenitrile (1.20 ml, 3.76 mmol) and diisopropylammonium tetrazolide (0.493 g, 2.881 mmol). The reaction mixture was stirred at ambient temperature while the progress was monitored by LCMS. Upon completion, the reaction mixture was concentrated in vacuo and purified by silicagel column chromatography (SiO$_2$ 50 g, 40% to 66% EtOAc in n-heptane with 1% TEA) to give 1.80 g of Compound 186 as a pale orange foam solid.

Compounds 196 and 197

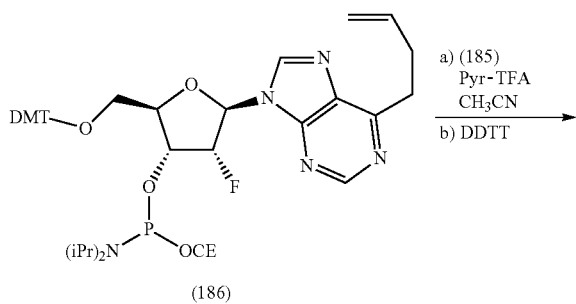

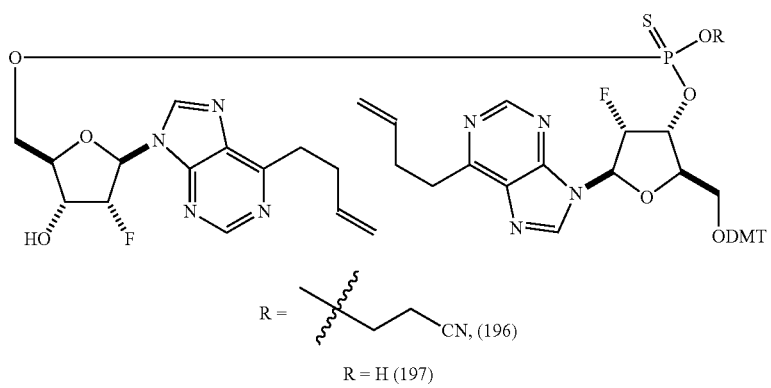

Compound 186 (1.8 g, 2.22 mmol) and Compound 185 (1.110 g, 2.664 mmol) were dissolved in acetonitrile (21.6 ml) and concentrated in vacuo. The same operation was repeated one more time. The resulting mixture was dissolved in acetonitrile (21.6 ml) and treated with pyridinium trifluoroacetate (0.514 g, 2.664 mmol) at ambient temperature. Upon complete reaction (monitored by LCMS), ((Dimethylamino-methylidene)amino)-3H-1,2,4-dithiazaoline-3-thione (0.911 g, 4.439 mmol) was added and the resulting mixture was stirred at ambient temperature. Upon complete sulfurization (monitored by LCMS), a sat'd aqueous NaHCO₃ solution (30 ml) was added and the resulting mixture was extracted three time with MTBE (30 mL each time). The combined organic layers were washed with 30% aqueous NaCl solution (20 ml), dried over MgSO₄, filtered, and concentrated in vacuo. Purification by silicagel column chromatography (SiO₂ 100 g, 0% to 10% MeOH in EtOAc with 1% TEA) gave 0.481 g of Compound 196 and 1.315 g of Compound 197.

Compound 196: LCMS: MS (ESI) m/z 1073.25 [M+Na]⁺
Compound 197: LCMS: MS (ESI) m/z 995.23 [M–H]⁻
Compound 188

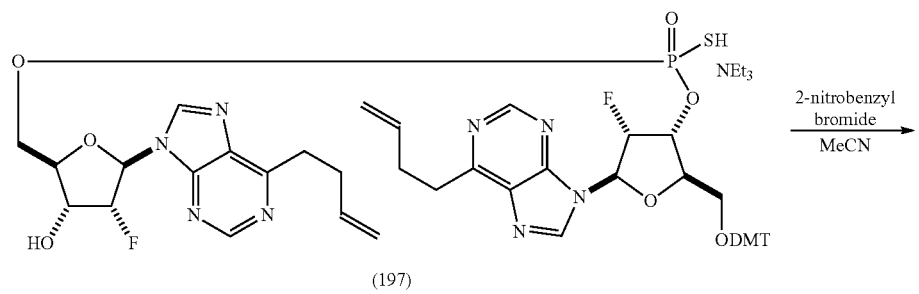

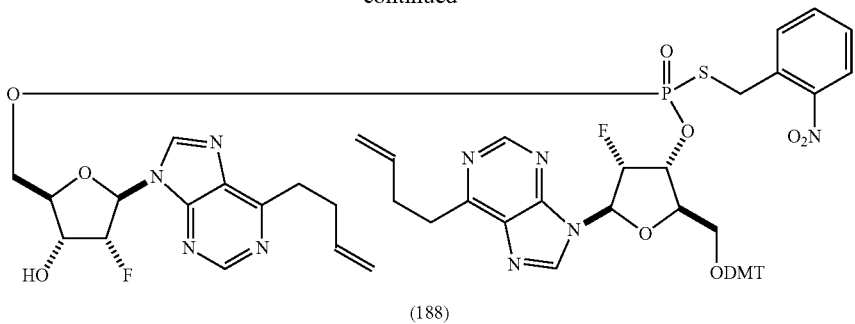

(188)

To a solution of TEA salt Compound 197 (1.315 g, 1.197 mmol) in MeCN (20 ml) at ambient temperature was added 2-nitrobenzyl bromide (0.388 g, 1.796 mmol). The resulting solution was stirred at ambient temperature while the reaction was monitored by LCMS. Upon completion, the reaction mixture was concentrated in vacuo and purified by silicagel column chromatography (SiO$_2$ 100 g, 0% to 5% MeOH in EtOAC) to give 0.90 g of Compound 188.

LCMS: MS (ESI) m/z 1154.29 [M+Na]$^+$

Compound 198

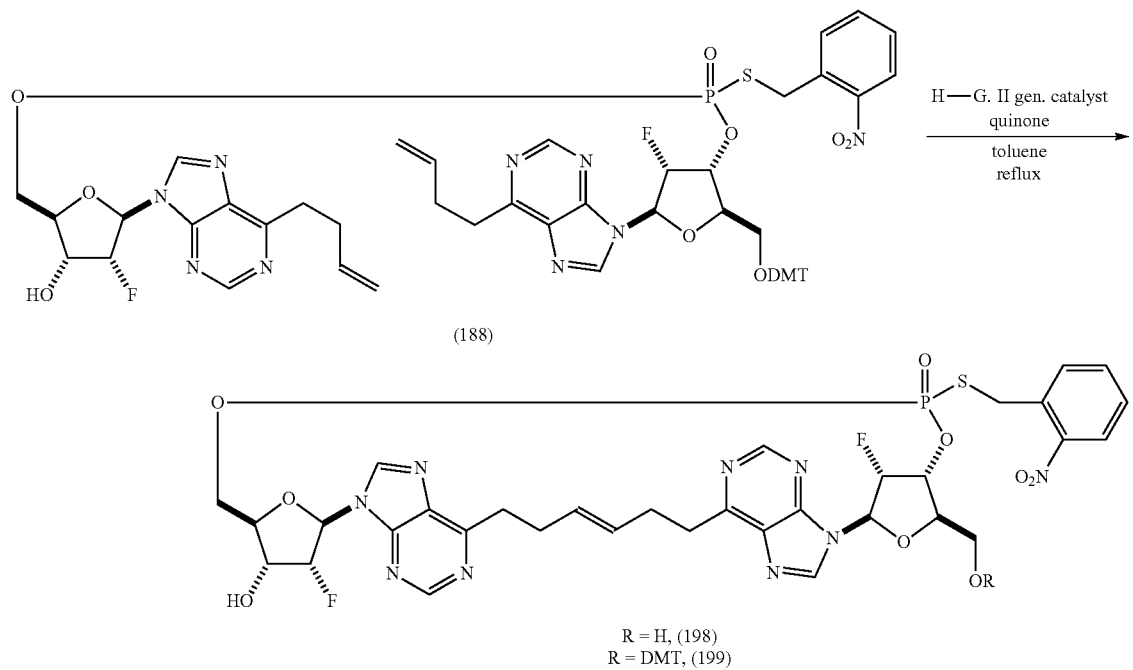

R = H, (198)
R = DMT, (199)

To a solution of Compound 188 (1.35 g, 1.192 mmol) in toluene (540 ml) at mild reflux (110-112° C. internal T) was added a solution of Hoveyda-Grubbs Catalyst 2nd Generation (0.187 g, 0.298 mmol) and Quinone (0.322 g, 2.981 mmol)) in toluene (20 mL). The resulting solution was stirred between 110-112° C. while the reaction was monitored by LCMS. After 4 h, additional catalyst (0.10 g, 0.16 mmol) was added and stirring continued at reflux. Upon completion, the reaction mixture was cooled to ambient temperature and treated with DMSO (2.54 ml, 35.8 mmol). After 3 h stirring, the reaction mixture was concentrated in vacuo and purified by silicagel column chromatography (SiO$_2$ 50 g, 0% to 15% MeOH in EtOAC) to give a mixture of Compound 198 and Compound 199. The mixture was dissolved in dichloromethane (2 mL) and treated with water (0.021 ml, 1.2 mmol) and 6% dichloroacetic acid (0.098 ml, 1.2 mmol) in dichloromethane (2 mL). After 10 min, the reaction was quenched with pyridine (1 ml) and concentrated in vacuo. The residue dissolved in dichloromethane (50 mL) and washed with 30% aqueous NaCl solution (15 mL each time) twice and dried over MgSO$_4$. Purification of the crude product by silicagel column chromatography (SiO$_2$ 50 g, 5% to 10% MeOH in DCM) gave 0.25 g of Compound 198.

Compound 199: LCMS: MS (ESI) m/z 1104.31 [M+H]+
Compound 198: LCMS: MS (ESI) m/z 802.16 [M+H]+
Compound 190

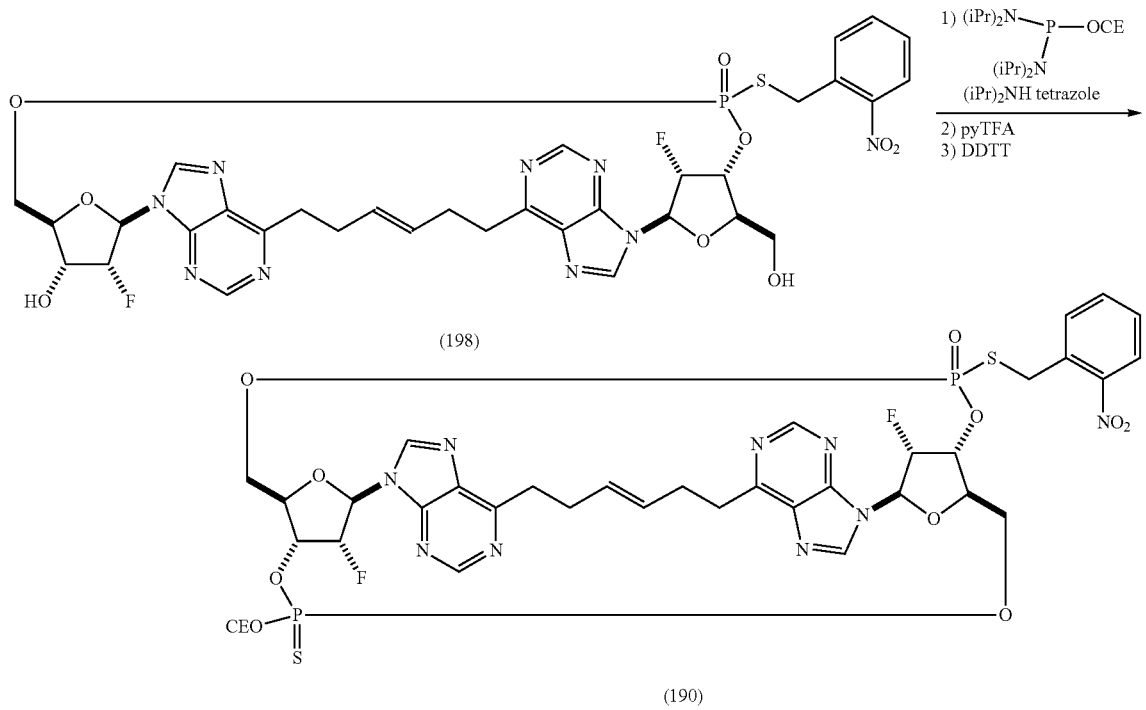

(198)

(190)

Compound 198 (0.233 g, 0.291 mmol) and 3-(Bis(diisopropylamino)phosphinooxy)propanenitrile (0.111 ml, 0.349 mmol) were dissolved in MeCN (10 mL) and concentrated in vacuo. The same operation repeated two more times. The resulting mixture was dissolved in dichloromethane (2.3 ml), cooled to 0-5° C., and treated diisopropylammonium tetrazolide (0.025 g, 0.145 mmol). The reaction mixture was warmed to ambient temperature overnight and then diluted with acetonitrile (2.3 ml). The resulting solution was added over 7 h via syringe pump into a solution of pyridine trifluoroacetate salt (0.168 g, 0.872 mmol) in MeCN (18.6 ml). 3-(Bis(diisopropylamino)phosphinooxy)propanenitrile (40 mg, 0.133 mmol) in MeCN (2 mL) was then added over 2 hours. After 1 h stirring, (E)-N,N-dimethyl-N'-(3-thioxo-3H-1,2,4-dithiazol-5-yl)formimidamide (0.119 g, 0.581 mmol) was added and the reaction solution was stirred until the sulfurization was complete (monitored by LCMS). Upon completion, the mixture was concentrated in vacuo, dissolved in MTBE (5 ml), and treated with a sat'd aqueous NaHCO$_3$ (3.50 ml) and water (1.2 ml). The layers were separated and the aqueous layer was extracted with a mixture of MTBE/EtOAc (5/3 ml). The combined organic layers were washed twice with 30% aqueous NaCl solution (2.3 ml), dried over MgSO$_4$, filtered, and concentrated in vacuo. Purification of the crude product by silicagel column chromatography (SiO$_2$ 25 g, 0% to 20% MeOH in EtOAc) gave 119 mg of Compound 190 (58 mg of faster eluting isomers and 61 mg of slower eluting isomers).

Compound 191 (SpRp Isomer)

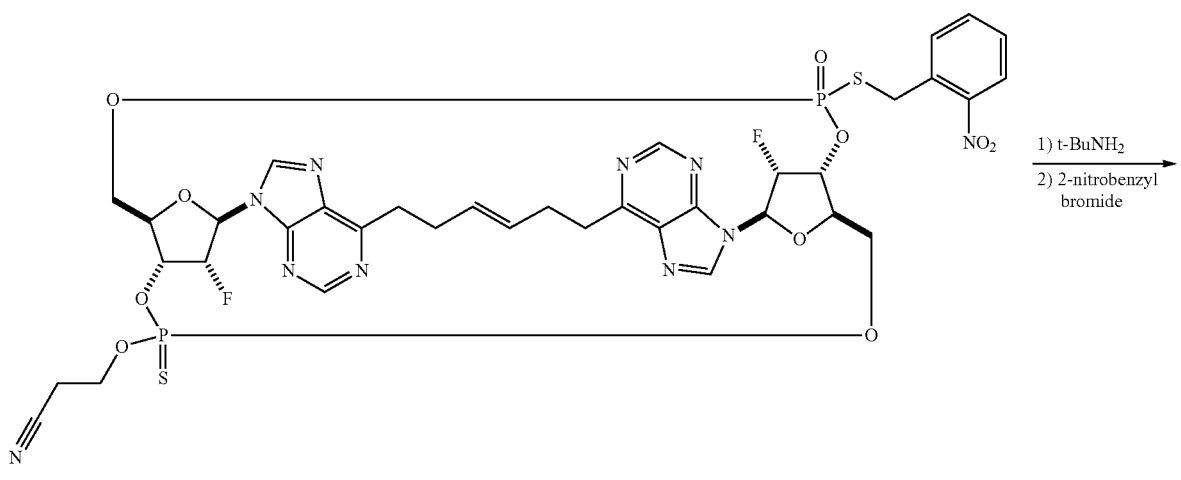

Faster eluting isomer
of (190)

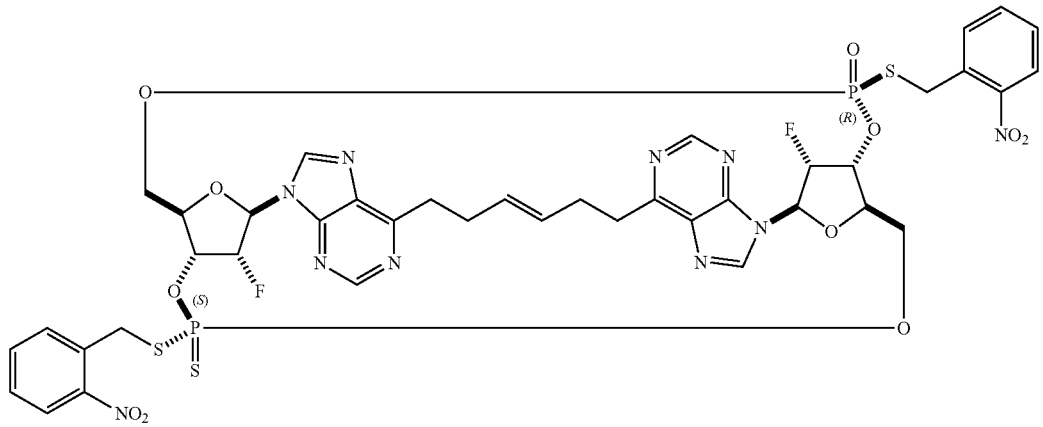

(191)

To a solution of the faster eluting isomers of Compound 190 (58 mg, 0.062 mmol) in dichloromethane (1.8 mL) was added tert-butylamine (1.2 ml, 11 mmol). The resulting solution was stirred at ambient temperature until all the starting material was consumed (monitored by LCMS). Upon completion, the reaction mixture was concentrated in vacuo, azeotroped with acetonitrile twice, and dissolved in acetonitrile (1.7 ml). To the resulting solution was added 1-(bromomethyl)-2-nitrobenzene (40.3 mg, 0.187 mmol). The reaction mixture was stirred at ambient temperature while the reaction was monitored by LCMS. Upon complete alkylation, the reaction mixture was concentrated in vacuo and purified by silicagel column chromatography (SiO$_2$ 10 g, 0% to 5% MeOH in EtOAC) to give 19 mg of Compound 191 (SpRp isomer).

$^1$H NMR (400 MHz, CHLOROFORM-d) δ=8.42 (s, 1H), 8.27 (s, 1H), 8.13 (dd, J=1.2, 8.2 Hz, 1H), 8.05 (s, 1H), 7.98 (d, J=7.8 Hz, 1H), 7.69-7.67 (m, 1H), 7.61-7.34 (m, 5H), 6.33 (d, J=17.2 Hz, 1H), 6.19 (d, J=19.9 Hz, 1H), 6.09-5.93 (m, 1H), 5.82-5.66 (m, 2H), 5.67 (dd, J=3.5, 50.8 Hz, 1H), 5.35-5.32 (m, 2H), 4.62-4.29 (m, 11H), 3.35-3.28 (m, 1H), 3.18-3.14 (m, 2H), 3.01-2.91 (m, 1H), 2.84-2.78 (m, 1H), 2.60-2.49 (m, 3H).

Compound Compound 192 (RpRp Isomer)

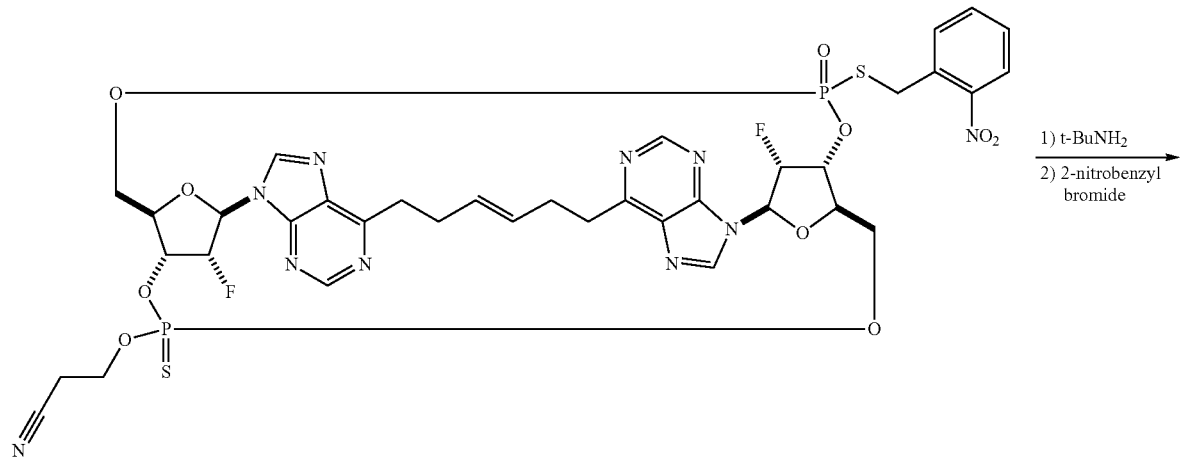

Slower eluting isomer of (190)

1) t-BuNH$_2$
2) 2-nitrobenzyl bromide

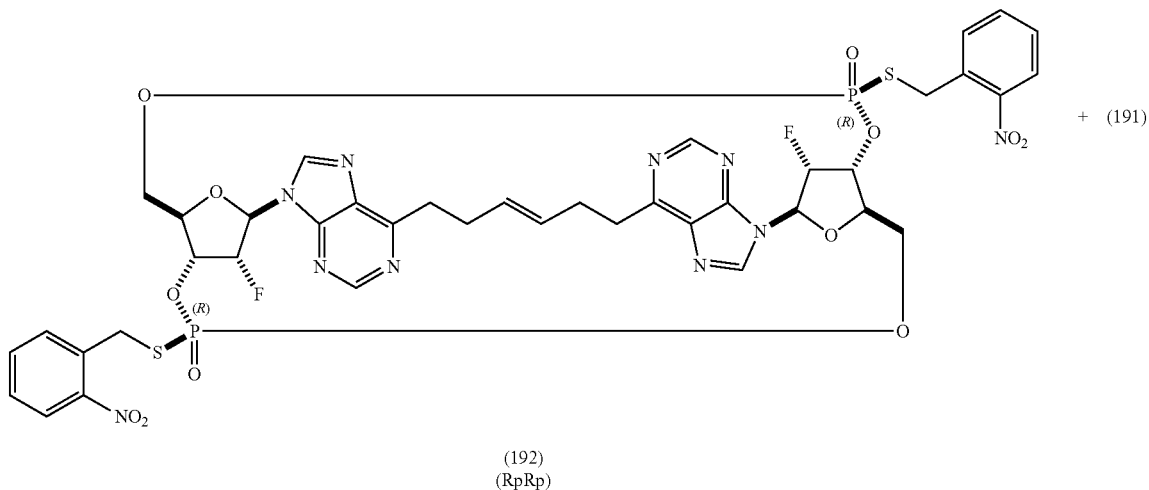

(192)
(RpRp)

The slower eluting isomer of Compound 190 (60 mg) was processed through the same reaction sequence as described in compound Compound 191 to give 14 mg of Compound 192 and 7 mg of Compound 191.

$^1$H NMR (400 MHz, CHLOROFORM-d) δ=8.18 (s, 2H), 8.10 (s, 2H), 8.10 (dd, J=1.0, 8.0 Hz, 2H), 7.66-7.57 (m, 4H), 7.53-7.46 (m, 2H), 6.31 (d, J=17.6 Hz, 2H), 6.19-6.05 (m, 2H), 5.84 (dd, J=4.3, 50.8 Hz, 2H), 5.39-5.30 (m, 2H), 4.58-4.46 (m, 6H), 4.45-4.39 (m, 2H), 4.19 (ddd, J=3.1, 6.3, 10.2 Hz, 2H), 3.32 (td, J=3.5, 15.6 Hz, 2H), 3.06 (td, J=6.3, 15.2 Hz, 2H), 2.67-2.57 (m, 4H).

Based upon synthetic methodology, NMR data (symmetric), HPLC retention time (slowest eluting isomer) and biological activities of Compound 34, which was derived from Compound 192, applicants believe that Compound 192 has RR phosphorous stereochemistry. This stereochemical assignment would be subject to confirmation by X-ray crystallography Compound 33

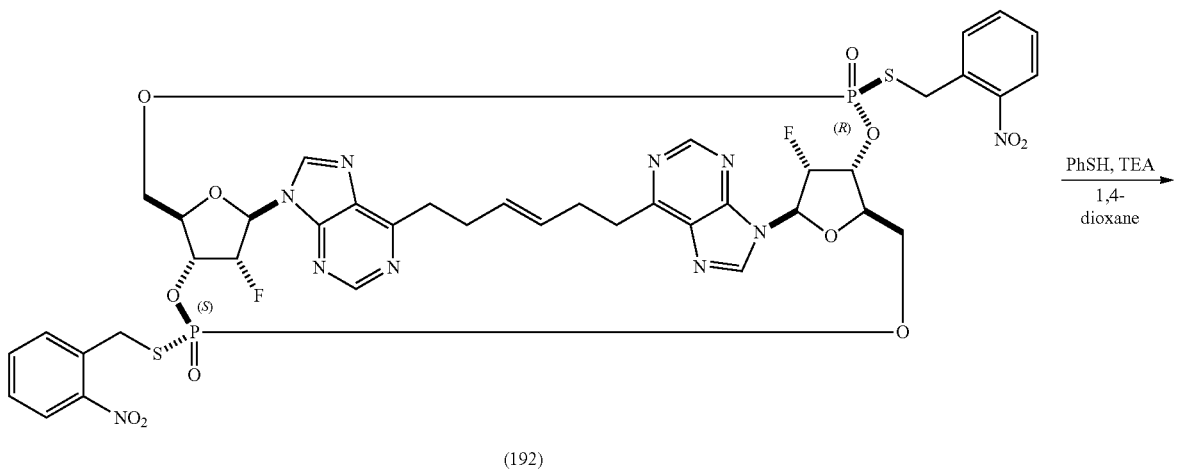

(192)

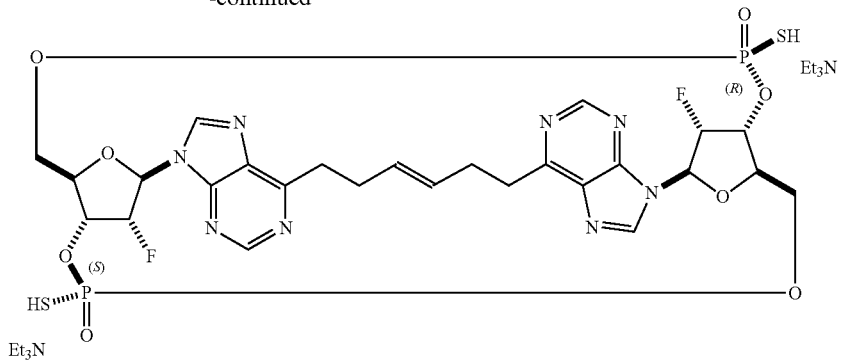

(33)

To a solution of Compound 192 (26 mg, 0.026 mmol) in 1,4-dioxane (0.52 ml) were added thiophenol (0.26 ml, 2.5 mmol) and then TEA (0.26 ml, 1.9 mmol). The resulting mixture was stirred at ambient temperature until the deprotection was complete (monitored by LCMS). Upon completion, water (2 mL) was added. The resulting mixture extracted three times with toluene (2 mL each time). The aqueous layer was concentrated in vacuo at 40-50° C. and dissolved in water (2 mL). The resulting mixture was extracted four times with a mixture of EtOAc/MTBE (1/1 mL each time). The aqueous layer was concentrated in vacuo to give bis-TEA salt of Compound 33.

$^1$H NMR (400 MHz, METHANOL-$d_4$) δ=9.06 (s, 1H), 8.73 (s, 1H), 8.56 (s, 1H), 8.47 (s, 1H), 6.43 (d, J=14.4 Hz, 1H), 6.38 (d, J=15.2 Hz, 1H), 6.27 (dd, J=3.5, 51.1 Hz, 1H), 5.63 (dd, J=2.7, 51.5 Hz, 1H), 5.30-5.14 (m, 2H), 5.06-4.91 (m, 2H), 4.58 (br d, J=12.5 Hz, 1H), 4.52-4.39 (m, 3H), 4.07 (dd, J=4.7, 11.7 Hz, 1H), 3.98 (dd, J=5.1, 12.5 Hz, 1H), 3.43-3.34 (m, 2H), 3.22 (q, J=7.2 Hz, 12H), 2.98-2.86 (m, 2H), 2.79-2.45 (m, 4H), 1.32 (t, J=7.4 Hz, 18H)

Compound 34

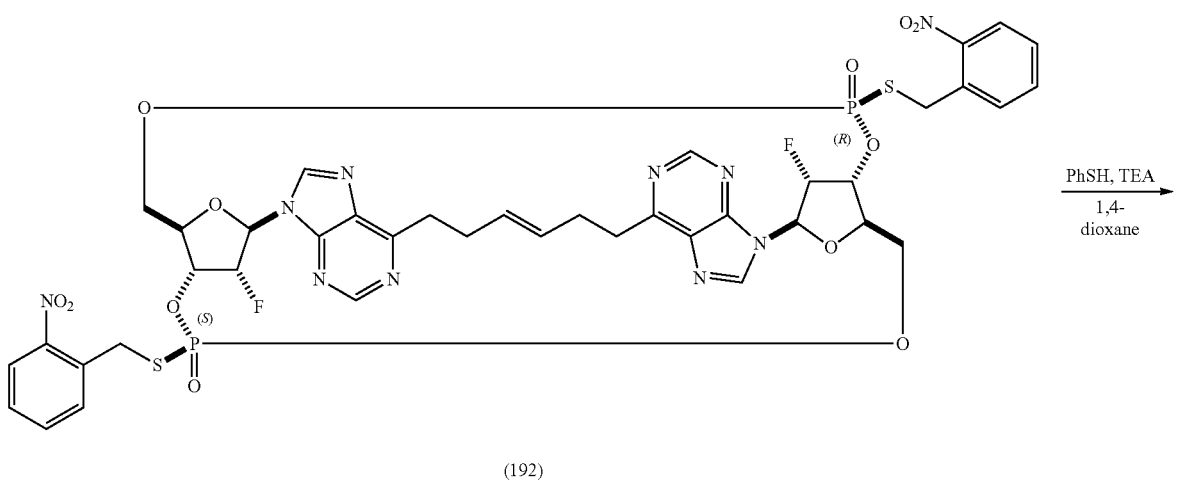

(192)

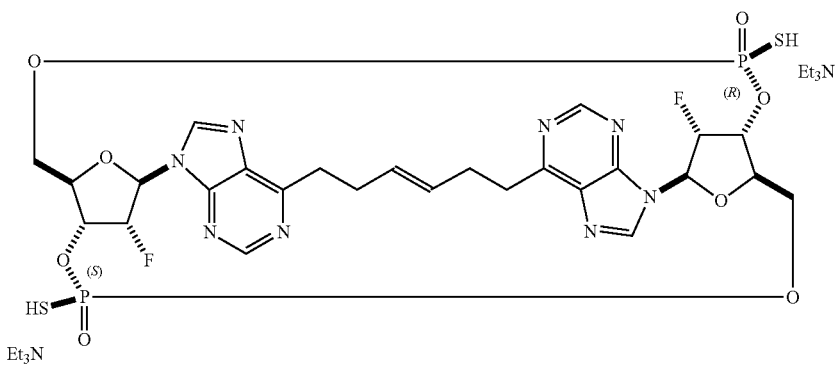

(34)

With Compound 192 as a starting material, Compound 34 was prepared via the same reaction sequence as described in Compound 33.
$^1$H NMR (400 MHz, METHANOL-d$_4$) δ=8.77 (s, 2H), 8.49 (s, 2H), 6.39 (d, J=15.2 Hz, 2H), 5.71 (dd, J=3.1, 51.2 Hz, 2H), 5.24-5.13 (m, 2H), 5.02 (dtd, J=3.1, 9.0, 25.4 Hz, 2H), 4.54 (br d, J=12.1 Hz, 2H), 4.42 (br d, J=9.8 Hz, 2H), 3.99 (dd, J=5.9, 12.1 Hz, 2H), 3.20 (q, J=7.3 Hz, 12H), 2.90 (ddd, J=3.5, 10.2, 14.1 Hz, 2H), 2.81-2.70 (m, 2H), 2.55-2.43 (m, 2H), 1.30 (t, J=7.4 Hz, 18H).
Example 22—Synthesis of Compound 35 and Compound 36
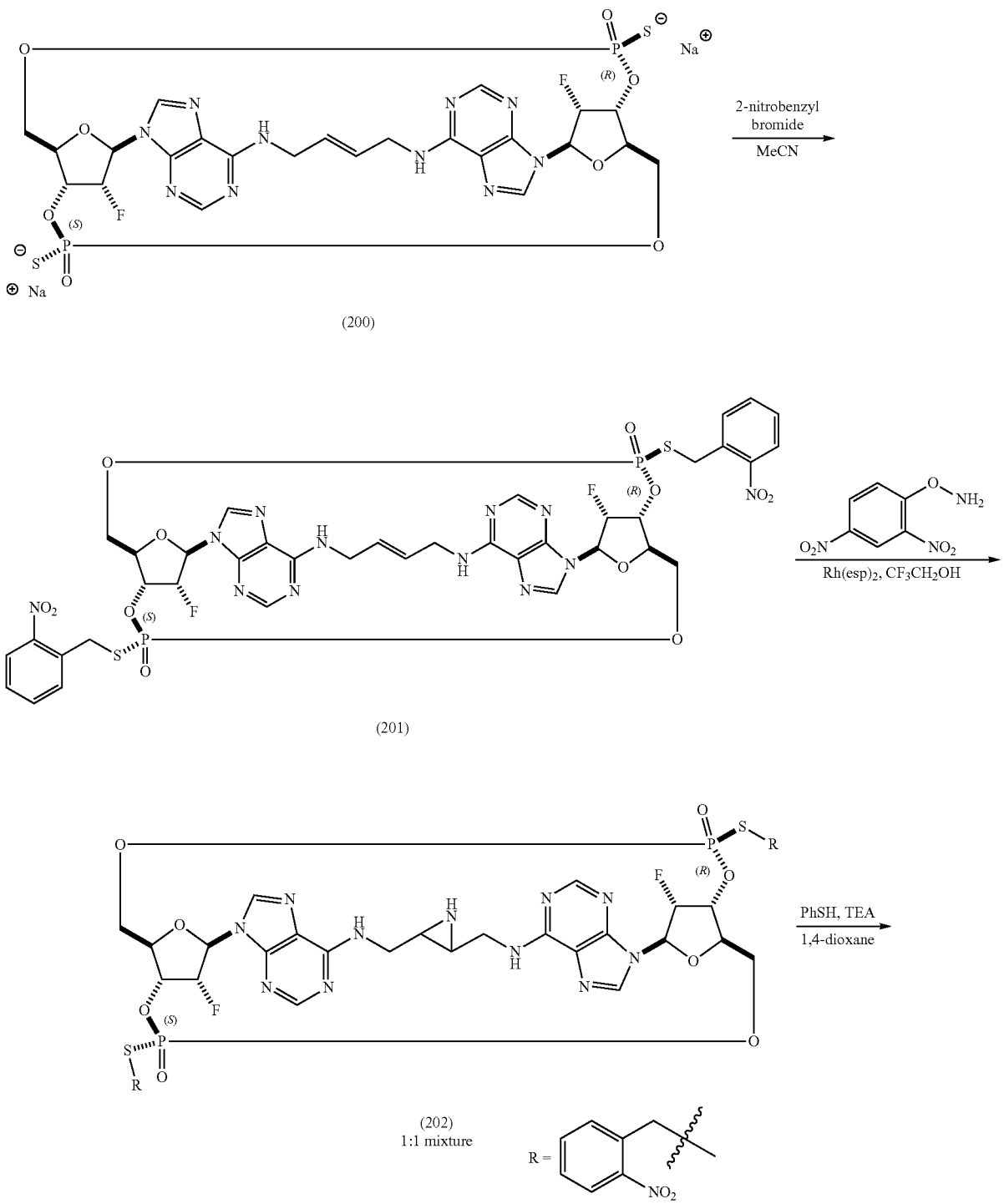

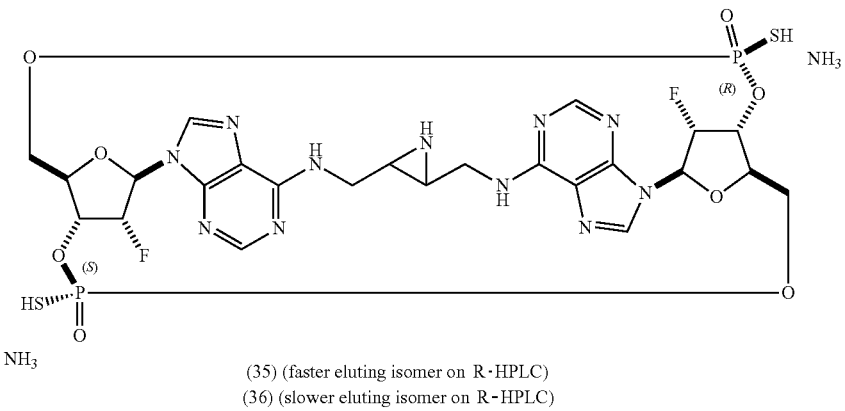

(35) (faster eluting isomer on R-HPLC)
(36) (slower eluting isomer on R-HPLC)

Compound 201

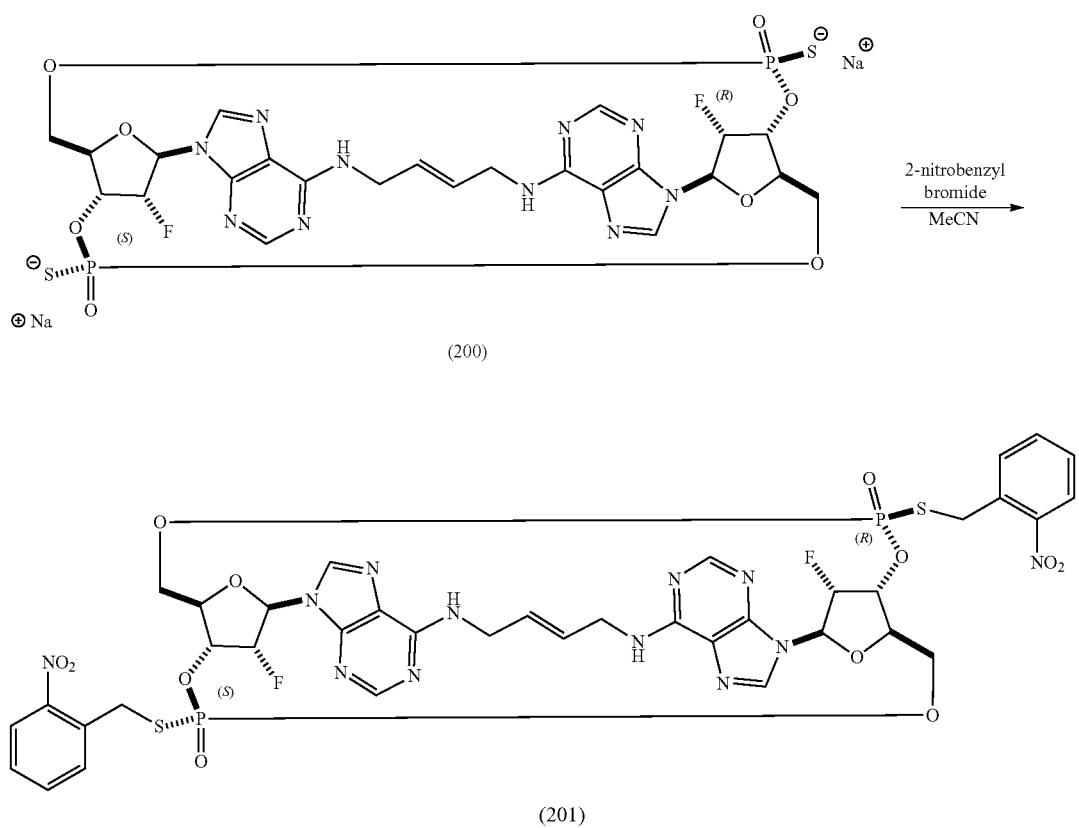

To di-sodium salt of Compound 200 (0.10 g, 0.126 mmol) were added 2-nitrobenzyl bromide (0.068 g, 0.316 mmol) and MeCN (2.0 ml). The resulting mixture was stirred at ambient temperature while the reaction was monitored by LCMS. Upon completion, the reaction mixture was concentrated in vacuo and purified by silicagel column chromatography (SiO$_2$ 10 g, 0% to 5% MeOH in DCM) to give 115 mg of Compound 201.

$^1$H NMR (400 MHz, CHLOROFORM-d) δ=8.13 (dd, J=0.8, 8.2 Hz, 1H), 8.06 (s, 1H), 8.03 (dd, J=1.0, 8.0 Hz, 1H), 7.80 (br s, 1H), 7.75 (s, 1H), 7.70-7.65 (m, 1H), 7.62-7.54 (m, 2H), 7.53-7.47 (m, 2H), 7.45-7.39 (m, 1H), 7.34-7.27 (m, 1H), 6.23 (br d, J=16.8 Hz, 1H), 6.14 (br d, J=18.8 Hz, 1H), 5.95 (br s, 2H), 5.77 (td, J=5.1, 15.2 Hz, 2H), 5.71 (td, J=5.1, 15.6 Hz, 1H), 5.63-5.55 (m, 1H), 5.47 (br d, J=11.7 Hz, 1H), 4.58-4.27 (m, 11H), 4.18-4.10 (m, 1H), 4.05-3.71 (m, 2H)

Compound 202

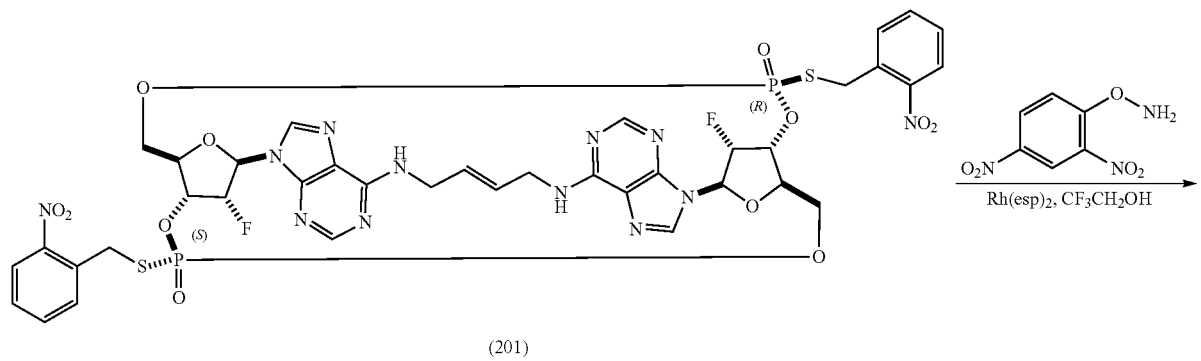

(201)

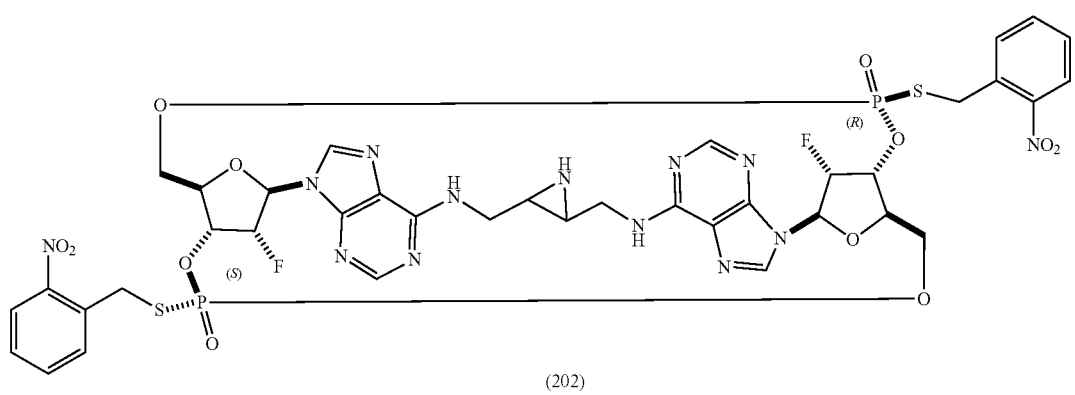

(202)

To a solution of Compound 201 (77 mg, 0.076 mmol) in 2,2,2-frifluoroethanol (2 ml) were added O-(2,4-Dinitrophenyl)hydroxylamine (36.5 mg, 0.183 mmol) and bis[rhodium (α,α,α',α'-tetramethyl-1,3-benzenedipropionic acid)] (5.74 mg, 0.015 mmol) in one portion. The mixture was stirred at ambient temperature overnight, diluted with DCM (10 mL) and treated with a sat'd aqueous NaHCO₃ solution (10 mL). The layers were separated and the aqueous layer was extracted twice with DCM (10 mL each). The combined organic layers were dried over MgSO₄ and purified by silicagel column chromatography (SiO₂ 10 g, 0% to 15% MeOH in EtOAc) to give 3.3 mg of Compound 202.

LCMS: MS m/z 1032.07 [M+H]$^+$

Compound 35 and Compound 36

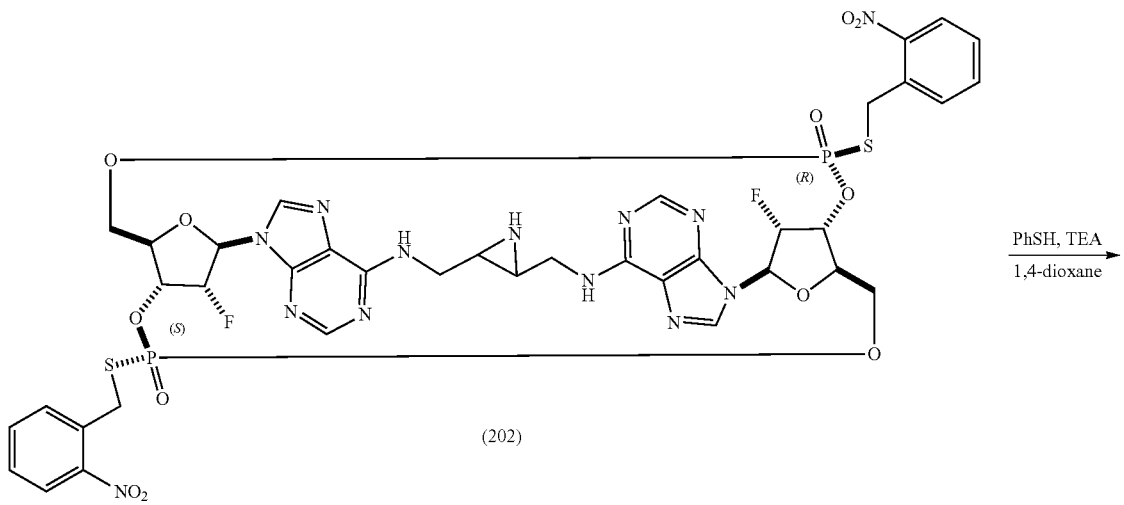

(202)

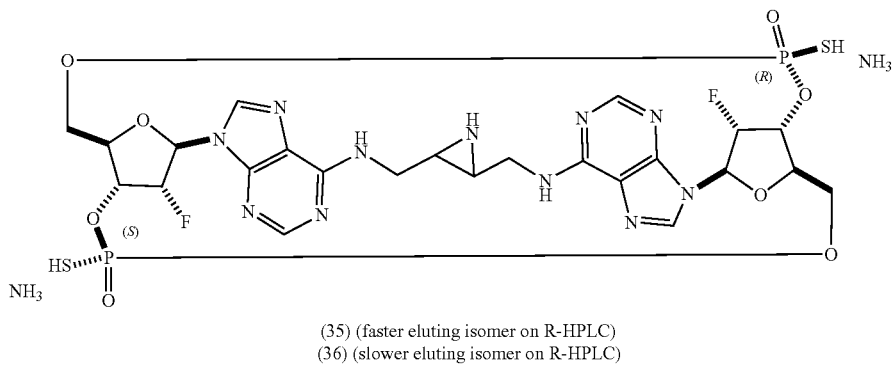

(35) (faster eluting isomer on R-HPLC)
(36) (slower eluting isomer on R-HPLC)

To a solution of Compound 202 (3.3 mg, 3.2 µmol) in 1,4-dioxane (0.40 ml) were added thiophenol (0.2 ml, 1.9 mmol) and TEA (0.2 ml, 1.4 mmol). The resulting mixture was stirred at ambient temperature while the reaction was monitored by LCMS. Upon completion, the reaction mixture was treated with water (2 mL) and extracted three times with toluene (2 mL each time). The aqueous layer was concentrated in vacuo at 40-50° C. and dissolved in water (1.5 ml). The resulting solid was filtered off, rinsing with water (0.5 mL). HPLC separation of the combined filtrates under the conditions described below gave Compound 35 (retention time: 8.4 min) and Compound 36 (retention time: 8.9 min)

Compound 35
LCMS: MS m/z 762.08 [M+H]$^+$

Compound 36
LCMS: MS m/z 762.22 [M+H]$^+$

Compound 35/Compound 36 Preparative HPLC Conditions:

| Instrument | Agilent 1200/1260 AS/FC |
|---|---|
| HPLC column | Waters Xterra C18, 10 × 100 mm # 3128 |
| Flow rate | 3.0 ml/min |
| Column temperature | 35° C. |
| mobile phase | A: 0.1% formic acid in water, B: 0.1% formic acid in acetonitrile |
| Gradient (B %) | 0 → 50 |
| Run time | 20 min |
| Injection volume | 50 ul (1 mg/ml in water) |
| detection | UV 260 nm |
| Retention times Compound 35 | 8.4 min |
| Compound 36 | 8.9 min |

Example-23—Synthesis of Compound 38 and Compound 39

Figure 13:
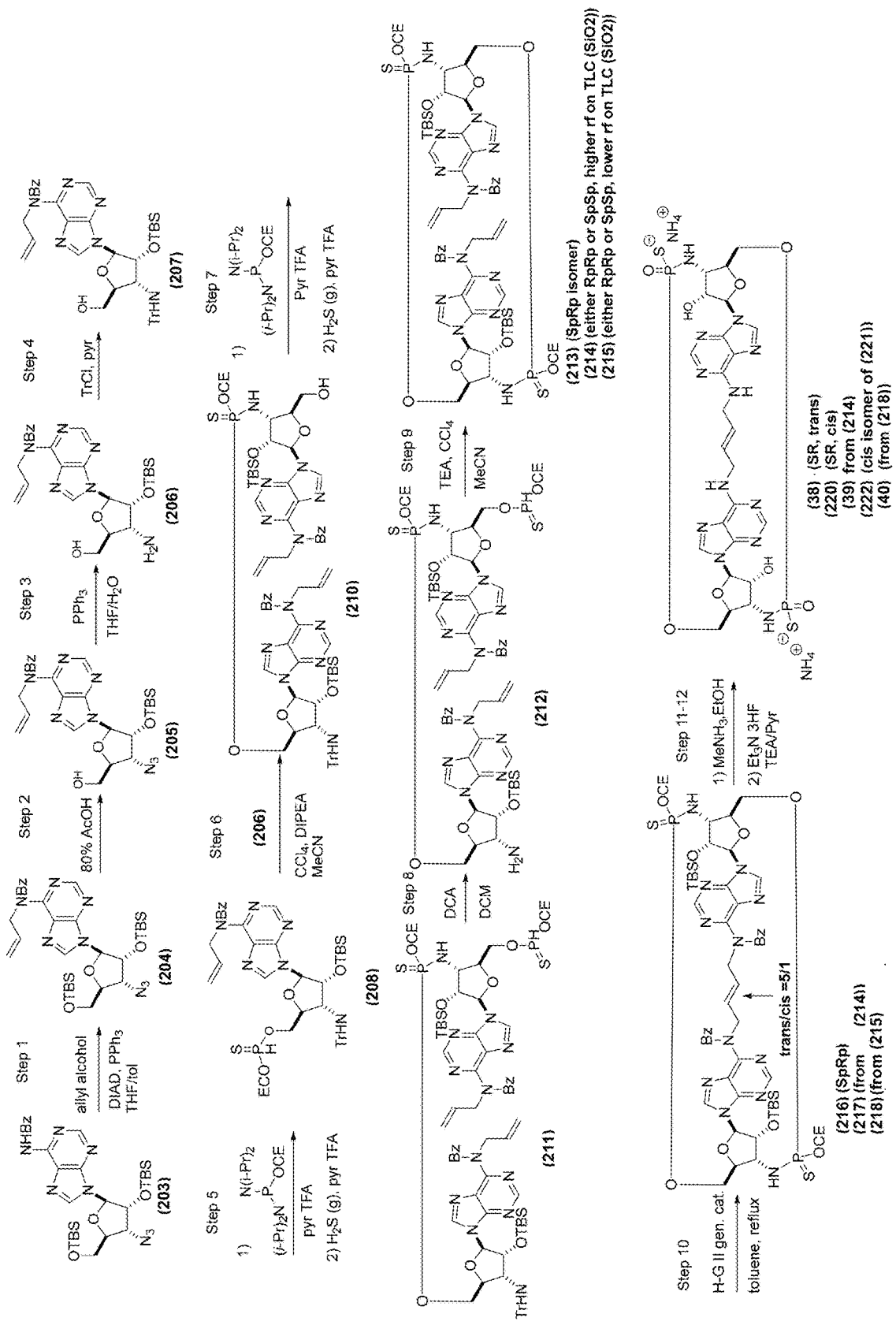
FIG. 13 shows an example of synthesis of Compound 38 and Compound 39.

FIG. 13 shows an example of synthesis of Compound 38 and Compound 39.

Step 1

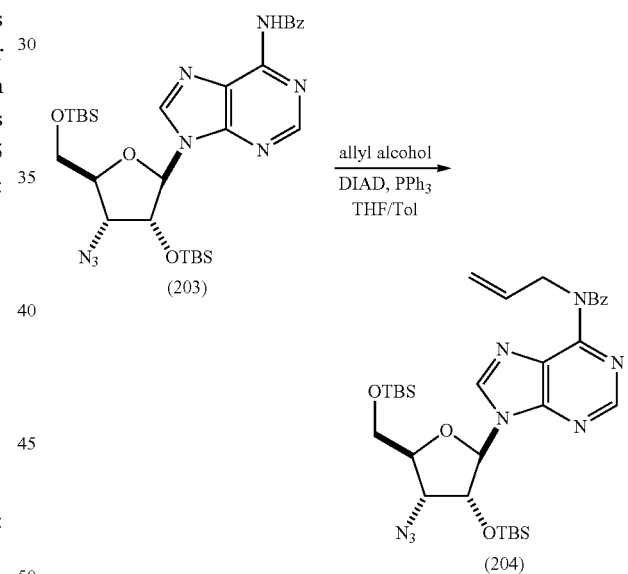

To a solution of Compound 203 (5.82 g, 9.314 mmol) and allyl alcohol (0.95 ml, 14 mmol) in THF (50 mL) at 0° C. was added a solution of DIAD (2.4 ml, 11.6 mmol) and triphenylphosphine (2.93 g, 11.2 mmol) in toluene (25 ml) while keeping the internal T below 10° C. The resulting solution was warmed to ambient temperature and stirred while the reaction was monitored by LCMS. Upon completion (5 h), the mixture was concentrated in vacuo and purified by silica gel column chromatography (100 g, 20% to 60% EtOAc in n-heptane) to give 4.56 g of Compound 204 as a pinkish oil.

Compound 204:
$^1$H NMR (400 MHz, CHLOROFORM-d) δ=8.55 (s, 1H), 8.24 (s, 1H), 7.46 (d, J=8.2 Hz, 2H), 7.31-7.23 (m, 1H), 7.20-7.10 (m, 2H), 6.02 (d, J=5.1 Hz, 1H), 6.07-5.95 (m, 1H), 5.21 (dd, J=1.6, 17.2 Hz, 1H), 5.05 (dd, J=1.4, 10.4 Hz, 1H), 5.00 (d, J=5.5 Hz, 2H), 4.82 (t, J=4.9 Hz, 1H), 4.22-4.16 (m, 1H), 4.05-4.00 (m, 2H), 3.82 (dd, J=2.5, 11.5 Hz, 1H), 0.95 (s, 9H), 0.81 (s, 9H), 0.14 (s, 3H), 0.13 (s, 3H), 0.00 (s, 3H), −0.23 (s, 3H).

Step 2

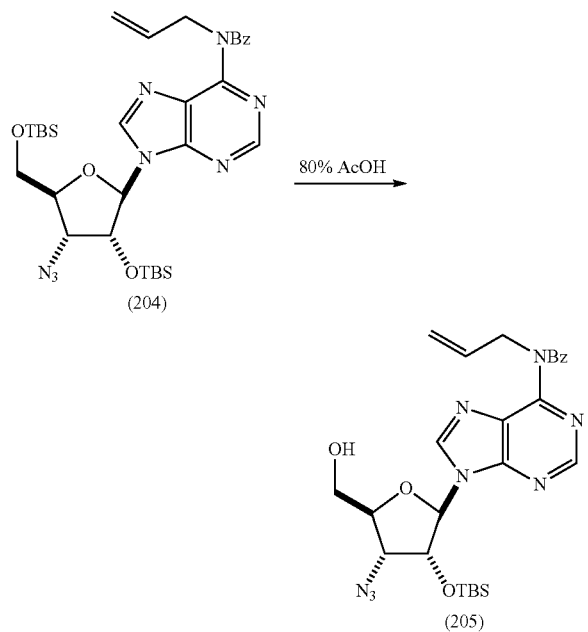

To Compound 204 (4.56 g, 6.858 mmol) was added acetic acid (80 ml) and water (20 ml). The resulting mixture was stirred at ambient temperature overnight and at 35° C. for 1 day. The resulting mixture was concentrated in vacuo and purified by silica gel column chromatography (SiO$_2$, 50 g, 33% to 60% EtOAc in n-heptane) to give 3.22 g of Compound 205 as a white foam solid.

Compound 205:

$^1$H NMR (400 MHz, CHLOROFORM-d) δ=8.56 (s, 1H), 7.88 (s, 1H), 7.51-7.47 (m, 2H), 7.32-7.27 (m, 1H), 7.20-7.16 (m, 2H), 6.06-5.95 (m, 1H), 5.72 (d, J=7.8 Hz, 1H), 5.26 (dd, J=5.5, 7.8 Hz, 1H), 5.20 (dd, J=1.6, 17.2 Hz, 1H), 5.06 (dd, J=1.6, 10.2 Hz, 1H), 5.03-4.98 (m, 2H), 4.23 (d, J=5.5 Hz, 1H), 4.14 (s, 1H), 3.92 (dd, J=1.6, 12.9 Hz, 1H), 3.68 (br d, J=12.9 Hz, 1H), 0.75 (s, 9H), −0.14 (s, 3H), −0.62 (s, 3H).

Step 3

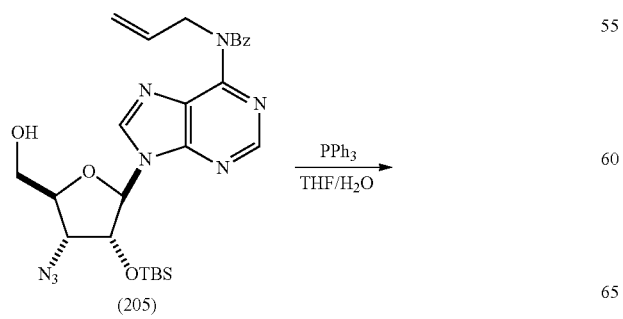

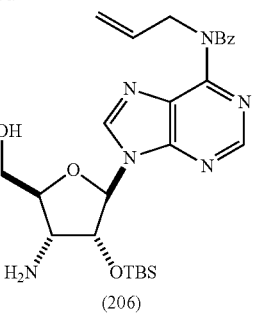

T a solution of Compound 205 (3.22 g, 5.847 mmol) in THF (120 mL) at ambient temperature were water (30 ml) and triphenylphosphine (2.454 g, 9.355 mmol). The resulting mixture was stirred at ambient temperature while the reaction was monitored by LCMS. Upon completion (18 h), the reaction mixture was concentrated in vacuo and azeotroped with MeCN three times. The residue was purified by silica gel column chromatography (SiO$_2$ (NH) 55 g, 20% to 100% EtOAc in n-heptane) to give 4.82 g of Compound 206 (63% purity assumed). The product was used in next the step without further purification.

Compound 206:

$^1$H NMR (400 MHz, CHLOROFORM-d) δ=8.56 (s, 1H), 7.92 (s, 1H), 7.54 (qd, J=1.6, 7.6 Hz, 2H), 7.31-7.27 (m, 1H), 7.19-7.15 (m, 2H), 6.07-5.94 (m, 1H), 5.84 (d, J=6.6 Hz, 1H), 5.50 (br d, J=10.6 Hz, 1H), 5.20 (dd, J=1.6, 17.2 Hz, 1H), 5.05 (dd, J=1.4, 10.4 Hz, 1H), 5.02-4.98 (m, 2H), 4.95-4.91 (m, 1H), 4.16-4.08 (m, 2H), 3.96 (dd, J=1.6, 12.9 Hz, 1H), 3.73 (dd, J=2.0, 5.5 Hz, 1H), 3.73-3.67 (m, 1H), 0.78 (s, 9H), −0.20 (s, 3H), −0.46 (s, 3H).

Step 4

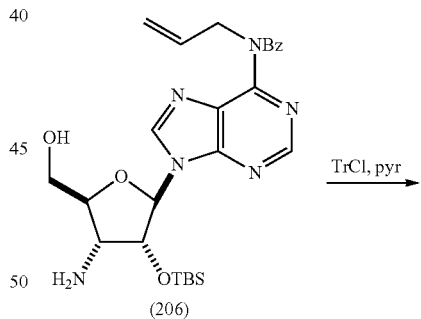

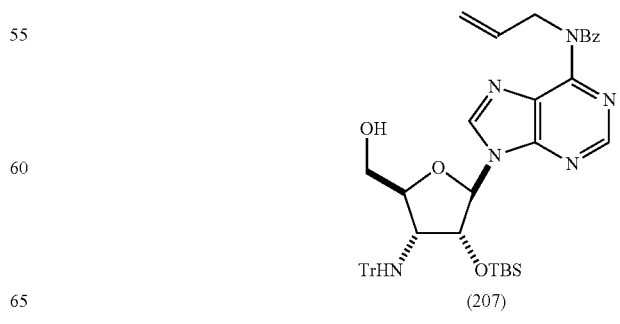

213

To a solution of Compound 206 (4.82 g, 63% purity, 5.72 mmol) in pyridine (39.0 ml) at ambient temperature were added TEA (1.3 ml, 8.6 mmol) and trityl-Cl (1.753 g, 6.289 mmol). Upon complete reaction (monitored by LC/MS), a sat'd NaHCO$_3$ solution (60 mL) was added. The resulting mixture was extracted three times with a mixture of MTBE/EtOAc (1/1, 70 mL each time). The combined organic layers washed with 30% aqueous NaCl solution (30 mL) and dried over MgSO$_4$, filtered and concentrated in vacuo. The residue was purified by silica gel column chromatography (SiO$_2$ 50 g pretreated with 1% TEA in EtOAc/n-heptane, 20% to 100% EtOAc in n-heptane with 1% TEA) to give 1.484 g of Compound 207 as a white solid.

Compound 207:

$^1$H NMR (400 MHz, CHLOROFORM-d) δ=8.49 (s, 1H), 8.10 (s, 1H), 7.50-7.46 (m, 8H), 7.31-7.22 (m, 7H), 7.20-7.14 (m, 5H), 6.11 (d, J=6.3 Hz, 1H), 6.07-5.94 (m, 1H), 5.20 (dd, J=1.2, 17.2 Hz, 1H), 5.06 (dd, J=1.4, 10.4 Hz, 1H), 5.03-4.98 (m, 2H), 4.84 (dd, J=3.1, 10.6 Hz, 1H), 4.52 (t, J=5.7 Hz, 1H), 3.78 (d, J=1.6 Hz, 1H), 3.64-3.57 (m, 1H), 3.26-3.16 (m, 3H), 0.77 (s, 9H), −0.18 (s, 3H), −0.63 (s, 3H).

Step 5

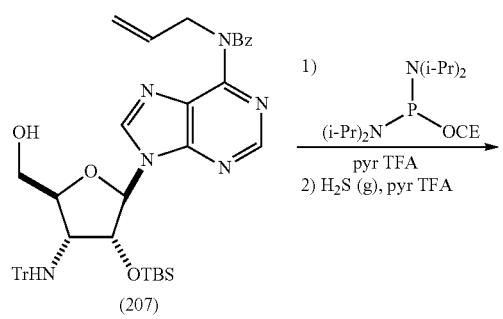

214

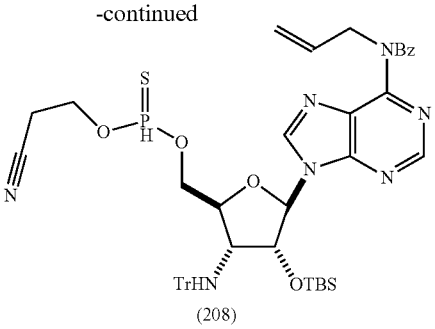

To a solution of Compound 207 (0.50 g, 0.652 mmol) in MeCN (6 mL) at ambient temperature were added 3-((bis(diisopropylamino)phosphaneyl)oxy)propanenitrile (0.393 g, 1.304 mmol) and pyridinium trifluoroacetate (0.113 g, 0.587 mmol). The resulting solution was stirred at ambient temperature while monitored by LCMS. Upon completion (1 h), the resulting solution was treated with hydrogen sulfide gas (bubbling) for 1 min followed by pyridinium trifluoroacetate (0.252 g, 1.304 mmol). The resulting solution was stirred at ambient temperature while monitored by LCMS. Upon completion (1 h), the resulting mixture was diluted with MTBE (60 mL). The resulting solution was washed with water (15 mL each time) twice and 30% aqueous NaCl solution (15 ml), and dried over Na$_2$SO$_4$, filtered and concentrated in vacuo. The residue was purified by silica gel column chromatography (SiO$_2$ 25 g, 25% to 40% EtOAc in n-heptane) to give 0.411 g of Compound 208 (1:1 P diastereomeric mixture) as a white foam solid.

Compound 208

(1:1 P diastereomeric mixture) $^1$H NMR (400 MHz, CHLOROFORM-d) δ=8.49 (s, 1H), 8.49 (s, 1H), 8.11 (s, 1H), 8.06 (s, 1H), 7.54-7.47 (m, 4H), 7.46-7.38 (m, 14H), 7.32-7.27 (m, 2H), 7.23-7.04 (m, 20H), 6.11-5.99 (m, 2H), 5.98 (d, J=2.0 Hz, 1H), 5.91 (d, J=1.6 Hz, 1H), 5.27 (dd, J=1.6, 6.3 Hz, 1H), 5.23 (dd, J=1.6, 6.3 Hz, 1H), 5.12 (dd, J=1.6, 6.3 Hz, 1H), 5.09 (dd, J=1.2, 6.3 Hz, 1H), 5.02 (br d, J=5.5 Hz, 4H), 4.57-4.45 (m, 2H), 4.43-4.34 (m, 1H), 4.32-4.04 (m, 8H), 3.23-3.19 (m, 1H), 3.10 (br s, 2H), 3.06-2.99 (m, 1H), 2.96-2.89 (m, 2H), 2.73 (dt, J=1.4, 6.4 Hz, 2H), 2.65 (t, J=6.3 Hz, 2H), 0.85 (s, 9H), 0.83 (s, 9H), 0.01 (s, 3H), −0.09 (s, 6H), −0.11 (s, 3H).

Step 6

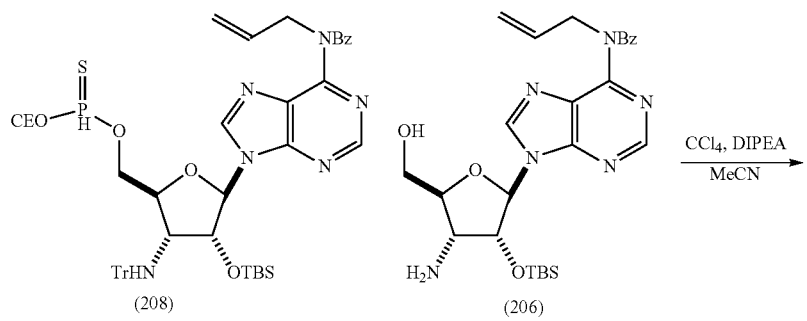

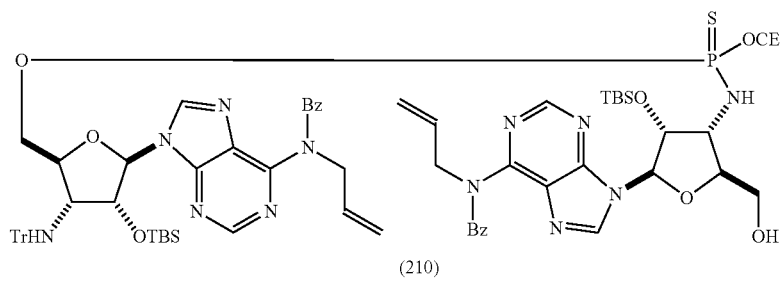

(210)

To a solution of Compound 208 (0.411 g, 0.457 mmol) and Compound 206 (0.293 g, 0.502 mmol) in acetonitrile (5 ml) at ambient temperature were added DIEA (0.16 ml, 0.91 mmol) and CCl$_4$ (0.18 ml, 1.8 mmol). The reaction mixture was stirred at ambient temperature while monitored by LCMS. Upon completion (1 h), the resulting mixture was concentrated in vacuo and purified by silica gel column chromatography (SiO$_2$ 25 g, 33% to 100% EtOAc in n-heptane) to give 0.461 g of Compound 210 (1:1 P diastereomeric mixture) as a white foam solid.

Compound 210:

$^1$H NMR (400 MHz, CHLOROFORM-d) δ=8.52 (s, 1H), 8.51 (s, 1H), 8.49 (s, 1H), 8.49 (s, 1H), 8.24 (s, 1H), 8.19 (s, 1H), 8.13 (s, 1H), 8.01 (s, 1H), 7.55-7.37 (m, 20H), 7.33-6.99 (m, 30H), 6.09-5.97 (m, 4H), 5.96 (d, J=2.7 Hz, 1H), 5.87 (d, J=1.2 Hz, 1H), 5.82 (d, J=4.7 Hz, 1H), 5.80 (d, J=3.9 Hz, 1H), 5.28-5.17 (m, 4H), 5.11-5.04 (m, 4H), 5.03-4.96 (m, 8H), 4.75 (t, J=5.1 Hz, 1H), 4.70 (t, J=4.5 Hz, 1H), 4.46-4.33 (m, 3H), 4.31-4.18 (m, 5H), 4.12-3.96 (m, 8H), 3.89 (br d, J=11.7 Hz, 1H), 3.78-3.67 (m, 3H), 3.57 (dd, J=2.9, 4.1 Hz, 1H), 3.56-3.44 (m, 2H), 3.08-3.01 (m, 2H), 2.99-2.93 (m, 1H), 2.91 (d, J=8.6 Hz, 1H), 2.77-2.73 (m, 1H), 2.72-2.53 (m, 4H), 0.84 (s, 9H), 0.84 (s, 9H), 0.84 (s, 9H), 0.82 (s, 9H), 0.00 (s, 3H), −0.05 (s, 6H), −0.08 (s, 3H), −0.12 (s, 3H), −0.15 (s, 3H), −0.18 (s, 3H), −0.18 (s, 3H).

Step 7

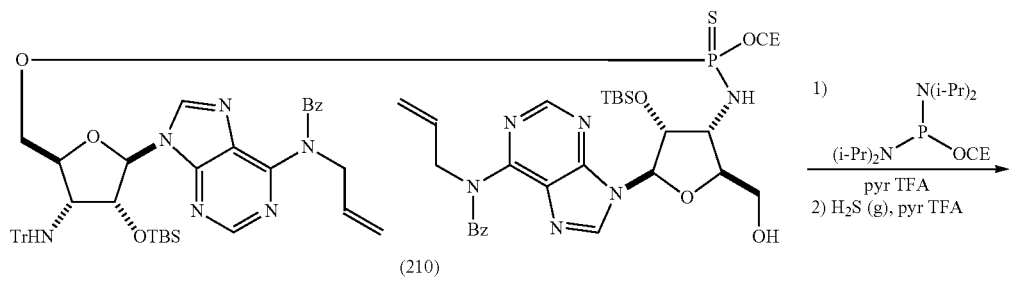

(210)

1) 
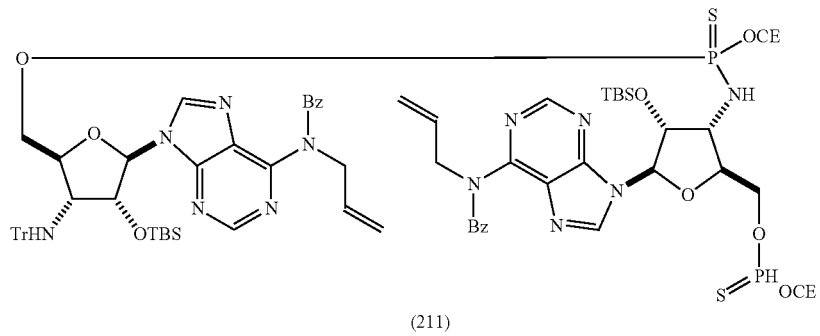

pyr TFA

2) H$_2$S (g), pyr TFA (211)

To a solution of Compound 210 (0.461 g, 0.324 mmol) in MeCN (5.5 ml) at ambient temperature were added 3-((bis(diisopropylamino)phosphaneyl)oxy)propanenitrile (0.195 g, 0.648 mmol) and pyridinium trifluoroacetate (0.050 g, 0.259 mmol). The resulting solution was stirred at ambient temperature while monitored by LCMS. Upon completion (40 min), the resulting solution was bubbled with hydrogen sulfide gas for 1 min and then treated with pyridinium trifluoroacetate (0.138 g, 0.713 mmol). Upon completion (monitored by LCMS), the resulting solution was diluted with MTBE (30 mL), washed with water (10 mL each) twice and 30% aqueous NaCl solution (10 ml), dried over Na$_2$SO$_4$, filtered and concentrated in vacuo. The residue was purified by silica gel column chromatography (SiO$_2$ 25 g, 33% to 60% EtOAc in n-heptane) to give 0.329 g of Compound 211 as a white foam solid.

Compound 211:
  LC/MS (ESI) m/z 1555.48 [M+H]$^+$.
Step 8

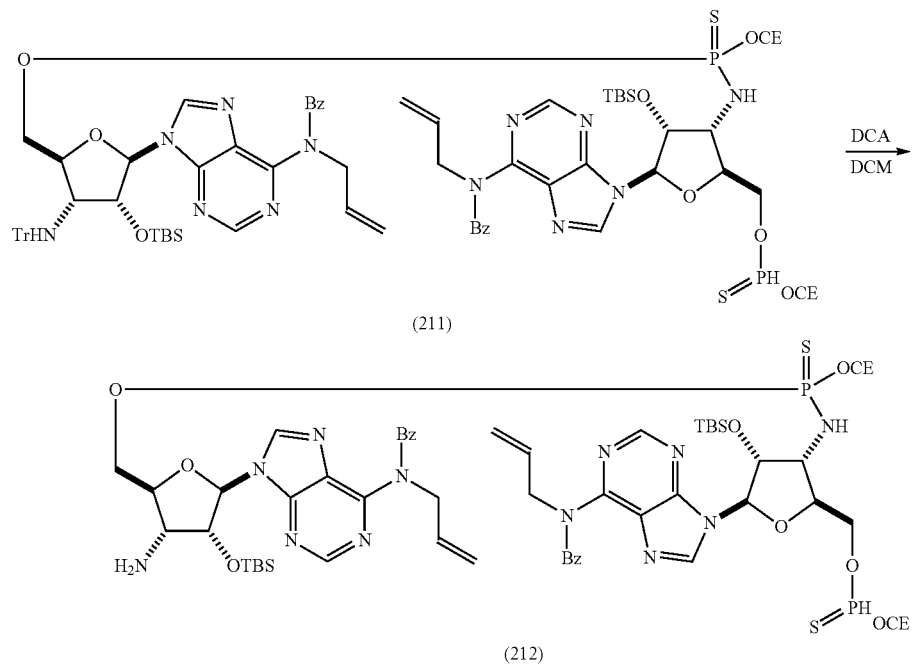

To a solution of Compound 211 (0.329 g, 0.211 mmol) in dichloromethane (7.2 ml) at ambient temperature were added water (0.032 ml, 1.8 mmol) and dichloroacetic acid (0.29 ml, 3.6 mmol). The resulting mixture was stirred at ambient temperature while monitored by LCMS. Upon completion (30 min), the reaction mixture was a sat'd NaHCO$_3$ solution (25 mL). The resulting mixture was extracted twice with DCM (30 mL each time). The combined organic layers were washed with 30% aqueous NaCl solution (20 mL), dried over MgSO$_4$, filtered and concentrated in vacuo. Crude product Compound 212 (0.278 g theoretical yield) was used in next step without further purification.

Compound 212:
  LC/MS (ESI) m/z 1313.40[M+H]$^+$.
Step 9

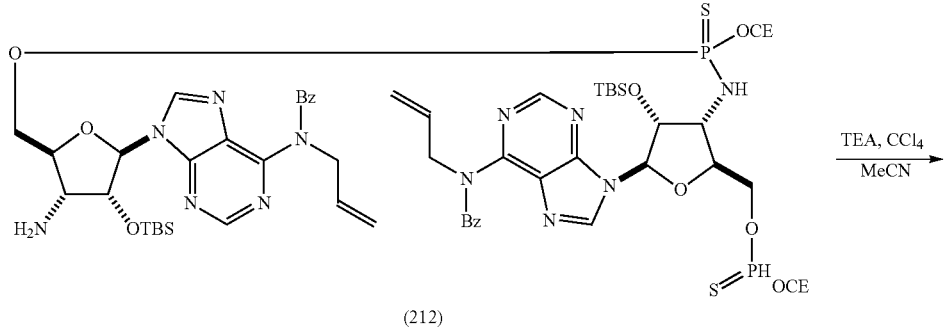

-continued

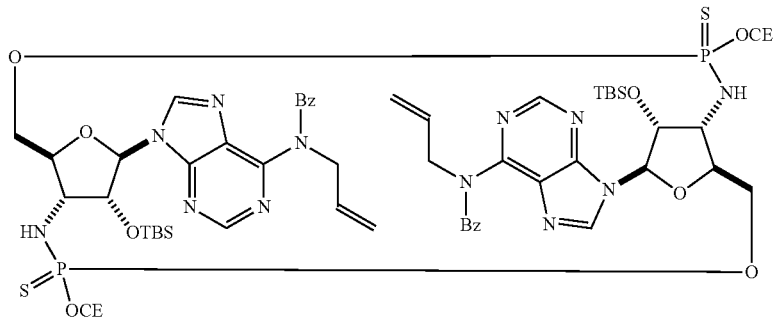

(213) (SpRp isomer)
(214) (either RpRp or SpSp, higher rf on TLC (SiO2))
(215) (either RpRp or SpSp, lower rf on TLC (SiO2))

To a solution of Compound 212 (0.278 g, 0.212 mmol) in MeCN (55.6 ml) at ambient temperature were added triethyl amine (1.0 ml, 7.2 mmol) and CCl$_4$ (1.0 ml, 10 mmol). The resulting solution was stirred at ambient temperature while monitored by LCMS. Upon completion (30 min), the reaction mixture was concentrated to ~20 mL in vacuo and diluted with MTBE (30 mL). The resulting mixture was washed with water (10 ml) and 30% aqueous NaCl solution (10 mL each) twice, dried over MgSO$_4$, filtered and concentrated in vacuo. The residue was purified by silica gel column chromatography (SiO$_2$ 25 g, 20% to 75% EtOAc in n-heptane) to give 71 mg of Compound 213 (SpRp isomer), 43 mg of Compound 214 (either RpRp or SpSp isomer, higher rf on TLC (SiO$_2$)), and 24 mg of Compound 215 (either RpRp or SpSp isomer, lower rf on TLC (SiO$_2$)).

Compound 213

(SpRp isomer) $^1$H NMR (400 MHz, CHLOROFORM-d) δ=8.58 (s, 1H), 8.44 (s, 1H), 8.42 (s, 1H), 8.12 (s, 1H), 7.46 (dd, J=7.2, 15.4 Hz, 4H), 7.36-7.27 (m, 2H), 7.18 (q, J=7.6 Hz, 4H), 6.09 (s, 1H), 5.98 (s, 1H), 6.06-5.95 (m, 2H), 5.25 (d, J=11.3 Hz, 1H), 5.21 (dd, J=1.4, 10.4 Hz, 1H), 5.12-5.03 (m, 3H), 5.00-4.92 (m, 3H), 4.87 (d, J=4.7 Hz, 1H), 4.60 (br d, J=11.7 Hz, 1H), 4.55 (d, J=3.9 Hz, 1H), 4.44 (br d, J=11.3 Hz, 1H), 4.39-4.32 (m, 2H), 4.26-4.08 (m, 8H), 3.75 (dd, J=11.3, 16.0 Hz, 1H), 3.49 (dd, J=8.2, 10.6 Hz, 1H), 2.82-2.72 (m, 3H), 2.61 (td, J=5.9, 17.2 Hz, 1H), 0.99 (s, 9H), 0.96 (s, 9H), 0.32 (s, 3H), 0.23 (s, 6H), 0.22 (s, 3H).

Compound 214

(either RpRp or SpSp isomer, higher rf on TLC (SiO$_2$) isomer): $^1$H NMR (400 MHz, CHLOROFORM-d) δ=8.60 (s, 2H), 8.18 (s, 2H), 7.50 (d, J=7.0 Hz, 4H), 7.37-7.31 (m, 2H), 7.25-7.21 (m, 4H), 6.05-5.93 (m, 4H), 5.22 (dd, J=1.6, 17.2 Hz, 2H), 5.09 (dd, J=1.0, 10.4 Hz, 2H), 5.00-4.83 (m, 6H), 4.61 (dd, J=1.2, 11.7 Hz, 2H), 4.25 (dq, J=4.3, 10.8 Hz, 2H), 4.09 (br dd, J=3.7, 10.4 Hz, 2H), 4.04 (td, J=5.5, 10.9 Hz, 2H), 3.99-3.88 (m, 4H), 3.70 (dd, J=11.9, 15.0 Hz, 2H), 2.71 (td, J=5.5, 17.1 Hz, 2H), 2.49-2.37 (m, 2H), 0.98 (s, 18H), 0.25 (s, 6H), 0.24 (s, 6H).

Compound 215

(either RpRp or SpSp isomer, lower rf on TLC (SiO$_2$) isomer): $^1$H NMR (400 MHz, CHLOROFORM-d) δ=8.54 (s, 2H), 8.06 (s, 2H), 7.47-7.44 (m, 4H), 7.32-7.27 (m, 2H), 7.20-7.15 (m, 4H), 6.06-5.95 (m, 2H), 5.92 (d, J=3.5 Hz, 2H), 5.22 (dd, J=1.2, 17.2 Hz, 2H), 5.07 (dd, J=1.4, 10.4 Hz, 2H), 5.04-4.94 (m, 6H), 4.62-4.52 (m, 2H), 4.46-4.40 (m, 2H), 4.40-4.22 (m, 8H), 3.81 (dd, J=6.6, 12.1 Hz, 2H), 2.89-2.71 (m, 4H), 0.88 (s, 18H), 0.08 (s, 6H), −0.07 (s, 6H).

Step 10

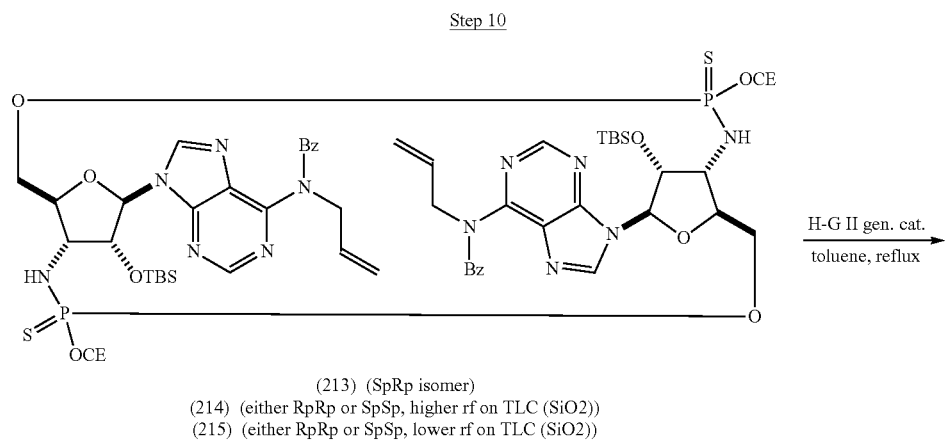

(213) (SpRp isomer)
(214) (either RpRp or SpSp, higher rf on TLC (SiO2))
(215) (either RpRp or SpSp, lower rf on TLC (SiO2))

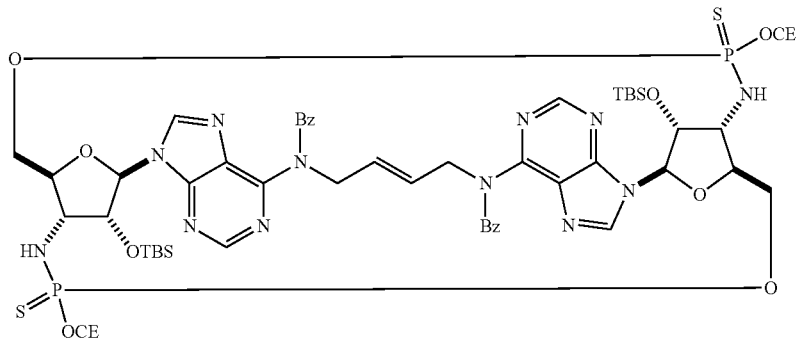

(216) (SpRp, trans/cis = 5/1)
(217) (either RpRp or SpSp, higher rf on TLC (SiO2) trans/cis = 5/1)
(218) (either RpRp or SpSp, lower rf on TLC (SiO2))

To a solution of Compound 213 (71 mg, 0.054 mmol) in toluene (28.4 ml) at reflux was added a solution of Hoveyda-Grubbs Catalyst 2nd Generation (17.0 mg, 0.027 mmol) and P-benzoquinone (11.70 mg, 0.108 mmol) in toluene (8 mL). The mixture was heated to reflux and reaction progress was monitored by LC/MS. After 3 h, additional catalyst (8.5 mg, 0.0135 mmol) in toluene (2.5 mL) was added and the reaction was continued for additional 2.5 hours. After cooling down, the mixture was concentrated in vacuo and purified by silica gel column chromatography (SiO$_2$ 10 g, 33% to 66% ethyl acetate in n-heptane) to give 17 mg of Compound 216 (trans/cis=5/1) as a brown dry foam.

Compound 216:
$^1$H NMR (trans isomer only, 400 MHz, CHLOROFORM-d) δ=8.37 (s, 1H), 8.34 (s, 1H), 8.24 (s, 1H), 8.20 (s, 1H), 7.41 (d, J=7.1 Hz, 2H), 7.36-7.27 (m, 3H), 7.24-7.13 (m, 5H), 5.97 (d, J=5.9 Hz, 2H), 5.75 (td, J=5.5, 15.2 Hz, 1H), 5.69 (td, J=5.5, 15.6 Hz, 1H), 5.07 (d, J=3.9 Hz, 1H), 5.03 (dd, J=5.1, 15.2 Hz, 1H), 4.94 (t, J=5.5 Hz, 2H), 4.85 (dd, J=5.1, 15.2 Hz, 1H), 4.74 (d, J=3.9 Hz, 1H), 4.67 (br d, J=12.1 Hz, 1H), 4.45 (br d, J=10.2 Hz, 1H), 4.42-4.34 (m, 2H), 4.28-4.19 (m, 2H), 4.19-4.06 (m, 4H), 3.96-3.84 (m, 1H), 3.82-3.68 (m, 1H), 3.56 (br dd, J=12.1, 14.5 Hz, 1H), 3.33 (dd, J=9.0, 10.9 Hz, 1H), 2.83-2.78 (m, 2H), 2.72 (td, J=5.6, 16.6 Hz, 1H), 2.39 (td, J=6.3, 17.2 Hz, 1H), 1.00 (s, 18H), 0.42 (s, 3H), 0.40 (s, 3H), 0.34 (s, 3H), 0.30 (s, 3H).

Compound 217
Compound 214 obtained from Step 9 was processed separately through Step 10 to give Compound 217 (5/1 mixture of trans/cis isomers).
$^1$H NMR (trans isomer only, 400 MHz, CHLOROFORM-d) δ=8.47 (s, 2H), 8.14 (s, 2H), 7.43-7.38 (m, 4H), 7.36-7.29 (m, 2H), 7.22 (t, J=7.0 Hz, 4H), 5.83 (s, 2H), 5.77 (t, J=3.3 Hz, 2H), 5.17 (d, J=3.5 Hz, 2H), 5.11-5.04 (m, 2H), 4.70 (br dd, J=3.5, 16.4 Hz, 2H), 4.62 (br d, J=12.1 Hz, 2H), 4.16-4.08 (m, 6H), 3.93 (br dd, J=3.7, 11.9 Hz, 2H), 3.74-3.64 (m, 2H), 3.49 (t, J=12.9 Hz, 2H), 2.42 (td, J=5.9, 18.4 Hz, 2H), 2.13 (ddd, J=5.5, 7.8, 16.8 Hz, 2H), 1.00 (s, 18H), 0.40 (s, 6H), 0.34 (s, 6H).

Compound 218
Compound 215 obtained from Step 9 was processed separately through Step 10 to give Compound 218.
$^1$H NMR (400 MHz, CHLOROFORM-d) δ=8.14 (s, 2H), 8.12 (s, 2H), 7.49-7.43 (m, 2H), 7.36-7.27 (m, 4H), 7.19-7.12 (m, 4H), 5.96 (s, 2H), 5.67-5.54 (m, 2H), 4.95-4.82 (m, 4H), 4.69 (d, J=4.3 Hz, 2H), 4.60-4.09 (m, 12H), 3.63 (dd, J=8.8, 16.2 Hz, 2H), 2.93 (td, J=5.9, 17.2 Hz, 2H), 2.82-2.72 (m, 2H), 0.99 (s, 18H), 0.30 (s, 6H), 0.27 (s, 6H).

Step 11

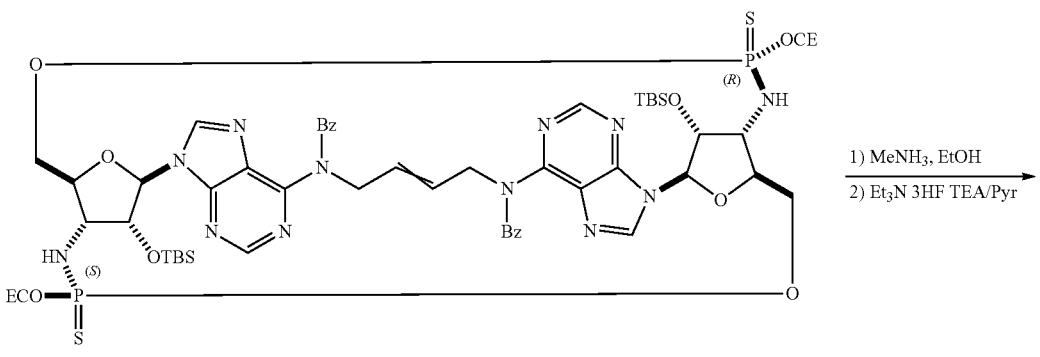

(216) (SpSp, trans/cis = 5/1)

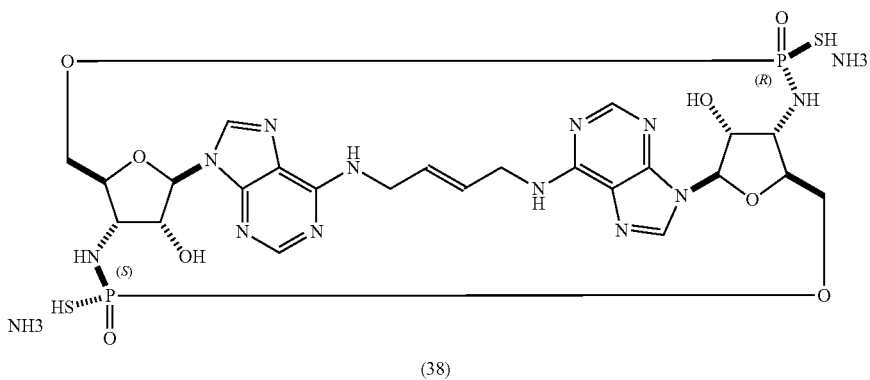

(38)

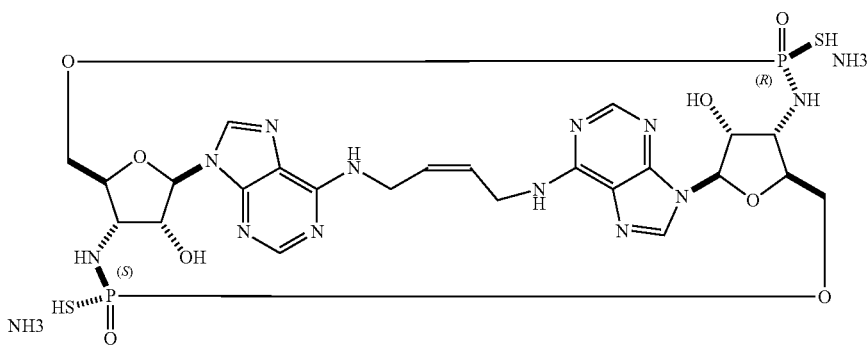

220

To Compound 216 (trans/cis=5/1, 17 mg, 0.013 mmol) was added a solution of methylamine solution (2 ml) (33% in EtOH) at ambient temperature. The resulting solution was stirred at ambient temperature while monitored by LCMS. Upon completion (1 h), the reaction mixture was concentrated in vacuo. To the residue were added pyridine (0.9 ml), TEA (0.45 ml) and triethylamine trihydrofluoride (0.36 ml, 2.2 mmol). The resulting mixture was stirred at 50-60° C. for 4 h and cooled to ambient temperature. Upon complete TBS deprotection (monitored by LCMS), the reaction mixture was treated with methoxytrimethylsilane (1.5 ml, 12 mmol) and stirred for 1 h. Water (3 mL) was added and the resulting mixture was extracted with toluene (3 ml each time) twice and EtOAc (2 mL each time) twice. The aqueous layer was filtered by syringe filter and the filtrate was subjected to preparative HPLC to give 5.3 mg of Compound 38 and 1.1 mg of Compound 220.

Compound 38 (SpRp, Trans):

$^1$H NMR (400 MHz, METHANOL-$d_4$) δ=9.27 (br s, 1H), 8.47 (br s, 1H), 8.21 (br s, 1H), 8.09 (br s, 1H), 6.19-5.96 (m, 2H), 5.94-5.71 (m, 2H), 5.13-4.68 (m, 2H), 4.55-4.39 (m, 2H), 4.38-4.23 (m, 1H), 4.20-3.91 (m, 5H), 3.75-3.50 (m, 4H).

Compound 220 (SpRp, Cis):

$^1$H NMR (400 MHz, METHANOL-$d_4$) δ=9.08 (s, 1H), 8.72 (br s, 1H), 8.55 (s, 1H), 8.24 (s, 1H), 8.18 (s, 1H), 6.22-6.14 (m, 2H), 6.10 (d, J=1.6 Hz, 2H), 5.01 (d, J=3.9 Hz, 1H), 4.41 (br d, J=9.8 Hz, 1H), 4.34-4.25 (m, 3H), 4.24-4.18 (m, 1H), 4.15 (dd, J=6.1, 11.5 Hz, 1H), 4.08-3.99 (m, 4H), 3.71-3.57 (m, 3H).

Compound 39 and Compound 222

Compound 217 was processed separately through Step 11 to give Compound 39 and Compound 222.

Compound 39 (trans isomer): $^1$H NMR (400 MHz, METHANOL-$d_4$) δ=8.83 (br s, 1H), 8.43 (br s, 1H), 8.17 (br s, 1H), 8.11 (br s, 1H), 6.17-5.95 (m, 2H), 5.93-5.63 (m, 2H), 5.10-4.78 (m, 2H), 4.69-4.53 (m, 1H), 4.52-4.35 (m, 2H), 4.12-3.92 (m, 5H), 3.76-3.44 (m, 4H).

Compound 222 (cis isomer): $^1$H NMR (400 MHz, METHANOL-$d_4$) δ=8.71 (br s, 2H), 8.18 (s, 2H), 6.17-6.06 (m, 4H), 4.37 (br d, J=9.8 Hz, 2H), 4.33 (d, J=3.9 Hz, 2H), 4.27 (br dd, J=7.0, 13.7 Hz, 2H), 4.06 (dd, J=7.0, 11.3 Hz, 2H), 4.19-4.03 (m, 2H), 4.01 (br d, J=9.8 Hz, 2H), 3.74 (ddd, J=3.9, 6.4, 10.5 Hz, 2H).

Compound 40

Compound 218 was processed separately through Step 11 to give Compound 40: $^1$H NMR (400 MHz, METHANOL-$d_4$) δ=9.34-8.88 (m, 2H), 8.73 (br s, 1H), 8.34-8.02 (m, 2H), 6.20-5.96 (m, 2H), 5.89 (br s, 2H), 5.25-4.95 (m, 2H), 4.76-4.64 (m, 1H), 4.47-4.22 (m, 2H), 4.20-4.07 (m, 2H), 4.07-3.93 (m, 2H), 3.82-3.55 (m, 3H), 3.54-3.38 (m, 2H)

Example 24—Synthesis of Compound 30

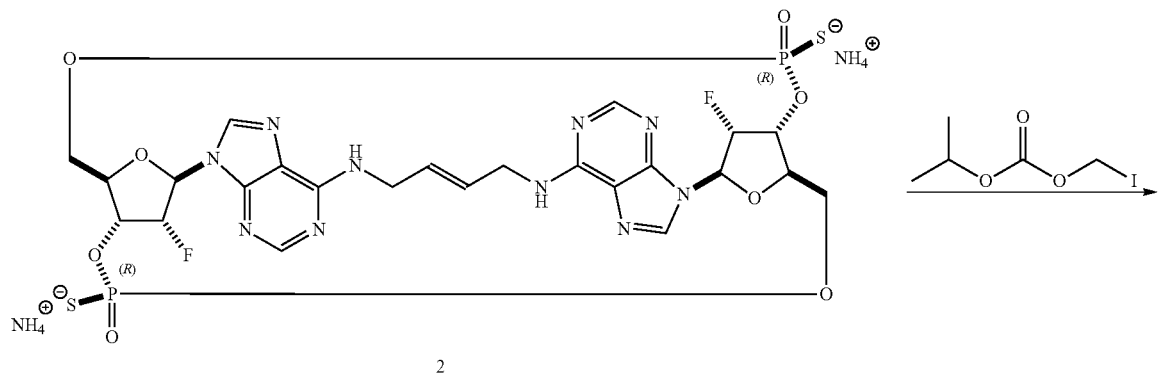

2

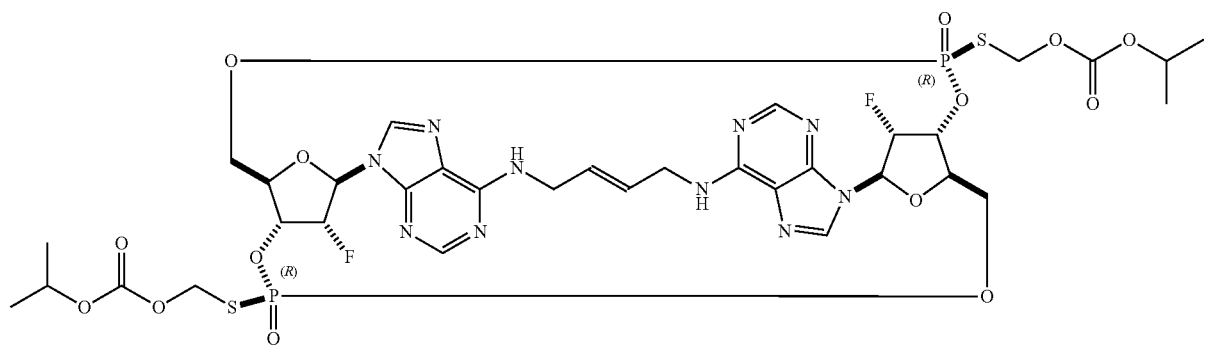

30

Compound 2 (1.1 mg, 1.4 μmol) was added into a solution of iodomethyl isopropyl carbonate (13.75 mg, 0.056 mmol) in acetone/water (0.4/0.10 ml) at ambient temperature. The resulting mixture was stirred at ambient temperature in darkness while the reaction was monitored by LCMS. Upon completion (2 h), the reaction mixture was diluted with water (0.4 ml) and extracted with n-neptane three time (0.5 mL each). Purification of the crude product in the aqueous layer provided 0.5 mg of Compound 30.

$^1$H NMR (400 MHz, CHLOROFORM-d) δ=7.92 (s, 2H), 7.72 (br s, 2H), 6.22 (d, J=17.2 Hz, 2H), 6.19-6.03 (m, 2H), 5.98 (br t, J=6.3 Hz, 2H), 5.82-5.77 (m, 2H), 5.68 (dd, J=2.3, 51.6 Hz, 1H), 5.54 (dd, J=10.9, 13.7 Hz, 2H), 5.48 (dd, J=10.9, 12.9 Hz, 2H), 4.94 (quin, J=6.2 Hz, 2H), 4.71-4.63 (m, 2H), 4.63-4.56 (m, 2H), 4.50-4.43 (m, 2H), 4.22-4.12 (m, 2H), 4.05-3.90 (m, 2H), 1.33 (d, J=4.3 Hz, 6H), 1.32 (d, J=4.3 Hz, 6H).

Example 103—HAQ STING Agonist Activity Reporter Assay

THP1-Dual™ Cells (InvivoGen, Cat #thpd-nfis) were applied for $EC_{50}$ determination. THP1 Dual™ Cells have been characterized to carry the HAQ STING genotype by the vendor Invivogen (Insight 201402-1). Cells were grown and maintained under conditions as recommended by manufacturer. The interferon regulatory factor (IRF) pathway induction described in manufacturer's manual was followed for $EC_{50}$ determination. In brief, cells were seeded and treated with different concentrations of compound for 20 hrs while incubated at 37° C., 5% $CO_2$. Cells were resuspended and QUANTI-Luc™ solution (Cat. #: rep-qlc1) was added. Resulting light emission was measured by luminometer (Envision, Perkin Elmer). Obtained signals were plotted and $EC_{50}$ was calculated with GraphPad Prism7 software.

$EC_{50}$ values are reported in Tables 4-8 below. The $EC_{50}$ values may be from a single assay or an average of multiple assays. Preceding each table is a structure used for review of that table.

TABLE 4

(VI)

[Structure of formula (VI): a cyclic dinucleotide analog with two adenine nucleosides connected by a linker containing (CH₂)ₘ–CH=CH–(CH₂)ₙ between the N6 positions, with phosphorothioate (or phosphate) linkages; Xa substituent at the 2' position of one sugar.]

| length | m | n | geometry | Xa at 2' | P chirality 2' side | 3' side | Compound Number | HAQ | WT | AQ | REF |
|---|---|---|---|---|---|---|---|---|---|---|---|
| 4 carbon linker | 1 | 1 | trans | Xa = OH | S | S | 223 | * | N/E | N/E | N/E |
| | | | | | S | R | 13 | 26.7 | N/E | N/E | N/E |
| | | | | | R | R | 14 | 58.2 | 69.8 | * | * |
| | | | cis | | S | R | 224 | * | N/E | N/E | N/E |
| | | | | | S | S | 225 | * | N/E | N/E | N/E |
| | | | | | | | | N/E | N/E | N/E | |
| | | | TBD | | Not applicable (phosphodiester) | | 226 | * | N/E | N/E | N/E |
| | | | TBD | | | | 227 | * | N/E | N/E | N/E |
| | | | | | | | 228 | * | N/E | N/E | N/E |

[Linker structure: –NH–CH₂–CH(OH)–CH(OH)–CH₂–NH–]

| | | | trans | Xa = F | S | R | 15 | 24.7 | 11.6 | 13.1 | 66.7 |
| | | | | | R | R | 16 | 28.8 | 25.7 | 20.4 | 66.7 |
| | | | cis | | R | R | 229 | * | N/E | N/E | N/E |
| 5 carbon linker | 2 | 1 | trans | Xa = OH | R | R | 230 | * | N/E | N/E | N/E |
| | | | Trans (2:1 mix) | | TBD | | 231 | * | | N/E | N/E |
| | | | Trans (3:1 mix) | | TBD | | 232 | * | N/E | N/E | N/E |
| | | | | | S | R | 233 | * | N/E | N/E | N/E |
| | 1 | 2 | trans | | S | R | 234 | * | N/E | N/E | N/E |
| | | | | | TBD | | 235 | * | | N/E | N/E |
| | | | | | TBD | | 236 | * | | N/E | N/E |
| | | | cis | | S | R | 237 | * | N/E | N/E | N/E |
| | | | | | TBD | | 238 | * | | N/E | N/E |
| | | | TBD | | R | R | 239 | * | N/E | N/E | N/E |
| | | | | | S | R | 240 | * | | | N/E |

[Linker structure: –NH–(CH₂)₄–NH–]

| 6 carbon linker | 2 | 2 | TBD | | S | R | 241 | * | N/E | N/E | N/E |
| | | | TBD | | S | R | 242 | * | N/E | N/E | N/E |
| | | | TBD | | R | R | 243 | * | N/E | N/E | N/E |

* Indicates activity was not measurable in the experimental concentration range.
"N/E" indicates "not evaluated."

Human STING EC50 (µM) was measured using the ammonium salt form of each compound in Table 4.

TABLE 5

(VII)

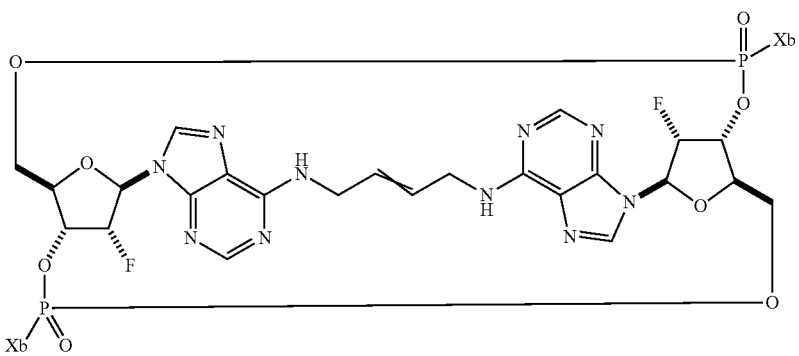

| 4 carbon linkers (between NH in chain) | P linkages chirality | P linkages Xb | Compound Number | Human STING EC50 (μM) HAQ | Human STING EC50 (μM) WT | Human STING EC50 (μM) AQ | Human STING EC50 (μM) REF |
|---|---|---|---|---|---|---|---|
| trans | — | OH | 9 | 39.2 | 18.0 | 30.9 | 31.7 |
|  | RR |  | 30 | N.D. | N.D. | N.D. | N.D. |

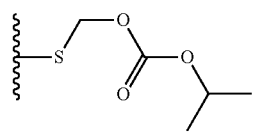 [SMILES: *SCOC(=O)OC(C)C]

| | P linkages chirality | P linkages Xb | Compound Number | HAQ | WT | AQ | REF |
|---|---|---|---|---|---|---|---|
|  | SR | —SH | 1 | 4.1 | 0.9 | 1.2 | 4.8 |
|  | SS |  | 3 | 16.4 | 9.9 | 13.7 | 42.7 |
|  | RR |  | 2 | 6.1 | 3.4 | 3.5 | 11.4 |
| Trans/cis mix | RR |  | 10 | 17.9 | 9.0 | 10.2 | 34.3 |
| cis | SS |  | 244 | * | >100 | >100 | >100 |
|  | RR |  | 4 | 10.6 | 3.9 | 8.2 | >100 |
|  | SR |  | 5 | 87.1 | 49.1 | >100 | >100 |
|  | SR |  | 6 | 10.5 | 5.7 | 9.0 | 42.0 | saturated

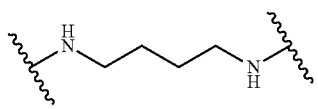

| | P linkages chirality | Compound Number | HAQ | WT | AQ | REF |
|---|---|---|---|---|---|---|
| 5C cis/trans | N.D. | 245 | * | N/E | N/E | N/E |
| TBD |  | 246 | * | N/E | N/E | N/E |
| 5C trans | N.D. | 8 | 69.7 | 68.7 | 81.0 | >100 |
| 5C trans | N.D. | 7** | 10.7 | 8.0 | 9.0 | 66.7 |
| 5C trans | N.D. | 37 | 87.2 | >100 | 82.2 | >100 |
| 5C trans | N.D. | 11 | 6.8 | N/E | N/E | N/E |
| 5C trans | N.D. | 12 | 8.2 | N/E | N/E | N/E |

\* Indicates activity was not measurable in the experimental concentration range.
\*\*Compound 7 is a 1:1 mixture of Compound 11 and Compound 12.
"N/E" indicates "not available."
"N.D." indicates "not determined."

Human STING EC50 (μM) was measured using the ammonium salt form of each compound listed in Table 5.

TABLE 6

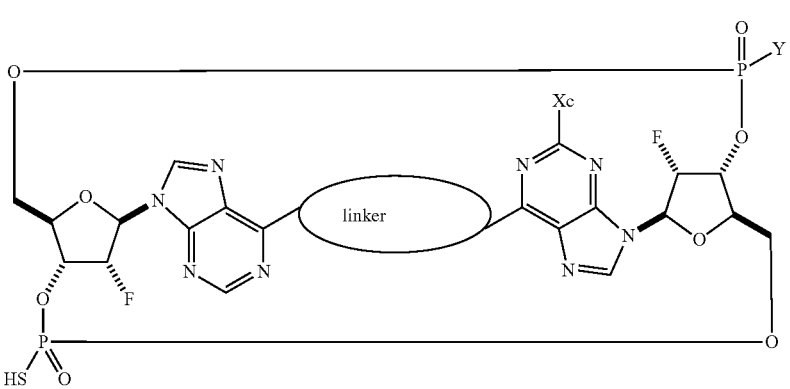

| Base pair | Xc = | Y = | linker | P geometry | P chirality | Compound Number | hSTING EC50 (μM) HAQ | hSTING EC50 (μM) REF |
|---|---|---|---|---|---|---|---|---|
| AG | NH₂ | SH | ⁻N\~\~\~O⁻ | cis | N.D. | 247 | * | N/E |
|  |  |  |  | trans |  | 22 | 41.2 | N/E |
|  |  |  |  |  | N.D. | 21 | 83.3 | N/E |
|  |  |  |  |  | TBD | 23 | 62.3 | N/E |
| AI | H |  |  | cis |  | 248 | * | N/E |
|  |  |  |  |  |  | 249 | * | N/E |
|  |  |  |  | trans |  | 18 | 2.3 | N/E |
|  |  |  |  |  |  | 19 | 94.1 | N/E |
|  |  |  |  |  |  | 20 | 2.8 | N/E |
| II |  |  | ⁻O\~\~O⁻ |  | RR | 26 | 2.3 | 7.4 |
| AA |  |  | \~\~\~ |  | SR | 33 | 21.5 | * |
|  |  |  |  |  | RR | 34 | 2.3 | * |
|  |  |  |  |  | SS | 250 | * | * |
|  |  |  | aziridine linker |  | SR | 35 | 44.5 | 67.2 |
|  |  |  |  |  | SR | 36 | 31.4 | 94.1 |
|  |  |  | diol linker |  | SR | 32 | 15.7 | * |
|  |  |  | alkyne linker |  | SR | 29 | 0.62 | 8.4 |
|  |  |  | deuterated linker | trans | SR | 25 | 0.73 | 3.0 |
|  | OH |  | ⁻N\~\~N⁻ |  | S | 27 | 9.8 | 27.6 |
|  |  |  |  |  | R | 28 | 10.2 | 18.4 |

* Indicates activity was not measurable in the experimental concentration range.
"N/E" indicates "not evaluated."
"N.D." indicates "not determined."

Human STING EC50 (μM) was measured using the ammonium salt form of each compound listed in Table 6 with the exception of Compound 26, Compound 31, Compound 33, and Compound 34, all of which were tested as bis-TEA salts.

TABLE 7

(IX)

[Chemical structure showing a cyclic dinucleotide with two adenine-like bases connected by a linker, with phosphorothioate groups]

| Base pair | linker | geometry | P chirality | Compound Number | hSTING EC50 (μM) HAQ | hSTING EC50 (μM) REF |
|---|---|---|---|---|---|---|
| AA | —N(H)—CH₂—CH=CH—CH₂—N(H)(CH₃)— (methyl on each N) | trans | S S or RR | 251 | * | * |
|  |  |  | SS or RR | 252 | * | * |
|  |  |  | RR | 31 | 20.2 | * |

\* Indicates activity was not measurable in the experimental concentration range.

Human STING EC50 (μM) was measured using the ammonium salt form of each compound in Table 7.

TABLE 8

[Chemical structure showing a cyclic dinucleotide with two purine bases connected by a linker, with Xd substituents and phosphorothioate/phosphoramidate groups]

| Xd = | linker | geometry | P chirality | Compound Number | hSTING EC50 (μM) HAQ | REF |
|---|---|---|---|---|---|---|
| OH | —N(H)(CH₃)—CH₂—CH=CH—CH₂—N(H)(CH₃)— | trans | SR | 38 | 79.9 | * |
|  |  |  | SS or RR | 39 | 29.6 | * |

\* Indicates activity was not measurable in the experimental concentration range.

Human STING EC50 (μM) was measured using the ammonium salt form of each compound in Table 8.

Example 104—STING Variant Specific Reporter Assay

Figure 6:
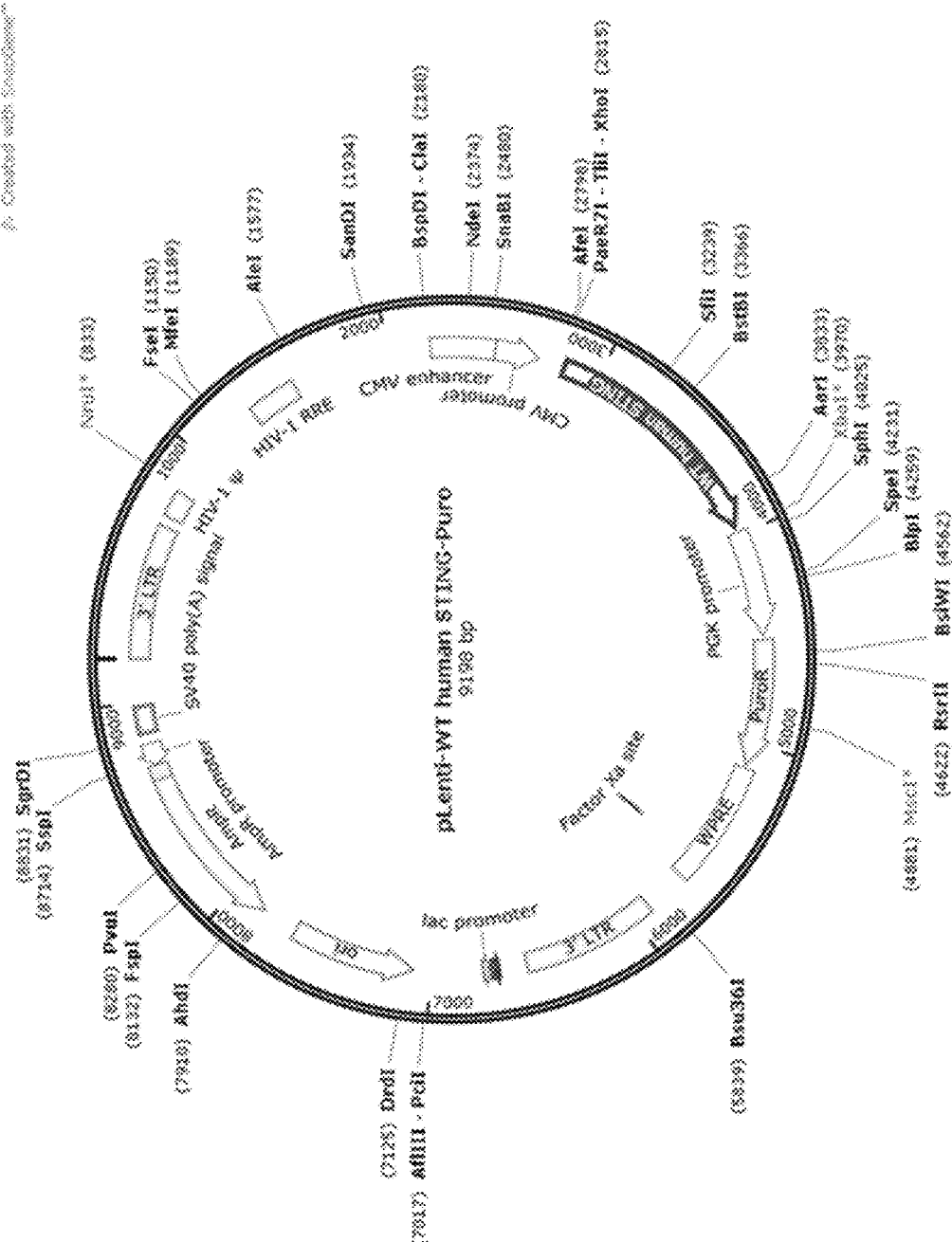
FIG. 6 shows an expression vector map for WT STING (pLenti-WT human STING-Puro).

Human STING has 4 major variants, including WT, HAQ, REF, and AQ variants. REF-STING, also referred to as R232H, for example, occurs in about 14% of the human population. Compared to the wild-type allele, R232H has decreased response to bacterial and metazoan cyclic dinucleotides. Details of these 4 major variants as well as other rare variants are reported by Yi G, et al., "Single nucleotide polymorphisms of human STING can affect innate immune response to cyclic dinucleotides" *PLoS One* 2013; 8:e77846. STING variant specific reporter cell lines were established by using THP1-Dual™ KO-STING cells (InvivoGen, Cat #thpd-kostg) and three STING variant protein expression vectors. The expression vector map for WT STING is shown in FIG. 6. For the other two expression vectors, different STING variant sequences were used in that vector, with the WT STING replaced by the appropriate nucleotide sequence.

STING variant-expressing vectors for WT-STING, REF-STING, and AQ-STING were prepared and stably transfected into THP1-Dual™ KO-STING cells to prepare STING variant-specific reporter assays for WT-STING, REF-STING and AQ-STING, respectively. $EC_{50}$ values were determined as described above in Example 103 for the HAQ STING agonist activity reporter assay. Results are shown below in Table 9. The DNA sequences used for these STING variants are shown in SEQ ID NO: 1 (Nucleotide Sequence of WT Human STING), SEQ ID NO: 2 (Nucleotide Sequence of REF Human STING), and SEQ ID NO: 3 (Nucleotide Sequence of AQ Human Sting).

WT Human STING:

(SEQ ID NO: 1)
atgccccactccagcctgcatccatccatcccgtgtcccaggggtcacgg ggcccagaaggcagccttggttctgctgagtgcctgcctggtgacccttg ggggctaggagagccaccagagcacactctccggtacctggtgctccacc tagcctccctgcagctgggactgctgttaaacggggtctgcagcctggct gaggagctgcgccacatccactccaggtaccggggcagctactggaggac tgtgcgggcctgcctgggctgccccctccgccgtggggccctgttgctgc tgtccatctatttctactactccctcccaaatgcggtcggcccgcccttc acttggatgcttgccctcctgggcctctcgcaggcactgaacatcctcct gggcctcaagggcctggccccagctgagatctctgcagtgtgtgaaaaag ggaatttcaacgtggcccatgggctggcatggtcatattacatcggatat ctgcggctgatcctgccagagctccaggcccggattcgaacttacaatca gcattacaacaacctgctacggggtgcagtgagccagcggctgtatattc tcctcccattggactgtggggtgcctgataacctgagtatggctgacccc aacattcgcttcctggataaactgccccagcagaccggtgaccgggctgg catcaaggatcgggtttacagcaacagcatctatgagcttctggagaacg ggcagcgggcgggcacctgtgtcctggagtacgccaccccttgcagact ttgtttgccatgtcacaatacagtcaagctggctttagccgggaggatag gcttgagcaggccaaactcttctgccggacacttgaggacatcctggcag atgcccctgagtctcagaacaactgccgcctcattgcctaccaggaacct gcagatgacagcagcttctcgctgtcccaggaggttctccggcacctgcg gcaggaggaaaaggaagaggttactgtgggcagcttgaagacctcagcg tgcccagtacctccacgatgtcccaagagcctgagctcctcatcagtgga atggaaaagcccctccctctccgcacggatttctcttga.

REF Human STING:

(SEQ ID NO: 2)
atgccccactccagcctgcatccatccatcccgtgtcccaggggtcacgg ggcccagaaggcagccttggttctgctgagtgcctgcctggtgacccttt gggggctaggagagccaccagagcacactctccggtacctggtgctccac ctagcctccctgcagctgggactgctgttaaacggggtctgcagcctggc tgaggagctgcgccacatccactccaggtaccggggcagctactggagga ctgtgcgggcctgcctgggctgccccctccgccgtggggccctgttgctg ctgtccatctatttctactactccctcccaaatgcggtcggcccgccctt cacttggatgcttgccctcctgggcctctcgcaggcactgaacatcctcc tgggcctcaagggcctggccccagctgagatctctgcagtgtgtgaaaaa gggaatttcaacgtggcccatgggctggcatggtcatattacatcggata tctgcggctgatcctgccagagctccaggcccggattcgaacttacaatc agcattacaacaacctgctacggggtgcagtgagccagcggctgtatatt ctcctcccattggactgtggggtgcctgataacctgagtatggctgaccc caacattcgcttcctggataaactgccccagcagaccggtgaccatgctg gcatcaaggatcgggtttacagcaacagcatctatgagcttctggagaac gggcagcgggcgggcacctgtgtcctggagtacgccaccccttgcagac tttgtttgccatgtcacaatacagtcaagctggctttagccgggaggata ggcttgagcaggccaaactcttctgccggacacttgaggacatcctggca gatgcccctgagtctcagaacaactgccgcctcattgcctaccaggaacc tgcagatgacagcagcttctcgctgtcccaggaggttctccggcacctgc ggcaggaggaaaaggaagaggttactgtgggcagcttgaagacctcagcg gtgcccagtacctccacgatgtcccaagagcctgagctcctcatcagtgg aatggaaaagcccctccctctccgcacggatttctcttga AQ Human STING:

(SEQ ID NO: 3)
atgccccactccagcctgcatccatccatcccgtgtcccaggggtcacgg ggcccagaaggcagccttggttctgctgagtgcctgcctggtgaccdttg ggggctaggagagccaccagagcacactctccggtacctggtgctccacc tagcctccctgcagctgggactgctgttaaacggggtctgcagcctggct gaggagctgcgccacatccactccaggtaccggggcagctactggaggac tgtgcgggcctgcctgggctgccccctccgccgtggggccctgttgctgc tgtccatctatttctactactccctcccaaatgcggtcggcccgcccttc acttggatgcttgccctcctgggcctctcgcaggcactgaacatcctcct gggcctcaagggcctggccccagctgagatctctgcagtgtgtgaaaaag ggaatttcaacgtggcccatgggctggcatggtcatattacatcggatat ctgcggctgatcctgccagagctccaggcccggattcgaacttacaatca gcattacaacaacctgctacggggtgcagtgagccagcggctgtatattc tcctcccattggactgtggggtgcctgataacctgagtatggctgacccc aacattcgcttcctggataaactgccccagcagaccgctgaccgagctgg catcaaggatcgggtttacagcaacagcatctatgagcttctggagaacg ggcagcgggcgggcacctgtgtcctggagtacgccaccccttgcagact ttgtttgccatgtcacaatacagtcaagctggctttagccgggaggatag gcttgagcaggccaaactcttctgccagacacttgaggacatcctggcag atgcccctgagtctcagaacaactgccgcctcattgcctaccaggaacct gcagatgacagcagcttctcgctgtcccaggaggttctccggcacctgcg gcaggaggaaaaggaagaggttactgtgggcagcttgaagacctcagcg tgcccagtacctccacgatgtcccaagagcctgagctcctcatcagtgga atggaaaagcccctccctctccgcacggatttctcttga

Example 105—Mouse STING Agonist Activity Reporter Assay

RAW-Lucia™ ISG Cells (InvivoGen, Cat #rawl-isg) were used for a mouse STING agonist reporter assay. $EC_{50}$ values were determined as described above in Example 103 in the HAQ STING agonist activity reporter assay. Results are shown below in Table 9.

Example 106—Differential Scanning Fluorimetry (DSF) Assay

A DSF assay was employed to measure the physical interaction between compound and recombinant STING protein. Truncated recombinant STING protein (a.a.155-341) (SEQ ID NO: 4) was expressed in *E. coli* and isolated for the assay, as described below. Assay matrix was prepared in 384-well plates to a final volume of 10 µL per well consisting of 1 µM recombinant STING protein (a.a. 155-341) (SEQ ID NO: 4), 100 mM PBS pH 7.4, supplemented with 100 mM KCl, 5×SYPRO orange dye and 50 µM compound (final DMSO conc. 0-1%). Assays were performed on a QuantStudio 12K Flex Real-Time PCR System using a temperature gradient from 25° C. to 95° C. at a rate of 0.05° C./min, and excitation and emission filters at 470 and 586 nm, respectively. According to the fluorescence derivative curves assigned by the Applied Biosystems® Protein Thermal Shift software (algorithm version 1.3.), the thermal melt (Tm) of the unbound and ligand bound recombinant STING protein and the difference in thermal melt (dTm D) was calculated.

In general, compounds with ΔTm values larger than 0 are considered to have a physical interaction with the tested protein, and the value of ΔTm is positively associated with compound binding affinity. Here, Compound 1a showed the ΔTm of 17.6 (Table 9), indicating physical interaction with STING protein.

TABLE 9

Compound 1a in vitro characterization

| Compound | Humans STING $EC_{50}$ (µM) | | | | Mouse STING $EC_{50}$ (µM) | DSF WT STING ΔTm (° C.) |
|---|---|---|---|---|---|---|
| | WT | HAQ | REF | AQ | | |
| 1a | 0.9 | 4.1 | 4.8 | 1.2 | 3.4 | 17.6 |

Example 107—Ex Vivo Human PBMC Stimulation Assay

Human blood from 5 healthy donors was collected using 10.0 mL BD Vacutainer Sodium heparin tubes (cat #367874). Peripheral blood mononuclear cell (PBMC) isolation was done using SIGMA ACCUSPIN 50 ml Tubes (cat #A2055) and sigma ACCUSPIN System-HISTOPAQUE-1077 (cat #A7054) using protocol provided by manufacturer. PBMC layer was harvested and washed with 1× Phosphate Buffered Saline (PBS) as suggested by Sigma. PBMC were counted and finally suspended @ 1×10e6/ml in RPMI (corning cat #10-041-CV) supplemented with 10% fetal bovine serum (FBS) (Gibco cat #20140.79). 1 ml of cell (1×10e6) were transferred into Falcon 5 mL Round Bottom Polypropylene Test Tube (cat #352063) and stimulated with different concentrations (0, 0.1, 1, 10 uM) for 24 hours in 5% CO2 incubator at 37° C.

After 24 hours of incubation the tubes were centrifuged at 1400 rpm for 5 minutes and supernatants were harvested. Supernatant were stored in −80° C. for subsequent IFNβ measurement. IFNβ measurement was done using Human IFN-β Base Kit (Meso Scale Diagnostics cat #K151ADA) and protocol provided by manufacturer was used. IFN-beta estimation was done by reading assay plate at MESO SECTOR Imager 2400 and using MSD Discovery Workbench 4.0 program. After 24 hours IFNβ protein was analyzed. The results showed that compound 1a can induce primary human PBMC IFNβ protein production in a dose-dependent manner.

Results shown in Table 10 reflect an average of measurements conducted using five different donors.

TABLE 10

Ex vivo human PBMC stimulation assay

| | PBS (Control) | Compound 1a | | |
|---|---|---|---|---|
| | | 0.1 µM | 1 µM | 10 µM |
| IFNβ (pg/mL) | 0 | 21.3 ± 17.8 | 227.5 ± 62.4 | 540.2 ± 215.0 |

For IFNβ mRNA quantification, total RNA was isolated using the RNeasy Mini Kit (Qiagen, Germany) according to the manufacturer's protocol. IFNβ mRNA was quantified by qPCR assay. In brief, total RNA (400 ng to 1000 ng) was converted to cDNA in a 60-µl reaction volume using SuperScript VILO MasterMix (Life Technologies, USA). Obtained cDNAs (10 ng) were subsequently amplified using Applied Biosystems TaqMan expression assays using RNA-specific primers for IFNB1 (Hs01077958_s1), and GAPDH (Hs99999905_m1). A qPCR analysis was performed with TaqMan Fast Advanced Master Mix (Life Technologies, USA) on the Applied Biosystems Quantstudio 12K Flex Real-Time PCR System, with an initial 2-min step at 50° C. followed by 95° C. for 2 s and 40 cycles of 95° C. for 1 s and 60° C. for 20 s. Relative gene expression was calculated after normalization against the reference gene GAPDH using the 2−ΔΔCT method. Calculations were done using the Applied Biosystems Quantstudio 12K Flex software v1.2.2. IFNβ mRNA fold changes vs. vehicle treated samples are summarized in Table 11. The results showed that compound 1a can induce IFNβ mRNA in primary PBMC in a dose- and time-dependent manner. Table 11 shows an average calculated from five different donors.

TABLE 11

Ex vivo human PBMC 3-hr & 24-hr stimulation assay (mRNA)

| IFNβ mRNA(fold changes vs. vehicle treated samples) | Compound 1a | | |
|---|---|---|---|
| | 0.1 µM | 1 µM | 10 µM |
| 3-hr treatment | 51.0 ± 21.7 | 219.8 ± 69.8 | 1973.3 ± 1023.0 |
| 24-hr treatment | 28.1 ± 28.9 | 10652.3 ± 4992.4 | 24157.3 ± 9224.2 |

Example 108—Anti-Cancer Effect of Compound 1a on the CT26 Dual Tumor Model

Compound 1a was tested for its anti-cancer activity in CT26 dual tumor model, which is a mouse colon cancer model. Female of 5-6 week old Balb/cJ mice (Jackson Labs, Bar Harbor, Me.) were implanted subcutaneously with CT26 tumor cells on both sides of each animals, $10^5$ cells for each side. For study A, treatment was started 5 days (1.25 mg/kg, 2.5 mg/kg and 5 mg/kg) after the tumor implantation, when the average tumors reached approximately 100 mm$^3$. For study B, treatment was started 8 days (0.6 mg/kg, and 10 mg/kg) after the tumor implantation, when the average tumors reached approximately 120 mm$^3$. The treatment scheme is described in Table 12 and Table 13.

TABLE 12

Dosing scheme for study A

| Group | No. of Animals | Treatment | Route and Schedule |
| --- | --- | --- | --- |
| A | 6 | Vehicle (1 × PBS) | I.T.*; single dose |
| B | 6 | 5 mg/kg compound 1a | I.T.; single dose |
| C | 6 | 2.5 mg/kg compound 1a | I.T.; single dose |
| D | 6 | 1.25 mg/kg compound 1a | I.T.; single dose |

*I.T. is intratumoral.

TABLE 13

Dosing scheme for study B

| Group | No. of Animals | Treatment | Route and Schedule |
| --- | --- | --- | --- |
| A | 5 | Vehicle (1 × PBS) | I.T.*; single dose |
| B | 5 | 10 mg/kg compound 1a | I.T.; single dose |
| C | 5 | 0.6 mg/kg compound 1a | I.T.; single dose |

*I.T. is intratumoral.

All the mice in the study have two subcutaneous CT26 tumors. The "treated tumor" indicates the tumor with compound direct administration, while "untreated tumor" indicates the tumor without direct compound administration. Tumor volume was followed throughout the experiment. Tumor volume is measured two times weekly after the start of treatment. Tumor burden is calculated from caliper measurements by the formula for the volume of a prolate ellipsoid (L×W$^2$)/2 where L and W are the respective orthogonal length and width measurements (mm).

Figure 7:
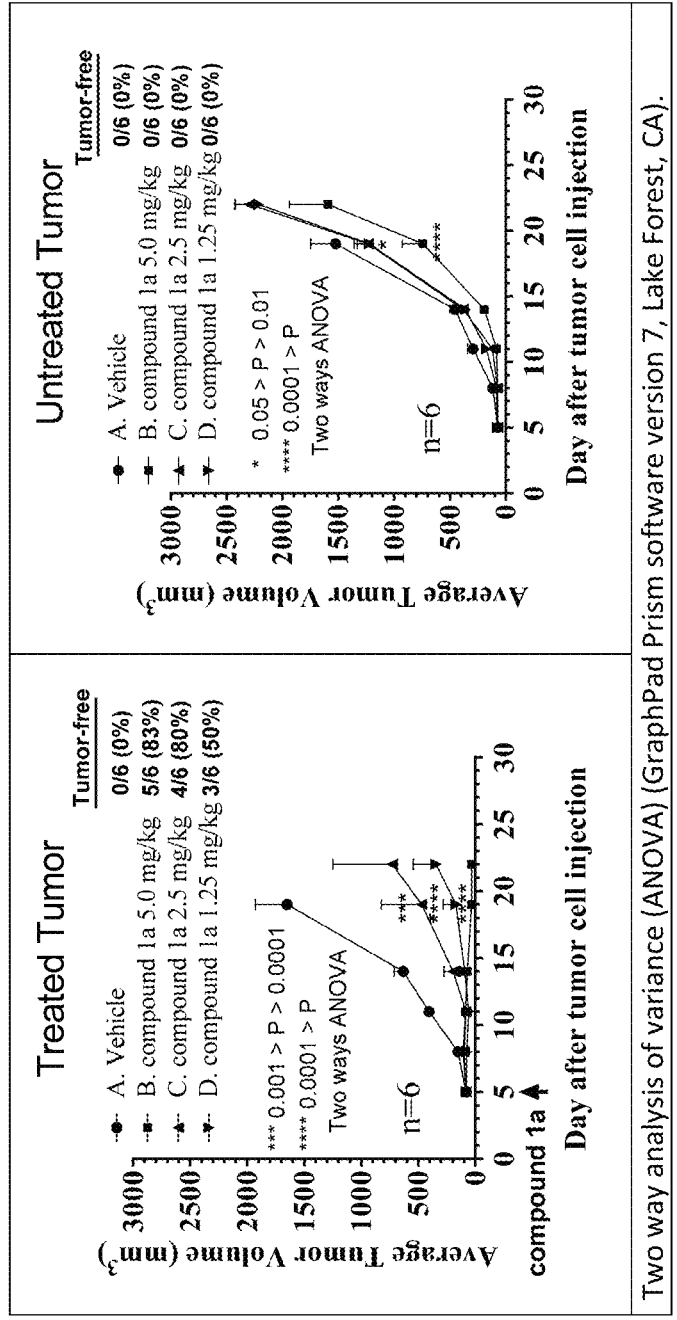
FIG. 7 and FIG. 8 accompany Example 108 and show curative activity of Compound 1a in a CT26 dual tumor model.
Figure 8:
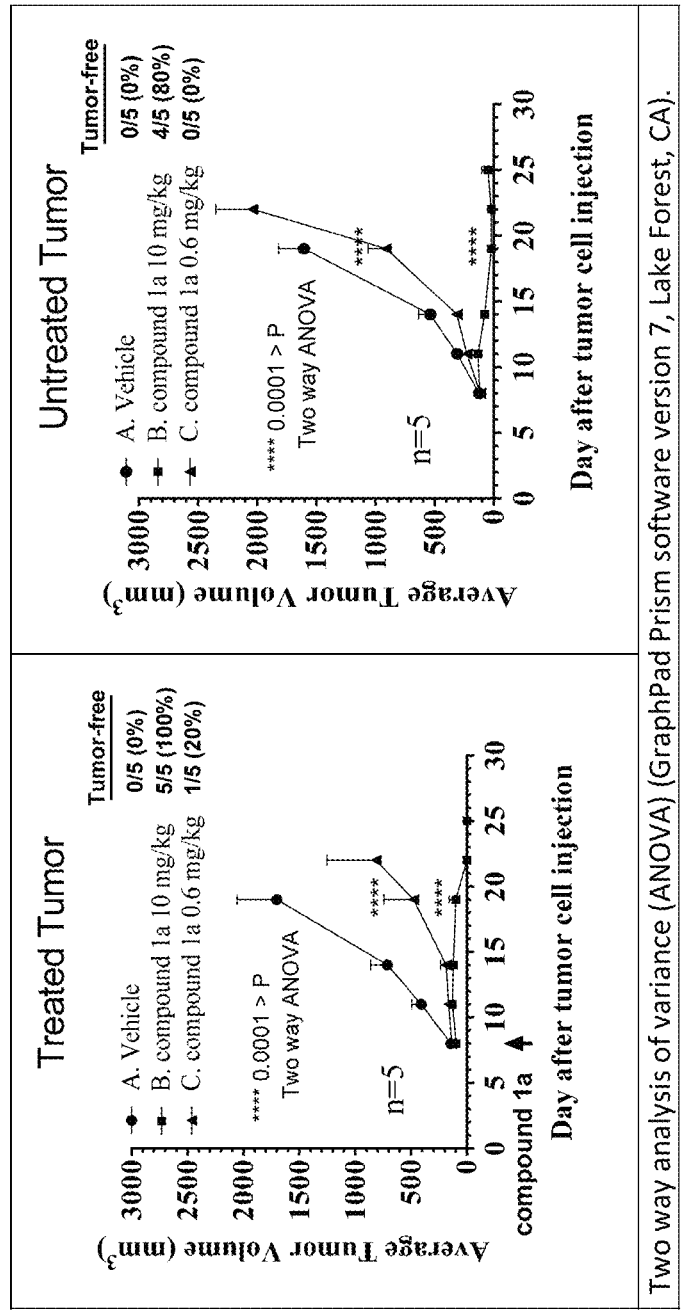

Compound 1a showed potent and curative activity in CT26 dual tumor model (FIG. 7 and FIG. 8). For treated tumors, a cure rate of 20% was detected even at the lowest dose tested in the study (FIG. 8, 0.6 mg/kg dose). At the same time, the highest dose (10 mg/kg) cured 100% of animals of that tumor at the end of study. For the untreated tumors, a dose-dependent anti-tumor effect was also evident. The top dose group (10 mg/kg) showed 80% curative effects; all the lower doses also showed tumor growth inhibition activity. Hence, a therapeutic window of 0.6 mg/kg to 10 mg/kg for compound 1a was observed, with anti-tumor activity seen not only locally but also systemically, based on effects at the non-injected distal tumor site. In conclusion, these results indicate that local administration of compound 1a can induce both local and systemic (abscopal) anti-cancer activity.

Example 109—Anti-Cancer Effect of Compound 1a on the CT26 Liver Metastatic Model Compound 1a was tested for its anti-cancer activity in a CT26 liver metastatic model. Anesthetized female 5-6 week-old BALB/cJ mice (Jackson Labs, Bar Harbor, Me.) were implanted intra-splenically with luciferase-expressing CT26 tumor cells (5×10$^5$ cells per mouse). A subsequent ten minute waiting period allowed tumor cells to circulate into the animals' livers. Spleens were then removed and animals were sutured and allowed to recover. Three days later, CT26 tumor cells (10$^5$ cells per mouse) were again implanted, this time subcutaneously (sc) under the right forelimb area, to enable development of a tumor mass for compound administration. Nine days after intra-splenic injection, compound (10 mg/kg) was administered intratumorally, a single time, into the sc tumor.

Figure 9:
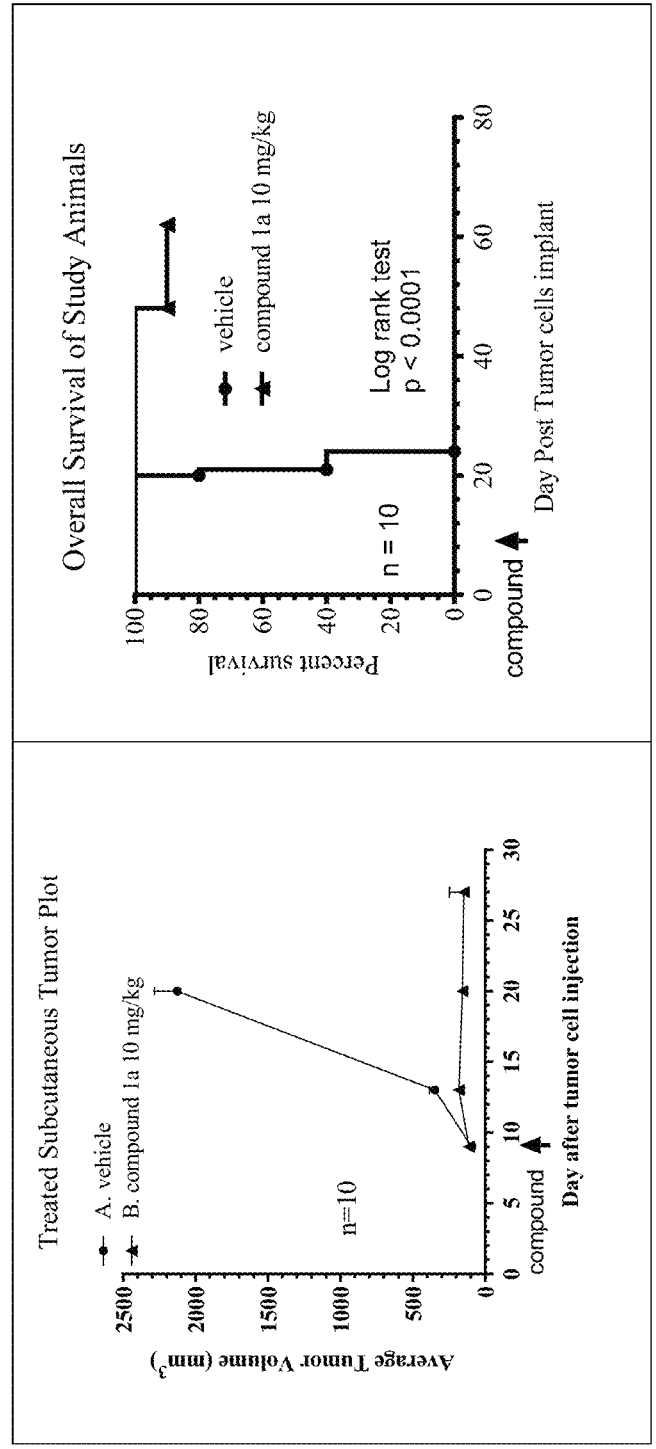
FIG. 9 accompanies Example 109 and shows a tumor volume plot for treated tumors and survival curve.

The local anti-cancer effect of compound was measured through its effect on the sc tumor, while the compound's abscopal effect was assessed by the overall survival of treated mice compared with vehicle-treated control mice, based on the detrimental effect of the growing tumor mass in each mouse liver. Compound 1a showed both potent activity towards the local sc tumors and also curative systemic activity in 9 of 10 treated animals (FIG. 9). These results indicate that local administration of compound 1a can induce both local and systemic (abscopal) anti-cancer activity including deep lesion such as in the liver.

Figure 10:
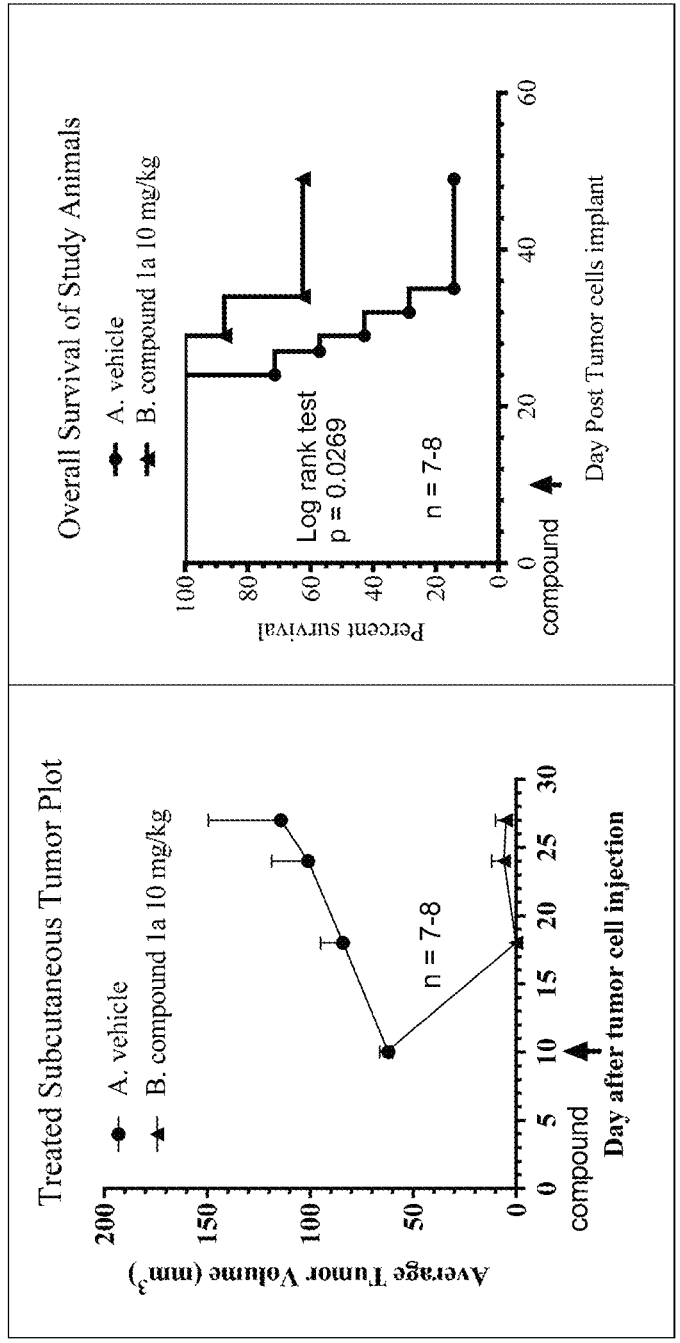
FIG. 10 accompanies Example 110 and shows a tumor volume plot for treated tumors and survival curve.

Example 110—Anti-Cancer Effect of Compound 1a on the GL261 Brain Orthotopic Model Compound 1a was tested for its anti-cancer activity in a GL261 brain orthotopic model. GL261 is a murine glioma cell line. Luciferase expressing GL261 mouse glioma cells (2×10$^4$ cells/mouse) were intra-cranially implanted into female 5-6 week-old B6 albino mice (Jackson Labs, Bar Harbor, Me.). Three to 4 days later, GL261 cells were implanted subcutaneously (10$^6$ cells/mouse) under the right forelimb area to allow development of a tumor mass for compound administration. Ten days after intra-cranial tumor cell implantation, compound (10 mg/kg) was administered intratumorally, a single time, into the sc tumor. The local anti-cancer effect of compound was measured through its effect on the sc tumor, while the compound's abscopal effect was assessed by the overall survival of treated mice compared with vehicle-treated control mice, based on the detrimental effect of the growing tumor mass in each mouse brain. Compound 1a showed both potent activity at local sc tumors and showed curative systemic activity in 5 of 8 treated animals (FIG. 10). These results indicate that local administration of compound 1a can induce both local and systemic (abscopal) anti-cancer activity including deep lesion such as in the brain.

Example 111—X-Ray Structure Confirming Complex with WT STING

To further understand the target-binding mechanism of our new compounds, the X-ray crystal structure of WT STING in complex with the compounds was determined.

A. Expression and Purification of WT STING C-Terminal Domain (Residue 155-341)

DNA sequence encoding human WT STING protein from amino acid 155 to 341 (SEQ ID NO: 4) was cloned into the pET21b vector, following a His-TEV-Sumo tag at its N-terminus (SEQ ID NO: 5). The sequence of the pET21b has been deposited in addgene and is available here: addgene-.org/vector-database/2550/; that sequence is incorporated by reference herein.

*E. coli* BL21 (DE3) codon plus cells were transformed with this plasmid, and the expression of recombinant protein was induced with 0.1 mM Isopropyl 3-D-1-thiogalactopyranoside (IPTG). Protein was purified from the soluble fraction of cell lysate by Ni-NTA affinity chromatography.

The His-TEV-Sumo tag was removed by sumo protease, and was separated from tag-free WT STING 155-341, using a second Ni-NTA affinity column. The protein was further purified by anion-exchange and size-exclusion chromatography, and was stored in buffer containing 20 mM Tris.HCl pH 7.5, and 150 mM NaCl at 35 mg/ml concentration.

B. Crystallization and Structure Determination of WT STING C-Terminal Domain in Complex with Compound 1

To co-crystallize WT STING 155-341, with Compound 1, the WT STING protein was diluted to 10 mg/ml using the storage buffer (20 mM Tris.HCl pH 7.5, and 150 mM NaCl) and mixed with Compound 1 (100 mM stock in DMSO) in molar ratio 1:5. The mixture was incubated for 4 hours at 4° C., and centrifuged at 13,000 rpm for 20 min before crystallization. Crystallization screen trays were set up using the hanging-drop vapor-diffusion method at 18° C. Crystals were grown by mixing 1 μL of WT STING/Compound 1 solution with an equal volume of well solution, containing 100 mM HEPES pH 7.5, 200 mM CaCl2, and 15% (wt/vol) PEG 8000. 20% (wt/vol) PEG 400 was used as cryoprotectant reagent when crystals were flash-frozen in liquid nitrogen. Diffraction datasets were collected with a Pilatus detector at SSRF BL19U1 beamline, and processed with HKL3000 and program SCALEPACK2MTZ in CCP4 software suite.

The structure of WT STING 155-341 bound to Compound 1 was determined by molecular replacement using program PHASER (Maximum Likelihood Molecular Replacement), with PDB ID 4F9E as the initial search model. The presence of Compound 1 between the dimer interface of WT STING was confirmed in a Fo-Fc difference map calculated with model phases. The model was built and completed manually with Coot program and refined with Refmac5 program in CCP4 software suite. The final refined structure was reported at a resolution of 2.38 Å in space group P212121 with unit cell measured at a=33.820, b=78.110, c=132.212, α=90.00, β=90.00, γ=90.00. Two copies of WT STING 155-341 were identified in each asymmetric unit binding to one molecule of Compound 1 at the dimer interface.

C. Interaction of Compound 1 with WT STING Observed in X-Ray Crystal Structure

Figure 11:
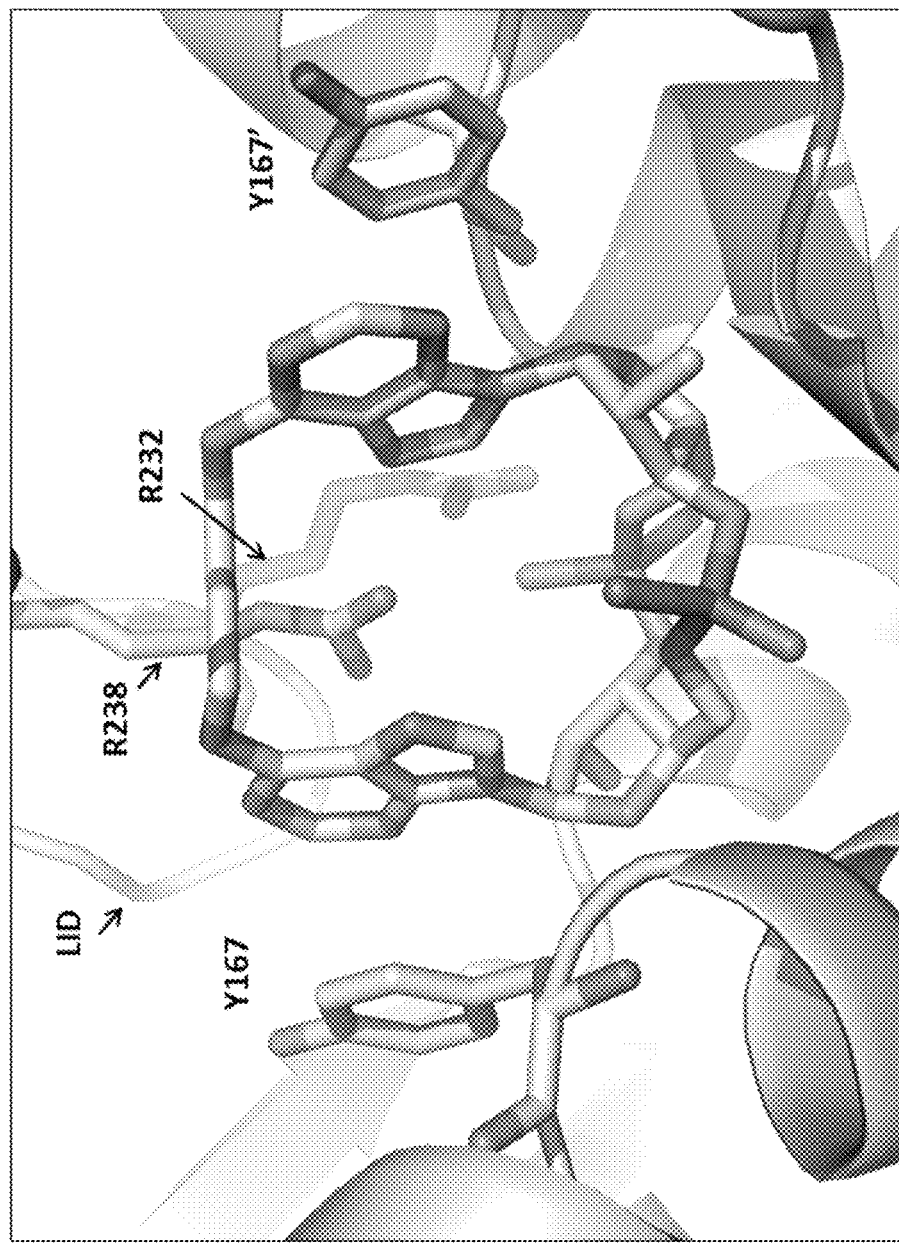
FIG. 11 shows a picture of the X-ray crystal structure of human WT STING in complex with Compound 1.

FIG. 11 shows a picture of the X-ray crystal structure of human WT STING in complex with Compound 1. We examined the X-ray crystal structure of human WT STING in complex with Compound 1, which was co-crystallized from a sample of Compound 1a. The compound binds at an interface pocket formed by a dimer of WT STING protein. The two faces of adenine base of the compound form π-π stacking interaction with Tyr240 and the guanidine group of Arg238, respectively. The trans olefin linker forms van der Waals interaction with aliphatic portion of the side chain of Arg 238. The fluorine substituent at the C2' position of ribose group of compound nests in a hydrophobic hole defined by Thr263, Pro264 and Tyr163. The negatively charged thiophosphate group of the compound forms salt bridge with Arg238 and H-bond interactions with Ser162 and Thr267, respectively. In addition, the thiophosphate group also forms electrostatic interaction with guanidine group of Arg 232. The LID loop region of WT STING, consisting of residue 226 to 243, wraps around the two base groups and the trans olefin linker.

Example 112—Determination of X-Ray Crystal Structure of REF STING in Complex with Compound 1

A. Expression and purification of REF STING C-terminal Domain (residue 155-341, SEQ ID NO: 6)

DNA sequence encoding human REF STING protein from amino acid 155 to 341 (SEQ ID NO: 6) was cloned into the pET21b vector, following a His-TEV-Sumo tag at its N-terminus (SEQ ID NO: 7). The sequence of the pET21b has been deposited in addgene and is available here: addgene.org/vector-database/2550/; that sequence is incorporated by reference herein.

*E. coli* BL21 (DE3) codon plus cells were transformed with this plasmid, and the expression of recombinant protein was induced with 0.1 mM Isopropyl β-D-1-thiogalactopyranoside (IPTG). Protein was purified from the soluble fraction of cell lysate by Ni-NTA affinity chromatography. The His-TEV-Sumo tag was removed by sumo protease, and was separated from tag-free REF STING_155-341 using a second Ni-NTA affinity column. The protein was further purified by anion-exchange and size-exclusion chromatography, and was stored in buffer containing 20 mM Tris.HCl pH 7.5, and 150 mM NaCl at 24 mg/ml concentration.

B. Crystallization and Structure Determination of REF STING C-Terminal Domain in Complex with Compound 1

To co-crystallize REF STING_155-341 with Compound 1, REF STING protein was diluted to 10 mg/ml using the storage buffer (20 mM Tris.HCl pH 7.5, and 150 mM NaCl) and mixed with Compound 1 (100 mM stock in DMSO) in molar ratio 1:5. The mixture was incubated for 4 hours at 4° C., and centrifuged at 13,000 rpm for 20 min before crystallization. Crystallization screen trays were set up using the hanging-drop vapor-diffusion method at 18° C. Crystals were grown by mixing 1 μL of REF STING/Compound 1 solution with an equal volume of well solution, containing 100 mM HEPES pH 7.5, 200 mM CaCl2, and 15% (wt/vol) PEG 8000. 20% (wt/vol) PEG 400 was used as cryoprotectant reagent when crystals were flash-frozen in liquid nitrogen. Diffraction datasets were collected with a Pilatus detector at SSRF BL18U1 beamline, and processed with HKL3000 and program SCALEPACK2MTZ in CCP4 software suite. This structure is shown in FIG. 12.

The structure of REF STING_155-341, bound to Compound 1 was determined by molecular replacement using program PHASER (Maximum Likelihood Molecular Replacement), using previously determined WT STING 155-341 structure (as described above) as the initial search model. The presence of Compound 1 between the dimer interface of REF STING, was confirmed in a Fo-Fc difference map calculated with model phases. The model was built and completed manually with Coot program and refined with Refmac5 program in CCP4 software suite. The final refined structure was reported at a resolution of 2.76 Å in space group P212121 with unit cell measured at a=33.733, b=77.831, c=131.689, α=90.00, β=90.00, γ=90.00. Two copies of REF STING 155-341 were identified in each asymmetric unit binding to one molecule of Compound 1 at the dimer interface.

C. Interaction of Compound 1 with REF STING Observed in X-Ray Crystal Structure

Figure 12:
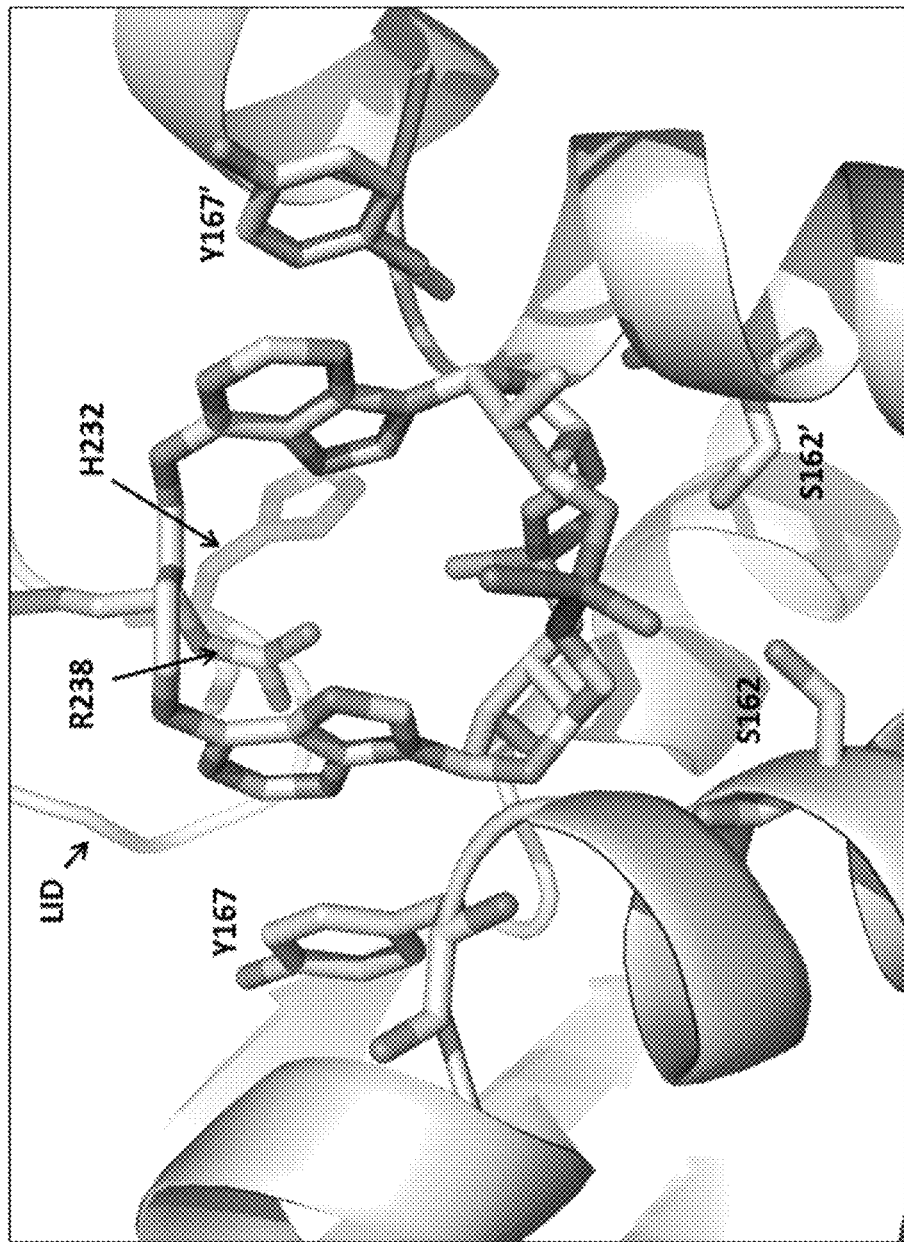
FIG. 12 shows human REF STING C-terminal Domain in complex with Compound 1.

FIG. 12 shows the X-ray crystal structure of human REF STING in complex with Compound 1, which was co-crystallized from a sample of Compound 1a. The compound binds at an interface pocket formed by a dimer of STING protein. The two faces of adenine base of the compound form π-π stacking interaction with Tyr240 and the guanidine group of Arg238, respectively. The trans olefin linker forms van der Waals interaction with the aliphatic portion of the side chain of Arg238 while the guanidine portion of the side chain of Arg238 forms π-π stacking interaction with the imidazole group of the side chain of His232 from outside. The olefin linker is in contact with the interacting pair of the side chains of Arg238 and His232. The fluorine substituent at the C2' position of ribose group of compound nests in a hydrophobic hole defined by Thr263, Pro264 and Tyr163. The negatively charged thiophosphate group of the compound forms salt bridge with Arg238 and H-bond interactions with Ser162 and Thr267, respectively. The LID loop region of REF STING, consisting of residue 226 to 243, wraps around the two base groups and the trans olefin linker.

Example 113—Comparisons

EC50 values were calculated for human STING assays of WT STING, HAQ STING, AQ STING, and REF STING, in head-to-head comparisons using Compound 1a of the present disclosure, a natural STING ligand (2'3' cGAMP), and the purported STING agonist ML RR-S2 CDA, as reported in Corrales, et al., "Direct Activation of STING in the Tumor Microenvironment Leads to Potent and Systemic Tumor Regression and Immunity," *Cell Reports* (2015) 11:1018-1030, which is incorporated by reference herein. Assays were conducted as described in examples set forth above. Note that reported assay values in Table 14 were limited to the assays conducted in the head-to-head comparisons and may not reflect averaged values determined over a greater number of trials as reported in Table 5 or elsewhere. Note further that "2'3' cGAMP" is the same as "ML cGAMP" as reported in the Cell Reports publication.

TABLE 14

| Compound | Kd (WT) (µM) | Human $EC_{50}$ (mM) (20-hr assay) | | | |
|---|---|---|---|---|---|
| | | WT | HAQ | AQ | REF |
| 2'3' cGAMP | 0.07 | 61.7 | 57.9 | 56.5 | 33-100 |
| ML RR-S2 CDA | 0.4 | 5.9 | 8.4 | 5.5 | >100 |
| Compound 1a | 0.04 | 0.6 | 1.9 | 1.0 | 3.9 |

Table 14 also reports dissociation binding constants (Kd) for the binding of human WT STING to each of the three tested compounds, as measured by isothermal titration calorimetry (ITC). ITC is a microcalorimetric titration technique that measures thermodynamic properties associated with intermolecular interactions. Based on these tests, Compound 1a appears to form the strongest bond with WT STING of the tested compounds.

Materials

Recombinant human wild type STING (aa, 139-379, H232R) protein was generated by expressing a construct in *E. coli* encoding a cytosolic domain of human WT STING comprising amino acids 139-379.

Reagents

Sources of reagents used in this study are shown below:

| Reagent | Source | Catalog No. |
|---|---|---|
| 1X PBS without Calcium or Magnesium | Corning | 21-040-CV |
| MilliQ-Deionized Water | MilliQ | Z000Q0V0T0 |
| Liquinox | Alconox | 1201 |
| NaOH | EM | SXO593-1 |
| Methanol | EMD Millipore | MX0475-1 |
| Compounds: | | |
| Compound 1a | | |
| 2'3' cGAMP | | |
| ML RR-S2 CDA | | |

Protein Buffer Preparation

STING protein was stored at −60° C. in 90 µL and 100 µL aliquots each at a concentration of 3.0 mg/mL and 20 mg/mL, respectively in PBS, pH 7.5 containing 5% glycerol. On the day of analysis, aliquots of the protein were thawed, diluted to 400 uL and buffer-exchanged into PBS using an Amicon Ultra centrifugal filter unit (10 k MW cutoff, 0.5 mL) with at least four 10 min 14000×g centrifugations with an Eppendorf microcentrifuge and then finally diluted to 20 µM to 30 µM (experiment-dependent) with 1×PBS. Protein concentration was determined using a Nanodrop 2000 spectrophotometer and a protein extinction coefficient of 22140 ($M^{-1}cm^{-1}$).

Sample Preparation

Two hundred L of 1 mM stock solutions of Compound 1a, 2'3' cGAMP, and ML RR-S2CDA were supplied by 1.5 mL microcentrifuge tubes. Prior to each experiment, the samples were diluted to concentrations of 200 uM to 500 uM (experiment-dependent).

Methods

Assays were performed on an Affinity ITC unit (TA Instruments no. 609003.901) equipped with the ITC cleaning accessory (TA Instruments no 601800.901). The STING protein solution, approximately 400 µL containing 20 µM to 30 µM STING protein, was pipetted into the 185 µL calorimeter cell allowing some acceptable overload. The reference cell contained an equivalent amount of Milli-Q water. Incubation was carried out at 25° C. with 20×2.5 µL injections of 100 µM to 300 µM compounds. The control software was ITC Run Ver. 3.3.0.0 (TA Instruments) was used to obtain the thermograms consisting of multiple peaks of raw heat (µcal/sec) representing the heat rate at each injection. The analysis software Nano Analyze Ver. 3.70 (TA Instruments) was used to baseline-correct, correct for blank or sample heat of dilution (at saturation) and to integrate the heat rate peaks producing graphed "Q" values. The resulting isotherms were fit with an independent model to derive the thermodynamic parameters.

The Kds and n values (molar ratios at the curve inflection points) were derived and reported. Optimal conditions for the concentrations of protein and ligand were derived from preliminary experiments.

Results

The heat rate thermograms and their resulting isotherms for the binding of the tested compounds to recombinant human wild type STING (aa, 139-379, H232R) were determined. The binding of each compound to STING was endothermic as indicated by the negative heat rates with exothermic (positive direction) heats of dilution (observed after the compound has achieved saturation of the protein). 2', 3' cGAMP has been shown to produce a similar endothermic response to various STING variants. Compound 1a provided the lowest Kd of 0.04 µM, followed by 2'3' cGAMP with a Kd of 0.07 µM and then ML RR-S2 CDA with a Kd of 0.40 µM. All compounds provided n values close to 0.5, suggesting that the STING protein was present as a dimer and bound 1 mol of compound per 2 mol of STING.

Example 114—Identification of Potential Metabolites

Compound 1a was incubated in hepatocytes of CD-1 mouse, Sprague Dawley rat, Beagle dog, Cynomolgus monkey, and human, to evaluate the formation of major metabolites.

Materials

Cryopreserved pooled hepatocytes were purchased from ThermoFisher Scientific (Waltham, Mass.), Xenotech, LLC (Kansas City, Kans.) and In Vitro ADMET Laboratories (Columbia, Md.), and the appropriate media were purchased from In Vitro ADMET Laboratories (Columbia, Md.) and Life Technologies (Carlsbad, Calif.). AOPI staining solution and phosphate buffer were obtained from Corning Life Sciences (Tewksbury, Mass.) and Nexcelom Bioscience (Lawrence, Mass.), respectively. All chemicals, reagents, and solvents used in analysis were of either analytical or HPLC grade.

Experimental Designs and Procedures

Hepatocyte Incubations

Compound 1a was weighed and dissolved in HPLC-water containing 0.12% formic acid PBS to make 1020 mmol/L. The solution was then diluted 2.5-fold individually to 4 mmol/L and then further diluted 21000-fold with the Williams' E medium containing 0.1% human serum albumin and 2 mmol/L L-glutamine to make the working stock solution with concentration of 20 µmol/L.

Prior to incubations, the cryopreserved hepatocytes were thawed in a water bath at 37° C. One tube of cryopreserved hepatocytes was added to each 50-mL conical tube of cryopreserved hepatocyte recovery medium (UCRM) obtained from In Vitro ADMET Laboratories (Columbia, Md.). The cells were spun in a Beckman centrifuge (Brea, Calif.) with a GH 3.8 rotor at 740 rpm for 10 minutes at room temperature 4° C. The supernatant was removed and the cells were re-suspended in plating media for counting.

After the cells were re-suspended in plating media, 20 µL of the re-suspension was transferred and mixed with 20 µL of AOPI staining solution. The solution was gently mixed and cells were counted using a Cellometer (Nexcelom, Lawrence, Mass.). After counting, the cells were then re-suspended at 1 or 2 million viable cells/mL in Williams' E media containing 2 mmol/L L-glutamine (pH 7.4).

The hepatocyte suspension (50 µL/well) was added into a 48-well plate. Fifty microliters of working stock solution containing Compound 1a (20 µmol/L) were added to start the reaction. The plate was placed into a tissue culture incubator (5% CO2/95% air humidified atmosphere and 37° C.), and the reactions were terminated with 200 µL of stop solution consisting of 100% methanol/acetonitrile (1/1, v/v) with 2010 ng/mL furosemide and 0.2 µmol/L (R)-propranolol at 5, 30, 60, 120, 180 and 240 minutes. The mixture was centrifuged and filtered, and the supernatant was collected for analysis. The final concentrations of cryopreserved hepatocytes were 1×106 cells/mL. The final incubation concentration of Compound 1a was 10 µmol/L.

LC-MS/MS Conditions for Metabolite Identification

The LC-MS/MS system was composed of a Shimadzu HPLC and an AB-SCIEX TripleTOF 5600 hybrid quadrupole and TOF mass spectrometer (Framingham, Mass.). The Shimadzu HPLC (Kyoto, Japan), consisted of a communications bus module (CBM-20A), an auto-sampler (SIL-30AC) with an attached rack changer (Rack Changer II) two pumps (LC-30AD) and a column oven (CTO-30A). The mass spectrometer was calibrated using the AB-SCIEX APCI both Negative and Positive Calibration Solutions (Framingham, Mass.). The samples obtained from incubations with hepatocytes were analyzed under both negative and positive scan modes. The basic analytical method and instrumental conditions are summarized below. Modification of the spectrometer settings was dependent on the necessity of the analyte.

LC-MS/MS Conditions:

| Chromatography Settings: | Shimadzu LC30AD |
|---|---|
| Column Type | Agilent Eclipse XDB-C8, 5µ, 2.1 × 150 mm, part# 993700-906, serial# USSN002817 |
| Mobile Phases | A: water/methanol = 95/5 (v/v) with 5 mM ammonium acetate<br>B: methanol/water = 95/5 (v/v) with 5 mM ammonium acetate |
| Gradients | 0-1 min at 1% B; 1-5 min linear to 10% B; 5-13 min linear to 95% B; 13-19.9 min at 95% B; 19.9-20 min linear to 1% B; 20-24 min at 1% B |
| Flow Rate | 0.4 mL/min |
| Analysis Time | 24 min |
| Sample Tray Temperature | 4° C. |
| Injection Volume | 15 µL |
| Mass Spectrometer Settings: | AB Sciex Hybrid Quadrupole-TOF LC-MS/MS Triple TOF 5600 |
| Ion Source | DuoSpray Ion Source |
| Polarity | Negative or Positive |
| Ion Spray Voltage (ISVF) | 4500 V or 5500 V |
| Temperature (TEM) | 550° C. |
| Curtain Gas (CUR) | 30 |
| GS1 | 50 |
| GS2 | 50 |
| TOF-MS Settings: | CE −5.000 or 5.000<br>DP −100.000 or 100.000<br>scan range: 120.0-1000.0 |
| TOF MS^2 Settings: | CE −60.000 or 60.000<br>CES 5.000<br>DP −100.000 or 100.000<br>Scan range: 100.0-1000.0 |

Data Analysis of Activity Data

Mass spectrometry data were acquired using AB-Sciex Analyst TF (Version 1.5.1; Framingham, Mass.). Chromatograms and spectra were obtained using AB-Sciex PeakView (Version 2.2.0.1; Framingham, Mass.). The comparison of relative peak areas for extracted ion chromatograms were based on ±0.0002 Da of the expected exact mass-to-charge ratio (m/z) for each analyte of interest.

Results

No metabolite was detected from the incubations with hepatocytes. Under the presented analytical conditions, Compound 1a showed a retention time of approximate 7.8 minutes. Under negative scan mode, Compound 1a showed the deprotonated molecular ion m/z 745 ($C_{24}H_{25}F_2N_{10}O_8P_2S_2^-$) and the doubly deprotonated molecular ion m/z 372 ($C_{24}H_{24}F_2N_{10}O_{18}P_2S_{22}^-$). The major MS/MS product ions with m/z 533 ($C_{19}H_{19}FN_{10}O_4PS^-$) and m/z 186 ($C_9H_8N_5^-$) were observed. Under positive scan mode, Compound 1a showed the protonated molecular ion m/z 747 ($C_{24}H_{27}F_2N_{10}O_8P_2S_2^+$) and the major MS/MS product ions with m/z 651 ($C_{24}H_{26}F_2N_{10}O_6PS^+$), m/z 252 ($C_{10}H_{11}FN_5O_2^+$), and m/z 188 ($C_9H_{10}N_5^+$). The MS and MS/MS data are confirmative to the structure of Compound 1a.

Compound 1a was stable in the incubations with hepatocytes of mouse, rat, dog, monkey, and human. No apparent metabolite of Compound 1a was identified in this study. In the samples obtained from incubations with hepatocytes, only Compound 1a itself could be detected and confirmed by the fragments of tandem mass spectrometry (MS/MS).

All documents referenced in this disclosure are incorporated by reference herein, though if any incorporated document contradicts this written specification, then this written specification shall control. Those of skill in the will recognize that various changes and modifications may be made to the material provided herein, and that that material is within the scope and spirit of the disclosure.

---

SEQUENCE LISTINGS

```
SEQ ID NO: 1 (WT Human STING):
atgccccactccagcctgcatccatccatcccgtgtcccaggggtcacggggcccagaaggcagccttggttctgctgagtgcctgcctggtga
cccttggggctaggagagccaccagagcacactctccggtacctggtgctccacctagcctccctgcagctgggactgctgttaaacggggt
ctgcagcctggctgaggagctgcgccacatccactccaggtaccggggcagctactggaggactgtgcgggcctgcctgggctgcccctcc
gccgtggggcctgttgctgctgtccatctatttctactactccctcccaaatgcggtcggcccgcccttcacttggatgcttgcctcctgggcctct
cgcaggcactgaacatcctcctgggcctcaagggcctggcccccagctgagatctctgcagtgtgtgaaaaagggaatttcaacgtggcccatgg
gctggcatggtcatattacatcggatatctgcggctgatcctgccagagctccaggcccggattcgaacttacaatcagcattacaacaacctgcta
cggggtgcagtgagccagcggctgtatattctcctcccattggactgtggggtgcctgataacctgagtatggctgaccccaacattcgcttcctg
gataaactgccccagcagaccggtgaccgggctggcatcaaggatcgggtttacagcaacagcatctatgagcttctggagaacgggcagcgg
gcgggcacctgtgtcctggagtacgccacccccttgcagactttgtttgccatgtcacaatacagtcaagctggctttagccgggaggataggctt
gagcaggccaaactcttctgccggacacttgaggacatcctggcagatgcccctgagtctcagaacaactgccgcctcattgcctaccaggaac
ctgcagatgacagcagcttctcgctgtcccaggaggttctccggcacctgcggcaggaggaaaaggaagaggttactgtgggcagcttgaaga
cctcagcggtgcccagtacctccacgatgtcccaagagcctgagctcctcatcagtggaatggaaaagcccctccctctccgcacggatttctctt
ga SEQ ID NO: 2 (REF Human STING):
atgccccactccagcctgcatccatccatcccgtgtcccaggggtcacggggcccagaaggcagccttggttctgctgagtgcctgcctggtga
cccttggggctaggagagccaccagagcacactctccggtacctggtgctccacctagcctccctgcagctgggactgctgttaaacggggt
ctgcagcctggctgaggagctgcgccacatccactccaggtaccggggcagctactggaggactgtgcgggcctgcctgggctgcccctcc
gccgtggggcctgttgctgctgtccatctatttctactactccctcccaaatgcggtcggcccgcccttcacttggatgcttgcctcctgggcctct
cgcaggcactgaacatcctcctgggcctcaagggcctggcccccagctgagatctctgcagtgtgtgaaaaagggaatttcaacgtggcccatgg
gctggcatggtcatattacatcggatatctgcggctgatcctgccagagctccaggcccggattcgaacttacaatcagcattacaacaacctgcta
cggggtgcagtgagccagcggctgtatattctcctcccattggactgtggggtgcctgataacctgagtatggctgaccccaacattcgcttcctg
gataaactgccccagcagaccggtgaccatgctggcatcaaggatcgggtttacagcaacagcatctatgagcttctggagaacgggcagcgg
gcgggcacctgtgtcctggagtacgccacccccttgcagactttgtttgccatgtcacaatacagtcaagctggctttagccgggaggataggctt
gagcaggccaaactcttctgccggacacttgaggacatcctggcagatgcccctgagtctcagaacaactgccgcctcattgcctaccaggaac
ctgcagatgacagcagcttctcgctgtcccaggaggttctccggcacctgcggcaggaggaaaaggaagaggttactgtgggcagcttgaaga
cctcagcggtgcccagtacctccacgatgtcccaagagcctgagctcctcatcagtggaatggaaaagcccctccctctccgcacggatttctctt
ga SEQ ID NO: 3 (AQ Human STING):
atgccccactccagcctgcatccatccatcccgtgtcccaggggtcacggggcccagaaggcagccttggttctgctgagtgcctgcctggtga
cccttggggctaggagagccaccagagcacactctccggtacctggtgctccacctagcctccctgcagctgggactgctgttaaacggggt
ctgcagcctggctgaggagctgcgccacatccactccaggtaccggggcagctactggaggactgtgcgggcctgcctgggctgcccctcc
gccgtggggcctgttgctgctgtccatctatttctactactccctcccaaatgcggtcggcccgcccttcacttggatgcttgcctcctgggcctct
cgcaggcactgaacatcctcctgggcctcaagggcctggcccccagctgagatctctgcagtgtgtgaaaaagggaatttcaacgtggcccatgg
gctggcatggtcatattacatcggatatctgcggctgatcctgccagagctccaggcccggattcgaacttacaatcagcattacaacaacctgcta
cggggtgcagtgagccagcggctgtatattctcctcccattggactgtggggtgcctgataacctgagtatggctgaccccaacattcgcttcctg
gataaactgccccagcagaccgctgaccgagctggcatcaaggatcgggtttacagcaacagcatctatgagcttctggagaacgggcagcgg
gcgggcacctgtgtcctggagtacgccacccccttgcagactttgtttgccatgtcacaatacagtcaagctggctttagccgggaggataggctt
gagcaggccaaactcttctgccagacacttgaggacatcctggcagatgcccctgagtctcagaacaactgccgcctcattgcctaccaggaac
ctgcagatgacagcagcttctcgctgtcccaggaggttctccggcacctgcggcaggaggaaaaggaagaggttactgtgggcagcttgaaga
cctcagcggtgcccagtacctccacgatgtcccaagagcctgagctcctcatcagtggaatggaaaagcccctccctctccgcacggatttctctt
ga SEQ ID NO: 4 (WT STING residues 155-341):
VAHGLAWSYYIGYLRLILPELQARIRTYNQHYNNLLRGAVSQRLYILLPLDCGVPDNLSMA
DPNIRELDKLPQQTGDRAGIKDRVYSNSIYELLENGQRAGTCVLEYATPLQTLFAMSQYSQA
GFSREDRLEQAKLFCRTLEDILADAPESQNNCRLIAYQEPADDSSFSLSQEVLRHLRQEEKEE
V SEQ ID NO: 5 (His-TEV-Sumo-WT STING 155-341)
MHHHHHHSSGVDLGTENLYFQSNAMSDSEVNQEAKPEVKPEVKPETHINLKVSDGSSEIFF
KIKKTTPLRRLMEAFAKRQGKEMDSLRFLYDGIRIQADQTPEDLDMEDNDIIEAHREQIGGG
SVAHGLAWSYYIGYLRLILPELQARIRTYNQHYNNLLRGAVSQRLYILLPLDCGVPDNLSM
ADPNIRELDKLPQQTGDRAGIKDRVYSNSIYELLENGQRAGTCVLEYATPLQTLFAMSQYSQ
AGFSREDRLEQAKLFCRTLEDILADAPESQNNCRLIAYQEPADDSSFSLSQEVLRHLRQEEKE
EV
```

SEQ ID NO: 6 (REF STING residues 155-341):
VAHGLAWSYYIGYLRLILPELQARIRTYNQHYNNLLRGAVSQRLYILLPLDCGVPDNLSMA
DPNIRELDKLPQQTGDHAGIKDRVYSNSIYELLENGQRAGTCVLEYATPLQTLFAMSQYSQ
AGFSREDRLEQAKLFCRTLEDILADAPESQNNCRLIAYQEPADDSSFSLSQEVLRHLRQEEKE
EV SEQ ID NO: 7 (His-TEV-Sumo-REF STING 155-341)
MHHHHHHSSGVDLGTENLYFQSNAMSDSEVNQEAKPEVKPETHINLKVSDGSSEIFF
KIKKTTPLRRLMEAFAKRQGKEMDSLRFLYDGIRIQADQTPEDLDMEDNDIIEAHREQIGGG
SVAHGLAWSYYIGYLRLILPELQARIRTYNQHYNNLLRGAVSQRLYILLPLDCGVPDNLSM
ADPNIRFLDKLPQQTGDHAGIKDRVYSNSIYELLENGQRAGTCVLEYATPLQTLFAMSQYS
QAGFSREDRLEQAKLFCRTLEDILADAPESQNNCRLIAYQEPADDSSFSLSQEVLRHLRQEE
KEEV

---

We claim:

1. A compound or pharmaceutically acceptable salt thereof, selected from the group consisting of:

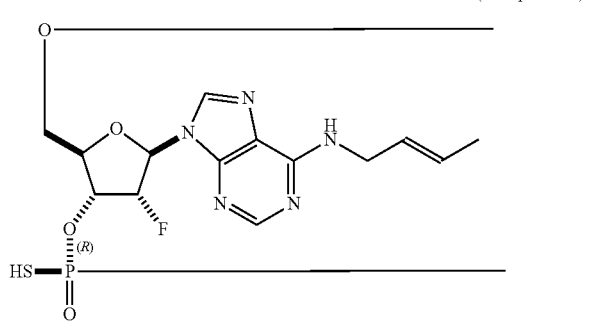
(Compound 2)

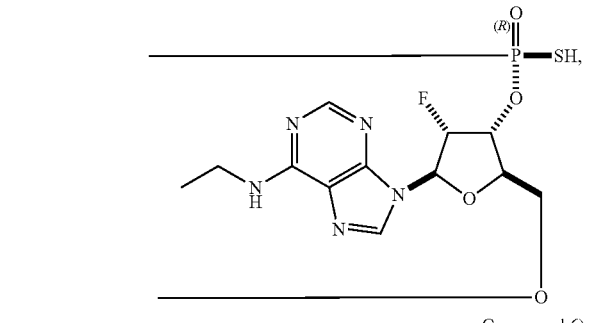
Compound 6)

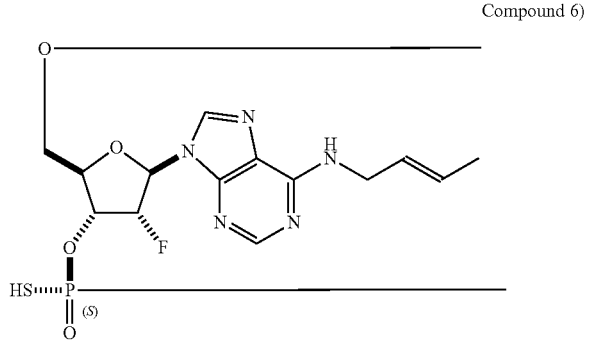
(Compound 26)

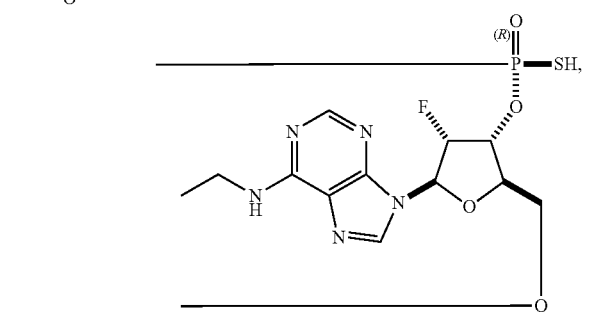

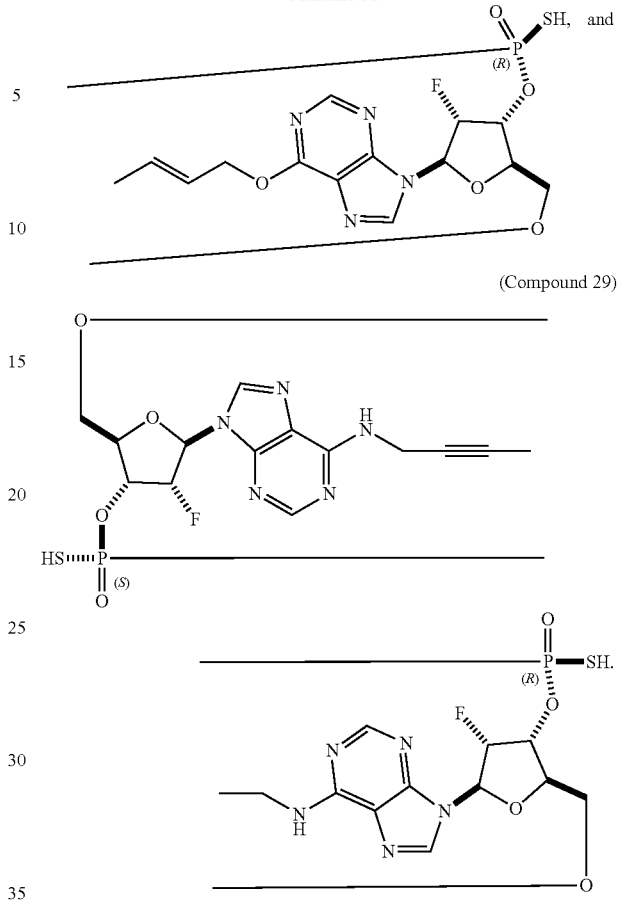
(Compound 29)

2. The compound or pharmaceutically acceptable salt of claim 1, wherein the compound or pharmaceutically acceptable salt is Compound 2 or a pharmaceutically acceptable salt thereof.

3. The compound or pharmaceutically acceptable salt of claim 2, wherein the compound is selected, and wherein the compound is Compound 2.

4. The compound or pharmaceutically acceptable salt of claim 2, wherein the pharmaceutically acceptable salt is selected, and wherein the pharmaceutically acceptable salt is a diammonium salt of Compound 2.

5. A pharmaceutical composition comprising a compound or pharmaceutically acceptable salt of claim 2 and a pharmaceutically acceptable excipient.

6. The compound or pharmaceutically acceptable salt of claim 1, wherein the compound or pharmaceutically acceptable salt is Compound 6 or a pharmaceutically acceptable salt thereof.

7. The compound or pharmaceutically acceptable salt of claim 6, wherein the compound is selected, and wherein the compound is Compound 6.

8. The compound or pharmaceutically acceptable salt of claim 6, wherein the pharmaceutically acceptable salt is selected, and wherein the pharmaceutically acceptable salt is a diammonium salt of Compound 6.

9. A pharmaceutical composition comprising a compound or pharmaceutically acceptable salt of claim 6 and a pharmaceutically acceptable excipient.

10. The compound or pharmaceutically acceptable salt of claim 1, wherein the compound or pharmaceutically acceptable salt is Compound 26 or a pharmaceutically acceptable salt thereof.

11. The compound or pharmaceutically acceptable salt of claim 10, wherein the compound is selected, and wherein the compound is Compound 26.

12. The compound or pharmaceutically acceptable salt of claim 10, wherein the pharmaceutically acceptable salt is selected, and wherein the pharmaceutically acceptable salt is a diammonium salt of Compound 26.

13. A pharmaceutical composition comprising a compound or pharmaceutically acceptable salt of claim 10 and a pharmaceutically acceptable excipient.

14. The compound or pharmaceutically acceptable salt of claim 10, wherein the pharmaceutically acceptable salt is selected, and wherein the pharmaceutically acceptable salt is a di-triethylamine salt of Compound 26.

15. The compound or pharmaceutically acceptable salt of claim 1, wherein the compound or pharmaceutically acceptable salt is Compound 29 or a pharmaceutically acceptable salt thereof.

16. The compound or pharmaceutically acceptable salt of claim 15, wherein the compound is selected, and wherein the compound is Compound 29.

17. The compound or pharmaceutically acceptable salt of claim 15, wherein the pharmaceutically acceptable salt is selected, and wherein the pharmaceutically acceptable salt is a diammonium salt of Compound 29.

18. A pharmaceutical composition comprising a compound or pharmaceutically acceptable salt of claim 15 and a pharmaceutically acceptable excipient.

\* \* \* \* \*